US012599675B2

(12) United States Patent
Heo et al.

(10) Patent No.:  US 12,599,675 B2
(45) Date of Patent:     Apr. 14, 2026

(54) CONJUGATE OF IMMUNE-STIMULATING IL-2 ANALOG AND PREPARATION METHOD THEREOF

(71) Applicant: HANMI PHARM. CO., LTD., Hwaseong-si (KR)

(72) Inventors: Yong Ho Heo, Hwaseong-si (KR); Euh Lim Oh, Hwaseong-si (KR); Da Hyeon Park, Hwaseong-si (KR); Jin Young Kim, Hwaseong-si (KR); Jun Sub Park, Hwaseong-si (KR); Yu Yon Kim, Hwaseong-si (KR); A Ram Lee, Hwaseong-si (KR); Sang Yun Kim, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 0 days.

(21) Appl. No.: 18/000,096

(22) PCT Filed: Mar. 31, 2022

(86) PCT No.: PCT/KR2022/004620
§ 371 (c)(1),
(2) Date: Nov. 28, 2022

(87) PCT Pub. No.: WO2022/211537
PCT Pub. Date: Oct. 6, 2022

(65) Prior Publication Data
US 2024/0009317 A1     Jan. 11, 2024

(30) Foreign Application Priority Data
Mar. 31, 2021     (KR) ........................ 10-2021-0042305

(51) Int. Cl.
*A61K 38/20*       (2006.01)
*A61K 47/68*       (2017.01)
*C07K 16/46*       (2006.01)

(52) U.S. Cl.
CPC .......... *A61K 47/68* (2017.08); *A61K 38/2013* (2013.01); *C07K 16/46* (2013.01)

(58) Field of Classification Search
None
See application file for complete search history.

(56) References Cited

FOREIGN PATENT DOCUMENTS

| KR | 10-2004-0086930 A | 10/2004 |
| KR | 10-2017-0070091 A | 6/2017 |
| KR | 10-2020-0078312 A | 7/2020 |
| KR | 10-2020-0086722 A | 7/2020 |
| WO | 96/032478 A1 | 10/1996 |
| WO | 97/034631 A1 | 9/1997 |
| WO | 2016/014428 A2 | 1/2016 |
| WO | 2016/164937 A2 | 10/2016 |
| WO | 2017/052329 A1 | 3/2017 |
| WO | 2018/089420 A1 | 5/2018 |
| WO | 2019/185705 A1 | 10/2019 |
| WO | 2020/020783 A1 | 1/2020 |
| WO | 2020/057646 A1 | 3/2020 |
| WO | 2020/260270 A1 | 12/2020 |
| WO | 2021/030633 A1 | 2/2021 |

OTHER PUBLICATIONS

Mestas et al ( J. of Immunology, 2004, 172, pp. 2731-238.*
Tufveson et al., Immunol. Rev, 1993, N: 136, pp. 100-109.*
Noessner (Front Cell Dev Biol, 2017, 1-7, 2017.*
Shanks et al ( Philosophy, Ethics and Humanities in Medicine, 2009, v.4, pp. 1-20.*
International Search Report for PCT/KR2022/004620 dated Jul. 12, 2022 [PCT/ISA/210].
Office Action dated Dec. 2, 2022 from the Australian Intellectual Property Office in AU Application No. 2022209248.
Communication dated Feb. 26, 2026 in Japanese Application No. 2023-555563.
Extended European Search Report dated Feb. 9, 2026 in Application No. 22781656.8.

* cited by examiner

*Primary Examiner* — Michail A Belyavskyi
(74) *Attorney, Agent, or Firm* — Sughrue Mion, PLLC

(57) ABSTRACT
The present invention relates to a long-acting conjugate of an interleukin-2 analog with altered binding affinity for interleukin-2 receptors.

12 Claims, 8 Drawing Sheets
Specification includes a Sequence Listing.

[Analog 21]          [Analog 41]          [Analog 52]

M : Marker (Unstained Ladder Thermo Fisher, 26614)
1 : Non-reduced interleukin-2 analog-3.4K PEG- FC fragment conjugate
2 : Reduced interleukin-2 analog-3.4K PEG- FC fragment conjugate primary tumor exposure          primary tumor re-exposure          secondary tumor re-exposure

- ○ negative control (drug not treated)
- ◆ aldesleukin (3.0 mg/kg, intraperitoneal)
- ■ interleukin-2 analog conjugate 21 (0.5 mg/kg, subcutaneous)
- ⬡ interleukin-2 analog conjugate 41 (0.5 mg/kg, subcutaneous)
- ▲ interleukin-2 analog conjugate 52 (0.5 mg/kg, subcutaneous)

- ● normal control (drug not treated)
- ○ negative control (drug not treated)
- ■ interleukin-2 analog conjugate 21 (0.5 mg/kg, subcutaneous)
- ▢ interleukin-2 analog conjugate 41 (0.5 mg/kg, subcutaneous)
- ▲ interleukin-2 analog conjugate 52 (0.5 mg/kg, subcutaneous)

Fig. 6A

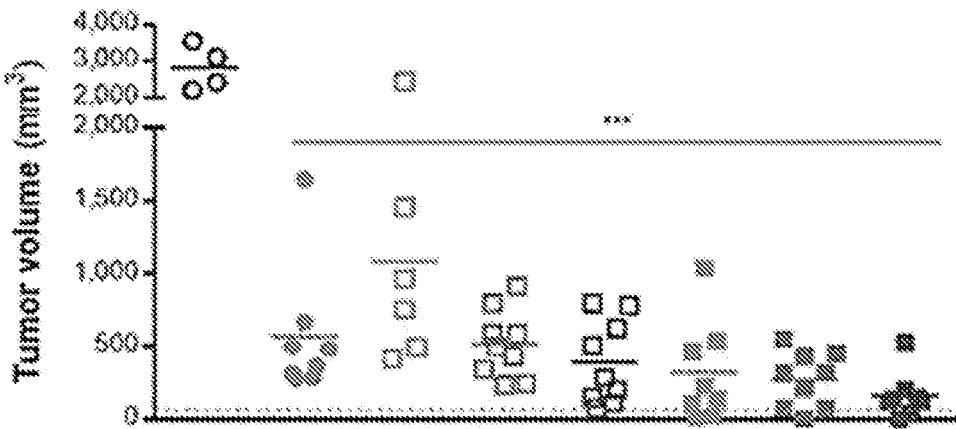

○  negative control (drug not treated)

◉  aldesleukin (3.0 mg/kg, intraperitoneal)

▢  interleukin-2 analog conjugate 86 (0.08 mg/kg, subcutaneous)

▢  interleukin-2 analog conjugate 86 (0.4 mg/kg, subcutaneous)

□  interleukin-2 analog conjugate 86 (2.0 mg/kg, subcutaneous)

▦  interleukin-2 analog conjugate 86 (4.0 mg/kg, subcutaneous)

▨  interleukin-2 analog conjugate 86 (6.0 mg/kg, subcutaneous)

■  interleukin-2 analog conjugate 86 (10.0 mg/kg, subcutaneous)

Fig. 6B

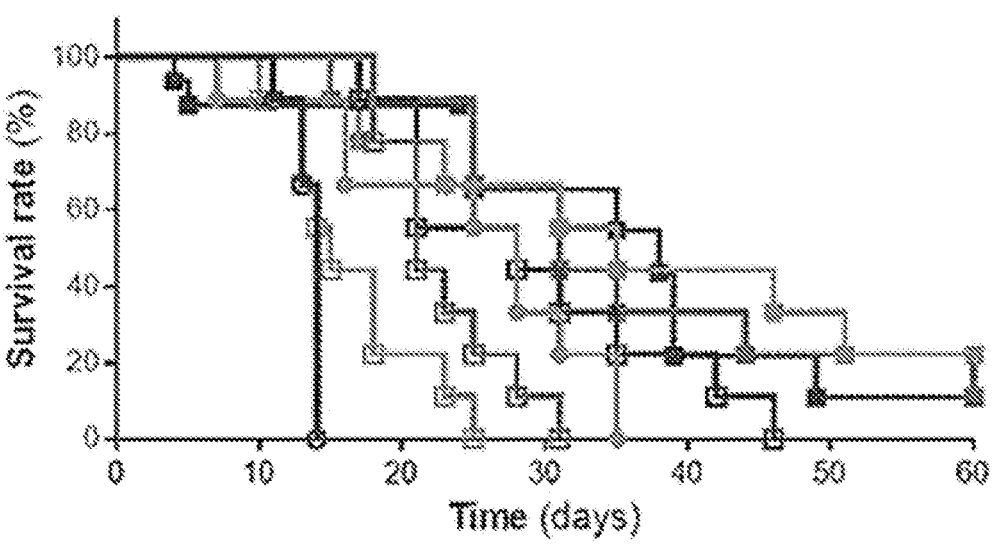

○ negative control (drug not treated)

◉ aldesleukin (3.0 mg/kg, intraperitoneal)

▢ interleukin-2 analog conjugate 86 (0.08 mg/kg, subcutaneous)

▢ interleukin-2 analog conjugate 86 (0.4 mg/kg, subcutaneous)

▢ interleukin-2 analog conjugate 86 (2.0 mg/kg, subcutaneous)

▦ interleukin-2 analog conjugate 86 (4.0 mg/kg, subcutaneous)

▨ interleukin-2 analog conjugate 86 (6.0 mg/kg, subcutaneous)

■ interleukin-2 analog conjugate 86 (10.0 mg/kg, subcutaneous)

1

CONJUGATE OF IMMUNE-STIMULATING IL-2 ANALOG AND PREPARATION METHOD THEREOF

CROSS REFERENCE TO RELATED APPLICATIONS

This application is a National Stage of International Application No. PCT/KR2022/004620 filed Mar. 31, 2022, claiming priority based on Korean Patent Application No. 10-2021-0042305 filed Mar. 31, 2021.

INCORPORATION BY REFERENCE OF SEQUENCE LISTING

The content of the electronically submitted sequence listing, file name: Q282192_Sequence_Listing_As_Filed.txt; size: 253,765 bytes; and date of creation: Nov. 23, 2021, filed herewith, is incorporated herein by reference in its entirety.

TECHNICAL FIELD

The present invention relates to a novel conjugate of an interleukin-2 analog, a preparation method thereof, and use thereof.

BACKGROUND ART

Interleukin-2 is an important immunostimulant with a molecular weight of about 15 kDa, which consists of a total of 133 amino acid residues, and activates various cells of the immune system including T cells and B cells. The high efficacy of interleukin-2 as an immunostimulant can be used for the treatment of various immune-related conditions including cancer and AIDS (Korean Patent Application Publication No. 10-2017-0070091). Currently, interleukin-2 (trademark name: Proleukin) is an FDA-approved drug for the treatment of metastatic renal cell carcinoma and metastatic melanoma. However, due to the severe toxicity associated with high-dose interleukin-2 therapy, the applicable patients are limited. In fact, this therapy is applied to only a small number of eligible patients. The toxicity associated with interleukin-2 includes severe fever, nausea, vomiting, vascular leak, severe hypotension, pulmonary edema, and vascular leak syndrome, which causes liver damage.

The interleukin-2 receptor has three kinds of subunit receptors. The subunit consists of an alpha chain (IL-2Rα, CD25), a beta chain (IL-2Rβ3 or CD122), and a gamma chain (IL-2Rγ or CD132). Interleukin-2 can exhibit various functions by binding to receptor subunits of various combinations. A single interleukin-2 alpha receptor is called a low-affinity interleukin-2 receptor, and it is not involved in signaling. A complex of interleukin-2 beta and gamma receptors binds to interleukin-2 with intermediate affinity. A complex of interleukin-2 alpha, beta, and gamma receptors binds to interleukin-2 with high affinity. The complex of interleukin-2 beta and gamma receptors is required for effective signal conversion through kinase activation in multiple signaling pathways. In particular, interleukin-2 beta- and gamma-binding receptors are prominent in CD8+ cells and natural killer (NK) cells. In addition, complexes of high-affinity interleukin-2 alpha, beta, and gamma receptors are usually found in CD4+ T regulatory cells (Treg), and recently they were also found in activated T cells. Since interleukin-2 beta receptors are distributed in CD8+ T cells or natural killer cells (NK cells) and are involved in the immune response in the body, studies have been conducted to develop therapeutic agents by increasing the activity of beta receptors for immune activation.

Meanwhile, despite the potential of interleukin-2 as a therapeutic agent for various immune-related conditions, there are still not many drugs which can reduce their doses while reducing toxicity and side effects, and thus there is an increasing demand for studies on new and improved drugs.

DISCLOSURE

Technical Problem

As part of the development of a therapeutic agent for immune-related diseases, it is required to develop a drug that includes an interleukin-2 analog and has excellent durability and pharmacological effect.

Technical Solution

An object of the present invention is to provide a long-acting conjugate including an interleukin-2 analog.

Another object of the present invention is to provide a method for preparing the long-acting conjugate.

Still another object of the present invention is to provide a pharmaceutical composition for preventing or treating cancer, including the interleukin-2 analog or a long-acting conjugate thereof.

Yet another object of the present invention is to provide a method for preventing or treating cancer, including administering the interleukin-2 analog, a long-acting conjugate thereof, or a composition including the same to an individual in need thereof.

Even another object of the present invention is to provide the use of the interleukin-2 analog, a long-acting conjugate thereof, or a composition including the same for the prevention or treatment of cancer.

Further another object of the present invention is to provide the use for a providing medicament for the prevention or treatment of cancer, including the interleukin-2 analog or a long-acting conjugate thereof, or a composition including the same.

Advantageous Effects

The interleukin-2 analog or a long-acting conjugate including the same is an analog which has an increased binding affinity for interleukin-2 beta receptors in vivo and has the effect of improving administration convenience and side effects for anticancer treatment purposes.

BRIEF DESCRIPTION OF DRAWINGS

In FIG. 3, the dose and serum concentration of the long-acting conjugate are shown based only on the weight occupied by the interleukin-2 analog region in the entire conjugate.

In FIG. 4, the dose of the long-acting conjugate is a value expressed based only on the weight occupied by the interleukin-2 analog region in the entire conjugate.

In FIGS. 5A and 5B are, the dose of the long-acting conjugate is a value expressed based only on the weight occupied by the interleukin-2 analog region in the entire conjugate.

FIGS. 6A and 6B are is the result of evaluating the anti-tumor efficacy of the long-acting conjugate of interleukin-2 analogs in an animal model of malignant melanoma. A shows the tumor size of the aldesleukin and interleukin-2 analog conjugate 86, and B is the result of confirming the survival rate of the aldesleukin and interleukin-2 analog conjugate 86. In FIGS. 6A and 6B are, the dose of the long-acting conjugate is a value expressed based only on the weight occupied by the interleukin-2 analog region in the entire conjugate.

BEST MODE

Figure 1:
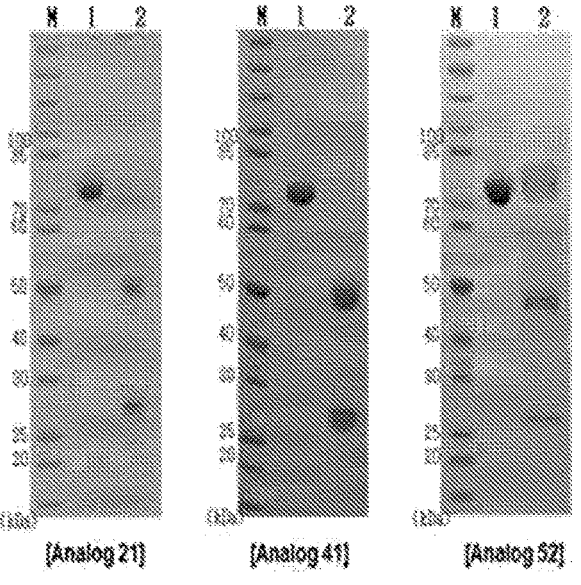
FIG. 1 is the SDS-PAGE result of the long-acting conjugate of interleukin-2 analogs (analogs 21, 41, and 52).

An aspect of the present invention provides a novel interleukin-2 analog (or IL-2 analog). The interleukin-2 analog is an interleukin-2 analog which has an increased binding affinity for interleukin-2 beta receptors compared to native interleukin-2 or aldesleukin (i.e., an interleukin-2 analog). The interleukin-2 analog may include a sequence in which one or more amino acids in native interleukin-2 are modified.

In a specific embodiment, the long-acting conjugate is characterized in that it is a long-acting conjugate represented by Chemical Formula 1 below:

$$X\text{-}L_a\text{-}F \qquad \text{[Chemical Formula 1]}$$

wherein, X is an interleukin-2 analog that when X does not form a part of the long-acting conjugate and is present alone, it is an interleukin-2 analog having an increased binding affinity for interleukin-2 beta receptors compared to aldesleukin;

L is a polyethylene glycol linker;

a is 0 or a natural number, with the proviso that when a is 2 or more, each L is independent of each other;

F is an immunoglobulin Fc region in the form of a dimer; and

— indicates a covalent linkage between X and L and between L and F;

wherein the interleukin-2 analog comprises a sequence in which one or more amino acids corresponding to positions 1, 12, 18, 19, 20, 22, 32, 35, 38, 42, 43, 45, 48, 49, 61, 68, 69, 74, 76, 80, 81, 82, 84, 85, 86, 87, 88, 89, 91, 92, 94, 95, 96, 125, 126, and 133 in native interleukin-2 are modified.

In another specific embodiment, the long-acting conjugate includes an interleukin-2 analog in which one or more amino acids in native interleukin-2 are mutated by one of the methods selected from the group consisting of substitution, addition, deletion, modification, and combinations thereof.

The long-acting conjugate according to any one of the previous specific embodiments is characterized in that the interleukin-2 alpha receptor binding affinity is changed compared to the native interleukin-2 or aldesleukin, and it includes the interleukin-2 analog having an increased binding affinity for interleukin-2 beta receptors as a part of the conjugate.

The long-acting conjugate according to any one of the previous specific embodiments is characterized in that it includes an interleukin-2 analog in which one or more amino acids are added to the amino acid corresponding to position 133 as a part of the conjugate.

The long-acting conjugate according to any one of the previous specific embodiments is characterized in that it includes an interleukin-2, as a part of the conjugate, in which the amino acid at position 1 is removed and the amino acid at position 125 is substituted with a different amino acid in the native interleukin-2.

The long-acting conjugate according to any one of the previous specific embodiments is characterized in that it includes an interleukin-2 analog further including 1 to 10 amino acid substitutions as a part of the conjugate.

The long-acting conjugate according to any one of the previous specific embodiments is characterized in that it includes an interleukin-2 analog, as a part of the conjugate, in which one or more amino acids at positions 18, 19, 20, 22, 38, 42, 43, 45, 61, 68, 69, 74, 80, 81, 84, 85, 86, 88, 89, 91, 92, 94, and 96 of the interleukin-2 analog are further substituted with different amino acids The long-acting conjugate according to any one of the previous specific embodiments is characterized in that it includes an interleukin-2 analog, as a part of the conjugate, in which one or more amino acids at positions 18, 22, 38, 42, 61, 68, 80, 81, 85, 86 and 92 are further substituted with different amino acids.

The long-acting conjugate according to any one of the previous specific embodiments includes any one of the following analogs as a part of an interleukin-2 analog:

(a) an interleukin-2 analog in which the amino acid at position 1 is removed and the amino acids at positions 125 and 32 are substituted with different amino acids in native interleukin-2;

(b) an interleukin-2 analog in which the amino acid at position 1 is removed and the amino acids at positions 125 and 35 are substituted with different amino acids in native interleukin-2;

(c) an interleukin-2 analog in which the amino acid at position 1 is removed and the amino acids at positions 125 and 38 are substituted with different amino acids in native interleukin-2;

(d) an interleukin-2 analog in which the amino acid at position 1 is removed and the amino acids at positions 125 and 42 are substituted with different amino acids in native interleukin-2;

(e) an interleukin-2 analog in which the amino acid at position 1 is removed and the amino acids at positions 125 and 43 are substituted with different amino acids in native interleukin-2;

(f) an interleukin-2 analog in which the amino acid at position 1 is removed and the amino acids at positions 125 and 48 are substituted with different amino acids in native interleukin-2;

(g) an interleukin-2 analog in which the amino acid at position 1 is removed and the amino acids at positions 125 and 49 are substituted with different amino acids in native interleukin-2;

(h) an interleukin-2 analog in which the amino acid at position 1 is removed and the amino acids at positions 125 and 76 are substituted with different amino acids in native interleukin-2;

(i) an interleukin-2 analog in which the amino acid at position 1 is removed and the amino acids at positions 125, 38, 42, 81, 92, 94, and 96 are substituted with different amino acids in native interleukin-2;

(j) an interleukin-2 analog in which the amino acid at position 1 is removed and the amino acids at positions 125 and 87 are substituted with different amino acids in native interleukin-2;

(k) an interleukin-2 analog in which the amino acid at position 1 is removed and the amino acids at positions 125, 38, and 42 are substituted with different amino acids in native interleukin-2;

(l) an interleukin-2 analog in which the amino acid at position 1 is removed and the amino acids at positions 125, 38, and 80 are substituted with different amino acids in native interleukin-2;

(m) an interleukin-2 analog in which the amino acid at position 1 is removed and the amino acids at positions 125, 38, and 84 are substituted with different amino acids in native interleukin-2;

(n) an interleukin-2 analog in which the amino acid at position 1 is removed and the amino acids at positions 125, 19, 38, and 42 are substituted with different amino acids in native interleukin-2;

(o) an interleukin-2 analog in which the amino acid at position 1 is removed and the amino acids at positions 125, 12, 38, and 42 are substituted with different amino acids in native interleukin-2;

(p) an interleukin-2 analog in which the amino acid at position 1 is removed and the amino acids at positions 125, 38, 42, and 61 are substituted with different amino acids in native interleukin-2;

(q) an interleukin-2 analog in which the amino acid at position 1 is removed and the amino acids at positions 125, 38, 42, and 84 are substituted with different amino acids in native interleukin-2;

(r) an interleukin-2 analog in which the amino acid at position 1 is removed and the amino acids at positions 125, 38, 42, and 88 are substituted with different amino acids in native interleukin-2;

(s) an interleukin-2 analog in which the amino acid at position 1 is removed and the amino acids at positions 125, 38, 42, and 89 are substituted with different amino acids in native interleukin-2;

(t) an interleukin-2 analog in which the amino acid at position 1 is removed and the amino acids at positions 125, 38, 42, and 91 are substituted with different amino acids in native interleukin-2;

(u) an interleukin-2 analog in which the amino acid at position 1 is removed and the amino acids at positions 125, 38, 42, and 94 are substituted with different amino acids in native interleukin-2;

(v) an interleukin-2 analog in which the amino acid at position 1 is removed and the amino acids at positions 125, 38, 42, and 126 are substituted with different amino acids in native interleukin-2;

(w) an interleukin-2 analog in which the amino acid at position 1 is removed and the amino acids at positions 125, 38, 80, and 84 are substituted with different amino acids in native interleukin-2;

(x) an interleukin-2 analog in which the amino acid at position 1 is removed and the amino acids at positions 125, 38, 94, and 96 are substituted with different amino acids in native interleukin-2;

(y) an interleukin-2 analog in which the amino acid at position 1 is removed and the amino acids at positions 125, 38, 81, and 92 are substituted with different amino acids in native interleukin-2;

(z) an interleukin-2 analog in which the amino acid at position 1 is removed and the amino acids at positions 125, 61, 81, and 92 are substituted with different amino acids in native interleukin-2;

(aa) an interleukin-2 analog in which the amino acid at position 1 is removed and the amino acids at positions 125, 38, 42, 81, and 92 are substituted with different amino acids in native interleukin-2;

(ab) an interleukin-2 analog in which the amino acid at position 1 is removed and the amino acids at positions 125, 38, 80, 81, and 92 are substituted with different amino acids in native interleukin-2;

(ac) an interleukin-2 analog in which the amino acid at position 1 is removed and the amino acids at positions 125, 38, 81, 84, and 92 are substituted with different amino acids in native interleukin-2;

(ad) an interleukin-2 analog in which the amino acid at position 1 is removed and the amino acids at positions 125, 20, 38, 42, 81, and 92 are substituted with different amino acids in native interleukin-2;

(ae) an interleukin-2 analog in which the amino acid at position 1 is removed and the amino acids at positions 125, 38, 42, 80, 81, and 92 are substituted with different amino acids in native interleukin-2;

(af) an interleukin-2 analog in which the amino acid at position 1 is removed and the amino acids at positions 125, 38, 42, 74, 81, and 92 are substituted with different amino acids in native interleukin-2;

(ag) an interleukin-2 analog in which the amino acid at position 1 is removed and the amino acids at positions 125, 38, 42, 81, 84, and 92 are substituted with different amino acids in native interleukin-2;

(ah) an interleukin-2 analog in which the amino acid at position 1 is removed and the amino acids at positions 125, 38, 42, 81, 88, and 92 are substituted with different amino acids in native interleukin-2;

(ai) an interleukin-2 analog in which the amino acid at position 1 is removed and the amino acids at positions 125, 38, 42, 85, 86, and 92 are substituted with different amino acids in native interleukin-2;

(aj) an interleukin-2 analog in which the amino acid at position 1 is removed and the amino acids at positions 125, 38, 80, 81, 85, and 92 are substituted with different amino acids in native interleukin-2;

(ak) an interleukin-2 analog in which the amino acid at position 1 is removed and the amino acids at positions 125, 38, 80, 81, 86, and 92 are substituted with different amino acids in native interleukin-2;

(al) an interleukin-2 analog in which the amino acid at position 1 is removed and the amino acids at positions 125, 80, 81, 85, 86, and 92 are substituted with different amino acids in native interleukin-2;

(am) an interleukin-2 analog in which the amino acid at position 1 is removed and the amino acids at positions 125, 38, 42, 45, 74, 81, and 92 are substituted with different amino acids in native interleukin-2;

(an) an interleukin-2 analog in which the amino acid at position 1 is removed and the amino acids at positions 125, 38, 42, 74, 80, 81, and 92 are substituted with different amino acids in native interleukin-2;

(ao) an interleukin-2 analog in which the amino acid at position 1 is removed and the amino acids at positions 125, 38, 42, 80, 81, 84, and 92 are substituted with different amino acids in native interleukin-2;

(ap) an interleukin-2 analog in which the amino acid at position 1 is removed and the amino acids at positions 125, 38, 42, 45, 80, 85, 86, and 92 are substituted with different amino acids in native interleukin-2;

(aq) an interleukin-2 analog in which the amino acid at position 1 is removed and the amino acids at positions 125, 38, 80, 81, 85, 86, and 92 are substituted with different amino acids in native interleukin-2;

(ar) an interleukin-2 analog in which the amino acid at position 1 is removed and the amino acids at positions 125, 42, 80, 81, 85, 86, and 92 are substituted with different amino acids in native interleukin-2;

(as) an interleukin-2 analog in which the amino acid at position 1 is removed and the amino acids at positions 125, 61, 80, 81, 85, 86, and 92 are substituted with different amino acids in native interleukin-2;

(at) an interleukin-2 analog in which the amino acid at position 1 is removed and the amino acids at positions 125, 69, 80, 81, 85, 86, and 92 are substituted with different amino acids in native interleukin-2;

(au) an interleukin-2 analog in which the amino acid at position 1 is removed and the amino acids at positions 125, 80, 81, 85, 86, 91, and 92 are substituted with different amino acids in native interleukin-2;

(av) an interleukin-2 analog in which the amino acid at position 1 is removed and the amino acids at positions 125, 18, 22, 80, 81, 85, 86, and 92 are substituted with different amino acids in native interleukin-2;

(aw) an interleukin-2 analog in which the amino acid at position 1 is removed and the amino acids at positions 125, 38, 42, 80, 81, 85, 86, and 92 are substituted with different amino acids in native interleukin-2;

(ax) an interleukin-2 analog in which the amino acid at position 1 is removed and the amino acids at positions 125, 38, 42, 45, 74, 80, 81, and 92 are substituted with different amino acids in native interleukin-2;

(ay) an interleukin-2 analog in which the amino acid at position 1 is removed and the amino acids at positions 125, 38, 68, 80, 81, 85, 86, and 92 are substituted with different amino acids in native interleukin-2;

(az) an interleukin-2 analog in which the amino acid at position 1 is removed and the amino acids at positions 125, 69, 74, 80, 81, 85, 86, and 92 are substituted with different amino acids in native interleukin-2;

(ba) an interleukin-2 analog in which the amino acid at position 1 is removed and the amino acids at positions 125, 80, 81, 84, 85, 86, 91, and 92 are substituted with different amino acids in native interleukin-2;

(bb) an interleukin-2 analog in which the amino acid at position 1 is removed and the amino acids at positions 125, 80, 81, 85, 86, 92, 94, and 96 are substituted with different amino acids in native interleukin-2;

(bc) an interleukin-2 analog in which the amino acid at position 1 is removed and the amino acids at positions 125, 18, 19, 22, 80, 81, 85, 86, and 92 are substituted with different amino acids in native interleukin-2;

(bd) an interleukin-2 analog in which the amino acid at position 1 is removed and the amino acids at positions 125, 18, 22, 38, 80, 81, 85, 86, and 92 are substituted with different amino acids in native interleukin-2;

(be) an interleukin-2 analog in which the amino acid at position 1 is removed and the amino acids at positions 125, 18, 22, 61, 80, 81, 85, 86, and 92 are substituted with different amino acids in native interleukin-2;

(bf) an interleukin-2 analog in which the amino acid at position 1 is removed and the amino acids at positions 125, 18, 22, 68, 80, 81, 85, 86, and 92 are substituted with different amino acids in native interleukin-2;

(bg) an interleukin-2 analog in which the amino acid at position 1 is removed and the amino acids at positions 125, 35, 38, 42, 80, 81, 85, 86, and 92 are substituted with different amino acids in native interleukin-2;

(bh) an interleukin-2 analog in which the amino acid at position 1 is removed and the amino acids at positions 125, 38, 42, 45, 80, 81, 85, 86, and 92 are substituted with different amino acids in native interleukin-2;

(bi) an interleukin-2 analog in which the amino acid at position 1 is removed and the amino acids at positions 125, 38, 42, 80, 81, 85, 86, 91, and 92 are substituted with different amino acids in native interleukin-2;

(bj) an interleukin-2 analog in which the amino acid at position 1 is removed and the amino acids at positions 125, 38, 42, 80, 81, 85, 86, 92, and 95 are substituted with different amino acids in native interleukin-2;

(bk) an interleukin-2 analog in which the amino acid at position 1 is removed and the amino acids at positions 125, 35, 38, 42, 74, 80, 81, 85, 86, and 92 are substituted with different amino acids in native interleukin-2;

(bl) an interleukin-2 analog in which the amino acid at position 1 is removed and the amino acids at positions 125, 38, 42, 43, 61, 80, 81, 85, 86, and 92 are substituted with different amino acids in native interleukin-2;

(bm) an interleukin-2 analog in which the amino acid at position 1 is removed and the amino acids at positions 125, 38, 42, 80, 81, 85, 86, 91, 92, and 95 are substituted with different amino acids in native interleukin-2;

(bn) an interleukin-2 analog in which the amino acid at position 1 is removed and the amino acids at positions 125, 35, 38, 42, 74, 80, 81, 82, 85, 86, and 92 are substituted with different amino acids in native interleukin-2;

(bo) an interleukin-2 analog in which the amino acid at position 1 is removed and the amino acids at positions 125, 80, 81, 86, and 92 are substituted with different amino acids in native interleukin-2; and (bp) an interleukin-2 analog in which the amino acid at position 1 is removed and the amino acids at positions 125, 80, 81, 85, and 86 are substituted with different amino acids in native interleukin-2.

The long-acting conjugate according to any one of the previous specific embodiments is characterized in that it includes an interleukin-2 analog including any one or more substitutions selected from the group consisting of the following amino acid substitutions:

(a) a substitution in which the amino acid at position 12 is substituted with valine or phenylalanine;

(b) a substitution in which the amino acid at position 18 is substituted with arginine;

(c) a substitution in which the amino acid at position 19 is substituted with tyrosine, valine, phenylalanine, or arginine;

(d) a substitution in which the amino acid at position 20 is substituted with valine or phenylalanine;

(e) a substitution in which the amino acid at position 22 is substituted with glutamic acid;

(f) a substitution in which the amino acid at position 32 is substituted with cysteine;

(g) a substitution in which the amino acid at position 35 is substituted with cysteine or glutamic acid;

(h) a substitution in which the amino acid at position 38 is substituted with alanine or aspartic acid;

(i) a substitution in which the amino acid at position 42 is substituted with lysine, alanine, or tryptophan;

(j) a substitution in which the amino acid at position 43 is substituted with cysteine, glutamic acid, or glutamine;

(k) a substitution in which the amino acid at position 45 is substituted with alanine;

(l) a substitution in which the amino acid at position 48 is substituted with cysteine;

(m) a substitution in which the amino acid at position 49 is substituted with cysteine;

(n) a substitution in which the amino acid at position 61 is substituted with glutamine, arginine, or aspartic acid;

(o) a substitution in which the amino acid at position 68 is substituted with aspartic acid or glutamine;

(p) a substitution in which the amino acid at position 69 is substituted with glycine;

(q) a substitution in which the amino acid at position 74 is substituted with histidine or alanine;

(r) a substitution in which the amino acid at position 76 is substituted with cysteine;

(s) a substitution in which the amino acid at position 80 is substituted with phenylalanine, tyrosine, valine, aspartic acid, or tryptophan;

(t) a substitution in which the amino acid at position 81 is substituted with aspartic acid, glutamic acid, or asparagine;

(u) a substitution in which the amino acid at position 82 is substituted with glycine or valine;

(v) a substitution in which the amino acid at position 84 is substituted with glutamic acid, valine, or phenylalanine;

(w) a substitution in which the amino acid at position 85 is substituted with valine, alanine, glycine, tryptophan, tyrosine, threonine, isoleucine, glutamic acid, or phenylalanine;

(x) a substitution in which the amino acid at position 86 is substituted with valine, alanine, glycine, or leucine;

(y) a substitution in which the amino acid at position 87 is substituted with cysteine;

(z) a substitution in which the amino acid at position 88 is substituted with glutamine, valine, or phenylalanine;

(aa) a substitution in which the amino acid at position 89 is substituted with phenylalanine;

(ab) a substitution in which the amino acid at position 91 is substituted with threonine, phenylalanine, or glutamic acid;

(ac) a substitution in which the amino acid at position 92 is substituted with phenylalanine, leucine, tyrosine, or tryptophan;

(ad) a substitution in which the amino acid at position 94 is substituted with phenyl alanine or valine;

(ae) a substitution in which the amino acid at position 95 is substituted with aspartic acid;

(af) a substitution in which the amino acid at position 96 is substituted with phenylalanine, valine, or isoleucine;

(ag) a substitution in which the amino acid at position 125 is substituted with serine; and (ah) a substitution in which the amino acid at position 126 is substituted with threonine.

The long-acting conjugate according to any one of the previous specific embodiments is characterized in that it includes an interleukin-2 analog including an amino acid sequence selected from the group consisting of SEQ ID NOS: 3 to 106.

The long-acting conjugate according to any one of the previous specific embodiments is characterized in that it includes an interleukin-2 analog of any one of the following analogs:

(a) an interleukin-2 analog, wherein the interleukin-2 analog is native interleukin-2 in which the amino acid at position 1 is removed and the amino acids at positions 125, 38, 42, 80, 81 and 92 are substituted with different amino acids;

(b) an interleukin-2 analog, wherein the interleukin-2 analog is native interleukin-2 in which the amino acid at position 1 is removed and the amino acids at positions 125, 80, 81, 85, 86, and 92 are substituted with different amino acids;

(c) an interleukin-2 analog, wherein the interleukin-2 analog is native interleukin-2 in which the amino acid at position 1 is removed and the amino acids at positions 125, 18, 22, 80, 81, 85, 86, and 92 are substituted with different amino acids;

(d) an interleukin-2 analog, wherein the interleukin-2 analog is native interleukin-2 in which the amino acid at position 1 is removed and the amino acids at positions 125, 38, 42, 80, 81, 85, 86, and 92 are substituted with different amino acids;

(e) an interleukin-2 analog, wherein the interleukin-2 analog is native interleukin-2 in which the amino acid at position 1 is removed and the amino acids at positions 125, 18, 22, 61, 80, 81, 85, 86, and 92 are substituted with different amino acids; and (f) an interleukin-2 analog, wherein the interleukin-2 analog is native interleukin-2 in which the amino acid at position 1 is removed and the amino acids at positions 125, 18, 22, 68, 80, 81, 85, 86, and 92 are substituted with different amino acids.

The long-acting conjugate according to any one of the previous specific embodiments is characterized in that it includes an interleukin-2 analog including any one or more amino acid substitutions selected from the group consisting of the following amino acid substitutions:

(a) a substitution in which the amino acid at position 18 is substituted with arginine;

(b) a substitution in which the amino acid at position 22 is substituted with glutamic acid;

(c) a substitution in which the amino acid at position 38 is substituted with alanine;

(d) a substitution in which the amino acid at position 42 is substituted with lysine;

(e) a substitution in which the amino acid at position 61 is substituted with aspartic acid;

(f) a substitution in which the amino acid at position 68 is substituted with aspartic acid;

(g) a substitution in which the amino acid at position 80 is substituted with phenylalanine;

(h) a substitution in which the amino acid at position 81 is substituted with glutamic acid;

(i) a substitution in which the amino acid at position 85 is substituted with valine;

(j) a substitution in which the amino acid at position 86 is substituted with valine;

(k) a substitution in which the amino acid at position 92 is substituted with phenylalanine; and (l) a substitution in which the amino acid at position 125 is substituted with serine.

The long-acting conjugate according to any one of the previous specific embodiments is characterized in that it includes an immunoglobulin Fc region which is derived from IgG, IgA, IgD, IgE, IgM, or a combination thereof, or a hybrid thereof.

The long-acting conjugate according to any one of the previous specific embodiments is characterized in that it includes an IgG4 Fc region.

The long-acting conjugate according to any one of the previous specific embodiments is characterized in that it includes an immunoglobulin Fc region which is non-glycosylated.

The long-acting conjugate according to any one of the preceding embodiments is characterized in that the immunoglobulin Fc region is derived from a human IgG4-derived non-glycosylated Fc region.

In the long-acting conjugate according to any one of the previous specific embodiments, the immunoglobulin Fc region has a structure in which two polypeptide chains are linked by a disulfide bond, and is linked only through a nitrogen atom in one of the two chains.

The long-acting conjugate according to any one of the previous specific embodiments is characterized in that the immunoglobulin Fc region includes a monomer having an amino acid sequence of SEQ ID NO: 438.

The long-acting conjugate according to any one of the previous specific embodiments is characterized in that the immunoglobulin Fc region is a homodimer of the monomers of the amino acid sequence of SEQ ID NO: 438.

The long-acting conjugate according to any one of the previous specific embodiments is characterized in that the immunoglobulin Fc region is linked through a nitrogen atom of the N-terminal proline thereof.

The long-acting conjugate according to any one of the previous specific embodiments is characterized in that the L contains ethylene glycol repeating units, and the formula weight of the ethylene glycol repeating unit moiety is in the range of 1 kDa to 100 kDa.

The long-acting conjugate according to any one of the previous specific embodiments is characterized in that one molecule of X is covalently linked to one of the Fc regions of the dimeric immunoglobulin Fc region through the polyethylene glycol linker.

The long-acting conjugate according to any one of the previous specific embodiments is characterized in that the ethylene glycol repeating unit has a formula of $[OCH_2CH_2]$ n, wherein n is a natural number, and the average molecular weight of the $[OCH_2CH_2]n$ region in the interleukin-2 analog conjugate, for example, the number average molecular weight is determined to be 1 kDa to 100 kDa.

The long-acting conjugate according to any one of the previous specific embodiments is characterized in that the value of n is determined such that the average molecular weight of the $[OCH_2CH_2]n$ region in the interleukin-2 analog conjugate, for example, the number average molecular weight is 3.4 kDa.

The long-acting conjugate according to any one of the previous specific embodiments is characterized in that a is 1, and one molecule of X is covalently linked to one of the Fc region chains of the dimeric immunoglobulin Fc region through a linker containing the ethylene glycol repeating units.

The long-acting conjugate according to any one of the previous specific embodiments is characterized in that one end of the linker is linked only to one of the two Fc region chains of the dimeric immunoglobulin Fc region.

As the long-acting conjugate according to any one of the previous specific embodiments, the conjugate is characterized in that one end of L is linked to F and the other end of L is linked to X by a covalent bond formed by reacting with an amine or thiol group of F and with an amine or thiol group of X, respectively.

Another aspect of the present invention provides a long-acting conjugate of an interleukin-2 analog, represented by Chemical Formula 2 below:

X—Z-Fc                    [Chemical Formula 2]

wherein X is an interleukin-2 analog including any one of polypeptide sequences selected from the amino acid sequence of SEQ ID NOS: 3 to 106;

Z is a polyethylene glycol linker having a molecular weight of 2 kDa to 30 kDa;

Fc is an immunoglobulin Fc region in the form of a dimer; and

— indicates a covalent linkage between X and Z and between Z and Fc;

wherein the long-acting conjugate is a long-acting conjugate in which one end of Z is covalently linked to only one polypeptide chain in the dimeric Fc region, and one molecule of X is covalently linked to the opposite end of Z.

In a specific embodiment, the interleukin-2 analog is characterized in that it includes any one of sequences selected from the group consisting of amino acid sequences of SEQ ID NOS: 10, 13, 14, 15, 16, 17, 20, 21, 22, 32, 35, 36, 42, 53, 54, 56, 58, 59, 60, 62, 71, 72, 74, 75, 76, 77, 78, 85, 87, 89, 91, 92, 93, 94, 95, 98, 99, 100, 101, 103, 104, 105, and 106.

In another specific embodiment, the interleukin-2 analog is characterized in that it includes any one of sequences selected from the group consisting of amino acid sequences of SEQ ID NOS: 10, 13, 14, 16, 17, 20, 21, 22, 32, 35, 36, 42, 53, 54, 87, 89, 91, 92, 93, 94, 98, 99, 100, 101, 103, 104, and 105.

The long-acting conjugate according to any one of the previous specific embodiments is characterized in that it includes an interleukin-2 analog including any one of sequences selected from the group consisting of the amino acid sequences of SEQ ID NOS: 22, 42, 53, 87, 105 and 106.

The interleukin-2 analog of the long-acting conjugate according to any one of the previous specific embodiments is characterized in that it further includes one or more amino acids at the C-terminus thereof.

Still another aspect of the present invention provides a long-acting conjugate of an interleukin-2 analog, represented by Chemical Formula 3 below:

X'—Z-Fc                    [Chemical Formula 3]

wherein X' is an interleukin-2 analog including an amino acid sequence represented by General Formula 1 below:

```
[General Formula 1]
                    (General Formula 1, SEQ ID NO: 212)
X1-P-T-S-S-S-T-K-K-T-Q-L-Q-L-E-H-L-X18-X19-D-L-

X22-M-I-L-N-G-I-N-N-Y-K-N-P-K-L-T-X38-M-L-T-X42-
```

-continued

```
X43-F-X45-M-P-K-K-A-T-E-L-K-H-L-Q-C-L-E-X61-E-L-K-

P-L-E-X68-V-L-N-L-A-X74-S-K-N-F-H-X80-X81-P-R-X84-

X85-X86-S-N-I-N-X91-X92-V-X94-E-X96-K-G-S-E-T-T-F-

M-C-E-Y-A-D-E-T-A-T-I-V-E-F-L-N-R-W-I-T-F-S-Q-S-I-

I-S-T-L-T
``` wherein in General Formula 1 above,

X1 is a deletion;

X18 is leucine (L) or arginine (R);

X19 is leucine (L) or tyrosine (Y);

X22 is glutamic acid (E) or glutamine (Q);

X38 is alanine (A), aspartic acid (D), or arginine (R);

X42 is alanine (A), phenylalanine (F), lysine (K), or tryptophan (W);

X43 is glutamic acid (E), lysine (K), or glutamine (Q);

X45 is alanine (A) or tyrosine (Y);

X61 is aspartic acid (D), glutamic acid (E), glutamine (Q), or arginine (R);

X68 is aspartic acid (D) or glutamic acid (E);

X74 is histidine (H) or glutamine (Q);

X80 is phenylalanine (F), leucine (L), valine (V), or tyrosine (Y);

X81 is aspartic acid (D), glutamic acid (E), or arginine (R);

X84 is aspartic acid (D) or glutamic acid (E);

X85 is alanine (A), glutamic acid (E), glycine (G), leucine (L), valine (V), tryptophan (W), or tyrosine (Y);

X86 is alanine (A), glycine (G), isoleucine (I), or valine (V);

X91 is threonine (T) or valine (V);

X92 is phenylalanine (F), isoleucine (I), or tyrosine (Y);

X94 is phenylalanine (F) or leucine (L);

X96 is phenylalanine (F) or leucine (L);

Z is a polyethylene glycol linker having a molecular weight of 2 kDa to 30 kDa;

Fc is an immunoglobulin Fc region in the form of a dimer; and

— indicates a covalent linkage between X' and Z and between Z and Fc;

wherein the long-acting conjugate is a long-acting conjugate in which one end of Z is covalently linked only to one polypeptide chain in the dimeric Fc region, and one molecule of X' is covalently linked to the opposite end of Z.

In a specific embodiment, in General Formula 1 above,

X43 is lysine (K);

X45 is tyrosine (Y);

X61 is aspartic acid (D), glutamic acid (E), or glutamine (Q);

X68 is glutamic acid (E);

X74 is glutamine (Q);

X80 is phenylalanine (F) or leucine (L);

X85 is leucine (L), valine (V), or tyrosine (Y);

X86 is isoleucine (I) or valine (V); and

X92 is phenylalanine (F) or isoleucine (I).

In another embodiment, the interleukin-2 analog further includes one or more amino acids at the C-terminus thereof.

Yet another aspect of the present invention provides a long-acting conjugate of an interleukin-2 analog, represented by Chemical Formula 4 below:

X"—Z-Fc                                    [Chemical Formula 4]

wherein X" is an interleukin-2 analog including an amino acid sequence represented by General Formula 2 below:

[General Formula 2]

(General Formula 2, SEQ ID NO: 213)
```
X1-P-T-S-S-S-T-K-K-T-Q-L-Q-L-E-H-L-X18-L-D-L-X22-

M-I-L-N-G-I-N-N-Y-K-N-P-K-L-T-X38-M-L-T-X42-K-F-Y-

M-P-K-K-A-T-E-L-K-H-L-Q-C-L-E-X61-E-L-K-P-L-E-X68-

V-L-N-L-A-Q-S-K-N-F-H-F-X81-P-R-D-X85-X86-S-N-I-N-

V-F-V-L-E-L-K-G-S-E-T-T-F-M-C-E-Y-A-D-E-T-A-T-I-V-

E-F-L-N-R-W-I-T-F-S-Q-S-I-I-S-T-L-T
```

X1 is a deletion;

X18 is leucine (L) or arginine (R);

X22 is glutamic acid (E) or glutamine (Q);

X38 is alanine (A) or arginine (R);

X42 is phenylalanine (F) or lysine (K);

X61 is aspartic acid (D) or glutamic acid (E);

X68 is aspartic acid (D) or glutamic acid (E);

X81 is aspartic acid (D) or glutamic acid (E);

X85 is leucine (L) or valine (V);

X86 is isoleucine (I) or valine (V);

Z is a polyethylene glycol linker having a molecular weight of 2 kDa to 30 kDa;

Fc is an immunoglobulin Fc region in the form of a dimer; and

— indicates a covalent linkage between X" and Z and between Z and Fc;

wherein the long-acting conjugate is a long-acting conjugate in which one end of Z is covalently linked only to one polypeptide chain in the dimeric Fc region, and one molecule of X" is covalently linked to the opposite end of Z.

In a specific embodiment, the interleukin-2 analog is characterized in that it includes any one of sequences selected from the group consisting of amino acid sequences of SEQ ID NOS: 22, 42, 53, 87, 105, and 106.

Even another aspect of the present invention provides a method for preparing a long-acting conjugate including an interleukin-2 analog, including: linking the interleukin-2 analog with an immunoglobulin Fc region through a non-peptidyl polymer.

In a specific embodiment, the interleukin-2 analog is characterized in that one or more amino acids selected from the group consisting of amino acids corresponding to positions 1, 12, 18, 19, 20, 22, 32, 35, 38, 42, 43, 45, 48, 49, 61, 68, 69, 74, 76, 80, 81, 82, 84, 85, 86, 87, 88, 89, 91, 92, 94, 95, 96, 125, 126, and 133 in native interleukin-2 are modified.

Further another aspect of the present invention provides a pharmaceutical composition for preventing or treating cancer, including an interleukin-2 analog or a long-acting conjugate thereof.

In a specific embodiment, the pharmaceutical composition is characterized in that it includes a pharmaceutically effective amount of a long-acting conjugate of an interleukin-2 analog and a pharmaceutically acceptable excipient.

In another specific embodiment, the interleukin-2 analog of the pharmaceutical composition is characterized in that it includes a sequence in which one or more amino acids corresponding to positions 1, 12, 18, 19, 20, 22, 32, 35, 38, 42, 43, 45, 48, 49, 61, 68, 69, 74, 76, 80, 81, 82, 84, 85, 86, 87, 88, 89, 91, 92, 94, 95, 96, 125, 126, and 133 in native interleukin-2 are modified.

The pharmaceutical composition according to any one of the previous specific embodiments is characterized in that it includes an interleukin-2 analog having an increased binding affinity for interleukin-2 beta receptors compared to aldesleukin.

The pharmaceutical composition according to any one of the previous specific embodiments is characterized in that the interleukin-2 analog is selected from the group consisting of SEQ ID NOS: 3 to 106.

The pharmaceutical composition according to any one of the previous specific embodiments is characterized in that the interleukin-2 analog is selected from the group consisting of SEQ ID NOS: 22, 42, 53, 87, 105, and 106.

The pharmaceutical composition according to any one of the previous specific embodiments is characterized in that the long-acting conjugate is represented by Chemical Formula 1 below:

$$X\text{-}L_a\text{-}F \qquad \text{[Chemical Formula 1]}$$

wherein, X is an interleukin-2 analog having an increased binding affinity for interleukin-2 beta receptors compared to aldesleukin;

L is a polyethylene glycol linker;

a is 0 or a natural number, with the proviso that when a is 2 or more, each L is independent of each other;

F is an immunoglobulin Fc region in the form of a dimer; and

— indicates a covalent linkage between X and L and between L and F.

The pharmaceutical composition according to any one of the previous specific embodiments is characterized in that the cancer is any one selected from the group consisting of metastatic renal cell cancer, metastatic melanoma, colorectal cancer, liver cancer, ovarian cancer, pancreatic cancer, gallbladder cancer, kidney cancer, colorectal cancer, lung cancer, skin cancer, melanoma, breast cancer, bladder cancer, and stomach cancer.

The pharmaceutical composition according to any one of the previous specific embodiments is characterized in that the composition exhibits high blood exposure, tumor growth inhibition and/or memory T-cell response relative to aldesleukin.

The pharmaceutical composition according to any one of the previous specific embodiments is characterized in that the pharmaceutical composition is administered via an intraperitoneal, intravenous, intramuscular, subcutaneous, intradermal, oral, topical, intranasal, intrapulmonary, or intrarectal route.

The pharmaceutical composition according to any one of the previous specific embodiments is characterized in that the pharmaceutical composition is administered at a time interval ranging from 1 week to 1 month.

Still further another aspect of the present invention provides a method for preventing or treating cancer, including: administering the interleukin-2 analog, a long-acting conjugate thereof, or a composition including the same to an individual in need thereof.

Still further another aspect of the present invention provides the use of the interleukin-2 analog, a long-acting conjugate thereof, or a composition including the same for the prevention or treatment of cancer.

Still further another aspect of the present invention provides the use for providing a medicament for the prevention or treatment of cancer, including the interleukin-2 analog or a long-acting conjugate thereof, or a composition including the same.

MODE FOR INVENTION

The details for carrying out the present invention will be described as follows. Meanwhile, respective descriptions and embodiments disclosed in the present invention may also be applied to other descriptions and embodiments. That is, all combinations of various elements disclosed in the present invention fall within the scope of the present invention. Further, the scope of the present invention cannot be considered to be limited by the specific description below. Furthermore, a number of papers and patent documents are referenced and cited throughout this specification. The disclosures of the cited papers and patent documents are incorporated herein by reference in their entirety to further clarify the level and scope of the subject matter to which the present invention pertains.

Over the entire specification of the present invention, the conventional one-letter and three-letter codes for amino acids are used. Additionally, the amino acids mentioned herein are abbreviated according to the nomenclature rules of the IUPAC-IUB as follows:

alanine A arginine R asparagine N aspartic acid D cysteine C glutamic acid E glutamine Q glycine G histidine H isoleucine 1 leucine L lysine K methionine M phenylalanine F proline P serine S threonine T tryptophan W tyrosine Y valine V As used herein, "Aib" may be used interchangeably with "2-aminoisobutyric acid" or "aminoisobutyric acid", and 2-aminoisobutyric acid and aminoisobutyric acid may be used interchangeably with each other.

One aspect of the present invention provides a long-acting conjugate including interleukin-2 analog.

Specifically, the long-acting conjugate may be represented by Chemical Formula 1 below:

$$X\text{-}L_a\text{-}F \qquad \text{[Chemical Formula 1]}$$

wherein, X is an interleukin-2 analog having an increased binding affinity for interleukin-2 beta receptors compared to aldesleukin;

L is a polyethylene glycol linker;

a is 0 or a natural number, with the proviso that when a is 2 or more, each L is independent of each other;

F is an immunoglobulin Fc region in the form of a dimer; and

— indicates a covalent linkage between X and L and between L and F.

The interleukin-2 analog of the long-acting conjugate of the present invention is characterized in that its binding affinity for interleukin-2 receptors is altered when it is present alone without forming a part of the conjugate, and in particular in that it has increased binding affinity for interleukin-2 beta receptors. Specifically, the interleukin-2 analog of the present invention may be one which has increased binding affinity for interleukin-2 beta receptors compared to native interleukin-2 or known aldesleukin, when it is present alone without forming a part of the conjugate, and more specifically one which also has altered (increased or decreased) binding affinity for interleukin-2 alpha receptors, and may include a sequence in which one or more amino acids in native interleukin-2 are modified.

As used herein, the term "interleukin-2 (IL-2)" refers to a type of cytokine which transmits signals in the immune system in vivo. The interleukin-2 is generally known as an important immunostimulator with a size of about 15 kDa.

As used herein, the term "interleukin-2 analog" refers to native interleukin-2 in which one or more amino acids in the sequence thereof are modified. Particularly in the present invention, the interleukin-2 analog may be an interleukin-2 analog which has reduced or increased binding affinity for interleukin-2 receptors compared to native interleukin-2, in which amino acids in native interleukin-2 are modified. Specifically, the interleukin-2 analog of the present invention may be one which is not naturally occurring.

The native interleukin-2 may be a human interleukin-2, and its sequence may be obtained from known databases, etc. Specifically, the native interleukin-2 may have an amino acid sequence of SEQ ID NO: 1, but is not limited thereto.

In the present invention, what is meant by "native interleukin-2 may have an amino acid sequence of SEQ ID NO: 1" is that not only the sequence which is the same as SEQ ID NO: 1, but also sequences which have a homology of 80%, 85%, 90%, 91%, 92%, 93%, 94%, 95%, 96%, 97%, 98%, or 99% or higher to SEQ ID NO: 1 belong to the scope of native interleukin-2 of the present invention; and that the corresponding position(s) of amino acid modification is(are) altered on the amino acid sequence of SEQ ID NO: 1 when sequences having a homology of 80%, 85%, 90%, 91%, 92%, 93%, 94%, 95%, 96%, 97%, 98%, or 99% or higher are aligned based on SEQ ID NO: 1.

In the present invention, what is meant by "one or more amino acids in the native sequence are altered" may be that a modification selected from the group consisting of substitution, addition, deletion, modification, and a combination thereof has occurred in at least one amino acid in the native sequence.

Specifically, the interleukin-2 analog of the present invention may include a sequence in which one or more amino acids corresponding to positions 1, 12, 18, 19, 20, 22, 32, 35, 38, 42, 43, 45, 48, 49, 61, 68, 69, 74, 76, 80, 81, 82, 84, 85, 86, 87, 88, 89, 91, 92, 94, 95, 96, 125, 126, and 133 in native interleukin-2 are modified. Specifically, the interleukin-2 analog of the present invention may be one in which the amino acid at position 1 is removed and the amino acid at position 125 is substituted with a different amino acid in native interleukin-2; and which further includes 1, 2, 3, 4, 5, 6, 7, 8, 9, 10, or more amino acid substitutions. Although not limited thereto, the amino acid at position 125 (i.e., cysteine) may be substituted with serine, and the amino acid(s) at which a further substitution occurs may be amino acids corresponding to positions 12, 18, 19, 20, 22, 32, 35, 38, 42, 43, 45, 48, 49, 61, 68, 69, 74, 76, 80, 81, 82, 84, 85, 86, 87, 88, 89, 91, 92, 94, 95, 96, 126, and 133.

Additionally, interleukin-2 analogs which include substitution, addition, deletion, modification, etc. of amino acid residues in addition to the positions for modification above to the extent that can be performed for the stability and increase of half-life of a peptide known in the art are also included within the scope of the present invention.

As used herein, the term "aldesleukin" or "interleukin-2 analog (aldesleukin)", which is a commercially available interleukin-2 analog, may be aldesleukin (trademark name: Proleukin®), and specifically may be one which has the amino acid sequence of SEQ ID NO: 2. In the present invention, these terms are used interchangeably with "interleukin-2 analog 1". The interleukin analog according to the present invention may have altered binding affinity for interleukin-2 alpha receptors and/or increased binding affinity for interleukin-2 beta receptors compared to the interleukin-2 analog 1.

Although interleukin-2 alpha receptors are not known to be involved in the signaling system of interleukin-2, they increase the binding affinity of interleukin-2 for other interleukin-2 receptors (beta or gamma receptors) by 10 to 100 times and are expressed in CD4$^+$ regulatory T cells, etc.

Since interleukin-2 beta receptors are mainly distributed in CD8$^+$ T cells or natural killer cells (NK cells) and have an important role of activating immune responses and macrophages, it is expected that tumor cell death and activation of the body's immune responses can be promoted through the activation of interleukin-2 beta receptors.

Accordingly, the interleukin-2 analog of the present invention which has increased binding affinity for interleukin-2 beta receptors can have a therapeutic effect where the suppression and death of tumors is increased while side effects are reduced.

In the present invention, the interleukin-2 analog may include a sequence in which the amino acid at position 1 is removed and the amino acid at position 125 is substituted with a different amino acid in native interleukin-2, and which further includes 1 to 10 amino acid modifications. For example, the interleukin-2 analog may include a sequence in which the amino acid at position 125 is substituted with serine and one or more amino acids at positions 12, 18, 19, 20, 22, 32, 35, 38, 42, 43, 45, 48, 49, 61, 68, 69, 74, 76, 80, 81, 82, 84, 85, 86, 87, 88, 89, 91, 92, 94, 95, 96, and 126 are substituted with different amino acids and/or one or more amino acids are added on the amino acid at position 133 in native interleukin-2, but the sequence is not limited thereto, and any interleukin-2 analog which has altered binding affinity for interleukin-2 alpha receptors and increased binding affinity for interleukin-2 beta receptors compared to native interleukin-2 and/or aldesleukin is included without limitation.

As an example of the interleukin-2 analog of the present invention, the interleukin-2 analog may be one in which one or more amino acids are added to the amino acid corresponding to position 133, but is not limited thereto. For the purpose of the present invention, the amino acids to be added are not limited with regard to the type or length thereof as long as the interleukin-2 analog has altered binding affinity for interleukin-2 alpha receptors and increased binding affinity for interleukin-2 beta receptors compared to native interleukin-2 or aldesleukin, and amino acids which are not naturally occurring and amino acids with a chemical modification can also be added in addition to natural amino acids.

In another embodiment, the interleukin-2 analog may be one in which the amino acid at position 1 is removed; the amino acid at position 125 is substituted with a different amino acid; and 1, 2, 3, 4, 5, 6, 7, 8, 9, or more amino acids among the amino acids at positions 18, 19, 20, 22, 38, 42, 43, 45, 61, 68, 69, 74, 80, 81, 84, 85, 86, 88, 89, 91, 92, 94, and 96 are substituted with different amino acids in native interleukin-2, but is not limited thereto.

In still another embodiment, the interleukin-2 analog may be one in which the amino acid at position 1 is removed; the amino acid at position 125 is substituted with a different amino acid; and 1, 2, 3, 4, 5, 6, 7, 8, 9, or more amino acids among the amino acids at positions 18, 19, 22, 38, 42, 43, 45, 61, 68, 74, 80, 81, 84, 85, 86, 88, 91, 92, 94, and 96 are substituted with different amino acids in native interleukin-2, but is not limited thereto.

In still another embodiment, the interleukin-2 analog may be one in which the amino acid at position 1 is removed; the amino acid at position 125 is substituted with a different amino acid; and one or more amino acids among the amino acids at positions 18, 22, 38, 42, 61, 68, 80, 81, 85, 86, and 92 are substituted with different amino acids in native interleukin-2, but is not limited thereto.

In still another embodiment, the interleukin-2 analog may be any one selected from the group consisting of the following analogs:

(a) an interleukin-2 analog in which the amino acid at position 1 is removed and the amino acids at positions 125 and 32 are substituted with different amino acids in native interleukin-2;

(b) an interleukin-2 analog in which the amino acid at position 1 is removed and the amino acids at positions 125 and 35 are substituted with different amino acids in native interleukin-2;

(c) an interleukin-2 analog in which the amino acid at position 1 is removed and the amino acids at positions 125 and 38 are substituted with different amino acids in native interleukin-2;

(d) an interleukin-2 analog in which the amino acid at position 1 is removed and the amino acids at positions 125 and 42 are substituted with different amino acids in native interleukin-2;

(e) an interleukin-2 analog in which the amino acid at position 1 is removed and the amino acids at positions 125 and 43 are substituted with different amino acids in native interleukin-2;

(f) an interleukin-2 analog in which the amino acid at position 1 is removed and the amino acids at positions 125 and 48 are substituted with different amino acids in native interleukin-2;

(g) an interleukin-2 analog in which the amino acid at position 1 is removed and the amino acids at positions 125 and 49 are substituted with different amino acids in native interleukin-2;

(h) an interleukin-2 analog in which the amino acid at position 1 is removed and the amino acids at positions 125 and 76 are substituted with different amino acids in native interleukin-2;

(i) an interleukin-2 analog in which the amino acid at position 1 is removed and the amino acids at positions 125, 38, 42, 81, 92, 94, and 96 are substituted with different amino acids in native interleukin-2;

(j) an interleukin-2 analog in which the amino acid at position 1 is removed and the amino acids at positions 125 and 87 are substituted with different amino acids in native interleukin-2;

(k) an interleukin-2 analog in which the amino acid at position 1 is removed and the amino acids at positions 125, 38, and 42 are substituted with different amino acids in native interleukin-2;

(l) an interleukin-2 analog in which the amino acid at position 1 is removed and the amino acids at positions 125, 38, and 80 are substituted with different amino acids in native interleukin-2;

(m) an interleukin-2 analog in which the amino acid at position 1 is removed and the amino acids at positions 125, 38, and 84 are substituted with different amino acids in native interleukin-2;

(n) an interleukin-2 analog in which the amino acid at position 1 is removed and the amino acids at positions 125, 19, 38, and 42 are substituted with different amino acids in native interleukin-2;

(o) an interleukin-2 analog in which the amino acid at position 1 is removed and the amino acids at positions 125, 12, 38, and 42 are substituted with different amino acids in native interleukin-2;

(p) an interleukin-2 analog in which the amino acid at position 1 is removed and the amino acids at positions 125, 38, 42, and 61 are substituted with different amino acids in native interleukin-2;

(q) an interleukin-2 analog in which the amino acid at position 1 is removed and the amino acids at positions 125, 38, 42, and 84 are substituted with different amino acids in native interleukin-2;

(r) an interleukin-2 analog in which the amino acid at position 1 is removed and the amino acids at positions 125, 38, 42, and 88 are substituted with different amino acids in native interleukin-2;

(s) an interleukin-2 analog in which the amino acid at position 1 is removed and the amino acids at positions 125, 38, 42, and 89 are substituted with different amino acids in native interleukin-2;

(t) an interleukin-2 analog in which the amino acid at position 1 is removed and the amino acids at positions 125, 38, 42, and 91 are substituted with different amino acids in native interleukin-2;

(u) an interleukin-2 analog in which the amino acid at position 1 is removed and the amino acids at positions 125, 38, 42, and 94 are substituted with different amino acids in native interleukin-2;

(v) an interleukin-2 analog in which the amino acid at position 1 is removed and the amino acids at positions 125, 38, 42, and 126 are substituted with different amino acids in native interleukin-2;

(w) an interleukin-2 analog in which the amino acid at position 1 is removed and the amino acids at positions 125, 38, 80, and 84 are substituted with different amino acids in native interleukin-2;

(x) an interleukin-2 analog in which the amino acid at position 1 is removed and the amino acids at positions 125, 38, 94, and 96 are substituted with different amino acids in native interleukin-2;

(y) an interleukin-2 analog in which the amino acid at position 1 is removed and the amino acids at positions 125, 38, 81, and 92 are substituted with different amino acids in native interleukin-2;

(z) an interleukin-2 analog in which the amino acid at position 1 is removed and the amino acids at positions 125, 61, 81, and 92 are substituted with different amino acids in native interleukin-2;

(aa) an interleukin-2 analog in which the amino acid at position 1 is removed and the amino acids at positions 125, 38, 42, 81, and 92 are substituted with different amino acids in native interleukin-2;

(ab) an interleukin-2 analog in which the amino acid at position 1 is removed and the amino acids at positions 125, 38, 80, 81, and 92 are substituted with different amino acids in native interleukin-2;

(ac) an interleukin-2 analog in which the amino acid at position 1 is removed and the amino acids at positions 125, 38, 81, 84, and 92 are substituted with different amino acids in native interleukin-2;

(ad) an interleukin-2 analog in which the amino acid at position 1 is removed and the amino acids at positions 125, 20, 38, 42, 81, and 92 are substituted with different amino acids in native interleukin-2;

(ae) an interleukin-2 analog in which the amino acid at position 1 is removed and the amino acids at positions 125, 38, 42, 80, 81, and 92 are substituted with different amino acids in native interleukin-2;

(af) an interleukin-2 analog in which the amino acid at position 1 is removed and the amino acids at positions 125, 38, 42, 74, 81, and 92 are substituted with different amino acids in native interleukin-2;

(ag) an interleukin-2 analog in which the amino acid at position 1 is removed and the amino acids at positions 125, 38, 42, 81, 84, and 92 are substituted with different amino acids in native interleukin-2;

(ah) an interleukin-2 analog in which the amino acid at position 1 is removed and the amino acids at positions 125, 38, 42, 81, 88, and 92 are substituted with different amino acids in native interleukin-2;

(ai) an interleukin-2 analog in which the amino acid at position 1 is removed and the amino acids at positions 125, 38, 42, 85, 86, and 92 are substituted with different amino acids in native interleukin-2;

(aj) an interleukin-2 analog in which the amino acid at position 1 is removed and the amino acids at positions 125, 38, 80, 81, 85, and 92 are substituted with different amino acids in native interleukin-2;

(ak) an interleukin-2 analog in which the amino acid at position 1 is removed and the amino acids at positions 125, 38, 80, 81, 86, and 92 are substituted with different amino acids in native interleukin-2;

(al) an interleukin-2 analog in which the amino acid at position 1 is removed and the amino acids at positions 125, 80, 81, 85, 86, and 92 are substituted with different amino acids in native interleukin-2;

(am) an interleukin-2 analog in which the amino acid at position 1 is removed and the amino acids at positions 125, 38, 42, 45, 74, 81, and 92 are substituted with different amino acids in native interleukin-2;

(an) an interleukin-2 analog in which the amino acid at position 1 is removed and the amino acids at positions 125, 38, 42, 74, 80, 81, and 92 are substituted with different amino acids in native interleukin-2;

(ao) an interleukin-2 analog in which the amino acid at position 1 is removed and the amino acids at positions 125, 38, 42, 80, 81, 84, and 92 are substituted with different amino acids in native interleukin-2;

(ap) an interleukin-2 analog in which the amino acid at position 1 is removed and the amino acids at positions 125, 38, 42, 45, 80, 85, 86, and 92 are substituted with different amino acids in native interleukin-2;

(aq) an interleukin-2 analog in which the amino acid at position 1 is removed and the amino acids at positions 125, 38, 80, 81, 85, 86, and 92 are substituted with different amino acids in native interleukin-2;

(ar) an interleukin-2 analog in which the amino acid at position 1 is removed and the amino acids at positions 125, 42, 80, 81, 85, 86, and 92 are substituted with different amino acids in native interleukin-2;

(as) an interleukin-2 analog in which the amino acid at position 1 is removed and the amino acids at positions 125, 61, 80, 81, 85, 86, and 92 are substituted with different amino acids in native interleukin-2;

(at) an interleukin-2 analog in which the amino acid at position 1 is removed and the amino acids at positions 125, 69, 80, 81, 85, 86, and 92 are substituted with different amino acids in native interleukin-2;

(au) an interleukin-2 analog in which the amino acid at position 1 is removed and the amino acids at positions 125, 80, 81, 85, 86, 91, and 92 are substituted with different amino acids in native interleukin-2;

(av) an interleukin-2 analog in which the amino acid at position 1 is removed and the amino acids at positions 125, 18, 22, 80, 81, 85, 86, and 92 are substituted with different amino acids in native interleukin-2;

(aw) an interleukin-2 analog in which the amino acid at position 1 is removed and the amino acids at positions 125, 38, 42, 80, 81, 85, 86, and 92 are substituted with different amino acids in native interleukin-2;

(ax) an interleukin-2 analog in which the amino acid at position 1 is removed and the amino acids at positions 125, 38, 42, 45, 74, 80, 81, and 92 are substituted with different amino acids in native interleukin-2;

(ay) an interleukin-2 analog in which the amino acid at position 1 is removed and the amino acids at positions 125, 38, 68, 80, 81, 85, 86, and 92 are substituted with different amino acids in native interleukin-2;

(az) an interleukin-2 analog in which the amino acid at position 1 is removed and the amino acids at positions 125, 69, 74, 80, 81, 85, 86, and 92 are substituted with different amino acids in native interleukin-2;

(ba) an interleukin-2 analog in which the amino acid at position 1 is removed and the amino acids at positions 125, 80, 81, 84, 85, 86, 91, and 92 are substituted with different amino acids in native interleukin-2;

(bb) an interleukin-2 analog in which the amino acid at position 1 is removed and the amino acids at positions 125, 80, 81, 85, 86, 92, 94, and 96 are substituted with different amino acids in native interleukin-2;

(bc) an interleukin-2 analog in which the amino acid at position 1 is removed and the amino acids at positions 125, 18, 19, 22, 80, 81, 85, 86, and 92 are substituted with different amino acids in native interleukin-2;

(bd) an interleukin-2 analog in which the amino acid at position 1 is removed and the amino acids at positions 125, 18, 22, 38, 80, 81, 85, 86, and 92 are substituted with different amino acids in native interleukin-2;

(be) an interleukin-2 analog in which the amino acid at position 1 is removed and the amino acids at positions 125, 18, 22, 61, 80, 81, 85, 86, and 92 are substituted with different amino acids in native interleukin-2;

(bf) an interleukin-2 analog in which the amino acid at position 1 is removed and the amino acids at positions 125, 18, 22, 68, 80, 81, 85, 86, and 92 are substituted with different amino acids in native interleukin-2;

(bg) an interleukin-2 analog in which the amino acid at position 1 is removed and the amino acids at positions 125, 35, 38, 42, 80, 81, 85, 86, and 92 are substituted with different amino acids in native interleukin-2;

(bh) an interleukin-2 analog in which the amino acid at position 1 is removed and the amino acids at positions 125, 38, 42, 45, 80, 81, 85, 86, and 92 are substituted with different amino acids in native interleukin-2;

(bi) an interleukin-2 analog in which the amino acid at position 1 is removed and the amino acids at positions 125, 38, 42, 80, 81, 85, 86, 91, and 92 are substituted with different amino acids in native interleukin-2;

(bj) an interleukin-2 analog in which the amino acid at position 1 is removed and the amino acids at positions 125, 38, 42, 80, 81, 85, 86, 92, and 95 are substituted with different amino acids in native interleukin-2;

(bk) an interleukin-2 analog in which the amino acid at position 1 is removed and the amino acids at positions 125, 35, 38, 42, 74, 80, 81, 85, 86, and 92 are substituted with different amino acids in native interleukin-2;

(bl) an interleukin-2 analog in which the amino acid at position 1 is removed and the amino acids at positions 125, 38, 42, 43, 61, 80, 81, 85, 86, and 92 are substituted with different amino acids in native interleukin-2;

(bm) an interleukin-2 analog in which the amino acid at position 1 is removed and the amino acids at positions 125, 38, 42, 80, 81, 85, 86, 91, 92, and 95 are substituted with different amino acids in native interleukin-2;

(bn) an interleukin-2 analog in which the amino acid at position 1 is removed and the amino acids at positions 125, 35, 38, 42, 74, 80, 81, 82, 85, 86, and 92 are substituted with different amino acids in native interleukin-2;

(bo) an interleukin-2 analog in which the amino acid at position 1 is removed and the amino acids at positions 125, 80, 81, 86, and 92 are substituted with different amino acids in native interleukin-2; and (bp) an interleukin-2 analog in which the amino acid at position 1 is removed and the amino acids at positions 125, 80, 81, 85, and 86 are substituted with different amino acids in native interleukin-2.

In particular, the amino acid substitutions included in the interleukin-2 analog may be any one or more selected from the group consisting of the following amino acid substitutions:

(a) a substitution in which the amino acid at position 12 is substituted with valine or phenylalanine;

(b) a substitution in which the amino acid at position 18 is substituted with arginine;

(c) a substitution in which the amino acid at position 19 is substituted with tyrosine, valine, phenylalanine, or arginine;

(d) a substitution in which the amino acid at position 20 is substituted with valine or phenylalanine;

(e) a substitution in which the amino acid at position 22 is substituted with glutamic acid;

(f) a substitution in which the amino acid at position 32 is substituted with cysteine;

(g) a substitution in which the amino acid at position 35 is substituted with cysteine or glutamic acid;

(h) a substitution in which the amino acid at position 38 is substituted with alanine or aspartic acid;

(i) a substitution in which the amino acid at position 42 is substituted with lysine, alanine, or tryptophan;

(j) a substitution in which the amino acid at position 43 is substituted with cysteine, glutamic acid, or glutamine;

(k) a substitution in which the amino acid at position 45 is substituted with alanine;

(l) a substitution in which the amino acid at position 48 is substituted with cysteine;

(m) a substitution in which the amino acid at position 49 is substituted with cysteine;

(n) a substitution in which the amino acid at position 61 is substituted with glutamine, arginine, or aspartic acid;

(o) a substitution in which the amino acid at position 68 is substituted with aspartic acid or glutamine;

(p) a substitution in which the amino acid at position 69 is substituted with glycine;

(q) a substitution in which the amino acid at position 74 is substituted with histidine or alanine;

(r) a substitution in which the amino acid at position 76 is substituted with cysteine;

(s) a substitution in which the amino acid at position 80 is substituted with phenylalanine, tyrosine, valine, aspartic acid, or tryptophan;

(t) a substitution in which the amino acid at position 81 is substituted with aspartic acid, glutamic acid, or asparagine;

(u) a substitution in which the amino acid at position 82 is substituted with glycine or valine;

(v) a substitution in which the amino acid at position 84 is substituted with glutamic acid, valine, or phenylalanine;

(w) a substitution in which the amino acid at position 85 is substituted with valine, alanine, glycine, tryptophan, tyrosine, threonine, isoleucine, glutamic acid, or phenylalanine;

(x) a substitution in which the amino acid at position 86 is substituted with valine, alanine, glycine, or leucine;

(y) a substitution in which the amino acid at position 87 is substituted with cysteine;

(z) a substitution in which the amino acid at position 88 is substituted with glutamine, valine, or phenylalanine;

(aa) a substitution in which the amino acid at position 89 is substituted with phenylalanine;

(ab) a substitution in which the amino acid at position 91 is substituted with threonine, phenylalanine, or glutamic acid;

(ac) a substitution in which the amino acid at position 92 is substituted with phenylalanine, leucine, tyrosine, or tryptophan;

(ad) a substitution in which the amino acid at position 94 is substituted with phenyl alanine or valine;

(ae) a substitution in which the amino acid at position 95 is substituted with aspartic acid;

(af) a substitution in which the amino acid at position 96 is substituted with phenylalanine, valine, or isoleucine;

(ag) a substitution in which the amino acid at position 125 is substituted with serine; and (ah) a substitution in which the amino acid at position 126 is substituted with threonine.

In still another embodiment, the interleukin-2 analog may be any one selected from the following interleukin-2 analogs:

(a) an interleukin-2 analog in which the amino acid at position 1 is removed and the amino acids at positions 125, 38, 42, 80, 81 and 92 are substituted with different amino acids in native interleukin-2 analog;

(b) an interleukin-2 analog in which the amino acid at position 1 is removed and the amino acids at positions 125, 80, 81, 85, 86, and 92 are substituted with different amino acids in native interleukin-2 analog;

(c) an interleukin-2 analog in which the amino acid at position 1 is removed and the amino acids at positions 125, 18, 22, 80, 81, 85, 86, and 92 are substituted with different amino acids in native interleukin-2 analog;

(d) an interleukin-2 analog in which the amino acid at position 1 is removed and the amino acids at positions 125, 38, 42, 80, 81, 85, 86, and 92 are substituted with different amino acids in native interleukin-2 analog;

(e) an interleukin-2 analog in which the amino acid at position 1 is removed and the amino acids at positions 125, 18, 22, 61, 80, 81, 85, 86, and 92 are substituted with different amino acids in native interleukin-2 analog; and (f) an interleukin-2 analog in which the amino acid at position 1 is removed and the amino acids at positions 125, 18, 22, 68, 80, 81, 85, 86, and 92 are substituted with different amino acids in native interleukin-2 analog.

In particular, the amino acid substitutions included in the interleukin-2 analog may be any one or more selected from the group consisting of the following amino acid substitutions:

(a) a substitution in which the amino acid at position 18 is substituted with arginine;

(b) a substitution in which the amino acid at position 22 is substituted with glutamic acid;

(c) a substitution in which the amino acid at position 38 is substituted with alanine;

(d) a substitution in which the amino acid at position 42 is substituted with lysine;

(e) a substitution in which the amino acid at position 61 is substituted with aspartic acid;

(f) a substitution in which the amino acid at position 68 is substituted with aspartic acid;

(g) a substitution in which the amino acid at position 80 is substituted with phenylalanine;

(h) a substitution in which the amino acid at position 81 is substituted with glutamic acid;

(i) a substitution in which the amino acid at position 85 is substituted with valine;

(j) a substitution in which the amino acid at position 86 is substituted with valine;

(k) a substitution in which the amino acid at position 92 is substituted with phenylalanine; and (l) a substitution in which the amino acid at position 125 is substituted with serine.

As used herein, the term "corresponding to" refers to an amino acid residue at a position listed in a peptide, or an amino acid residue which is similar, identical, or homologous to a residue listed in a peptide. Confirmation of the amino acid at the corresponding position may be determining a specific amino acid in a sequence that refers to a specific sequence.

For example, each amino acid residue in the amino acid sequence can be numbered by aligning any amino acid sequence with SEQ ID NO: 1, and based on the same, referring to the numerical position of the amino acid residue corresponding to the amino acid residue of SEQ ID NO: 1.

As such an alignment, for example, the Needleman-Wunsch algorithm (Needleman and Wunsch, 1970, J. Mol. Biol. 48:443-453), the Needle program of the EMBOSS package (EMBOSS: The European Molecular Biology Open Software Suite, Rice et al., 2000), (*Trends Genet.* 16:276-277), etc. may be used, but the available programs are not limited thereto, and a sequence alignment program known in the art, a pairwise sequence comparison algorithm, etc. may be used appropriately.

In the present invention, even if expressed as a specific position of an amino acid in a peptide, such expression may refer to a corresponding position in a reference sequence.

In another embodiment, the interleukin-2 analog may include, essentially consist of, or consist of an amino acid sequence which is selected from the group consisting of SEQ ID NOS: 3 to 106, but is not limited thereto.

Additionally, even if the interleukin-2 analog is expressed as "an interleukin-2 analog consisting of a particular SEQ ID NO" in the present invention, it does not exclude a mutation that may occur by the addition of a meaningless sequence upstream or downstream of the amino acid sequence of the corresponding SEQ ID NO, or a mutation that may occur naturally, or a silent mutation thereof, as long as the inter-leukin-2 analog has an activity identical or equivalent to the interleukin-2 analog consisting of the amino acid sequence of the corresponding SEQ ID NO, and even if the sequence addition or mutation is present, the interleukin-2 analog apparently belongs to the scope of the present invention.

The interleukin-2 analog of the present invention may include an amino acid sequence which has a homology or identity of 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% or higher to the amino acid sequences of SEQ ID NOS: 3 to 106, but is not limited thereto.

In a specific embodiment, the interleukin-2 analog of the present invention may include, essentially consist of, or consist of an amino acid sequence which is selected from the group consisting of SEQ ID NOS: 21, 41, 52, 86, 104, and 105, but is not limited thereto.

As used herein, the terms "homology" and "identity" refer to a degree of relatedness between two given amino acid sequences or nucleotide sequences and may be expressed as a percentage.

Sequence homology or identity of a conserved polynucle-otide or polypeptide may be determined by a standard alignment algorithm, and default gap penalties established by a program to be used may be used in combination. Substantially, homologous or identical sequences may generally hybridize with all or part of the sequences under moderately or highly stringent conditions. It is apparent that hybridization also includes hybridization of a polynucle-otide with a polynucleotide, which includes a general codon or a codon where codon degeneracy is considered.

The terms homology and identity can frequently be used interchangeably.

Whether any two nucleotide or peptide sequences have homology, similarity, or identity may be determined by, for example, a known computer algorithm (e.g., the "FASTA" program) using default parameters as in Pearson et al. (1988) *Proc. Natl. Acad. Sci. USA* 85:2444). Alternatively, they may be determined using the Needleman-Wunsch algorithm (Needleman and Wunsch, 1970, *J. Mol. Biol.* 48:443-453) as performed in the Needleman program of the EMBOSS package (EMBOSS: The European Molecular Biology Open Software Suite, Rice et al., 2000, *Trends Genet.* 16:276-277) (version 5.0.0 or later) (including GCG program package (Devereux, J. et al., *Nucleic Acids Research* 12:387 (1984)), BLASTP, BLASTN, FASTA (Atschul, S. F. et al., *J Molec Biol* 215:403 (1990); *Guide to Huge Computers, Martin J. Bishop, ed.*, Academic Press, San Diego, 1994, and CAR-ILLO et al. (1988) *SIAM J Applied Math* 48:1073). For example, homology, similarity, or identity may be determined using BLAST or ClustalW of the National Center for Biotechnology Information.

Homology, similarity, or identity of nucleotide or peptide sequences may be determined by comparing sequence information using the GAP computer program (e.g., Needleman et al. (1970), *J Mol Biol* 48:443) as disclosed in Smith and Waterman, *Adv. Appl. Math* (1981) 2:482. Briefly, the GAP program defines homology, similarity, or identity as the number of similar aligned symbols (i.e., nucleotides or amino acids), divided by the total number of symbols in the shorter of the two sequences. The default parameters for the GAP program may include: (1) a unary comparison matrix (containing a value of 1 for identities and 0 for nonidentities) and the weighted comparison matrix (or EDNA-FULL (EMBOSS version of NCBI NUC4.4) substitution matrix) of Gribskov et al. (1986) *Nucl. Acids Res.* 14:6745, as disclosed by Schwartz and Dayhoff, eds., *Atlas Of Protein Sequence And Structure*, National Biomedical Research Foundation, pp. 353-358 (1979); (2) a penalty of 3.0 for each gap and an additional 0.10 penalty for each symbol in each gap (or gap open penalty 10, gap extension penalty 0.5); and (3) no penalty for end gaps. Therefore, the terms "homology" and "identity", as used herein, represent relatedness between sequences.

The above may be applied to other embodiments or other aspects of the present invention, but is not limited thereto.

The interleukin-2 analog of the present invention may be used as a novel interleukin-2 substitute that alters its in vitro activity by weakening or increasing the binding affinity of the interleukin-2 analog for interleukin-2 alpha and/or beta receptors. In particular, the interleukin-2 analog of the present invention can be used as an effective therapeutic agent due to its activities for the two types of receptors because it not only has an increased binding affinity for beta receptors but also has altered (i.e., increased or decreased) binding affinity for alpha receptors.

In the present invention, such modification for preparing analogs of interleukin-2 includes all of the modifications using L-type or D-type amino acids and/or non-natural amino acids; and/or a modification of native sequence, for example, a modification of a side chain functional group, an intramolecular covalent bonding (e.g., a ring formation between side chains), methylation, acylation, ubiquitination, phosphorylation, aminohexanation, biotinylation, etc.

Additionally, the modification includes all of those where one or more amino acids are added to the amino and/or carboxy terminus of native interleukin-2.

As the amino acids to be substituted or added, not only the 20 amino acids commonly observed in human proteins, but also atypical amino acids or those which are not naturally occurring can be used. Commercial sources of atypical amino acids include Sigma-Aldrich, ChemPep Inc., and Genzyme Pharmaceuticals. The peptides including these amino acids and typical peptide sequences may be synthesized and purchased from commercial suppliers for peptide synthesis, e.g., American Peptide Company, Bachem (USA), or Anygen (Korea).

Amino acid derivatives may be obtained in the same manner, and as one such example, 4-imidazoacetic acid, etc. may be used.

Additionally, the interleukin-2 analog according to the present invention may be in a modified form where the N-terminus and/or C-terminus, etc. of the interleukin-2 is chemically modified or protected by organic groups, or amino acids may be added to the terminus of the peptide, etc. for its protection from proteases in vivo while increasing its stability.

In particular, in the case of a chemically synthesized peptide, its N- and C-termini are electrically charged, and thus the N-terminus of the peptide may be acetylated and/or C-terminus of the peptide may be amidated to remove the charge, but the peptide is not particularly limited thereto.

The interleukin-2 analog of the present invention may be synthesized by a solid-phase synthesis method, and may also be produced by a recombinant method, or may be prepared commercially, but is not limited thereto.

Further, the interleukin-2 analog of the present invention may be synthesized by a method well-known in the art, according to its length, e.g., by an automatic peptide synthesizer, and may also be produced by genetic engineering technology.

Specifically, the interleukin-2 analog of the present invention may be prepared by a standard synthesis method, a recombinant expression system, or any other method known in the art. Accordingly, the interleukin-2 analog of the present invention may be synthesized by many methods including, for example, the following methods:

(a) a method of synthesizing a peptide by a solid-phase or liquid-phase method stepwise or by fragment assembly, followed by isolation and purification of the final peptide product;

(b) a method of expressing a nucleic acid construct encoding a peptide in a host cell and recovering the expression product from the host cell culture; or (c) a method of performing an in vitro cell-free expression of a nucleic acid construct encoding a peptide and recovering the expression product therefrom; or a method of obtaining peptide fragments by any combination of the methods (a), (b), and (c), obtaining a peptide by linking the peptide fragments, and then recovering the peptide.

In the present invention, the binding affinity of any interleukin-2 analog (or a long-acting conjugate including the same) for native interleukin-2 receptors can be measured using surface plasmon resonance (SPR), which is a method for measuring the affinity for the receptors.

Specifically, in the SPR analysis, a method, using the protein-ligand binding principle, in which the interleukin-2 receptor is immobilized to the sensor chip and the interleukin-2 analog diluted in the experimental buffer using a serial dilution method is flowed to induce binding to the immobilized receptor, and then, only the experimental buffer was flowed at the same flow rate to induce the dissociation of the interleukin-2 analog with the receptor, thereby measuring the binding affinity; or a method in which an antibody for a human immunoglobulin Fc region is immobilized to a sensor chip, then the interleukin-2 receptor to which the Fc region is bound is immobilized, and the interleukin-2 analog is flowed to measure binding affinity may be used, but the method is not limited thereto.

More specifically, biotin-labeled human interleukin-2 receptors were immobilized to a streptavidin biosensor chip, and the long-acting conjugate of the interleukin-2 analog diluted to HBS-P+ buffer using a two-fold serial dilution method was flowed at a flow rate of 20 μL/min for 3 minutes, and only the HBS-P+ buffer was flowed at the same flow rate to induce the dissociation between the interleukin-2 receptors and the long-acting conjugate of the interleukin-2 analog, and the obtained association constant and dissociation constant were used to measure the binding affinity according to the 1:1 binding fitting model using the Biaevaluation program, but is not limited thereto.

More specifically, the interleukin-2 analog of the present invention may have a reduced or increased binding affinity for interleukin-2 alpha receptors compared to the native interleukin-2 or interleukin-2 analog (aldesleukin; or interleukin-2 analog 1).

Specifically, the interleukin-2 analog of the present invention may have binding affinity for interleukin-2 alpha receptors of about 0.001-fold or greater, about 0.005-fold or greater, about 0.01-fold or greater, about 0.05-fold or greater, about 0.1-fold or greater, about 0.3-fold or greater, about 0.5-fold or greater, about 0.7-fold or greater, about 0.9-fold or greater, about 1.1-fold or greater, about 1.3-fold or greater, about 1.5-fold or greater, or about 1.7-fold or greater compared to the binding affinity of native interleukin-2 or aldesleukin for interleukin-2 alpha receptors, but the numerical value of the binding affinity is not limited, and the value will belong to the scope of the present invention as long as there is a change in the binding affinity compared to that of native interleukin-2 or aldesleukin.

Alternatively, based on the binding affinity of aldesleukin for interleukin-2 alpha receptors (set at 100%), the interleukin-2 analog of the present invention may have no binding affinity for interleukin-2 alpha receptors or have binding affinity for interleukin-2 alpha receptors of about 1% or greater, about 5% or greater, about 7% or greater, about 10% or greater, about 15% or greater, about 20% or greater, about 30% or greater, about 50% or greater, about 70% or greater, about 90% or greater, about 100% or greater, about 150% or greater, or about 200% or greater, but the numerical value of the binding affinity is not limited, and the value will belong to the scope of the present invention as long as there is a change in the binding affinity compared to that of native interleukin-2 or aldesleukin.

Additionally, the interleukin-2 analog of the present invention may specifically have binding affinity for interleukin-2 beta receptors of about 0.1-fold or greater, about 0.3-fold or greater, about 0.5-fold or greater, about 0.7-fold or greater, about 1.0-fold or greater, about 10-fold or greater, about 20-fold or greater, about 30-fold or greater, about 40-fold or greater, about 50-fold or greater, about 60-fold or greater, about 70-fold or greater, about 80-fold or greater, about 90-fold or greater, or about 100-fold or greater compared to the binding affinity of native interleukin-2 or aldesleukin for interleukin-2 beta receptors, but the numerical value of the binding affinity is not limited, and the value will belong to the scope of the present invention as long as there is a change or increase in the binding affinity compared to that of native interleukin-2 or aldesleukin.

Alternatively, based on the binding affinity of aldesleukin for interleukin-2 beta receptors (set at 100%), the interleukin-2 analog of the present invention may have binding affinity for interleukin-2 beta receptors of about 5% or greater, about 9% or greater, about 10% or greater, about 20% or greater, about 30% or greater, about 50% or greater, about 100% or greater, about 200% or greater, about 500% or greater, about 700% or greater, about 1,000% or greater, about 1,500% or greater, about 3,000% or greater, about 5,000% or greater, about 7,000% or greater, about 10,000% or greater, about 12,000% or greater, about 15,000% or greater, about 20,000% or greater, or about 25,000%, but the numerical value of the binding affinity is not limited, and the value will belong to the scope of the present invention as long as there is an increase in the binding affinity compared to that of native interleukin-2 or aldesleukin.

As used herein, the term "about" refers to a range which includes all of ±0.5, ±0.4, ±0.3, ±0.2, ±0.1, etc. and includes all of the values that are equivalent or similar to those following the values, but the range is not limited thereto.

The interleukin-2 analog of the present invention is characterized in that it has altered binding affinity for interleukin-2 alpha receptors and increased binding affinity for interleukin-2 beta receptors compared to native interleukin-2 or aldesleukin.

In a specific embodiment of the present invention, for the preparation of the interleukin-2 analog of the present invention, an interleukin-2 analog, into which a modification was introduced based on native interleukin-2 (SEQ ID NO: 1), was prepared. The interleukin-2 analog prepared in the present invention may be one which includes any one amino acid sequence among SEQ ID NOS: 3 to 106, or may be one which is encoded by any one nucleotide sequence among SEQ ID NOS: 108 to 211.

The nucleic acid encoding the interleukin-2 analog of the present invention may be one which is modified so that a modification (deletion, substitution, and/or addition of an amino acid) can be introduced into an amino acid at a particular position in a nucleotide sequence encoding the native interleukin-2 of SEQ ID NO: 1, and specifically, the interleukin-2 analog of the present invention may include a nucleotide sequence encoding any one amino acid sequence among SEQ ID NOS: 3 to 106. For example, the nucleic acid of the present invention may have or include a nucleotide sequence of any one among SEQ ID NOS: 108 to 211.

The nucleotide sequence of the present invention may be modified variously in the coding region within a range not altering the amino acid sequence of the interleukin-2 analog of the present invention, considering codon degeneracy or the codons preferred in the organism where the nucleic acid of the present invention is to be expressed. Specifically, the nucleic acid of the present invention may have or include a nucleotide sequence which has a homology or identity of 70% or higher, 75% or higher, 80% or higher, 85% or higher, 90% or higher, 95% or higher, 96% or higher, 97% or higher, 98% or higher, and less than 100% to any one of the sequences of SEQ ID NOS: 108 to 211; or may consist of or essentially consist of a nucleotide sequence which has a homology or identity of 70% or higher, 75% or higher, 80% or higher, 85% or higher, 90% or higher, 95% or higher, 96% or higher, 97% or higher, 98% or higher, and less than 100% to any one of the sequences of SEQ ID NOS: 108 to 211, but the nucleic acid is not limited thereto.

Additionally, the nucleic acid of the present invention can include, without limitation, a probe which can be prepared from a known gene sequence (e.g., a sequence that can hybridize with a sequence complementary to all or part of the nucleic acid sequence of the present invention under stringent conditions). The "stringent conditions" refer to conditions that enable specific hybridization between polynucleotides. Such conditions are described in detail in the literature (see J. Sambrook et al., Molecular Cloning, *A Laboratory Manual,* 2nd Edition, Cold Spring Harbor Laboratory press, Cold Spring Harbor, New York, 1989; F. M. Ausubel et al., *Current Protocols in Molecular Biology,* John Wiley & Sons, Inc., New York, 9.50-9.51, 11.7-11.8).

Hybridization requires that two nucleic acids have complementary sequences, although mismatches between bases may be possible depending on hybridization stringency. The term "complementary" is used to describe the relationship between nucleotide bases that can hybridize to each other. For example, with respect to DNA, adenine is complementary to thymine, and cytosine is complementary to guanine. Accordingly, the nucleic acid of the present invention can include isolated nucleic acid fragments complementary to the entire sequence as well as substantially similar nucleic acid sequences.

The appropriate stringency for hybridizing polynucleotides depends on the length of the polynucleotides and the degree of complementarity, and variables are well known in the art (e.g., Sambrook et al., supra).

The homology and identity are as described above.

Further, the interleukin-2 analog of the present invention may have an increased in vivo half-life, compared to native interleukin-2 or aldesleukin, but is not particularly limited thereto. For example, the interleukin-2 analog of the present invention may be in the form of a long-acting conjugate having an increased half-life by linking a biocompatible material (e.g., an immunoglobulin Fc region) for increasing the half-life to the interleukin-2 analog directly or via a linker, but is not limited thereto.

The long-acting conjugate according to the present invention not only includes an interleukin-2 analog with increased binding affinity for the interleukin-2 beta receptors, but also binds to an immunoglobulin Fc region as a representative carrier for increasing its half-life, thereby increasing the half-life of the interleukin-2 analog, increasing blood exposure, and increasing in vivo immune response, and thus, growth inhibition and reduction of cancer cells can be effectively achieved.

Another aspect for implementing the present invention provides a long-acting conjugate of an interleukin-2 analog.

In the present invention, the long-acting conjugate of an interleukin-2 analog may be in the form, in which a biocompatible material capable of increasing the in vivo half-life thereof is linked to the interleukin-2 analog. In the present invention, the biocompatible material may be used interchangeably with a carrier.

In the present invention, the long-acting conjugate may exhibit increased duration of the efficacy as compared with the interleukin-2 analog to which the carrier is not linked, and in the present invention, such a conjugate is referred to as a "long-acting conjugate" or "conjugate"

Meanwhile, the conjugate may be one which does not occur naturally.

In one specific embodiment of the present invention, the long-acting conjugate may be a long-acting conjugate represented by Chemical Formula 1 below:

$$X\text{-}L_a\text{-}F \qquad \text{[Chemical Formula 1]}$$

wherein, X is an interleukin-2 analog having an increased binding affinity for interleukin-2 beta receptors compared to aldesleukin;

L is a polyethylene glycol linker;

a is 0 or a natural number, with the proviso that when a is 2 or more, each L is independent of each other;

F is an immunoglobulin Fc region in the form of a dimer; and

— indicates a covalent linkage.

More specifically, X and L, and L and F may be linked to each other via a covalent bond. In particular, the conjugate is a conjugate, in which X, L, and F are linked via covalent bonds, respectively, as in the order of Chemical Formula 1.

Further, F may be directly linked to X (i.e., a is 0 in Chemical Formula 1), or may be linked through a linker (L).

In the present invention, the interleukin-2 analog may correspond to an element of one moiety constituting the conjugate. Specifically, it corresponds to X in Chemical Formula 1 above, and the interleukin-2 analog is the same as described above.

In the conjugate, F is a material capable of increasing the half-life of X, i.e., the interleukin-2 analog, and it corresponds to an element of one moiety constituting the conjugate of the present invention.

F and X may be linked to each other by a covalent chemical bond, and F and X may be linked to each other via L by a covalent chemical bond.

Specifically, F is an immunoglobulin Fc region, and the immunoglobulin Fc region may be an IgG Fc region or a non-glycosylated IgG4 Fc region, but is not particularly limited thereto.

As a specific embodiment of the present invention, F (immunoglobulin Fc region) is a dimer consisting of two polypeptide chains, and may have a structure in which one end of L is linked only to one of the two polypeptide chains, but not limited thereto.

One or more amino acid side chains within the peptide of the present invention may be attached to the biocompatible material in order to increase in vivo solubility and/or half-life, and/or to increase bioavailability thereof. These modifications may reduce the clearance of therapeutic proteins and peptides.

The above-described biocompatible material may be soluble (amphipathic or hydrophilic) and/or non-toxic and/or pharmaceutically acceptable.

Further, F may be directly linked to X (i.e., a is 0 in Chemical Formula 1), or may be linked through a polyethylene glycol linker (L).

In one specific embodiment, the long-acting conjugate of the present invention may be one in which an interleukin-2 analog and an immunoglobulin Fc region are linked, but is not limited thereto.

In the present invention, the "immunoglobulin Fc region" refers to a region including a heavy chain constant region 2 (CH2) and/or a heavy chain constant region 3 (CH3), excluding heavy chain and light chain variable regions of the immunoglobulin. The immunoglobulin Fc region may be an element constituting the moiety of the conjugate of the present invention. Specifically, the immunoglobulin Fc region corresponds to F in Chemical Formula 1 above.

In the present specification, the Fc region encompasses not only a native sequence obtained from papain digestion of an immunoglobulin, but also derivatives thereof, for example, variants, in which one or more amino acid residues in the native sequence are converted by deletion, insertion, non-conservative or conservative substitution, or a combination thereof, and thus become different from the native sequence, etc.

The above derivatives, substituents, and variants are required to retain FcRn-binding ability. In the present invention, F may be a human immunoglobulin region, but is not limited thereto. In the present specification, "biocompatible material" or "carrier" may refer to the Fc region.

F (e.g., an immunoglobulin Fc region) has a structure, in which two polypeptide chains are linked to each other via a disulfide bond, only via a nitrogen atom of one chain of the two chains, but is not limited thereto. The linkage via the nitrogen atom may be linked via reductive amination to an epsilon amino group or the N-terminal amino group of lysine.

The reductive amination reaction refers to a reaction in which an amine group or an amino group of a reactant reacts with an aldehyde (i.e., a functional group capable of reductive amination) of another reactant to produce an amine, and then forms an amine bond by a reduction reaction. It is an organic synthesis reaction well known in the art.

In a specific embodiment of the long-acting conjugate of the present invention, the immunoglobulin Fc region is linked to the linker via a nitrogen atom at the N-terminus thereof.

Such an immunoglobulin Fc region may include a hinge region in the heavy chain constant region, but is not limited thereto.

In the present invention, the immunoglobulin Fc region may include a specific hinge sequence at the N-terminus.

As used herein, the term "hinge sequence" refers to a region that is located in the heavy chain and forms a dimer of the immunoglobulin Fc region through an inter-disulfide bond.

In the present invention, the hinge sequence may be altered to have only one cysteine residue by deleting a part in a hinge sequence having the following amino acid sequence, but is not limited thereto:

Glu-Ser-Lys-Tyr-Gly-Pro-Pro-Cys-Pro-Ser-Cys-Pro (SEQ ID NO: 418).

The hinge sequence may include only one cysteine residue by deleting a cysteine residue at position 8 or 11 in the hinge sequence of SEQ ID NO: 418. The hinge sequence of the present invention may include only one cysteine residue and may consist of 3 to 12 amino acids, but is not limited thereto. More specifically, the hinge sequence of the present invention may have the following sequence:

```
                                    (SEQ ID NO: 419)
Glu-Ser-Lys-Tyr-Gly-Pro-Pro-Pro-Ser-Cys-Pro, (SEQ ID NO: 420)
Glu-Ser-Lys-Tyr-Gly-Pro-Pro-Cys-Pro-Ser-Pro, (SEQ ID NO: 421)
Glu-Ser-Lys-Tyr-Gly-Pro-Pro-Cys-Pro-Ser, (SEQ ID NO: 422)
Glu-Ser-Lys-Tyr-Gly-Pro-Pro-Cys-Pro-Pro, (SEQ ID NO: 423)
Lys-Tyr-Gly-Pro-Pro-Cys-Pro-Ser, (SEQ ID NO: 424)
Glu-Ser-Lys-Tyr-Gly-Pro-Pro-Cys, (SEQ ID NO: 425)
Glu-Lys-Tyr-Gly-Pro-Pro-Cys, (SEQ ID NO: 426)
Glu-Ser-Pro-Ser-Cys-Pro, (SEQ ID NO: 427)
Glu-Pro-Ser-Cys-Pro, (SEQ ID NO: 428)
Pro-Ser-Cys-Pro, (SEQ ID NO: 429)
Glu-Ser-Lys-Tyr-Gly-Pro-Pro-Ser-Cys-Pro, (SEQ ID NO: 430)
Lys-Tyr-Gly-Pro-Pro-Pro-Ser-Cys-Pro, (SEQ ID NO: 431)
Glu-Ser-Lys-Tyr-Gly-Pro-Ser-Cys-Pro, (SEQ ID NO: 432)
Glu-Ser-Lys-Tyr-Gly-Pro-Pro-Cys, (SEQ ID NO: 433)
Lys-Tyr-Gly-Pro-Pro-Cys-Pro, (SEQ ID NO: 434)
Glu-Ser-Lys-Pro-Ser-Cys-Pro, (SEQ ID NO: 435)
Glu-Ser-Pro-Ser-Cys-Pro, (SEQ ID NO: 436)
Glu-Pro-Ser-Cys, (SEQ ID NO: 437)
Ser-Cys-Pro.
```

More specifically, the hinge sequence may include an amino acid sequence of SEQ ID NO: 428 (Pro-Ser-Cys-Pro) or SEQ ID NO: 437 (Ser-Cys-Pro), but is not limited thereto.

In a more specific embodiment of the long-acting conjugate of the present invention, in the conjugate, the N-terminus of the immunoglobulin Fc region is proline. In this conjugate, the Fc region is linked to the linker via a nitrogen atom of the proline.

In an embodiment of the long-acting conjugate of the present invention, the immunoglobulin Fc region may have a dimer form in which two chains of the immunoglobulin Fc region form a homodimer or a heterodimer due to the presence of a hinge sequence. The conjugate of Chemical Formula 1 of the present invention may be in the form in which one end of the linker is linked to one chain of the immunoglobulin Fc region of the dimer, but is not limited thereto.

As used herein, the term "N-terminus" refers to the amino terminus of a protein or polypeptide, and includes the extreme end of the amino terminus or includes up to 1, 2, 3, 4, 5, 6, 7, 8, 9, or 10 or more amino acids from the extreme end. The immunoglobulin Fc region of the present invention may include a hinge sequence at the N-terminus, but is not limited thereto.

Further, the immunoglobulin Fc region of the present invention may be an extended Fc region including a part or the entirety of the heavy chain constant region 1 (CH1) and/or light chain constant region 1 (CL1), excluding the heavy chain and light chain variable regions of an immunoglobulin, as long as it has an effect substantially equivalent or improved, as compared to its native form. Further, the immunoglobulin Fc region may be a region in which a part of a significantly long amino acid sequence corresponding to CH2 and/or CH3 is removed.

For example, the immunoglobulin Fc region of the present invention may be 1) CH1 domain, CH2 domain, CH3 domain, and CH4 domain, 2) CH1 domain and CH2 domain, 3) CH1 domain and CH3 domain, 4) CH2 domain and CH3 domain, 5) a combination between one or two or more domains among CH1 domain, CH2 domain, CH3 domain and CH4 domain, and an immunoglobulin hinge region (or a part of the hinge region), and 6) a dimer between each domain of the heavy chain constant region and the light chain constant region, but is not limited thereto.

In the present invention, the immunoglobulin Fc region may be a dimer or multimer consisting of single-chain immunoglobulins consisting of domains of the same origin, but is not limited thereto.

Further, in an embodiment of the long-acting conjugate of the present invention, the immunoglobulin Fc region F is a dimer consisting of two polypeptide chains, wherein the dimeric Fc region F and X may be covalently linked to each other via one identical linker L containing ethylene glycol repeating units. In a specific embodiment, X is covalently linked only to one polypeptide chain of the two polypeptide chains of the dimeric Fc region F via the linker L. In a more specific embodiment, only one X molecule is covalently linked via L to one polypeptide chain, to which X is linked, of the two polypeptide chains of the dimeric Fc region F. In the most specific embodiment, F is a homodimer.

In another specific embodiment, the immunoglobulin Fc region F is a dimer consisting of two polypeptide chains, and one end of L is linked only to one polypeptide chain of the two polypeptide chains, but is not limited thereto.

In another embodiment of the long-acting conjugate of the present invention, it is also possible for two molecules of X to bind symmetrically to one Fc region in a dimeric form. In particular, the immunoglobulin Fc region and X may be linked to each other via the linker (L), but are not limited to the above-described examples.

Further, the immunoglobulin Fc region of the present invention includes the native amino acid sequence as well as sequence derivatives thereof. The amino acid sequence derivative means that one or more amino acid residues in the natural amino acid sequence have a different sequence due to deletion, insertion, non-conservative or conservative substitution, or a combination thereof.

For example, amino acid residues at positions 214 to 238, 297 to 299, 318 to 322, or 327 to 331 in IgG Fc, which are known to be important for linkage, may be used as the sites suitable for variation.

Further, various types of derivatives are possible, for example, those where the site capable of forming a disulfide bond is removed, those where several N-terminal amino acids are removed from native Fc, those where a methionine residue is added to the N-terminus of native Fc, etc. Further, complement binding sites, e.g., C1q binding sites, or antibody-dependent cell-mediated cytotoxicity (ADCC) sites may be removed to remove the effector function. The techniques for preparing the sequence derivatives of the immunoglobulin Fc region are disclosed in International Publication Nos. WO 97/34631, WO 96/32478, etc.

Amino acid exchanges in a protein or peptide that do not alter the entire activity of a molecule are well known in the art (H. Neurath, R. L. Hill, *The Proteins*, Academic Press, New York, 1979). The most common exchanges occur between amino acid residues of Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, Asp/Gly. In some cases, amino acids may be modified by phosphorylation, sulfation, acrylation, glycosylation, methylation, farnesylation, acetylation, amidation, etc.

The Fc derivatives described above may be those which exhibit the same biological activity as that of the Fc region of the present invention, and have increased structural stability of the Fc region against heat, pH, etc.

Further, such an Fc region may be obtained from a native type isolated from humans or animals such as cows, goats, pigs, mice, rabbits, hamsters, rats, guinea pigs, etc., or may be their recombinants or derivatives obtained from transformed animal cells or microorganisms. In particular, the method of obtaining from a native form is a method of isolating whole immunoglobulins from human or animal organisms and then treating them with a protease. When treated with papain, the native form is digested into Fab and Fc, and when treated with pepsin, it is cleaved into pF' c and F(ab)₂. Fc or pF' c may be isolated using size exclusion chromatography, etc. In a more specific embodiment, the Fc region may be a recombinant immunoglobulin Fc region, in which a human-derived Fc region is obtained from a microorganism.

In addition, the immunoglobulin Fc region may have natural glycans or increased or decreased glycans compared to the natural type, or be in a deglycosylated form. The increase, decrease, or removal of glycans of the immunoglobulin Fc may be achieved by any methods commonly used in the art such as a chemical method, an enzymatic method, and a genetic engineering method using a microorganism. In particular, the immunoglobulin Fc region obtained by removing glycans shows a significant decrease in binding affinity to a complement c1q and a decrease in or loss of antibody-dependent cytotoxicity or complement-dependent cytotoxicity, and thus unnecessary immune responses are not induced thereby in living organisms. Based thereon, a deglycosylated or aglycosylated immunoglobulin Fc region may be more suitable as a drug carrier in view of the objects of the present invention.

As used herein, the term "deglycosylation" refers to a Fc region from which glycan is removed using an enzyme and the term "aglycosylation" refers to a Fc region that is not glycosylated and produced in prokaryotes, more specifically *E. coli*.

Meanwhile, the immunoglobulin Fc region may be derived from humans or animals including cows, goats, pigs, mice, rabbits, hamsters, rats, guinea pigs, etc., and in a more specific embodiment, it may be derived from humans.

Further, the immunoglobulin Fc region may be an Fc region derived from IgG, IgA, IgD, IgE, IgM, or a combination or hybrid thereof. In a more specific embodiment, it may be derived from IgG or IgM, which are the most abundant proteins in human blood, and in an even more specific embodiment, it may be derived from IgG, which is known to enhance the half-lives of ligand binding proteins. In a more specific embodiment, the immunoglobulin Fc region may be an IgG4 Fc region, and in a most specific embodiment, the immunoglobulin Fc region may be an aglycosylated Fc region derived from a human IgG4, but is not limited thereto.

In addition, in a specific embodiment, the immunoglobulin Fc region may be a human IgG4 Fc fragment in the form of a homodimer in which two monomers are linked to each other via a disulfide bond (inter-chain) formed between cysteines that are amino acids located at position 3 of each monomer. In particular, each monomer of the homodimer has or may have two disulfide bonds (intra-chain), i.e., a disulfide bond formed between cysteines at positions 35 and 95 and a disulfide bond formed between cysteines at positions 141 and 199.

Each monomer may consist of 221 amino acids and the number of amino acids constituting the homodimer may be 442 in total, without being limited thereto. Specifically, the immunoglobulin Fc fragment may be in the form of a homodimer in which two monomers each having an amino acid sequence of SEQ ID NO: 438 (consisting of 221 amino acids) are linked to each other via a disulfide bond between cysteines at position 3 of each monomer, wherein the monomers of the homodimer each independently have an intra-chain disulfide bond formed between cysteines at positions 35 and 95 and an intra-chain disulfide bond formed between cysteines at positions 141 and 199, without being limited thereto.

F of Chemical Formula 1 may include a monomer of the amino acid sequence of SEQ ID NO: 438, and F may be a homodimer of the monomer of the amino acid sequence of SEQ ID NO: 438, but is not limited thereto.

In an embodiment, the immunoglobulin Fc region may be a homodimer including an amino acid sequence of SEQ ID NO: 439 (consisting of 442 amino acids), but is not limited thereto.

In a specific embodiment, the immunoglobulin Fc region and X may not be glycosylated, but are not limited thereto.

Meanwhile, as used herein, the term "combination" means that polypeptides encoding single-chain immunoglobulin Fc regions of the same origin are linked to a single-chain polypeptide of a different origin to form a dimer or multimer. In other words, a dimer or a multimer may be prepared from two or more fragments selected from the group consisting of Fc regions of IgG Fc, IgA Fc, IgM Fc, IgD Fc, and IgE.

As used herein, the term "hybrid" means that sequences corresponding to two or more immunoglobulin Fc regions of different origins are present in a single-chain immunoglobulin constant region. In the present invention, various hybrid forms are possible. In other words, the hybrid domain may be composed of one to four domains selected from the group consisting of CH1, CH2, CH3, and CH4 of IgG Fc, IgM Fc, IgA Fc, IgE Fc, and IgD Fc, and may include a hinge region.

Meanwhile, IgG may be divided into the IgG1, IgG2, IgG3, and IgG4 subclasses, and the present invention may include combinations or hybrids thereof, specifically the IgG2 and IgG4 subclasses, and most specifically the Fc fragment of IgG4, which rarely has effector functions such as complement-dependent cytotoxicity (CDC).

Further, the above-described conjugate may have increased duration of efficacy, as compared with the native interleukin-2 or aldesleukin, or as compared with X not modified with F, and such a conjugate may be not only in the above-described form but also in the form, in which it is encapsulated in biodegradable nanoparticles, but is not limited thereto.

In Chemical Formula 1, L is a polyethylene glycol linker.

As used herein, the term "polyethylene glycol linker" includes a biocompatible polymer in which two or more ethylene glycol repeating units are conjugated. The repeating units are linked to each other through any covalent bond, not a peptide bond.

The polyethylene glycol linker may be an element constituting the moiety of the conjugate of the present invention, and corresponds to L in Chemical Formula 1. In the present specification, the linker may be used interchangeably with "non-peptidyl linker" or "non-peptidyl polymer".

In La, a may be 1 or more, and when a is 2 or more, L may be independent of each other.

In a specific embodiment, the conjugate may be one in which F and X are covalently linked to each other via a non-peptidyl linker including a reactive group capable of binding to F (specifically an immunoglobulin Fc region) and X (specifically an interleukin-2 analog) at both ends.

Specifically, in the present invention, the non-peptidyl linker may include reactive groups at ends thereof to form a conjugate through a reaction with other components constituting the conjugate. When the non-peptidyl linker having reactive functional groups at both ends bind to X and F of Chemical Formula 1 via respective reactive groups to form the conjugate, the non-peptidyl linker or non-peptidyl polymer may be referred to as a non-peptidyl polymer linker moiety or a non-peptidyl linker moiety.

In a specific embodiment, L (polyethylene glycol linker) may be a linker containing ethylene glycol repeating units, for example, polyethylene glycol, but is not limited thereto. As used herein, the polyethylene glycol is a term including all of an ethylene glycol homopolymer, a PEG copolymer, or a monomethyl-substituted PEG polymer (mPEG), but is not particularly limited thereto. Further, derivatives thereof that are known in the art and derivatives that may be easily prepared by ordinary skill in the art are also included in the scope of the present invention.

The polyethylene glycol linker may include the ethylene glycol repeating units while including, at the ends thereof, functional groups used in the preparation of a conjugate before being formed into the conjugate. In the long-acting conjugate according to the present invention, X and F may be linked to each other though the functional groups, but it is not limited thereto. In the present invention, the non-peptidyl linker may include two or three or more functional groups, wherein the respective functional groups are the same as or different from each other, but is not limited thereto.

Specifically, the linker may be polyethylene glycol (PEG) represented by Chemical Formula 5 below, but is not limited thereto:

[Chemical Formula 5]

Here, n=10 to 2400, n=10 to 480, or n=50 to 250, but is not limited thereto.

In the long-acting conjugate, the PEG moiety may include a structure of $—(CH_2CH_2O)_n—$ and an oxygen atom interposed between the linking element and $—(CH_2CH_2O)_n—$, but is not limited thereto.

In a specific embodiment, the ethylene glycol repeating unit may be represented by, for example, $[OCH_2CH_2]_n$, wherein the value of n is a natural number and may be determined such that an average molecular weight, for example, a number average molecular weight of the $[OCH_2CH_2]_n$ site in the conjugate of an interleukin-2 analog is more than 0 kDa to about 100 kDa, but is not limited thereto. In another embodiment, the value of n is a natural number and may be determined such that an average molecular weight, for example, a number average molecular weight of the $[OCH_2CH_2]_n$ site in the peptide conjugate may be about 1 kDa to about 100 kDa, about 1 kDa to about 80 kDa, about 1 kDa to about 50 kDa, about 1 kDa to about 30 kDa, about 1 kDa to about 25 kDa, about 1 kDa to about 20 kDa, about 1 kDa to about 15 kDa, about 1 kDa to about 13 kDa, about 1 kDa to about 11 kDa, about 1 kDa to about 10 kDa, about 1 kDa to about 8 kDa, about 1 kDa to about 5 kDa, about 1 kDa to about 3.4 kDa, about 3 kDa to about 30 kDa, about 3 kDa to about 27 kDa, about 3 kDa to about 25 kDa, about 3 kDa to about 22 kDa, about 3 kDa to about 20 kDa, about 3 kDa to about 18 kDa, about 3 kDa to about 16 kDa, about 3 kDa to about 15 kDa, about 3 kDa to about 13 kDa, about 3 kDa to about 11 kDa, about 3 kDa to about 10 kDa, about 3 kDa to about 8 kDa, about 3 kDa to about 5 kDa, about 3 kDa to about 3.4 kDa, about 8 kDa to about 30 kDa, about 8 kDa to about 27 kDa, about 8 kDa to about 25 kDa, about 8 kDa to about 22 kDa, about 8 kDa to about 20 kDa, about 8 kDa to about 18 kDa, about 8 kDa to about 16 kDa, about 8 kDa to about 15 kDa, about 8 kDa to about 13 kDa, about 8 kDa to about 11 kDa, about 8 kDa to about 10 kDa, about 9 kDa to about 15 kDa, about 9 kDa to about 14 kDa, about 9 kDa to about 13 kDa, about 9 kDa to about 12 kDa, about 9 kDa to about 11 kDa, about 9.5 kDa to about 10.5 kDa, or about 10 kDa, but is not limited thereto.

Further, in a specific embodiment, the conjugate may have a structure in which the interleukin-2 analog and the immunoglobulin Fc region (F) are covalently linked to each other via the linker (L) including ethylene glycol repeating units, but is not limited thereto.

In another specific embodiment, in the long-acting conjugate, L may be a linker including ethylene glycol repeating units, and F may be a dimeric immunoglobulin Fc region. More specifically, one X molecule is covalently linked to one Fc region of the dimeric immunoglobulin Fc region via the linker containing ethylene glycol repeating units, but is not limited thereto. In still another specific embodiment, one end of the linker containing ethylene glycol repeating units may be linked only to one Fc region chain of two Fc region chains of the dimeric immunoglobulin Fc region, but is not limited thereto.

The molecular weight of the polyethylene glycol linker that can be used in the present invention may be in the range of more than 0 kDa to 200 kDa, specifically in the range of about 1 kDa to 100 kDa, about 1 kDa to 50 kDa, about 1 kDa to 30 kDa, about 2 kDa to 30 kDa, about 1 kDa to 20 kDa, more specifically in the range of about 3.4 kDa to kDa, and much more specifically about 3.4 kDa, but is not limited thereto.

In addition, as the non-peptidyl linker of the present invention conjugated to the polypeptide corresponding to F, not only one type of polymer but also a combination of different types of polymers may be used.

As used herein, the term "about" includes all of the ranges including ±0.5, ±0.4, ±0.3, ±0.2, ±0.1, etc., and includes all values in a range equal to or similar to the value following the term "about", but is not limited thereto.

Specifically, the non-peptidyl linker may have reactive groups at both ends thereof in a state where F and X are not bound thereto, and may bind with F and X via the reactive groups.

In a specific embodiment, both ends of the linker may bind to a thiol group, an amino group, or a hydroxyl group of the immunoglobulin Fc region, and a thiol group, an amino group, an azide group, or a hydroxyl group of the interleukin-2 analog (X), but are not limited thereto.

Specifically, the linker may include, at both ends thereof, reactive groups capable of binding to the immunoglobulin Fc region and the interleukin-2 analog (X), respectively, specifically reactive groups capable of binding to a thiol group of cysteine; an amino group located at the N-terminus, lysine, arginine, glutamine, and/or histidine; and/or a hydroxyl group at the C-terminus of the immunoglobulin Fc region; and a thiol group of cysteine; an amino group of lysine, arginine, glutamine, and/or histidine; an azide group of azido-lysine; and/or a hydroxyl group of the interleukin-2 analog (X), but is not limited thereto.

More specifically, the reactive group of the linker may be one or more selected from the group consisting of an aldehyde group, a maleimide group, and a succinimide derivative, but is not limited thereto.

In the above, examples of the aldehyde group may include a propionaldehyde group, or a butyraldehyde group, but are not limited thereto.

In the above, examples of the succinimide derivative may include succinimidyl valerate, succinimidyl methylbutanoate, succinimidyl methylpropionate, succinimidyl butanoate, succinimidyl propionate, N-hydroxysuccinimide, hydroxy succinimidyl, succinimidyl carboxymethyl, or succinimidyl carbonate, but are not limited thereto.

The linker may be linked to the immunoglobulin Fc region F and the interleukin-2 analog X via the reactive groups to be converted into a linker moiety.

Further, a final product produced by reductive alkylation via aldehyde bonds is more stable than a linkage formed by an amide bond. The aldehyde reactive group selectively reacts with the N-terminus at low pH while forming a covalent bond with a lysine residue at high pH, e.g., at a pH of 9.0.

In addition, the reactive groups of both ends of the linker may be the same as or different from each other, for example, aldehyde groups may be provided at both ends, and a maleimide group may be provided at one end and an aldehyde group, a propionaldehyde group, or a butyraldehyde group may be provided at the other end.

However, the reactive groups are not particularly limited as long as F, specifically the immunoglobulin Fc region, and X may be linked to the respective ends of the linker.

For example, the linker may include a maleimide group at one end and an aldehyde group, a propionaldehyde group, or a butyraldehyde group at the other end, as reactive groups.

When polyethylene glycol having hydroxyl reactive groups at both ends is used as a linker, the long-acting conjugate of an interleukin-2 analog of the present invention may be prepared by activating the hydroxyl groups to various reactive groups by known chemical reactions, or using commercially available polyethylene glycol having modified reactive groups.

In a specific embodiment, the polymer may be linked to a cysteine residue of X, more specifically a —SH group of cysteine, but is not limited thereto.

Specifically, the reactive group of the linker may be linked to the —SH group of the cysteine residue, and all of those described above will be applied to the reactive group. When maleimide-PEG-aldehyde is used, the maleimide group may be linked to the —SH group of X via a thioether bond, and the aldehyde group may be linked to the —NH$_2$ group of F, specifically the immunoglobulin Fc, via a reductive amination, but is not limited thereto.

In another specific embodiment, the linker may be linked to the lysine residue of X, more specifically the amino group of the lysine, but is not limited thereto.

In addition, in the conjugate, the reactive group of the linker may be linked to —NH$_2$ located at the N-terminus of the immunoglobulin Fc region, but is not limited thereto.

Further, in the conjugate, the interleukin-analog according to the present invention may be linked to the linker having reactive groups via the C-terminus, but this is merely an example.

As used herein, the term "C-terminus" refers to a carboxy terminus of a peptide, and with respect to the objects of the present invention, it refers to a site capable of binding with the linker. For example, the C-terminus may include all of an amino acid residue at the extreme end of the C-terminus and amino acid residues near the C-terminus, and specifically include the 1$^{st}$ to 20$^{th}$ amino acid residues from the extreme end, but is not limited thereto.

Further, the above-described conjugate may have increased duration of efficacy, as compared with X not modified with F, and such a conjugate may be not only in the above-described form but also in a form, in which it is encapsulated in biodegradable nanoparticles.

Still another aspect for implementing the present invention provides a long-acting conjugate, in which an interleukin-2 analog including any one amino acid sequence selected from the group consisting of amino acid sequences of SEQ ID NOS: 3 to 106 and an immunoglobulin Fc region are linked through a linker.

The interleukin-2 analog, the linker, and the long-acting conjugate including the same are as described above.

Yet another aspect for implementing the present invention provides a long-acting conjugate of an interleukin-2 analog represented by Chemical Formula 2 below:

$$X—Z-Fc \qquad \text{[Chemical Formula 2]}$$

wherein X is an interleukin-2 analog including any one of polypeptide sequences selected from the amino acid sequence of SEQ ID NOS: 3 to 106;

Z is a polyethylene glycol linker having a molecular weight of 2 kDa to 30 kDa;

Fc is an immunoglobulin Fc region in the form of a dimer; and

— indicates a covalent linkage between X and Z and between Z and Fc;

wherein the long-acting conjugate is a long-acting conjugate in which one end of Z is covalently linked only to one polypeptide chain in the dimeric Fc region, and one molecule of X is covalently linked to the opposite end of Z.

The interleukin-2 analog, the linker, the Fc region, and the long-acting conjugate including the same are as described above.

In a specific embodiment, the interleukin-2 analog may include, essentially consist of, or consist of any one of sequences selected from the group consisting of amino acid sequences of SEQ ID NOS: 10, 13, 14, 15, 16, 17, 20, 21, 22, 32, 35, 36, 42, 53, 54, 56, 58, 59, 60, 62, 71, 72, 74, 75, 76, 77, 78, 85, 87, 89, 91, 92, 93, 94, 95, 98, 99, 100, 101, 103, 104, 105, and 106, but is not limited thereto.

In another specific embodiment, the interleukin-2 analog may include, essentially consist of, or consist of any one of sequences selected from the group consisting of amino acid sequences of SEQ ID NOS: 10, 13, 14, 16, 17, 20, 21, 22, 32, 35, 36, 42, 53, 54, 87, 89, 91, 92, 93, 94, 98, 99, 100, 101, 103, 104, and 105, but is not limited thereto.

In still another specific embodiment, the interleukin-2 analog may include, essentially consist of, or consist of any one of sequences selected from the group consisting of amino acid sequences of SEQ ID NOS: 22, 42, 53, 87, 105 and 106, but is not limited thereto.

Further, the interleukin-2 analog may be one further including one or more amino acids at the C-terminus thereof.

Even another aspect for implementing the present invention provides a long-acting conjugate of an interleukin-2 analog represented by Chemical Formula 3 below:

$$\text{X'—Z-Fc} \qquad \text{[Chemical Formula 3]}$$

wherein X' is an interleukin-2 analog including an amino acid sequence represented by General Formula 1 below:

[General Formula 1]

(General Formula 1, SEQ ID NO: 212)

X1-P-T-S-S-S-T-K-K-T-Q-L-Q-L-E-H-L-X18-X19-D-L-

X22-M-I-L-N-G-I-N-N-Y-K-N-P-K-L-T-X38-M-L-T-X42-

X43-F-X45-M-P-K-K-A-T-E-L-K-H-L-Q-C-L-E-X61-E-L-K-

P-L-E-X68-V-L-N-L-A-X74-S-K-N-F-H-X80-X81-P-R-X84-

X85-X86-S-N-I-N-X91-X92-V-X94-E-X96-K-G-S-E-T-T-F-

M-C-E-Y-A-D-E-T-A-T-I-V-E-F-L-N-R-W-I-T-F-S-Q-S-I-

I-S-T-L-T in General Formula 1 above,

X1 is a deletion;

X18 is leucine (L) or arginine (R);

X19 is leucine (L) or tyrosine (Y);

X22 is glutamic acid (E) or glutamine (Q);

X38 is alanine (A), aspartic acid (D), or arginine (R);

X42 is alanine (A), phenylalanine (F), lysine (K), or tryptophan (W);

X43 is glutamic acid (E), lysine (K), or glutamine (Q);

X45 is alanine (A) or tyrosine (Y);

X61 is aspartic acid (D), glutamic acid (E), glutamine (Q), or arginine (R);

X68 is aspartic acid (D) or glutamic acid (E);

X74 is histidine (H) or glutamine (Q);

X80 is phenylalanine (F), leucine (L), valine (V), or tyrosine (Y);

X81 is aspartic acid (D), glutamic acid (E), or arginine (R);

X84 is aspartic acid (D) or glutamic acid (E);

X85 is alanine (A), glutamic acid (E), glycine (G), leucine (L), valine (V), tryptophan (W), or tyrosine (Y);

X86 is alanine (A), glycine (G), isoleucine (I), or valine (V);

X91 is threonine (T) or valine (V);

X92 is phenylalanine (F), isoleucine (I), or tyrosine (Y);

X94 is phenylalanine (F) or leucine (L);

X96 is phenylalanine (F) or leucine (L);

Z is a polyethylene glycol linker having a molecular weight of 2 kDa to 30 kDa;

Fc is an immunoglobulin Fc region in the form of a dimer; and

— indicates a covalent linkage between X' and Z and between Z and Fc;

wherein the long-acting conjugate is a long-acting conjugate in which one end of Z is covalently linked only to one polypeptide chain in the dimeric Fc region, and one molecule of X' is covalently linked to the opposite end of Z.

The interleukin-2 analog, the linker, the Fc region, and the long-acting conjugate including the same are as described above.

In General Formula 1 above, one or more amino acids may be added to threonine (T) corresponding to X133, but is not limited thereto.

Specifically, the interleukin-2 analog may include, essentially consist of, or consist of any one of sequences selected from the group consisting of amino acid sequences of SEQ ID NOS: 10, 13, 14, 15, 16, 17, 20, 21, 22, 32, 35, 36, 42, 53, 54, 56, 58, 59, 60, 62, 71, 72, 74, 75, 76, 77, 78, 85, 87, 89, 91, 92, 93, 94, 95, 98, 99, 100, 101, 103, 104, 105, and 106, but is not limited thereto.

Such an interleukin-2 analog may have an increased binding affinity for beta receptors compared to aldesleukin or native interleukin-2, but is not limited thereto.

In a specific embodiment, in General Formula 1,

X43 is lysine (K);

X45 is tyrosine (Y);

X61 is aspartic acid (D), glutamic acid (E), or glutamine (Q);

X68 is glutamic acid (E);

X74 is glutamine (Q);

X80 is phenylalanine (F) or leucine (L);

X85 is leucine (L), valine (V), or tyrosine (Y);

X86 is isoleucine (I) or valine (V); and

X92 is phenylalanine (F) or isoleucine (I), but is not limited thereto.

Specifically, the interleukin-2 analog is characterized in that it includes any one of sequences selected from the group consisting of amino acid sequences of SEQ ID NOS: 10, 13, 14, 16, 17, 20, 21, 22, 32, 35, 36, 42, 53, 54, 87, 89, 91, 92, 93, 94, 98, 99, 100, 101, 103, 104, and 105, but is not limited thereto.

The interleukin-2 analog of the present invention may further include one or more amino acids at the C-terminus thereof, but is not limited thereto.

Further another aspect for implementing the present invention provides a long-acting conjugate of an interleukin-2 analog represented by Chemical Formula 4 below:

$$\text{X''—Z-Fc} \qquad \text{[Chemical Formula 4]}$$

wherein X'' is an interleukin-2 analog including an amino acid sequence represented by General Formula 2 below:

[General Formula 2]

```
            (General Formula 2, SEQ ID NO: 213)
X1-P-T-S-S-S-T-K-K-T-Q-L-Q-L-E-H-L-X18-L-D-L-X22-

M-I-L-N-G-I-N-N-Y-K-N-P-K-L-T-X38-M-L-T-X42-K-F-Y-

M-P-K-K-A-T-E-L-K-H-L-Q-C-L-E-X61-E-L-K-P-L-E-X68-

V-L-N-L-A-Q-S-K-N-F-H-F-X81-P-R-D-X85-X86-S-N-I-N-

V-F-V-L-E-L-K-G-S-E-T-T-F-M-C-E-Y-A-D-E-T-A-T-I-V-

E-F-L-N-R-W-I-T-F-S-Q-S-I-I-S-T-L-T
```

X1 is a deletion;

X18 is leucine (L) or arginine (R);

X22 is glutamic acid (E) or glutamine (Q);

X38 is alanine (A) or arginine (R);

X42 is phenylalanine (F) or lysine (K);

X61 is aspartic acid (D) or glutamic acid (E);

X68 is aspartic acid (D) or glutamic acid (E);

X81 is aspartic acid (D) or glutamic acid (E);

X85 is leucine (L) or valine (V);

X86 is isoleucine (I) or valine (V);

Z is a polyethylene glycol linker having a molecular weight of 2 kDa to 30 kDa;

Fc is an immunoglobulin Fc region in the form of a dimer; and

— indicates a covalent linkage between X" and Z and between Z and Fc;

wherein the long-acting conjugate is a long-acting conjugate in which one end of Z is covalently linked only to one polypeptide chain in the dimeric Fc region, and one molecule of X" is covalently linked to the opposite end of Z.

The interleukin-2 analog, the linker, the Fc region, and the long-acting conjugate including the same are as described above.

Specifically, the interleukin-2 analog may include any one of sequences selected from the group consisting of amino acid sequences of SEQ ID NOS: 22, 42, 53, 87, 105 and 106, but is not limited thereto.

In addition, in General Formula 2, one or more amino acids may be added to threonine (T) corresponding to X133, or one or more amino acids may be further included at the C-terminus of the interleukin-2 analog, but is not limited thereto.

Still further another aspect for implementing the present invention provides a long-acting conjugate including an interleukin-2 analog.

The interleukin-2 analog and the long-acting conjugate including the same are as described above.

Specifically, the method may include a step of linking the interleukin-2 analog, into which a modification was introduced into one or more amino acids selected from the group consisting of amino acids corresponding to positions 1, 12, 18, 19, 20, 22, 32, 35, 38, 42, 43, 45, 48, 49, 61, 68, 69, 74, 76, 80, 81, 82, 84, 85, 86, 87, 88, 89, 91, 92, 94, 95, 96, 125, 126, and 133 in native interleukin-2, with a biocompatible material (e.g., an immunoglobulin Fc region) via a linker (e.g., a non-peptidyl polymer).

The method of preparing a long-acting conjugate of the present invention may further include a step of introducing a modification into one or more amino acids selected from the group consisting of amino acids corresponding to positions 1, 12, 18, 19, 20, 22, 32, 35, 38, 42, 43, 45, 48, 49, 61, 68, 69, 74, 76, 80, 81, 82, 84, 85, 86, 87, 88, 89, 91, 92, 94, 95, 96, 125, 126, and 133 in native interleukin-2, but the method is not limited by specific steps or orders thereof as long as a long-acting conjugate, in which the interleukin-2 analog according to the present invention is linked to a biocompatible substance (e.g., immunoglobulin Fc region), is prepared.

In addition, the method of preparing a long-acting conjugate of the present invention may further include the steps of: a) culturing a transformant containing a nucleic acid encoding the interleukin-2 analog to express the interleukin-2 analog; and b) isolating and purifying the expressed interleukin-2 analog, but is not limited thereto.

The nucleic acid encoding the interleukin-2 analog may include or (essentially) consist of a nucleotide sequence of any one of SEQ ID NOS: 109 to 212, but is not limited thereto.

The medium used for culturing a transformant in the present invention must meet the requirements for culturing host cells in an appropriate manner. The carbon sources that can be included in the medium for the growth of host cells can be appropriately selected as a decision by those skilled in the art according to the type of transformants being produced, and appropriate culture conditions can be adopted to control the time and amount of culture.

Sugar sources that can be used may include sugars and carbohydrates (e.g., glucose, saccharose, lactose, fructose, maltose, starch, and cellulose); oils and fats (e.g., soybean oil, sunflower oil, castor oil, coconut oil, etc.); fatty acids (e.g., palmitic acid, stearic acid, and linoleic acid); alcohols (e.g., glycerol and ethanol); and organic acids (e.g., acetic acid). These materials can be used individually or as a mixture.

Nitrogen sources that can be used may include peptone, yeast extract, gravy, malt extract, corn steep liquor, soybean meal, and urea, or inorganic compounds (e.g., ammonium sulfate, ammonium chloride, ammonium phosphate, ammonium carbonate, and ammonium nitrate). Nitrogen sources can also be used individually or as a mixture.

Phosphorous sources that can be used may include potassium dihydrogen phosphate or dipotassium hydrogen phosphate, or corresponding sodium-containing salts thereof. In addition, the culture medium may contain a metal salt (e.g., magnesium sulfate and iron sulfate) required for growth.

Finally, in addition to these materials, essential growth materials (e.g., amino acids and vitamins) may be used. In addition, suitable precursors for culture media may be used. The above-mentioned raw materials can be added in a batch or continuous mode in a manner appropriate to the culture during the cultivation. Basic compounds (e.g., sodium hydroxide, potassium hydroxide, and ammonia) or acidic compounds (e.g., phosphoric acid and sulfuric acid) can be used in an appropriate manner to adjust the pH of the culture. In addition, antifoaming agents (e.g., fatty acid polyglycol esters) may be used to inhibit bubble generation. In order to maintain aerobic conditions, oxygen or oxygen-containing gas (e.g., air) is injected into the culture.

Culturing of the transformant according to the present invention is usually performed at a temperature of 20° C. to 45° C., specifically 25° C. to 40° C. In addition, the culture is continued until the maximum amount of the desired interleukin-2 analog is obtained, and for this purpose, the culture can usually last for 10 to 160 hours.

As described above, if the appropriate culture conditions are established depending on the host cell, the transformant according to the present invention will produce an interleukin-2 analog, and depending on the composition of the vector and the characteristics of the host cell, the interleukin-2 analog produced can be secreted into the cytoplasm of the host cell, into the periplasmic space, or extracellularly.

Proteins expressed in the host cell or outside thereof can be purified in a conventional manner. Examples of purification methods include salting out (e.g.: ammonium sulfate precipitation, sodium phosphate precipitation, etc.), solvent precipitation (e.g., protein fractionation precipitation using acetone, ethanol, etc.), dialysis, gel filtration, ion exchange, chromatography (e.g., reverse-phase column chromatography), ultrafiltration, etc. and can be used alone or in combination.

Further, the interleukin-2 analog prepared by a peptide synthesis method may be linked to a biocompatible substance (e.g., an immunoglobulin Fc region) via a non-peptidyl polymer. Since the sequences of the interleukin-2 analogs of the present invention are already provided, the synthesis of peptides can be performed using a known peptide synthesis method.

The interleukin-2 analog is as described above.

Still further another aspect for implementing the present invention provides a long-acting conjugate prepared by the method above.

Unless specified otherwise herein, the description in the detailed description or claims with respect to "interleukin-2 analog" according to the present invention or a "conjugate", in which an interleukin-2 analog is covalently linked to a biocompatible material, may be applied to the forms, which include not only the corresponding interleukin-2 analog or conjugate but also the salts of the corresponding interleukin-2 analog or conjugate (e.g., pharmaceutically acceptable salts of the interleukin-2 analog), or solvates thereof. Accordingly, even in a case where an "interleukin-2 analog" or "conjugate" is merely described herein, the description may also be equally applied to a particular salt thereof, a particular solvate thereof, and a particular solvate of the particular salt thereof. These salts may be, for example, in a form where any pharmaceutically acceptable salts are used. The kind of the salt is not particularly limited. However, the salt is preferably one that is safe and effective to a subject, e.g., a mammal, but is not particularly limited thereto.

The term "pharmaceutically acceptable" refers to a material which can be effectively used for a desired purpose without causing excessive toxicity, irritation, allergic reactions, etc. within the scope of medical judgment.

As used herein, the term "pharmaceutically acceptable salt" includes salts which are derived from pharmaceutically acceptable inorganic acids, organic acids, or bases. Examples of suitable acids include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, benzenesulfonic acid, etc. Salts derived from suitable bases may include alkali metals (e.g., sodium, potassium, etc.), alkaline earth metals (e.g., magnesium, etc.), ammonium, etc.

Additionally, as used herein, the term "solvate" refers to a complex formed between the interleukin-2 analog according to the present invention or a salt thereof and a solvent molecule.

Still further another aspect for implementing the present invention provides a composition including an interleukin-2 analog or a long-acting conjugate thereof. The interleukin-2 analog and the long-acting conjugate thereof are as described above. The composition according to the present invention may be a pharmaceutical composition, and in a specific embodiment, it may be a pharmaceutical composition with the use for preventing or treating cancer.

The composition according to the present invention may include an interleukin-2 analog or a long-acting conjugate thereof, and specifically may include a pharmacologically effective amount of an interleukin-2 analog or a long-acting conjugate thereof. In addition, it may further include a pharmaceutically acceptable carrier.

In a specific embodiment of the composition according to the present invention, the composition may include an interleukin-2 analog including any one amino acid sequence selected from the group consisting of SEQ ID NOS: 3 to 106; or a long-acting conjugate including the same, and more specifically an interleukin-2 analog including any one amino acid sequence selected from the group consisting of SEQ ID NOS: 22, 42, 53, 87, 105, and 106; or a long-acting conjugate including the interleukin-2 analog, but is not limited thereto.

As used herein, the term "pharmaceutically effective amount" may refer to a safe administration dose in which the interleukin-2 or a conjugate thereof exhibits cancer prevention or treatment effects, but does not show toxicity or side effects to patients, and may refer to an administration dose capable of exhibiting significant activities on interleukin-2 receptors, specifically beta and/or alpha receptors.

The composition according to the present invention may exhibit one or more of the following properties, but is not limited as long as it exhibits an increased immune response and anticancer effect, etc. based on increased binding affinity for interleukin-2 beta receptors:

(i) high blood exposure relative to aldesleukin;

(ii) high tumor growth inhibition compared to aldesleukin, (iii) high memory T cell-generating response compared to aldesleukin.

Interleukin-2, known as a T cell growth factor, is a protein involved in immunomodulation, and has the activity of proliferating T cells, stimulating B cells, and secreting γ-interferon by acting on T cells. Based on the immunomodulatory activity of interleukin-2, cancer prevention or treatment effects can be obtained by removing cancer cells using the body's immune system.

In particular, the interleukin-2 analog of the present invention has an increased binding affinity for interleukin-2 beta receptors, which play a major role in signal transduction, leading to a more effective anticancer effect in the immune system of an individual. In addition, the long-acting conjugate including the interleukin-2 analog exhibits excellent bioavailability due to increased blood exposure as the duration of efficacy is increased while having increased binding affinity for interleukin-2 beta receptors, and consequently exhibiting excellent tumor growth inhibition and memory T cell-producing ability, thereby showing effective cancer prevention or treatment effects.

Specifically, the long-acting conjugate of an interleukin-2 analog of the present invention may have no binding affinity or may have binding affinity for interleukin-2 alpha receptors of about 0.001-fold or greater, about 0.005-fold or greater, about 0.01-fold or greater, about 0.05-fold or greater, about 0.1-fold or greater, about 0.3-fold or greater, about 0.5-fold or greater, about 0.6-fold or greater, about 0.7-fold or greater, about 0.8-fold or greater, about 0.9-fold or greater, about 1.1-fold or greater, about 1.3-fold or greater, about 1.5-fold or greater, or about 1.7-fold or greater compared to the binding affinity of native interleukin-2, aldesleukin, or the long-acting conjugate including the same for interleukin-2 alpha receptors, but the numerical value of the binding affinity is not limited, and the value will belong to the scope of the present invention as long as there is a change in the binding affinity compared to that of native interleukin-2 or aldesleukin.

Additionally, the long-acting conjugate of an interleukin-2 analog of the present invention may specifically have binding affinity for interleukin-2 beta receptors of about 0.1-fold or greater, about 0.3-fold or greater, about 0.5-fold or greater, about 0.7-fold or greater, about 1.0-fold or greater, about 10-fold or greater, about 20-fold or greater, about 30-fold or greater, about 40-fold or greater, about 50-fold or greater, about 60-fold or greater, about 70-fold or greater, about 80-fold or greater, about 90-fold or greater, about 100-fold or greater, about 130-fold or greater, about 150-fold or greater, and about 200-fold or greater compared to the binding affinity of native interleukin-2, aldesleukin, or the long-acting conjugate including the same for interleukin-2 beta receptors, but the numerical value of the binding affinity is not limited, and the value will belong to the scope of the present invention as long as there is a change or increase in the binding affinity compared to that of native interleukin-2 or aldesleukin.

In the present invention, the cancer may be any one selected from the group consisting of colorectal cancer, liver cancer, ovarian cancer, pancreatic cancer, gallbladder cancer, kidney cancer, lung cancer, skin cancer, melanoma, breast cancer, bladder cancer, and stomach cancer, or may be metastatic cancer, but is not limited thereto. It may also include metastatic renal cell carcinoma or metastatic melanoma.

As used herein, the term "prevention" refers to all kinds of actions associated with inhibition or delay of cancer or tumor by administering the interleukin-2 analog (e.g., the interleukin-2 analog itself or a long-acting conjugate form in which a biocompatible material is bound thereto), or a composition including the same.

As used herein, the term "treatment" refers to all kinds of actions associated with the improvement or advantageous changes in symptoms of cancer by administering the interleukin-2 analog (e.g., the interleukin-2 analog itself or a long-acting conjugate form in which a biocompatible material is bound thereto), or a composition including the same.

The use of the interleukin-2 analog of the present invention or a long-acting conjugate thereof has great advantages of improving the quality of life of patients by reducing the number of administrations to chronic patients who are subjected to daily administration due to a dramatic increase in blood exposure, blood half-life, and in vivo duration of efficacy.

The pharmaceutical composition of the present invention may further include a pharmaceutically acceptable carrier or diluent. Such a pharmaceutically acceptable carrier or diluent may be one which does not occur naturally.

As used herein, the term "pharmaceutically acceptable" refers to an amount sufficient to exhibit therapeutic effects without causing side-effects, and may be easily determined by those of ordinary skill in the art, based on factors well known in the medical field such as the type of disease, a patient's age, body weight, health status, gender, and sensitivity to drug, administration route, administration method, frequency of administration, duration of treatment, and a drug used in combination or concurrently.

The pharmaceutical composition including the interleukin-2 analog of the present invention or a long-acting conjugate thereof may further include a pharmaceutically acceptable excipient. Although the excipient is not particularly limited, a binder, a lubricant, a disintegrator, a solubilizer, a dispersant, a stabilizer, a suspending agent, a coloring agent, and a flavoring agent may be used for oral administration, a buffer, a preservative, an analgesic, a solubilizer, an isotonic agent, and a stabilizer may be used in combination for injectable preparations, and a base, an excipient, a lubricant, a preservative, etc. may be used for topical administration.

The composition of the present invention may be formulated into various forms in combination with the above-mentioned pharmaceutically acceptable excipient. For example, for oral administration, the composition may be formulated into tablets, troches, capsules, elixirs, suspensions, syrups, wafers, etc. For injectable preparations, the composition may be formulated into a single-dose ampoule or multidose form. The composition may also be formulated into solutions, suspensions, tablets, pills, capsules, sustained-release preparations, etc.

Meanwhile, examples of the carrier, excipient, and diluent suitable for formulation may include lactose, dextrose, sucrose, sorbitol, mannitol, xylitol, erythritol, maltitol, starch, acacia, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, or mineral oils. Also, the composition may further include a filler, an anti-coagulant, a lubricant, a humectant, a flavoring agent, a preservative, etc.

In addition, the pharmaceutical composition of the present invention may have any one formulation selected from the group consisting of tablets, pills, powders, granules, capsules, suspensions, formulations for internal use, emulsions, syrups, sterilized aqueous solutions, non-aqueous solvents, lyophilized preparations, and suppositories.

Also, the composition may be formulated in a unit dosage form suitable for administration into a patient's body, specifically in a form useful for administration of protein medicines, according to a method commonly used in the art, and administered via an oral administration route or a parenteral administration route such as an intradermal, intravenous, intramuscular, intraarterial, intramedullary, intrathecal, intraventricular, intrapulmonary, transdermal, subcutaneous, intraperitoneal, intranasal, intestinal, topical, sublingual, vaginal, or rectal route using an administration method commonly used in the art, but is not limited thereto.

In addition, the conjugate may be used in combination with various carriers permitted as medicaments such as a saline solution or an organic solvent. As the medicaments, carbohydrates such as glucose, sucrose, or dextran, antioxidants such as ascorbic acid or glutathione, chelating agents, low-molecular-weight proteins, or other stabilizers may be used to improve stability or absorbability.

Still further another aspect for implementing the present invention provides a method for preventing or treating cancer, including administering an interleukin-2 analog, a long-acting conjugate thereof, or a pharmaceutical composition including the same to an individual in need thereof.

The interleukin-2 analog and/or long-acting conjugate of the interleukin-2 analog, composition including the same, cancer, prevention and treatment are as described above.

As used herein, the individual refers to an individual having cancer or suspected of having cancer, and may refer to mammals such as humans, rats, livestock, etc., but any individual that may be treated with the interleukin-2 analog and/or conjugate, or a composition including the same may be included without limitation.

As used herein, the term "administration" refers to an introduction of a particular material (e.g., interleukin-2 analog or long-acting conjugate thereof) to a patient by an appropriate manner. The composition may be, but is not particularly limited to, administered by a general route that enables the delivery of the composition to a target tissue in vivo, for example, intraperitoneal, intravenous, intramuscular, subcutaneous, intradermal, oral, topical, intranasal, intrapulmonary, and intrarectal administration.

The method of the present invention may include administering the pharmaceutical composition including the interleukin-2 analog or a long-acting conjugate thereof at a pharmaceutically effective amount. The suitable total daily dose should be determined within appropriate medical judgment by a physician, and administered once or several times in divided doses. For the purpose of the present invention, the specific therapeutically effective dose for any particular patient may be preferably applied differently, depending on various factors well known in the medical art, including the kind and degree of the response to be achieved, specific compositions including whether other agents are occasionally used therewith or not, the patient's age, body weight, general health conditions, gender and diet, the time and route of administration, secretion rate of the composition, duration of treatment, other drugs used in combination or concurrently with the specific composition, and like factors well-known in the medical arts.

In the method of the present invention, the dosage and frequency during administration are determined according to the type of drug, an active ingredient, along with several related factors such as the disease to be treated, the route of administration, patient's age, gender and weight, and disease severity. Specifically, the composition of the present invention may include the interleukin-2 analog or the long-acting conjugate including the same in a pharmaceutically effective amount, but is not limited thereto.

The inclusion of the interleukin-2 analog or the long-acting conjugate in a pharmaceutically effective amount means the degree to which the desired pharmacological activity (e.g., prevention, improvement or treatment of cancer) can be obtained due to the interleukin-2 analog or the long-acting conjugate, or may additionally mean a pharmaceutically acceptable level as a level that does not cause toxicity or side effects in the administered individual, but is not limited thereto. Such a pharmaceutically effective amount may be comprehensively determined in consideration of administration frequency, patient, formulation, etc.

The pharmaceutical composition of the present invention may contain the component (active ingredient) in an amount of 0.01% to 99% by weight to volume, but is not particularly limited thereto.

The total effective dose of the composition of the present invention may be administered to a patient in a single dose or may be administered for a long period of time in multiple doses according to a fractionated treatment protocol. In the pharmaceutical composition of the present invention, the content of the active ingredient may vary depending on the disease severity. Specifically, a preferred total daily dose of the interleukin-2 analog of the present invention or a long-acting conjugate thereof may be about 0.0001 mg to 500 mg per 1 kg of body weight of a patient. However, the effective dose of the interleukin-2 analog or a conjugate thereof is determined considering various factors including a patient's age, body weight, health conditions, gender, disease severity, diet, and excretion rate, in addition to administration route of the pharmaceutical composition and treatment frequency. In this regard, those skilled in the art may easily determine the effective dose suitable for the particular use of the composition of the present invention. The pharmaceutical composition according to the present invention is not particularly limited to the formulation, and administration route and mode, as long as it shows the effects of the present invention.

The pharmaceutical composition of the present invention may have excellent in vivo duration and titer, thereby remarkably reducing the number and frequency of administration of the pharmaceutical preparation of the present invention. The pharmaceutical composition may be administered by intraperitoneal, intravenous, intramuscular, subcutaneous, intradermal, oral, topical, intranasal, intrapulmonary, or intrarectal route, but the administration is not limited to a specific route of administration as long as the desired pharmacological effect can be obtained.

In an example, the pharmaceutical composition of the present invention may be administered once a week, once every two weeks, once every three weeks, once every four weeks, or once a month, or may be administered once or multiple times at a time interval ranging from 1 week to 1 month, but the frequency is not limited thereto.

Still further aspect for implementing the present invention provides the use of the interleukin-2 analog, a long-acting conjugate thereof, or a composition including the same in the preparation of medicaments for prevention or treatment of cancer.

The interleukin-2 analog and/or long-acting conjugate thereof, or composition including the same, cancer, prevention, treatment, route of administration, and frequency of administration are the same as described above.

Still further aspect for implementing the present invention provides the use of the interleukin-2 analog, a long-acting conjugate thereof, or a composition including the same in the prevention or treatment of cancer.

The interleukin-2 analog and/or long-acting conjugate thereof, or composition including the same, cancer, prevention, treatment, route of administration, and frequency of administration are the same as described above.

Meanwhile, unless otherwise required by context in the present specification, expressions such as "include", "including", "containing", etc. mean that they include a specified integer or group of integers, but it should be understood that these expressions do not exclude other integers or a set of integers.

Hereinafter, the present invention will be described in more detail with reference to the following Examples. However, these Examples are only for describing the present invention in more detail only, and the scope of the present invention is not intended to be limited by these Examples.

Example 1: Preparation of Expression Vectors for Native Interleukin-2 and Interleukin-2 Analogs For the preparation of expression vectors for native interleukin-2 encoding 133 amino acids, an interleukin-2 that was synthesized based on the reported interleukin-2 sequence (NM_000586.3; SEQ ID NO: 1) was cloned into the pET-22b vector (Novagen). Additionally, a novel interleukin-2 analog was prepared in which an amino acid(s) of interleukin-2 were modified using the interleukin-2 as a template.

The PCR conditions for the amplification of the interleukin-2 analog were 16 cycles of a process consisting of 95° C. for 30 seconds, 55° C. for 60 seconds, and 65° C. for 6.5 minutes. In order to confirm whether the amino acid(s) at the desired position had been correctly substituted, sequence analysis was performed on the mutagenesis product obtained under the conditions above. As a result, it was confirmed that the modifications shown in Table 1 below were found based on the native type at the desired mutation positions for each interleukin-2 analog. The thus-obtained expression vectors were named pET22b-interleukin-2 analogs 1 to 105.

Table 1 below shows the altered sequences of amino acids and analog names for each. In order to prepare these interleukin-2 analogs, forward (F) and reverse (R) primers were synthesized, and then PCR was performed to amplify each analog gene.

In Table 1 below, analog 1 represents aldesleukin, and primer nos. 1 to 204 correspond to SEQ ID NOS: 214 to 417, respectively.

TABLE 1

| Types of Interleukin-2 Analogs, Modification Positions and Altered Sequences thereof | | |
|---|---|---|
| Analog | Modification Positions and Altered Sequences Thereof | Primer # |
| 1 | desA1, C125S | 197, 198, 201, 202 |
| 2 | desA1, C125S, S87C | 197, 198, 201, 202, 149, 150 |
| 3 | desA1, C125S, K32C | 197, 198, 201, 202, 19, 20 |
| 4 | desA1, C125S, K35C | 197, 198, 201, 202, 21, 22 |
| 5 | desA1, C125S, K43C | 197, 198, 201, 202, 47, 48 |
| 6 | desA1, C125S, K48C | 197, 198, 201, 202, 53, 54 |
| 7 | desA1, C125S, K49C | 197, 198, 201, 202, 55, 56 |
| 8 | desA1, C125S, K76C | 197, 198, 201, 202, 73, 74 |
| 9 | desA1, C125S, R38A | 197, 198, 201, 202, 25, 26 |
| 10 | desA1, C125S, F42K | 197, 198, 201, 202, 35, 36 |
| 11 | desA1, C125S, F42A | 197, 198, 201, 202, 33, 34 |
| 12 | desA1, C125S, R38A, F42K | 197, 198, 201, 202, 25, 26, 35, 36 |
| 13 | desA1, C125S, R38A, F42A | 197, 198, 201, 202, 25, 26, 33, 34 |
| 14 | desA1, C125S, L19Y, R38A, F42K | 197, 198, 201, 202, 13, 14, 25, 26, 35, 36 |
| 15 | desA1, C125S, R38A, F42K, D84E | 197, 198, 201, 202, 25, 26, 35, 36, 109, 110 |
| 16 | desA1, C125S, R38A, F42K, N88Q | 197, 198, 201, 202, 25, 26, 35, 36, 153, 154 |
| 17 | desA1, C125S, R38A, F42K, V91T | 197, 198, 201, 202, 25, 26, 35, 36, 165, 166 |
| 18 | desA1, C125S, R38A, F42K, E61Q | 197, 198, 201, 202, 25, 26, 35, 36, 59, 60 |
| 19 | desA1, C125S, R38A, F42K, R81D, I92F | 197, 198, 201, 202, 25, 26, 35, 36, 97, 98, 167, 168 |
| 20 | desA1, C125S, R38A, F42K, L85V, I86V, I92F | 197, 198, 201, 202, 25, 26, 35, 36, 139, 140, 167, 168 |
| 21 | desA1, C125S, R38A, F42K, L80F, R81D, L85V, I86V, I92F | 197, 198, 201, 202, 25, 26, 35, 36, 79, 80, 167, 168 |
| 22 | desA1, C125S, L12V, R38A, F42K | 197, 198, 201, 202, 3, 4, 25, 26, 35, 36 |
| 23 | desA1, C125S, L12F, R38A, F42K | 197, 198, 201, 202, 1, 2, 25, 26, 35, 36 |
| 24 | desA1, C125S, L19V, R38A, F42K | 197, 198, 201, 202, 11, 12, 25, 26, 35, 36 |
| 25 | desA1, C125S, L19F, R38A, F42K | 197, 198, 201, 202, 9, 10, 25, 26, 35, 36 |
| 26 | desA1, C125S, R38A, F42K, I89F | 197, 198, 201, 202, 25, 26, 35, 36, 157, 158 |
| 27 | desA1, C125S, R38A, F42K, V91F | 197, 198, 201, 202, 25, 26, 35, 36, 163, 164 |
| 28 | desA1, C125S, R38A, F42K, L94V | 197, 198, 201, 202, 25, 26, 35, 36 |
| 29 | desA1, C125S, R38A, F42K, Q126T | 197, 198, 201, 202, 25, 26, 35, 36, 199, 200 |
| 30 | desA1, C125S, R38A, R81D, I92F | 197, 198, 201, 202, 27, 28, 97, 98, 169, 170 |
| 31 | desA1, C125S, R38A, D84E | 197, 198, 201, 202, 27, 28, 109, 110 |
| 32 | desA1, C125S, R38A, R81D, D84E, I92F | 197, 198, 201, 202, 27, 28, 95, 96, 169, 170 |
| 33 | desA1, C125S, R38A, L80F | 197, 198, 201, 202, 27, 28, 77, 78 |
| 34 | desA1, C125S, R38A, L80F, D84E | 197, 198, 201, 202, 27, 28, 77, 78, 109, 110 |
| 35 | desA1, C125S, R38A, L94F, L96F | 197, 198, 201, 202, 27, 28, 189, 190 |
| 36 | desA1, C125S, R38A, L94F, L96V | 197, 198, 201, 202, 27, 28, 193, 194 |
| 37 | desA1, C125S, R38A, L94F, L96I | 197, 198, 201, 202, 27, 28, 191, 192 |
| 38 | desA1, C125S, R38A, F42K, R81D, I92F, L94F, L96F | 197, 198, 201, 202, 25, 26, 35, 36, 97, 98, 175, 176 |
| 39 | desA1, C125S, R38A, F42K, R81D, I92F, L94F, L96V | 197, 198, 201, 202, 25, 26, 35, 36, 97, 98, 179, 180 |
| 40 | desA1, C125S, R38A, F42K, R81D, I92F, L94F, L96I | 197, 198, 201, 202, 25, 26, 35, 36, 97, 98, 177, 178 |
| 41 | desA1, C125S, L80F, R81D, L85V, I86V, I92F | 197, 198, 201, 202, 25, 26, 29, 30, 35, 36, 41, 42, 79, 80, 167, 168 |

TABLE 1-continued

| Analog | Modification Positions and Altered Sequences Thereof | Primer # |
|---|---|---|
| 42 | desA1, C125S, R38A, F42K, R81E, I92F | 197, 198, 201, 202, 25, 26, 35, 36, 103, 104, 169, 170 |
| 43 | desA1, C125S, R38A, F42K, R81D, I92L | 197, 198, 201, 202, 25, 26, 35, 36, 99, 100, 183, 184 |
| 44 | desA1, C125S, R38A, F42K, R81D, D84V, I92F | 197, 198, 201, 202, 25, 26, 35, 36, 99, 100, 113, 114, 169, 170 |
| 45 | desA1, C125S, R38A, F42K, R81D, D84F, I92F | 197, 198, 201, 202, 25, 26, 35, 36, 99, 100, 111, 112, 169, 170 |
| 46 | desA1, C125S, D20V, R38A, F42K, R81D, I92F | 197, 198, 201, 202, 17, 18, 25, 26, 35, 36, 99, 100, 169, 170 |
| 47 | desA1, C125S, D20F, R38A, F42K, R81D, I92F | 197, 198, 201, 202, 15, 16, 25, 26, 35, 36, 99, 100, 169, 170 |
| 48 | desA1, C125S, R38A, F42K, R81D, N88V, I92F | 197, 198, 201, 202, 25, 26, 35, 36, 99, 100, 155, 156, 169, 170 |
| 49 | desA1, C125S, R38A, F42K, R81D, N88F, I92F | 197, 198, 201, 202, 25, 26, 35, 36, 99, 100, 151, 152, 169, 170 |
| 50 | desA1, C125S, F42K, L80F, R81D, L85V, I86V, I92F | 197, 198, 201, 202, 25, 26, 29, 30, 35, 36, 79, 80, 139, 140, 169, 170 |
| 51 | desA1, C125S, E61Q, R81D, I92F | 197, 198, 201, 202, 59, 60, 99, 100, 169, 170 |
| 52 | desA1, C125S, R38A, F42K, L80F, R81D, I92F | 197, 198, 201, 202, 25, 26, 35, 36, 79, 80, 169, 170 |
| 53 | desA1, C125S, R38A, F42K, L80F, R81D, D84E, I92F | 197, 198, 201, 202, 25, 26, 35, 36, 79, 80, 95, 96, 169, 170 |
| 54 | desA1, C125S, R38A, F42K, Q74H, R81D, I92F | 197, 198, 201, 202, 25, 26, 35, 36, 71, 72, 99, 100, 169, 170 |
| 55 | desA1, C125S, R38A, F42K, Q74H, L80F, R81D, I92F | 197, 198, 201, 202, 25, 26, 35, 36, 71, 72, 79, 80, 169, 170 |
| 56 | desA1, C125S, R38A, F42K, Y45A, Q74H, R81D, I92F | 197, 198, 201, 202, 25, 26, 35, 36, 49, 50, 71, 72, 99, 100, 169, 170 |
| 57 | desA1, C125S, R38A, F42K, Y45A, Q74H, L80F, R81D, I92F | 197, 198, 201, 202, 25, 26, 35, 36, 49, 50, 71, 72, 79, 80, 169, 170 |
| 58 | desA1, C125S, R38A, F42K, L80F, R81D, L85A, I86A, I92F | 197, 198, 201, 202, 25, 26, 35, 36, 79, 80, 115, 116, 167, 168 |
| 59 | desA1, C125S, R38A, F42K, L80F, R81D, L85A, I86A, I92Y | 197, 198, 201, 202, 25, 26, 35, 36, 79, 80, 115, 116, 187, 188 |
| 60 | desA1, C125S, R38A, Y45A, L80Y, L85A, I86A, I92Y | 197, 198, 201, 202, 27, 28, 35, 36, 41, 42, 51, 52, 93, 94, 115, 116, 187, 188 |
| 61 | desA1, C125S, R38A, F42K, L80Y, R81D, L85G, I86V, I92Y | 197, 198, 201, 202, 25, 26, 35, 36, 87, 88, 125, 126, 187, 188 |
| 62 | desA1, C125S, R38A, L80W, R81E, L85G, I86A, I92F | 197, 198, 201, 202, 27, 28, 35, 36, 41, 42, 85, 86, 123, 124, 171, 172 |
| 63 | desA1, C125S, R38A, F42K, L80D, R81E, L85T, I86G, I92F | 197, 198, 201, 202, 25, 26, 35, 36, 75, 76, 133, 134, 167, 168 |
| 64 | desA1, C125S, R38A, F42K, L80Y, R81N, L85V, I86V, I92F | 197, 198, 201, 202, 25, 26, 35, 36, 91, 92, 139, 140, 167, 168 |
| 65 | desA1, C125S, R38A, F42K, L80Y, R81E, L85V, I86V, I92F | 197, 198, 201, 202, 25, 26, 35, 36, 89, 90, 139, 140, 167, 168 |
| 66 | desA1, C125S, R38A, F42K, L80F, R81E, L85F, I86V, I92F | 197, 198, 201, 202, 25, 26, 35, 36, 81, 82, 121, 122, 167, 168 |
| 67 | desA1, C125S, R38A, F42K, L80Y, R81D, L85F, I86V, I92W, E95D | 197, 198, 201, 202, 25, 26, 35, 36, 87, 88, 121, 122, 185, 186, 195, 196 |
| 68 | desA1, C125S, R38A, F42K, L80F, R81E, L85I, I86V, V91E, I92F | 197, 198, 201, 202, 25, 26, 35, 36, 81, 82, 127, 128, 159, 160, 167, 168 |
| 69 | desA1, C125S, R38A, F42K, L80Y, R81E, L85F, I86L, V91E, I92W, E95D | 197, 198, 201, 202, 25, 26, 35, 36, 89, 90, 119, 120, 161, 162, 185, 186, 195, 196 |
| 70 | desA1, C125S, R38A, F42K, L80Y, R81D, L85V, I86V, I92F | 197, 198, 201, 202, 25, 26, 35, 36, 87, 88, 139, 140, 167, 168 |
| 71 | desA1, C125S, R38A, F42K, L80F, R81E, L85V, I86V, I92F | 197, 198, 201, 202, 25, 26, 35, 36, 81, 82, 139, 140, 167, 168 |
| 72 | desA1, C125S, R38A, F42K, L80F, R81D, L85V, I86G, I92F | 197, 198, 201, 202, 25, 26, 35, 36, 79, 80, 135, 136, 167, 168 |
| 73 | desA1, C125S, R38A, F42K, L80F, R81D, L85W, I86V, I92F | 197, 198, 201, 202, 25, 26, 35, 36, 79, 80, 141, 142, 167, 168 |
| 74 | desA1, C125S, R38D, F42K, L80Y, R81D, L85V, I86V, I92F | 197, 198, 201, 202, 31, 32, 35, 36, 87, 88, 139, 140, 167, 168 |
| 75 | desA1, C125S, R38A, F42K, Y45A, L80F, R81E, L85V, I86V, I92F | 197, 198, 201, 202, 25, 26, 35, 36, 51, 52, 81, 82, 139, 140, 167, 168 |
| 76 | desA1, C125S, R38A, F42K, K43Q, E61R, L80F, R81D, L85V, I86G, I92F | 197, 198, 201, 202, 25, 26, 39, 40, 61, 62, 79, 80, 135, 136, 167, 168 |
| 77 | desA1, C125S, R38A, F42K, K43E, E61R, L80F, R81D, L85W, I86V, I92F | 197, 198, 201, 202, 25, 26, 37, 38, 61, 62, 79, 80, 143, 144, 167, 168 |

TABLE 1-continued

Types of Interleukin-2 Analogs, Modification Positions and Altered Sequences thereof

| Analog | Modification Positions and Altered Sequences Thereof | Primer # |
|---|---|---|
| 78 | desA1, C125S, K35E, R38A, F42K, L80F, R81E, L85V, I86V, I92F | 197, 198, 201, 202, 23, 24, 25, 26, 35, 36, 81, 82, 139, 140, 167, 168 |
| 79 | desA1, C125S, K35E, R38A, F42K, Q74H, L80F, R81E, L85V, I86V, I92F | 197, 198, 201, 202, 23, 24, 25, 26, 35, 36, 71, 72, 81, 82, 139, 140, 167, 168 |
| 80 | desA1, C125S, K35E, R38A, F42K, Q74H, L80F, R81E, P82G, L85V, I86V, I92F | 197, 198, 201, 202, 23, 24, 25, 26, 35, 36, 71, 72, 81, 82, 105, 106, 139, 140, 167, 168 |
| 81 | desA1, C125S, K35E, R38A, F42K, Q74H, L80F, R81E, P82V, L85V, I86V, I92F | 197, 198, 201, 202, 23, 24, 25, 26, 35, 36, 71, 72, 81, 82, 107, 108, 139, 140, 167, 168 |
| 82 | desA1, C125S, L18R, Q22E, L80F, R81D, L85E, I86V, I92F | 197, 198, 201, 202, 7, 8, 25, 26, 29, 30, 35, 36, 43, 44, 79, 80, 117, 118, 167, 168 |
| 83 | desA1, C125S, L18R, L19R, Q22E, L80F, R81D, L85E, I86V, I92F | 197, 198, 201, 202, 5, 6, 25, 26, 29, 30, 35, 36, 43, 44, 79, 80, 117, 118, 167, 168 |
| 84 | desA1, C125S, L18R, Q22E, L80V, R81D, L85E, I86V, I92F | 197, 198, 201, 202, 7, 8, 25, 26, 29, 30, 35, 36, 43, 44, 83, 84, 117, 118, 167, 168 |
| 85 | desA1, C125S, L80F, R81E, L85V, I86V, I92F | 197, 198, 201, 202, 25, 26, 29, 30, 35, 36, 43, 44, 81, 82, 139, 140, 167, 168 |
| 86 | desA1, C125S, L18R, Q22E, L80F, R81E, L85V, I86V, I92F | 197, 198, 201, 202, 7, 8, 25, 26, 29, 30, 35, 36, 43, 44, 81, 82, 139, 140, 167, 168 |
| 87 | desA1, C125S, L18R, L19R, Q22E, L80F, R81E, L85V, I86V, I92F | 197, 198, 201, 202, 5, 6, 25, 26, 29, 30, 35, 36, 43, 44, 81, 82, 139, 140, 167, 168 |
| 88 | desA1, C125S, E61D, L80F, R81E, L85V, I86V, I92F | 197, 198, 201, 202, 25, 26, 29, 30, 35, 36, 43, 44, 57, 58, 81, 82, 139, 140, 167, 168 |
| 89 | desA1, C125S, R38A, E68Q, L80F, R81E, L85V, I86V, I92F | 197, 198, 201, 202, 27, 28, 35, 36, 43, 44, 65, 66, 81, 82, 139, 140, 167, 168 |
| 90 | desA1, C125S, F42W, L80F, R81E, L85V, I86V, I92F | 197, 198, 201, 202, 25, 26, 29, 30, 45, 46, 81, 82, 139, 140, 167, 168 |
| 91 | desA1, C125S, E61Q, L80F, R81E, L85V, I86V, I92F | 197, 198, 201, 202, 25, 26, 29, 30, 35, 36, 43, 44, 59, 60, 81, 82, 139, 140, 167, 168 |
| 92 | desA1, C125S, L80F, R81E, L85V, I86V, V91T, I92F | 197, 198, 201, 202, 25, 26, 29, 30, 35, 36, 43, 44, 81, 82, 139, 140, 147, 148, 167, 168 |
| 93 | desA1, C125S, L80F, R81E, D84E, L85V, I86V, V91T, I92F | 197, 198, 201, 202, 25, 26, 29, 30, 35, 36, 43, 44, 81, 82, 101, 102, 139, 140, 167, 168 |
| 94 | desA1, C125S, L80F, R81E, L85V, I86V, I92F, L94F, L96F | 197, 198, 201, 202, 25, 26, 29, 30, 35, 36, 43, 44, 81, 82, 139, 140, 173, 174 |
| 95 | desA1, C125S, V69G, L80F, R81E, L85V, I86V, I92F | 197, 198, 201, 202, 25, 26, 29, 30, 35, 36, 43, 44, 67, 68, 81, 82, 139, 140, 167, 168 |
| 96 | desA1, C125S, V69G, Q74A, L80F, R81E, L85V, I86V, I92F | 197, 198, 201, 202, 25, 26, 29, 30, 35, 36, 43, 44, 69, 70, 81, 82, 139, 140, 167, 168 |
| 97 | desA1, C125S, R38A, L80F, R81D, I92F | 197, 198, 201, 202, 27, 28, 35, 36, 41, 42, 79, 80, 167, 168 |
| 98 | desA1, C125S, R38A, L80F, R81E, L85V, I92F | 197, 198, 201, 202, 27, 28, 35, 36, 41, 42, 81, 82, 137, 138, 167, 168 |
| 99 | desA1, C125S, R38A, L80F, R81E, I86V, I92F | 197, 198, 201, 202, 27, 28, 35, 36, 41, 42, 81, 82, 131, 132, 167, 168 |
| 100 | desA1, C125S, L80F, R81E, L85Y, I86V, I92F | 197, 198, 201, 202, 25, 26, 29, 30, 35, 36, 41, 42, 81, 82, 145, 146, 167, 168 |
| 101 | desA1, C125S, L80F, R81E, I86A, I92F | 197, 198, 201, 202, 25, 26, 29, 30, 35, 36, 41, 42, 81, 82, 129, 130, 167, 168 |
| 102 | desA1, C125S, L80F, R81E, L85V, I86V | 197, 198, 201, 202, 25, 26, 29, 30, 35, 36, 41, 42, 81, 82, 139, 140, 181, 182 |
| 103 | desA1, C125S, L18R, Q22E, R38A, L80F, R81E, L85V, I86V, I92F | 197, 198, 201, 202, 7, 8, 27, 28, 35, 36, 41, 42, 81, 82, 139, 140, 167, 168 |
| 104 | desA1, C125S, L18R, Q22E, E61D, L80F, R81E, L85V, I86V, I92F | 197, 198, 201, 202, 7, 8, 25, 26, 29, 30, 35, 36, 41, 42, 57, 58, 81, 82, 139, 140, 167, 168 |

TABLE 1-continued

| Types of Interleukin-2 Analogs, Modification Positions and Altered Sequences thereof | | |
| --- | --- | --- |
| Analog | Modification Positions and Altered Sequences Thereof | Primer # |
| 105 | desA1, C125S, L18R, Q22E, E68D, L80F, R81E, L85V, I86V, I92F | 197, 198, 201, 202, 7, 8, 25, 26, 29, 30, 35, 36, 41, 42, 63, 64, 81, 82, 139, 140, 167, 168 |

In Table 1 above, desA1 represents a deletion of alanine, which is the first amino acid in interleukin-2.

Table 2 below shows full-length protein sequences of interleukin-2 analogs. The letters shown in bold in Table 2 represent the positions for modification.

TABLE 2

| | Sequences of Interleukin-2 Analogs | | |
| --- | --- | --- | --- |
| Analog | Protein Sequence | SEQ ID NO: of Proteins | SEQ ID NO: of Nucleotides |
| 1 | PTSSSTKKT QLQLEHLLLD LQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFSQSIIS TLT | 2 | 107 |
| 2 | PTSSSTKKT QLQLEHLLLD LQMILNGINN YKNPKLTRML TFKFYMPKKA TELKHLQCLE EELKPLEEVL NLAQSKNFHL RPRDLICNIN VIVLELKGSE TTFMCEYADE TATIVEFLNR WITFSQSIIS TLT | 3 | 108 |
| 3 | PTSSSTKKT QLQLEHLLLD LQMILNGINN YCNPKLTRML TFKFYMPKKA TELKHLQCLE EELKPLEEVL NLAQSKNFHL RPRDLISNIN VIVLELKGSE TTFMCEYADE TATIVEFLNR WITFSQSIIS TLT | 4 | 109 |
| 4 | PTSSSTKKT QLQLEHLLLD LQMILNGINN YKNPCLTRML TFKFYMPKKA TELKHLQCLE EELKPLEEVL NLAQSKNFHL RPRDLISNIN VIVLELKGSE TTFMCEYADE TATIVEFLNR WITFSQSIIS TLT | 5 | 110 |
| 5 | PTSSSTKKT QLQLEHLLLD LQMILNGINN YKNPKLTRML TFCFYMPKKA TELKHLQCLE EELKPLEEVL NLAQSKNFHL RPRDLISNIN VIVLELKGSE TTFMCEYADE TATIVEFLNR WITFSQSIIS TLT | 6 | 111 |
| 6 | PTSSSTKKT QLQLEHLLLD LQMILNGINN YKNPKLTRML TFKFYMPCKA TELKHLQCLE EELKPLEEVL NLAQSKNFHL RPRDLISNIN VIVLELKGSE TTFMCEYADE TATIVEFLNR WITFSQSIIS TLT | 7 | 112 |
| 7 | PTSSSTKKT QLQLEHLLLD LQMILNGINN YKNPKLTRML TFKFYMPKCA TELKHLQCLE EELKPLEEVL NLAQSKNFHL RPRDLISNIN VIVLELKGSE TTFMCEYADE TATIVEFLNR WITFSQSIIS TLT | 8 | 113 |
| 8 | PTSSSTKKT QLQLEHLLLD LQMILNGINN YKNPKLTRML TFKFYMPKKA TELKHLQCLE EELKPLEEVL NLAQSCNFHL RPRDLISNIN VIVLELKGSE TTFMCEYADE TATIVEFLNR WITFSQSIIS TLT | 9 | 114 |
| 9 | PTSSSTKKT QLQLEHLLLD LQMILNGINN YKNPKLTAML TFKFYMPKKA TELKHLQCLE EELKPLEEVL NLAQSKNFHL RPRDLISNIN VIVLELKGSE TTFMCEYADE TATIVEFLNR WITFSQSIIS TLT | 10 | 115 |
| 10 | PTSSSTKKT QLQLEHLLLD LQMILNGINN YKNPKLTRML TKKFYMPKKA TELKHLQCLE EELKPLEEVL NLAQSKNFHL RPRDLISNIN VIVLELKGSE TTFMCEYADE TATIVEFLNR WITFSQSIIS TLT | 11 | 116 |
| 11 | PTSSSTKKT QLQLEHLLLD LQMILNGINN YKNPKLTRML TAKFYMPKKA TELKHLQCLE EELKPLEEVL NLAQSKNFHL RPRDLISNIN VIVLELKGSE TTFMCEYADE TATIVEFLNR WITFSQSIIS TLT | 12 | 117 |
| 12 | PTSSSTKKT QLQLEHLLLD LQMILNGINN YKNPKLTAML TKKFYMPKKA TELKHLQCLE EELKPLEEVL NLAQSKNFHL RPRDLISNIN VIVLELKGSE TTFMCEYADE TATIVEFLNR WITFSQSIIS TLT | 13 | 118 |
| 13 | PTSSSTKKT QLQLEHLLLD LQMILNGINN YKNPKLTAML TAKFYMPKKA TELKHLQCLE EELKPLEEVL NLAQSKNFHL RPRDLISNIN VIVLELKGSE TTFMCEYADE TATIVEFLNR WITFSQSIIS TLT | 14 | 119 |
| 14 | PTSSSTKKT QLQLEHLLYD LQMILNGINN YKNPKLTAML TKKFYMPKKA TELKHLQCLE EELKPLEEVL NLAQSKNFHL RPRDLISNIN VIVLELKGSE TTFMCEYADE TATIVEFLNR WITFSQSIIS TLT | 15 | 120 |

TABLE 2-continued

| | | SEQ ID NO: of | SEQ ID NO: of |
|---|---|---|---|
| Analog | Protein Sequence | Proteins | Nucleotides |
| 15 | PTSSSTKKT QLQLEHLLLD LQMILNGINN YKNPKLTAML TKKFYMPKKA<br>TELKHLQCLE EELKPLEEVL NLAQSKNFHL RPRELISNIN VIVLELKGSE<br>TTFMCEYADE TATIVEFLNR WITFSQSIIS TLT | 16 | 121 |
| 16 | PTSSSTKKT QLQLEHLLLD LQMILNGINN YKNPKLTAML TKKFYMPKKA<br>TELKHLQCLE EELKPLEEVL NLAQSKNFHL RPRDLISQIN VIVLELKGSE<br>TTFMCEYADE TATIVEFLNR WITFSQSIIS TLT | 17 | 122 |
| 17 | PTSSSTKKT QLQLEHLLLD LQMILNGINN YKNPKLTAML TKKFYMPKKA<br>TELKHLQCLE EELKPLEEVL NLAQSKNFHL RPRDLISNIN TIVLELKGSE<br>TTFMCEYADE TATIVEFLNR WITFSQSIIS TLT | 18 | 123 |
| 18 | PTSSSTKKT QLQLEHLLLD LQMILNGINN YKNPKLTAML TKKFYMPKKA<br>TELKHLQCLE QELKPLEEVL NLAQSKNFHL RPRDLISNIN VIVLELKGSE<br>TTFMCEYADE TATIVEFLNR WITFSQSIIS TLT | 19 | 124 |
| 19 | PTSSSTKKT QLQLEHLLLD LQMILNGINN YKNPKLTAML TKKFYMPKKA<br>TELKHLQCLE EELKPLEEVL NLAQSKNFHL DPRDLISNIN VFVLELKGSE<br>TTFMCEYADE TATIVEFLNR WITFSQSIIS TLT | 20 | 125 |
| 20 | PTSSSTKKT QLQLEHLLLD LQMILNGINN YKNPKLTAML TKKFYMPKKA<br>TELKHLQCLE EELKPLEEVL NLAQSKNFHL RPRDVVSNIN VFVLELKGSE<br>TTFMCEYADE TATIVEFLNR WITFSQSIIS TLT | 21 | 126 |
| 21 | PTSSSTKKT QLQLEHLLLD LQMILNGINN YKNPKLTAML TKKFYMPKKA<br>TELKHLQCLE EELKPLEEVL NLAQSKNFHF DPRDVVSNIN VFVLELKGSE<br>TTFMCEYADE TATIVEFLNR WITFSQSIIS TLT | 22 | 127 |
| 22 | PTSSSTKKT QVQLEHLLLD LQMILNGINN YKNPKLTAML TKKFYMPKKA<br>TELKHLQCLE EELKPLEEVL NLAQSKNFHL RPRDLISNIN VIVLELKGSE<br>TTFMCEYADE TATIVEFLNR WITFSQSIIS TLT | 23 | 128 |
| 23 | PTSSSTKKT QFQLEHLLLD LQMILNGINN YKNPKLTAML TKKFYMPKKA<br>TELKHLQCLE EELKPLEEVL NLAQSKNFHL RPRDLISNIN VIVLELKGSE<br>TTFMCEYADE TATIVEFLNR WITFSQSIIS TLT | 24 | 129 |
| 24 | PTSSSTKKT QLQLEHLLVD LQMILNGINN YKNPKLTAML TKKFYMPKKA<br>TELKHLQCLE EELKPLEEVL NLAQSKNFHL RPRDLISNIN VIVLELKGSE<br>TTFMCEYADE TATIVEFLNR WITFSQSIIS TLT | 25 | 130 |
| 25 | PTSSSTKKT QLQLEHLLFD LQMILNGINN YKNPKLTAML TKKFYMPKKA<br>TELKHLQCLE EELKPLEEVL NLAQSKNFHL RPRDLISNIN VIVLELKGSE<br>TTFMCEYADE TATIVEFLNR WITFSQSIIS TLT | 26 | 131 |
| 26 | PTSSSTKKT QLQLEHLLLD LQMILNGINN YKNPKLTAML TKKFYMPKKA<br>TELKHLQCLE EELKPLEEVL NLAQSKNFHL RPRDLISNFN VIVLELKGSE<br>TTFMCEYADE TATIVEFLNR WITFSQSIIS TLT | 27 | 132 |
| 27 | PTSSSTKKT QLQLEHLLLD LQMILNGINN YKNPKLTAML TKKFYMPKKA<br>TELKHLQCLE EELKPLEEVL NLAQSKNFHL RPRDLISNIN FIVLELKGSE<br>TTFMCEYADE TATIVEFLNR WITFSQSIIS TLT | 28 | 133 |
| 28 | PTSSSTKKT QLQLEHLLLD LQMILNGINN YKNPKLTAML TKKFYMPKKA<br>TELKHLQCLE EELKPLEEVL NLAQSKNFHL RPRDLISNIN VIVVELKGSE<br>TTFMCEYADE TATIVEFLNR WITFSQSIIS TLT | 29 | 134 |
| 29 | PTSSSTKKT QLQLEHLLLD LQMILNGINN YKNPKLTAML TKKFYMPKKA<br>TELKHLQCLE EELKPLEEVL NLAQSKNFHL RPRDLISNIN VIVLELKGSE<br>TTFMCEYADE TATIVEFLNR WITFSTSIIS TLT | 30 | 135 |
| 30 | PTSSSTKKT QLQLEHLLLD LQMILNGINN YKNPKLTAML TFKFYMPKKA<br>TELKHLQCLE EELKPLEEVL NLAQSKNFHL DPRDLISNIN VFVLELKGSE<br>TTFMCEYADE TATIVEFLNR WITFSQSIIS TLT | 31 | 136 |
| 31 | PTSSSTKKT QLQLEHLLLD LQMILNGINN YKNPKLTAML TFKFYMPKKA<br>TELKHLQCLE EELKPLEEVL NLAQSKNFHL RPRELISNIN VIVLELKGSE<br>TTFMCEYADE TATIVEFLNR WITFSQSIIS TLT | 32 | 137 |
| 32 | PTSSSTKKT QLQLEHLLLD LQMILNGINN YKNPKLTAML TFKFYMPKKA<br>TELKHLQCLE EELKPLEEVL NLAQSKNFHL DPRELISNIN VFVLELKGSE<br>TTFMCEYADE TATIVEFLNR WITFSQSIIS TLT | 33 | 138 |

TABLE 2-continued

Sequences of Interleukin-2 Analogs

| Analog | Protein Sequence | SEQ ID NO: of Proteins | SEQ ID NO: of Nucleotides |
|--------|------------------|------------------------|---------------------------|
| 33 | PTSSSTKKT QLQLEHLLLD LQMILNGINN YKNPKLTAML TFKFYMPKKA TELKHLQCLE EELKPLEEVL NLAQSKNFHF RPRDLISNIN VIVLELKGSE TTFMCEYADE TATIVEFLNR WITFSQSIIS TLT | 34 | 139 |
| 34 | PTSSSTKKT QLQLEHLLLD LQMILNGINN YKNPKLTAML TFKFYMPKKA TELKHLQCLE EELKPLEEVL NLAQSKNFHF RPRELISNIN VIVLELKGSE TTFMCEYADE TATIVEFLNR WITFSQSIIS TLT | 35 | 140 |
| 35 | PTSSSTKKT QLQLEHLLLD LQMILNGINN YKNPKLTAML TFKFYMPKKA TELKHLQCLE EELKPLEEVL NLAQSKNFHL RPRDLISNIN VIVFEFKGSE TTFMCEYADE TATIVEFLNR WITFSQSIIS TLT | 36 | 141 |
| 36 | PTSSSTKKT QLQLEHLLLD LQMILNGINN YKNPKLTAML TFKFYMPKKA TELKHLQCLE EELKPLEEVL NLAQSKNFHL RPRDLISNIN VIVFEVKGSE TTFMCEYADE TATIVEFLNR WITFSQSIIS TLT | 37 | 142 |
| 37 | PTSSSTKKT QLQLEHLLLD LQMILNGINN YKNPKLTAML TFKFYMPKKA TELKHLQCLE EELKPLEEVL NLAQSKNFHL RPRDLISNIN VIVFEIKGSE TTFMCEYADE TATIVEFLNR WITFSQSIIS TLT | 38 | 143 |
| 38 | PTSSSTKKT QLQLEHLLLD LQMILNGINN YKNPKLTAML TFKFYMPKKA TELKHLQCLE EELKPLEEVL NLAQSKNFHL DPRDLISNIN VFVFEFKGSE TTFMCEYADE TATIVEFLNR WITFSQSIIS TLT | 39 | 144 |
| 39 | PTSSSTKKT QLQLEHLLLD LQMILNGINN YKNPKLTAML TFKFYMPKKA TELKHLQCLE EELKPLEEVL NLAQSKNFHL DPRDLISNIN VFVFEVKGSE TTFMCEYADE TATIVEFLNR WITFSQSIIS TLT | 40 | 145 |
| 40 | PTSSSTKKT QLQLEHLLLD LQMILNGINN YKNPKLTAML TKKFYMPKKA TELKHLQCLE EELKPLEEVL NLAQSKNFHL DPRDLISNIN VFVFEIKGSE TTFMCEYADE TATIVEFLNR WITFSQSIIS TLT | 41 | 146 |
| 41 | PTSSSTKKT QLQLEHLLLD LQMILNGINN YKNPKLTRML TFKFYMPKKA TELKHLQCLE EELKPLEEVL NLAQSKNFHF DPRDVVSNIN VFVLELKGSE TTFMCEYADE TATIVEFLNR WITFSQSIIS TLT | 42 | 147 |
| 42 | PTSSSTKKT QLQLEHLLLD LQMILNGINN YKNPKLTAML TKKFYMPKKA TELKHLQCLE EELKPLEEVL NLAQSKNFHL EPRDLISNIN VFVLELKGSE TTFMCEYADE TATIVEFLNR WITFSQSIIS TLT | 43 | 148 |
| 43 | PTSSSTKKT QLQLEHLLLD LQMILNGINN YKNPKLTAML TKKFYMPKKA TELKHLQCLE EELKPLEEVL NLAQSKNFHL DPRDLISNIN VLVLELKGSE TTFMCEYADE TATIVEFLNR WITFSQSIIS TLT | 44 | 149 |
| 44 | PTSSSTKKT QLQLEHLLLD LQMILNGINN YKNPKLTAML TKKFYMPKKA TELKHLQCLE EELKPLEEVL NLAQSKNFHL DPRVLISNIN VFVLELKGSE TTFMCEYADE TATIVEFLNR WITFSQSIIS TLT | 45 | 150 |
| 45 | PTSSSTKKT QLQLEHLLLD LQMILNGINN YKNPKLTAML TKKFYMPKKA TELKHLQCLE EELKPLEEVL NLAQSKNFHL DPRFLISNIN VFVLELKGSE TTFMCEYADE TATIVEFLNR WITFSQSIIS TLT | 46 | 151 |
| 46 | PTSSSTKKT QLQLEHLLLV LQMILNGINN YKNPKLTAML TKKFYMPKKA TELKHLQCLE EELKPLEEVL NLAQSKNFHL DPRDLISNIN VFVLELKGSE TTFMCEYADE TATIVEFLNR WITFSQSIIS TLT | 47 | 152 |
| 47 | PTSSSTKKT QLQLEHLLLF LQMILNGINN YKNPKLTAML TKKFYMPKKA TELKHLQCLE EELKPLEEVL NLAQSKNFHL DPRDLISNIN VFVLELKGSE TTFMCEYADE TATIVEFLNR WITFSQSIIS TLT | 48 | 153 |
| 48 | PTSSSTKKT QLQLEHLLLD LQMILNGINN YKNPKLTAML TKKFYMPKKA TELKHLQCLE EELKPLEEVL NLAQSKNFHL DPRDLISVIN VFVLELKGSE TTFMCEYADE TATIVEFLNR WITFSQSIIS TLT | 49 | 154 |
| 49 | PTSSSTKKT QLQLEHLLLD LQMILNGINN YKNPKLTAML TKKFYMPKKA TELKHLQCLE EELKPLEEVL NLAQSKNFHL DPRDLISFIN VFVLELKGSE TTFMCEYADE TATIVEFLNR WITFSQSIIS TLT | 50 | 155 |
| 50 | PTSSSTKKT QLQLEHLLLD LQMILNGINN YKNPKLTRML TKKFYMPKKA TELKHLQCLE EELKPLEEVL NLAQSKNFHF DPRDVVSNIN VFVLELKGSE TTFMCEYADE TATIVEFLNR WITFSQSIIS TLT | 51 | 156 |

TABLE 2-continued

| | Sequences of Interleukin-2 Analogs | | |
| --- | --- | --- | --- |
| Analog | Protein Sequence | SEQ ID NO: of Proteins | SEQ ID NO: of Nucleotides |
| 51 | PTSSSTKKT QLQLEHLLLD LQMILNGINN YKNPKLTRML TFKFYMPKKA TELKHLQCLE QELKPLEEVL NLAQSKNFHL DPRDLISNIN VFVLELKGSE TTFMCEYADE TATIVEFLNR WITFSQSIIS TLT | 52 | 157 |
| 52 | PTSSSTKKT QLQLEHLLLD LQMILNGINN YKNPKLTAML TKKFYMPKKA TELKHLQCLE EELKPLEEVL NLAQSKNFHF DPRDLISNIN VFVLELKGSE TTFMCEYADE TATIVEFLNR WITFSQSIIS TLT | 53 | 158 |
| 53 | PTSSSTKKT QLQLEHLLLD LQMILNGINN YKNPKLTAML TKKFYMPKKA TELKHLQCLE EELKPLEEVL NLAQSKNFHF DPRELISNIN VFVLELKGSE TTFMCEYADE TATIVEFLNR WITFSQSIIS TLT | 54 | 159 |
| 54 | PTSSSTKKT QLQLEHLLLD LQMILNGINN YKNPKLTAML TKKFYMPKKA TELKHLQCLE EELKPLEEVL NLAHSKNFHL DPRDLISNIN VFVLELKGSE TTFMCEYADE TATIVEFLNR WITFSQSIIS TLT | 55 | 160 |
| 55 | PTSSSTKKT QLQLEHLLLD LQMILNGINN YKNPKLTAML TKKFYMPKKA TELKHLQCLE EELKPLEEVL NLAHSKNFHF DPRDLISNIN VFVLELKGSE TTFMCEYADE TATIVEFLNR WITFSQSIIS TLT | 56 | 161 |
| 56 | PTSSSTKKT QLQLEHLLLD LQMILNGINN YKNPKLTAML TKKFAMPKKA TELKHLQCLE EELKPLEEVL NLAHSKNFHL DPRDLISNIN VFVLELKGSE TTFMCEYADE TATIVEFLNR WITFSQSIIS TLT | 57 | 162 |
| 57 | PTSSSTKKT QLQLEHLLLD LQMILNGINN YKNPKLTAML TKKFAMPKKA TELKHLQCLE EELKPLEEVL NLAHSKNFHF DPRDLISNIN VFVLELKGSE TTFMCEYADE TATIVEFLNR WITFSQSIIS TLT | 58 | 163 |
| 58 | PTSSSTKKT QLQLEHLLLD LQMILNGINN YKNPKLTAML TKKFYMPKKA TELKHLQCLE EELKPLEEVL NLAQSKNFHF DPRDAASNIN VFVLELKGSE TTFMCEYADE TATIVEFLNR WITFSQSIIS TLT | 59 | 164 |
| 59 | PTSSSTKKT QLQLEHLLLD LQMILNGINN YKNPKLTAML TKKFYMPKKA TELKHLQCLE EELKPLEEVL NLAQSKNFHF DPRDAASNIN VYVLELKGSE TTFMCEYADE TATIVEFLNR WITFSQSIIS TLT | 60 | 165 |
| 60 | PTSSSTKKT QLQLEHLLLD LQMILNGINN YKNPKLTAML TKKFAMPKKA TELKHLQCLE EELKPLEEVL NLAQSKNFHY RPRDAASNIN VYVLELKGSE TTFMCEYADE TATIVEFLNR WITFSQSIIS TLT | 61 | 166 |
| 61 | PTSSSTKKT QLQLEHLLLD LQMILNGINN YKNPKLTAML TKKFYMPKKA TELKHLQCLE EELKPLEEVL NLAQSKNFHY DPRDGVSNIN VYVLELKGSE TTFMCEYADE TATIVEFLNR WITFSQSIIS TLT | 62 | 167 |
| 62 | PTSSSTKKT QLQLEHLLLD LQMILNGINN YKNPKLTAML TKKFYMPKKA TELKHLQCLE EELKPLEEVL NLAQSKNFHW EPRDGASNIN VFVLELKGSE TTFMCEYADE TATIVEFLNR WITFSQSIIS TLT | 63 | 168 |
| 63 | PTSSSTKKT QLQLEHLLLD LQMILNGINN YKNPKLTAML TKKFYMPKKA TELKHLQCLE EELKPLEEVL NLAQSKNFHD EPRDTGSNIN VFVLELKGSE TTFMCEYADE TATIVEFLNR WITFSQSIIS TLT | 64 | 169 |
| 64 | PTSSSTKKT QLQLEHLLLD LQMILNGINN YKNPKLTAML TKKFYMPKKA TELKHLQCLE EELKPLEEVL NLAQSKNFHY NPRDVVSNIN VYVLELKGSE TTFMCEYADE TATIVEFLNR WITFSQSIIS TLT | 65 | 170 |
| 65 | PTSSSTKKT QLQLEHLLLD LQMILNGINN YKNPKLTAML TKKFYMPKKA TELKHLQCLE EELKPLEEVL NLAQSKNFHY EPRDVVSNIN VFVLELKGSE TTFMCEYADE TATIVEFLNR WITFSQSIIS TLT | 66 | 171 |
| 66 | PTSSSTKKT QLQLEHLLLD LQMILNGINN YKNPKLTAML TKKFYMPKKA TELKHLQCLE EELKPLEEVL NLAQSKNFHF EPRDFVSNIN VFVLELKGSE TTFMCEYADE TATIVEFLNR WITFSQSIIS TLT | 67 | 172 |
| 67 | PTSSSTKKT QLQLEHLLLD LQMILNGINN YKNPKLTAML TKKFYMPKKA TELKHLQCLE EELKPLEEVL NLAQSKNFHY DPRDFVSNIN VWVLD LKGSE TTFMCEYADE TATIVEFLNR WITFSQSIIS TLT | 68 | 173 |
| 68 | PTSSSTKKT QLQLEHLLLD LQMILNGINN YKNPKLTAML TKKFYMPKKA TELKHLQCLE EELKPLEEVL NLAQSKNFHF EPRDIVSNIN EFVLELKGSE TTFMCEYADE TATIVEFLNR WITFSQSIIS TLT | 69 | 174 |

TABLE 2-continued

Sequences of Interleukin-2 Analogs

| Analog | Protein Sequence | SEQ ID NO: of Proteins | SEQ ID NO: of Nucleotides |
|---|---|---|---|
| 69 | PTSSSTKKT QLQLEHLLLD LQMILNGINN YKNPKLTAML TKKFYMPKKA TELKHLQCLE EELKPLEEVL NLAQSKNFHY EPRDFLSNIN EWVLDLKGSE TTFMCEYADE TATIVEFLNR WITFSQSIIS TLT | 70 | 175 |
| 70 | PTSSSTKKT QLQLEHLLLD LQMILNGINN YKNPKLTAML TKKFYMPKKA TELKHLQCLE EELKPLEEVL NLAQSKNFHY DPRDVVSNIN VFVLELKGSE TTFMCEYADE TATIVEFLNR WITFSQSIIS TLT | 71 | 176 |
| 71 | PTSSSTKKT QLQLEHLLLD LQMILNGINN YKNPKLTAML TKKFYMPKKA TELKHLQCLE EELKPLEEVL NLAQSKNFHF EPRDVVSNIN VFVLELKGSE TTFMCEYADE TATIVEFLNR WITFSQSIIS TLT | 72 | 177 |
| 72 | PTSSSTKKT QLQLEHLLLD LQMILNGINN YKNPKLTAML TKKFYMPKKA TELKHLQCLE EELKPLEEVL NLAQSKNFHF DPRDVGSNIN VFVLELKGSE TTFMCEYADE TATIVEFLNR WITFSQSIIS TLT | 73 | 178 |
| 73 | PTSSSTKKT QLQLEHLLLD LQMILNGINN YKNPKLTAML TKKFYMPKKA TELKHLQCLE EELKPLEEVL NLAQSKNFHF DPRDWVSNIN VFVLELKGSE TTFMCEYADE TATIVEFLNR WITFSQSIIS TLT | 74 | 179 |
| 74 | PTSSSTKKT QLQLEHLLLD LQMILNGINN YKNPKLTDML TKKFYMPKKA TELKHLQCLE EELKPLEEVL NLAQSKNFHY DPRDVVSNIN VFVLELKGSE TTFMCEYADE TATIVEFLNR WITFSQSIIS TLT | 75 | 180 |
| 75 | PTSSSTKKT QLQLEHLLLD LQMILNGINN YKNPKLTAML TKKFAMPKKA TELKHLQCLE EELKPLEEVL NLAQSKNFHF EPRDVVSNIN VFVLELKGSE TTFMCEYADE TATIVEFLNR WITFSQSIIS TLT | 76 | 181 |
| 76 | PTSSSTKKT QLQLEHLLLD LQMILNGINN YKNPKLTAML TKQFYMPKKA TELKHLQCLE RELKPLEEVL NLAQSKNFHF DPRDVGSNIN VFVLELKGSE TTFMCEYADE TATIVEFLNR WITFSQSIIS TLT | 77 | 182 |
| 77 | PTSSSTKKT QLQLEHLLLD LQMILNGINN YKNPKLTAML TKEFYMPKKA TELKHLQCLE RELKPLEEVL NLAQSKNFHF DPRDWVSNIN VFVLELKGSE TTFMCEYADE TATIVEFLNR WITFSQSIIS TLT | 78 | 183 |
| 78 | PTSSSTKKT QLQLEHLLLD LQMILNGINN YKNPELTAML TKKFYMPKKA TELKHLQCLE EELKPLEEVL NLAQSKNFHF EPRDVVSNIN VFVLELKGSE TTFMCEYADE TATIVEFLNR WITFSQSIIS TLT | 79 | 184 |
| 79 | PTSSSTKKT QLQLEHLLLD LQMILNGINN YKNPELTAML TKKFYMPKKA TELKHLQCLE EELKPLEEVL NLAHSKNFHF EPRDVVSNIN VFVLELKGSE TTFMCEYADE TATIVEFLNR WITFSQSIIS TLT | 80 | 185 |
| 80 | PTSSSTKKT QLQLEHLLLD LQMILNGINN YKNPELTAML TKKFYMPKKA TELKHLQCLE EELKPLEEVL NLAHSKNFHF EGRDVVSNIN VFVLELKGSE TTFMCEYADE TATIVEFLNR WITFSQSIIS TLT | 81 | 186 |
| 81 | PTSSSTKKT QLQLEHLLLD LQMILNGINN YKNPELTAML TKKFYMPKKA TELKHLQCLE EELKPLEEVL NLAHSKNFHF EVRDVVSNIN VFVLELKGSE TTFMCEYADE TATIVEFLNR WITFSQSIIS TLT | 82 | 187 |
| 82 | PTSSSTKKT QLQLEHLRLD LEMILNGINN YKNPKLTRML TFKFYMPKKA TELKHLQCLE EELKPLEEVL NLAQSKNFHF DPRDEVSNIN VFVLELKGSE TTFMCEYADE TATIVEFLNR WITFSQSIIS TLT | 83 | 188 |
| 83 | PTSSSTKKT QLQLEHLRRD LEMILNGINN YKNPKLTRML TFKFYMPKKA TELKHLQCLE EELKPLEEVL NLAQSKNFHF DPRDEVSNIN VFVLELKGSE TTFMCEYADE TATIVEFLNR WITFSQSIIS TLT | 84 | 189 |
| 84 | PTSSSTKKT QLQLEHLRLD LEMILNGINN YKNPKLTRML TFKFYMPKKA TELKHLQCLE EELKPLEEVL NLAQSKNFHV DPRDEVSNIN VFVLELKGSE TTFMCEYADE TATIVEFLNR WITFSQSIIS TLT | 85 | 190 |
| 85 | PTSSSTKKT QLQLEHLLLD LQMILNGINN YKNPKLTRML TFKFYMPKKA TELKHLQCLE EELKPLEEVL NLAQSKNFHF EPRDVVSNIN VFVLELKGSE TTFMCEYADE TATIVEFLNR WITFSQSIIS TLT | 86 | 191 |
| 86 | PTSSSTKKT QLQLEHLRLD LEMILNGINN YKNPKLTRML TFKFYMPKKA TELKHLQCLE EELKPLEEVL NLAQSKNFHF EPRDVVSNIN VFVLELKGSE TTFMCEYADE TATIVEFLNR WITFSQSIIS TLT | 87 | 192 |

TABLE 2-continued

Sequences of Interleukin-2 Analogs

| Analog | Protein Sequence | SEQ ID NO: of Proteins | SEQ ID NO: of Nucleotides |
|---|---|---|---|
| 87 | PTSSSTKKT QLQLEHLRRD LEMILNGINN YKNPKLTRML TFKFYMPKKA TELKHLQCLE EELKPLEEVL NLAQSKNFHF EPRDVVSNIN VFVLELKGSE TTFMCEYADE TATIVEFLNR WITFSQSIIS TLT | 88 | 193 |
| 88 | PTSSSTKKT QLQLEHLLLD LQMILNGINN YKNPKLTRML TFKFYMPKKA TELKHLQCLE DELKPLEEVL NLAQSKNFHF EPRDVVSNIN VFVLELKGSE TTFMCEYADE TATIVEFLNR WITFSQSIIS TLT | 89 | 194 |
| 89 | PTSSSTKKT QLQLEHLLLD LQMILNGINN YKNPKLTAML TFKFYMPKKA TELKHLQCLE EELKPLEQVL NLAQSKNFHF EPRDVVSNIN VFVLELKGSE TTFMCEYADE TATIVEFLNR WITFSQSIIS TLT | 90 | 195 |
| 90 | PTSSSTKKT QLQLEHLLLD LQMILNGINN YKNPKLTRML TWKFYMPKKA TELKHLQCLE EELKPLEEVL NLAQSKNFHF EPRDVVSNIN VFVLELKGSE TTFMCEYADE TATIVEFLNR WITFSQSIIS TLT | 91 | 196 |
| 91 | PTSSSTKKT QLQLEHLLLD LQMILNGINN YKNPKLTRML TFKFYMPKKA TELKHLQCLE QELKPLEEVL NLAQSKNFHF EPRDVVSNIN VFVLELKGSE TTFMCEYADE TATIVEFLNR WITFSQSIIS TLT | 92 | 197 |
| 92 | PTSSSTKKT QLQLEHLLLD LQMILNGINN YKNPKLTRML TFKFYMPKKA TELKHLQCLE EELKPLEEVL NLAQSKNFHF EPRDVVSNIN TFVLELKGSE TTFMCEYADE TATIVEFLNR WITFSQSIIS TLT | 93 | 198 |
| 93 | PTSSSTKKT QLQLEHLLLD LQMILNGINN YKNPKLTRML TFKFYMPKKA TELKHLQCLE EELKPLEEVL NLAQSKNFHF EPREVVSNIN TFVLELKGSE TTFMCEYADE TATIVEFLNR WITFSQSIIS TLT | 94 | 199 |
| 94 | PTSSSTKKT QLQLEHLLLD LQMILNGINN YKNPKLTRML TFKFYMPKKA TELKHLQCLE EELKPLEEVL NLAQSKNFHF EPRDVVSNIN VFVFEFKGSE TTFMCEYADE TATIVEFLNR WITFSQSIIS TLT | 95 | \|200 |
| 95 | PTSSSTKKT QLQLEHLLLD LQMILNGINN YKNPKLTRML TFKFYMPKKA TELKHLQCLE EELKPLEEGL NLAQSKNFHF EPRDVVSNIN VFVLELKGSE TTFMCEYADE TATIVEFLNR WITFSQSIIS TLT | 96 | 201 |
| 96 | PTSSSTKKT QLQLEHLLLD LQMILNGINN YKNPKLTRML TFKFYMPKKA TELKHLQCLE EELKPLEEGL NLAASKNFHF EPRDVVSNIN VFVLELKGSE TTFMCEYADE TATIVEFLNR WITFSQSIIS TLT | 97 | 202 |
| 97 | PTSSSTKKT QLQLEHLLLD LQMILNGINN YKNPKLTAML TFKFYMPKKA TELKHLQCLE EELKPLEEVL NLAQSKNFHF DPRDLISNIN VFVLELKGSE TTFMCEYADE TATIVEFLNR WITFSQSIIS TLT | 98 | 203 |
| 98 | PTSSSTKKT QLQLEHLLLD LQMILNGINN YKNPKLTAML TFKFYMPKKA TELKHLQCLE EELKPLEEVL NLAQSKNFHF EPRDVISNIN VFVLELKGSE TTFMCEYADE TATIVEFLNR WITFSQSIIS TLT | 99 | 204 |
| 99 | PTSSSTKKT QLQLEHLLLD LQMILNGINN YKNPKLTAML TFKFYMPKKA TELKHLQCLE EELKPLEEVL NLAQSKNFHF EPRDLVSNIN VFVLELKGSE TTFMCEYADE TATIVEFLNR WITFSQSIIS TLT | 100 | 205 |
| 100 | PTSSSTKKT QLQLEHLLLD LQMILNGINN YKNPKLTRML TFKFYMPKKA TELKHLQCLE EELKPLEEVL NLAQSKNFHF EPRDYVSNIN VFVLELKGSE TTFMCEYADE TATIVEFLNR WITFSQSIIS TLT | 101 | 206 |
| 101 | PTSSSTKKT QLQLEHLLLD LQMILNGINN YKNPKLTRML TFKFYMPKKA TELKHLQCLE EELKPLEEVL NLAQSKNFHF EPRDLASNIN VFVLELKGSE TTFMCEYADE TATIVEFLNR WITFSQSIIS TLT | 102 | 207 |
| 102 | PTSSSTKKT QLQLEHLLLD LQMILNGINN YKNPKLTRML TFKFYMPKKA TELKHLQCLE EELKPLEEVL NLAQSKNFHF EPRDVVSNIN VIVLELKGSE TTFMCEYADE TATIVEFLNR WITFSQSIIS TLT | 103 | 208 |
| 103 | PTSSSTKKT QLQLEHLRLD LEMILNGINN YKNPKLTAML TFKFYMPKKA TELKHLQCLE EELKPLEEVL NLAQSKNFHF EPRDVVSNIN VFVLELKGSE TTFMCEYADE TATIVEFLNR WITFSQSIIS TLT | 104 | 209 |

TABLE 2-continued

Sequences of Interleukin-2 Analogs

| Analog | Protein Sequence | SEQ ID NO: of Proteins | SEQ ID NO: of Nucleotides |
|--------|------------------|------------------------|---------------------------|
| 104 | PTSSSTKKT QLQLEHLRLD LEMILNGINN YKNPKLTRML TFKFYMPKKA TELKHLQCLE DELKPLEEVL NLAQSKNFHF EPRDVVSNIN VFVLELKGSE TTFMCEYADE TATIVEFLNR WITFSQSIIS TLT | 105 | 210 |
| 105 | PTSSSTKKT QLQLEHLRLD LEMILNGINN YKNPKLTRML TFKFYMPKKA TELKHLQCLE EELKPLEDVL NLAQSKNFHF EPRDVVSNIN VFVLELKGSE TTFMCEYADE TATIVEFLNR WITFSQSIIS TLT | 106 | 211 |

Example 2: Expression of Interleukin-2 Analogs

A recombinant interleukin-2 analog under the control of T7 promoter was expressed using the expression vectors prepared in Example 1. An expression *E. coli* strain, *E. coli* BL21DE3 (*E. coli* B F⁻dcm ompT hsdS(r_B⁻m_B⁻) gal λ(DE3); Novagen), was transformed with each recombinant interleukin-2 analog expression vector. As for the transformation method, a method recommended by Novagen was used. Each single colony, in which each recombinant expression vector was transformed, was collected, inoculated into a 2× Luria Broth medium containing ampicillin (50 μg/mL), and cultured at 37° C. for 15 hours. Each recombinant strain culture solution and the 2× LB medium containing 30% glycerol were mixed at a 1:1 (v/v) ratio, and each 1 mL of the mixture was dispensed into a cryo-tube, and stored at −150° C. This was used as a cell stock for the production of a recombinant protein.

For the expression of each recombinant interleukin-2 analog, one vial of each cell stock was dissolved, inoculated into 500 mL of 2× LB, and cultured with shaking at 37° C. for 14 to 16 hours. When the absorbance value at 600 nm reached 4.0 or higher, the culture was terminated, and this was used as a seed culture solution. The seed culture was inoculated into 1.6 L of a fermentation medium, and initial fermentation was started Using a 5 L fermentor (Bioflo-320, NBS, USA). Culture conditions were maintained at a pH of 6.70 using a temperature of 37° C., an air volume of 2.0 L/min (1 vvm), a stirring speed of 650 rpm, and 30% aqueous ammonia. As for the fermentation process, when nutrients in the culture medium were limited, fed-batch culture was performed by adding an additional medium (feeding solution). The growth of the strain was observed by absorbance, and a final concentration of 500 μM IPTG was introduced at an absorbance value of 70 or higher. The culture was performed further until for about 23 to 25 hours after the introduction of IPTG, and after termination of the culture, and the recombinant strain was recovered using a centrifuge and stored at −80° C. until use.

Example 3: Extraction and Refolding of Interleukin-2 Analogs

In order to convert the interleukin-2 analogs from the interleukin-2 analog expressing *E. coli* obtained in Example 2 in a soluble form, cells were disrupted and refolded. Cell pellets corresponding to 100 mL of the culture were suspended in 1-200 mL of a lysis buffer solution (20 mM Tris-HCl (pH 9.0), 1 mM EDTA (pH 9.0), 0.2 M NaCl, 0.5% Triton X-100), and the recombinant *E. coli* cells were disrupted at 15,000 psi using a microfluidizer. After centrifugation at 13,900 g for 30 minutes, the supernatant was discarded, and the pellet was washed with 400 mL of a first washing buffer solution (50 mM Tris-HCl (pH 8.0), 5 mM EDTA (pH 9.0)). After centrifugation under the same conditions as above, the supernatant was discarded, and the pellet was washed with 400 mL of a second washing buffer solution (50 mM Tris-HCl (pH 8.0), 5 mM EDTA (pH 9.0), 2% Triton X-100). After centrifugation under the same conditions as above, the supernatant was discarded, and the pellet was washed with 400 mL of a third washing buffer solution (50 mM Tris-HCl (pH 8.0), 5 mM EDTA (pH 9.0), 1% sodium deoxycholorate). After centrifugation under the same conditions as above, the supernatant was discarded, and the pellet was washed with 400 mL of a fourth washing buffer solution (50 mM Tris-HCl (pH 8.0), 5 mM EDTA (pH 9.0), 1 M NaCl). The resultant was subjected to centrifugation under the same conditions as above and washing, and *E. coli* inclusion bodies were obtained therefrom. The pellet of the washed inclusion bodies was resuspended in 400 mL of soluble/reducing buffer (6 M guanidine, 100 mM Tris (pH 8.0), 2 mM EDTA (pH 9.0), 50 mM DTT) and stirred at 50° C. for 30 minutes. To the soluble/reduced interleukin-2 analogs, 100 mL of distilled water was added to dilute the 6 M guanidine to 4.8 M guanidine, and then the resultant was centrifuged at 13,900 g for 30 minutes and the pellet discarded to obtain only the solution therein. To the diluted solution was additionally added 185.7 mL of distilled water, and the 4.8 M guanidine was diluted to 3.5 M guanidine, and the pH was adjusted to 5.0 using 100% acetic acid. The pH-adjusted solution was stirred at room temperature for one hour. The solution with precipitated impurities was centrifuged at 13,900 g for 30 minutes, and the supernatant was discarded and the pellet washed with a final washing buffer solution (3.5 M guanidine, 20 mM sodium acetate (pH 5.0), 5 mM DTT). The resultant was centrifuged under the same conditions as above to obtain a pellet. The washed interleukin-2 analogs were dissolved in 400 mL of a refolding buffer solution (6 mM guanidine, 100 mM Tris (pH 8.0), 0.1 mM CuCl₂). The refolding process was performed by stirring the mixed solution at 4° C. for 15 to 24 hours.

Example 4: Size-Exclusion Column Chromatography

The interleukin-2 analog refolding solution obtained in Example 3 was concentrated to less than 1 mL to be applied to a size-exclusion column for purification. The column was equilibrated with a buffer solution (2 M guanidine, 100 mM Tris (pH 8.0)) before introducing with the refolding solution and was eluted by flowing a buffer solution thereto after the introduction of the refolding solution. Since the eluted sample contained guanidine, it was replaced with a stabilized solution (10 mM sodium acetate (pH 4.5), 5% trehalose), and the purity was measured through RP-HPLC and peptide mapping analysis. The sample was used in the experiment when its measured purity reached 80% or higher.

Example 5: Evaluation of Binding Affinity of Interleukin-2 Analogs for Receptors In order to measure the binding affinity of the interleukin-2 analogs obtained in Example 4 for each of interleukin-2 alpha receptors and beta receptors, surface plasmon resonance measurement (BIACORE T200, GE Healthcare) was used. The binding affinity of the prepared analogs for the alpha receptors and beta receptors was measured, and the binding affinity of each of the prepared analogs was compared with that of an interleukin-2 analog 1 (aldesleukin).

First, an anti-human immunoglobulin antibody (Abcam, #ab97221) was immobilized to CM5 chips (GE Healthcare) by as much as about 5,000 RU (resonance unit) through amine coupling, and then, the immunoglobulin antibody was finally immobilized by allowing the interleukin-2 alpha receptors (SYMANSIS, #4102H) or interleukin-2 beta receptors (SYMANSIS, #4122H), to each of which a human immunoglobulin Fc region was bound, to bind to each immunoglobulin antibody using an antigen-antibody binding reaction. Thereafter, the recombinant interleukin-2 analog prepared above was diluted to HBS-P+ buffer (Cytiva, BR100671) using a two-fold serial dilution method at various concentrations and was flowed onto the CM5 chips, to which the interleukin-2 receptors were finally immobilized, to measure the binding affinity of each interleukin-2 receptor.

The measurement of binding affinity consisted of measurements of an association rate constant ($k_a$) and a dissociation rate constant ($k_d$), in which the binding rate was measured by flowing each interleukin-2 analog at a flow rate of 10 μL/min for 3 minutes while the dissociation rate was measured from each interleukin-2 receptor by flowing only the HBS-P+ buffer for the same period of time and at the same flow rate. After the measurement was completed, the binding affinity for the receptors was evaluated according to the 1:1 binding fitting model in the Biaevaluation program.

Relative Binding Affinity$(K_D)(\%)$=Binding Affinity of Analog 1(aldesleukin)$(K_D)$/Binding Affinity of Analog$(K_D)$×100

In Table 3 below, the expression "cannot be defined" indicates that the corresponding physical quantity cannot be defined for the corresponding receptor because no binding to the receptor was observed in the surface plasmon resonance measurement.

TABLE 3

Relative Binding Affinity of Interleukin-2 Analogs for Interleukin-2 Alpha or Beta Receptors Compared to Analog 1 (Aldesleukin)

| Interleukin-2 Receptor | Test Material | Relative Binding Affinity (%) |
| --- | --- | --- |
| Alpha Receptor | analog 1 | 100.0 |
| | analog 9 | 74.5 |
| | analog 12 | cannot be defined |
| | analog 13 | 1.1 |
| | analog 15 | cannot be defined |
| | analog 16 | 0.2 |
| | analog 17 | 29.6 |
| | analog 19 | cannot be defined |
| | analog 20 | cannot be defined |
| | analog 21 | cannot be defined |

TABLE 3-continued

Relative Binding Affinity of Interleukin-2 Analogs for Interleukin-2 Alpha or Beta Receptors Compared to Analog 1 (Aldesleukin)

| Interleukin-2 Receptor | Test Material | Relative Binding Affinity (%) |
| --- | --- | --- |
| | analog 31 | 5.0 |
| | analog 34 | 9.4 |
| | analog 35 | 31.7 |
| | analog 41 | 121.3 |
| | analog 52 | cannot be defined |
| | analog 53 | cannot be defined |
| | analog 86 | 71.1 |
| | analog 88 | 101.5 |
| | analog 90 | 98.4 |
| | analog 91 | 7.9 |
| | analog 92 | 97.3 |
| | analog 93 | 92.8 |
| | analog 95 | 10.7 |
| | analog 96 | 14.9 |
| | analog 97 | 18.8 |
| | analog 98 | 7.7 |
| | analog 99 | 19.9 |
| | analog 100 | 29.1 |
| | analog 101 | 24.7 |
| | analog 102 | 151.4 |
| | analog 103 | 6.1 |
| | analog 104 | 122.4 |
| | analog 105 | 246.8 |
| Beta Receptor | analog 01 | 100.0 |
| | analog 09 | 337.4 |
| | analog 12 | 166.2 |
| | analog 13 | 148.6 |
| | analog 14 | 129.7 |
| | analog 15 | 98.1 |
| | analog 16 | 1261.8 |
| | analog 17 | 9.4 |
| | analog 18 | 35.3 |
| | analog 19 | 455.0 |
| | analog 20 | 156.5 |
| | analog 21 | 14,084.2 |
| | analog 24 | 37.9 |
| | analog 25 | 21.7 |
| | analog 31 | 235.7 |
| | analog 34 | 321.8 |
| | analog 35 | 232.7 |
| | analog 41 | 22,776.2 |
| | analog 52 | 3,821.1 |
| | analog 53 | 690.7 |
| | analog 55 | 3,025.7 |
| | analog 57 | 2,569.7 |
| | analog 58 | 7,771.2 |
| | analog 59 | 1,533.5 |
| | analog 61 | 1,039.1 |
| | analog 70 | 10,199.2 |
| | analog 71 | 17,083.8 |
| | analog 73 | 1,591.8 |
| | analog 74 | 8,153.4 |
| | analog 75 | 9,571.2 |
| | analog 76 | 1,040.4 |
| | analog 77 | 644.4 |
| | analog 84 | 710.7 |
| | analog 86 | 18,745.8 |
| | analog 88 | 13,856.6 |
| | analog 90 | 12,776.2 |
| | analog 91 | 7,361.9 |
| | analog 92 | 1,510.3 |
| | analog 93 | 696.8 |
| | analog 94 | 35.5 |
| | analog 95 | 17.1 |
| | analog 96 | 229.3 |
| | analog 97 | 3,019.4 |
| | analog 98 | 11,084.5 |
| | analog 99 | 1,509.1 |
| | analog 100 | 2,534.1 |
| | analog 101 | 113.1 |
| | analog 102 | 4,452.0 |
| | analog 103 | 13,100.0 |
| | analog 104 | 25,439.8 |
| | analog 105 | 26,837.8 |

As explicitly shown in the test results (FIGS. 1 and 2 and Table 3), it was confirmed that the interleukin-2 analogs of the present invention had no binding affinity, reduced/increased binding affinity for interleukin-2 alpha receptors compared to the interleukin-2 analog 1, etc., thus showing an altered binding affinity for interleukin-2 alpha receptors compared to native interleukin-2 or aldesleukin. In contrast, as for the interleukin-2 beta receptors, the interleukin-2 analogs of the present invention showed a stronger binding affinity of up to 100-fold compared to native interleukin-2 or aldesleukin. From the above results, it was confirmed that the amino acid sequence of the interleukin-2 analog has an effect on its binding to the interleukin-2 alpha or beta receptors. These results suggest that the binding affinity for interleukin-2 receptors can be altered by substituting an amino acid at a specific position.

These experimental results suggest that the interleukin-2 analogs according to the present invention have altered binding affinity for interleukin-2 alpha receptors and interleukin-2 beta receptors and thus can be used in the development of various drugs based on the same.

Example 6: Coupling Reaction of Interleukin-2 Analog and Polyethylene Glycol (3.4K PEG) Linker and Purification of Interleukin-2 Analog Linked Material In order to prepare a long-acting conjugate in which the interleukin-2 analog obtained in Example 4 was bound to the immunoglobulin Fc region, a linked material in which the interleukin-2 analog was linked to one end of a polyethylene glycol (PEG) linker was first prepared. Interleukin-2 analogs 21, 41, 52, 86, 104 and 105 were used for the preparation of the linked material, and as the PEG linker, polyethylene glycol (ALD(2)3.4K PEG manufactured by NOF, Japan) with a molecular weight of 3.4 kDa and in which hydroxy hydrogens at both ends were modified with propylaldehyde groups were conjugated to the N-terminus of the interleukin-2 analogs. The molar ratio of an interleukin-2 analog: PEG linker was 1:15 to 1:20, and they were reacted at 2° C. to 10° C. for 1 hour while the concentration of the interleukin-2 analogs was 1 mg/mL or less. Herein, the reaction was carried out under 100 mM potassium phosphate (pH 5.5), and 20 mM sodium cyanoborohydride (SCB) was added as a reducing agent. After changing the reaction solution to 20 mM triethylamine (pH 8.0) buffer using a desalting column, an interleukin-2 analog-3.4K PEG linked material was obtained by purification via Fractogel® EMD TMAE (S) (Merck Millipore) or Source 15Q (Cytiva) column using the concentration gradients of triethylamine (pH 8.0) and sodium chloride.

Example 7: Preparation of Long-Acting Conjugate of Interleukin-2 Analog-3.4K PEG-Immunoglobulin Fc Region In order to prepare a long-acting conjugate of an interleukin-2 analog-3.4K PEG-immunoglobulin Fc region, the mole ratio of the interleukin-2 analog-3.4K PEG linked material obtained using the method of Example 6 and the immunoglobulin Fc region (SEQ ID NO: 438) was set to 1:10, and the total protein concentration was set to 30 mg/mL to carry out the reaction at 2° C. to 10° C. for 15 to 16 hours. Herein, 100 mM potassium phosphate (pH 6.0) was used as a reaction solution, and 20 mM sodium cyanoborohydride was added as a reducing agent. In the immunoglobulin region used at this time, two monomers having the amino acid sequence of SEQ ID NO: 423 (consisting of 221 amino acids) form a homodimer through a disulfide bond between cysteine, which is the 3rd amino acid of each monomer, and the monomers of the homodimer each independently form an internal disulfide bond between cysteines at positions 35 and 95 and an internal disulfide bond between cysteines at positions 141 and 199, respectively.

TABLE 4

| Protein Sequences of Immunoglobulin Fc | | |
|---|---|---|
| Name | Protein Sequence | SEQ ID NO: |
| Immuno- globulin Fc | PSCPAPEFLG GPSVFLFPPK PKDTLMISRT PEVTCVVVDV SQEDPEVQFN WYVDGVEVHN AKTKPREEQF NSTYRVVSVL TVLHQDWLNG KEYKCKVSNK GLPSSIEKTI SKAKGQPREP QVYTLPPSQE EMTKNQVSLT CLVKGFYPSD IAVEWESNGQ PENNYKTTPP VLDSDGSFFL YSRLTVDKSR WQEGNVFSCS VMHEALHNHY TQKSLSLSLG K | 438 |

Figure 2:
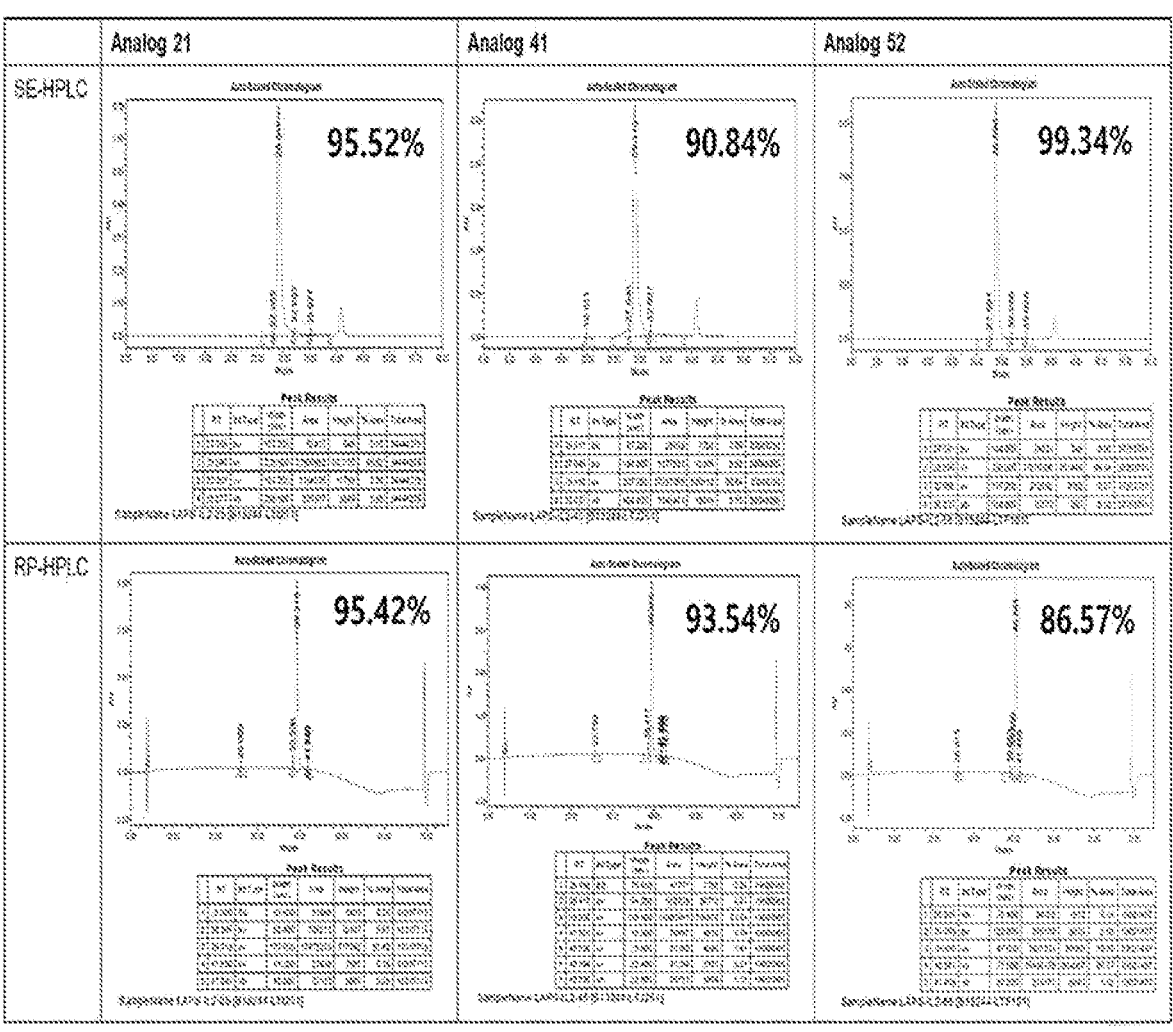
FIG. 2 is the result of analyzing purity of the long-acting conjugate of interleukin-2 analogs (analogs 21, 41, and 52).

After the reaction was completed, the unreacted immunoglobulin Fc region was removed from the reaction solution by Butyl FF (Cytiva) using Bis-Tris (pH 6.5) and sodium chloride, and the reaction solution was purified using sodium citrate buffer (pH 5.5) and ammonium sulfate by Source 15ISO (Cytiva) to obtain an interleukin-2 analog-3.4K PEG-immunoglobulin Fc region conjugate (long-acting conjugate) in which the N-terminus of the interleukin-2 analog is linked to one end of a 3.4 kDa PEG linker, and the opposite end of the 3.4 kDa PEG linker is linked to the nitrogen of the N-terminal proline of the Fc region. The long-acting conjugate was analyzed by SDS-PAGE, RP-HPLC, SE-HPLC (FIGS. 1 and 2).

Example 8: Evaluation of Interleukin-2 Receptor Binding Affinity of Interleukin-2 Analog Conjugates Surface plasma resonance (SPR, BIACORE T200, GE Healthcare) was used to measure the respective receptor binding affinity of the interleukin-2 analog long-acting conjugate obtained in Example 7 and the interleukin-2 alpha and beta receptors.

Specifically, biotin-labeled human interleukin-2 receptor alpha and beta subunits (ACROBiosystems) were each immobilized to a streptavidin biosensor chip (SA chip, Cytiva) at about 100 RU and 500 RU, and interleukin-2 analog long-acting conjugates diluted in HBS-EP+ buffer (Cytiva, BR100669) using a two-fold dilution method or aldesleukin were flowed at a flow rate of 20 μL/min. After the binding process for 3 minutes, only HBS-EP+ buffer was flowed for 3 minutes at the same flow rate to induce dissociation of the interleukin-2 analog long-acting conjugate or aldesleukin from the interleukin-2 receptors, and the binding affinity was calculated through the obtained association constant and dissociation constant. The binding affinity for the receptors was evaluated according to the 1:1 binding fitting model in the Biaevaluation program. Intrinsic interleukin-2 receptor binding affinity of the evaluated interleukin-2 analog conjugates was confirmed, and in particular, a clear difference in binding affinity between each candidate substance was confirmed in the interleukin-2 receptor alpha subunit. With reference to the results in detail, the interleukin-2 analog conjugates 21 and 52 did not bind to the interleukin-2 receptor alpha subunit, and the interleukin analog conjugates 41, 86, 104, and 105 showed a relative binding affinity of 50.8%, 65.2%, 81.0%, and 112.9% compared to aldesleukin. In the case of the interleukin-2 receptor beta subunit, higher binding affinity was confirmed compared to aldesleukin in all interleukin-2 analog conjugates including interleukin-2 analog conjugates 21 and 52.

Table 5 below summarizes the relative binding affinity (%) of the interleukin-2 analog long-acting conjugates prepared for each alpha and beta receptor compared with the binding affinity of aldesleukin. In Table 5, the corresponding long-acting conjugate is indicated by the number of the interleukin-2 analog constituting the same (e.g., the long-acting conjugate of an interleukin-2 analog 21 is indicated as "interleukin-2 analog conjugate 21").

TABLE 5

Figure 3A:
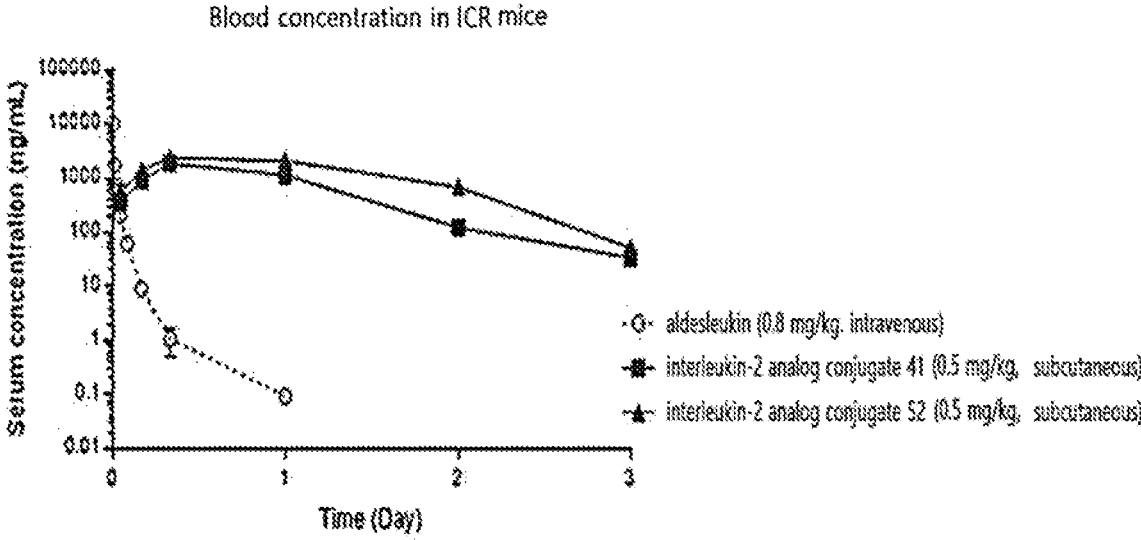
FIG. 3A and FIG. 3B show the results of analyzing the pharmacokinetics of the long-acting conjugate of interleukin-2 analogs in ICR and C57BL/6 mice. A is the results of analyzing the pharmacokinetics of an interleukin-2 analog conjugate 41 and interleukin-2 analog conjugate 52 in ICR mice, and B is the results of analyzing the pharmacokinetics of an interleukin-2 analog conjugate 21, interleukin-2 analog conjugate 86, interleukin-2 analog conjugate 104, and interleukin-2 analog conjugate 105 in C57BL/6 mice.
Figure 3B:
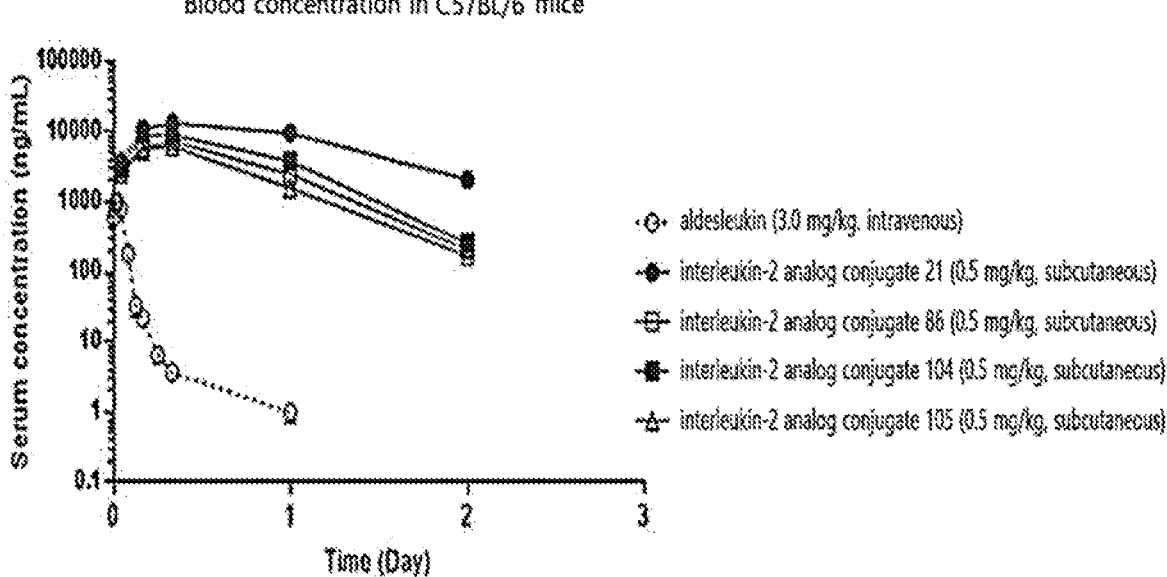

| Interleukin-2 Receptor Binding Affinity of Interleukin-2 Analog Conjugates | | |
|---|---|---|
| Material for Evaluation | Interleukin-2 Receptor Alpha Subunit Relative Binding Affinity (%) | Interleukin-2 Receptor Beta Subunit Relative Binding Affinity (%) |
| Aldesleukin | 100.0 | 100.0 |
| Interleukin-2 analog conjugate 21 | — | 5,426.6 |
| Interleukin-2 analog conjugate 41 | 50.8 | 5,483.0 |
| Interleukin-2 analog conjugate 52 | — | 2,271.8 |
| Interleukin-2 analog conjugate 86 | 65.2 | 15,393.1 |
| Interleukin-2 analog conjugate 104 | 81.0 | 13,423.5 |
| Interleukin-2 analog conjugate 105 | 112.9 | 13,293.8 | leukin-2 analog conjugate 105) were subcutaneously, intravenously, or intraperitoneally injected into normal mice. In the group in which the interleukin-2 analog conjugates were subcutaneously injected, blood was drawn from 3 animals via retro-orbital blood collection after 1, 4, 8, 24, 48, 72, and 96 hours, and in the group to which aldesleukin was administered by intravenous or intraperitoneal route, blood was drawn in the same manner from 3 animals at 0.08, 0.25, 0.5, 1, 1.5, 2, 3, 4, 6, 8, and 24 hours. Blood drawn from each group was centrifuged and separated into serum, and interleukin-2 analog conjugates and aldesleukin in the blood were quantified by ELISA using a human interleukin-2 antibody. As a result, the interleukin-2 analog conjugates exhibited higher blood exposure levels in normal mice of ICR and C57BL/6 lineage compared to aldesleukin (FIG. 3A and FIG. 3B, Tables 6 and 7). In the dose, AUC, and concentration values of the conjugates shown in the table below, the amount of conjugate (mg, ng) was expressed based on only the weight occupied by the interleukin-2 analog region among the entire conjugate.

TABLE 6

| Pharmacokinetics of Interleukin-2 Analog Conjugates in ICR Mice | | | |
|---|---|---|---|
| | Aldesleukin | Interleukin-2 analog conjugate 41 | Interleukin-2 analog conjugate 52 |
| Administration dose and route | 0.8 mg/kg (intravenous injection) | 0.5 mg/kg (subcutaneous injection) | 0.5 mg/kg (subcutaneous injection) |
| AUC (ng/mL × hr) | 2,463.8 | 43,511.2 | 82,579.4 |
| $C_0$ or $C_{max}$ (ng/mL) | 20,183.2 | 1,887.9 | 2,370.5 |
| $T_{1/2}$ (hr) | 1.4 | 8.5 | 9.0 |

TABLE 7

| Pharmacokinetics of Interleukin-2 Analog Conjugates in C57BL/6 Mice | | | | | |
|---|---|---|---|---|---|
| | Aldesleukin | Interleukin-2 analog conjugate 21 | Interleukin-2 analog conjugate 86 | Interleukin-2 analog conjugate 104 | Interleukin-2 analog conjugate 105 |
| Administration dose and route | 3.0 mg/kg (intraperitoneal injection) | 0.5 mg/kg (subcutaneous injection) | 0.5 mg/kg (subcutaneous injection) | 0.5 mg/kg (subcutaneous injection) | 0.5 mg/kg (subcutaneous injection) |
| AUC (ng/mL × hr) | 1,458.2 | 375,794.2 | 136,373.5 | 186,068.4 | 107,487.6 |
| $C_0$ or $C_{max}$ (ng/mL) | 1,018.6 | 13,319.0 | 7,371.1 | 9,288.3 | 6302.1 |

Example 9: Pharmacokinetic Evaluation of Interleukin-2 Analog Long-Acting Conjugates It was confirmed whether medicaments using the interleukin-2 analogs and the long-acting conjugate had excellent blood exposure and bioavailability based on the interleukin-2 analogs confirmed in Examples 5 and 7, and the binding ability of the long-acting conjugates including the same for the interleukin-2 receptors.

Specifically, the present inventors compared and analyzed the pharmacokinetics of an interleukin-2 analog long-acting conjugates and aldesleukin in ICR and C57BL/6 lineage normal mouse models.

More specifically, the control group administered with aldesleukin and the experimental group administered with the interleukin-2 analog conjugates (interleukin-2 analog conjugate 21, interleukin-2 analog conjugate 41, interleukin-2 analog conjugate 52, interleukin-2 analog conjugate 86, interleukin-2 analog conjugate 104, and inter- As can be seen from the above results, the interleukin-2 analog conjugates according to the present invention exhibited a higher blood distribution compared to aldesleukin through intravenous or intraperitoneal injection, despite being administered by the subcutaneous route. These results suggest that when the drug is administered, a larger amount of the interleukin-2 analog conjugate is exposed to the blood even when a smaller amount is administered compared to human recombinant interleukin-2, and that the convenience of administration can be secured.

Example 10: Evaluation of Anticancer Efficacy of Interleukin-2 Analog Long-Acting Conjugates In order to investigate the therapeutic efficacy of the interleukin-2 analog conjugates, tumor size and individual mortality were evaluated after each administration of interleukin-2 analog conjugate 21, interleukin-2 analog conjugate 41 and the interleukin-2 analog 52, and aldesleukin as a control material into CT26 colon tumor syngeneic mouse model.

Specifically, CT26 cells (ATCC) cultured in a cell culture flask were subcutaneously injected into the legs of BALB/c mice, and after a few days, when tumors were observed with the naked eye, 7 mice were assigned to each group so that the tumors were similar in size. To each group, 0.5 mg/kg of an interleukin-2 analog conjugate 21, interleukin-2 analog conjugate 41, and interleukin-2 analog conjugate 52 were repeatedly administered by subcutaneous route once a week for a total of two times. Herein, the dosage of the long-acting conjugate represents the weight of only the interleukin-2 analog region among the corresponding conjugate. In the aldesleukin administration group, 3.0 mg/kg of proleukin (Novartis) was administered once a day by the intraperito-neal route for 5 consecutive days, and after a 2-day rest, additional administration was performed for 5 days according to the same schedule.

Figure 4:
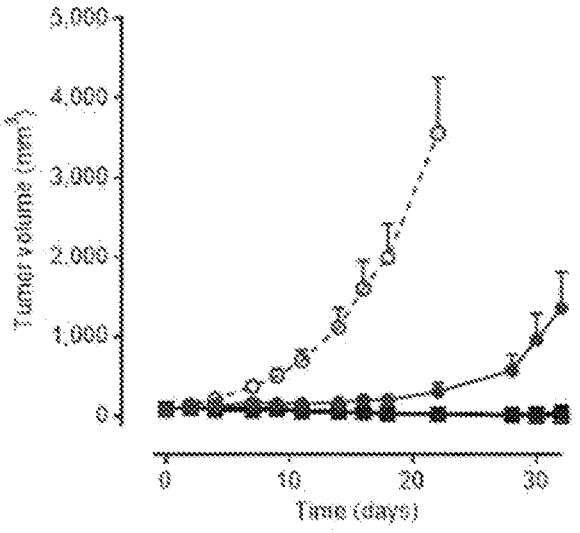
FIG. 4 shows the results of confirming the anticancer effect in an animal model of an interleukin-2 analog conjugate 21, interleukin-2 analog conjugate 41, and interleukin-2 analog conjugate 52 in mice.

Body weight and individual death were observed for 32 days from the first administration date, and based on the results, excellent anticancer efficacy was confirmed in all the interleukin-2 analog conjugate administration groups. In particular, complete remission was observed in all individu-als in the group administered with interleukin-2 analog conjugate 41. In contrast, in the group administered with aldesleukin, 2 out of 7 mice died, and only 2 mice showed complete remission. It is interpreted that the interleukin-2 analog conjugate according to the present invention strongly binds to the human interleukin-2 receptor beta subunit by altering the amino acid sequence, thereby exhibiting excel-lent anticancer effect (FIG. 4). In addition, the long-acting conjugate structure to which the human immunoglobulin Fc region is linked enables high blood exposure to increase the dosing interval, thereby suggesting that it is possible to provide administration convenience to patients and medical staff by converting the conventional injection therapy to a subcutaneous route.

Example 11: Evaluation of Memory T Cell Responses According to Repeated Exposure of Tumors Following the anticancer efficacy evaluation of Example 10, the response of memory T cells according to repeated exposure of tumors was evaluated. Specifically, for the individuals whose complete remission was confirmed after the anticancer efficacy evaluation was completed, CT26 cells were administered subcutaneously in the same manner as the first exposure, on 42 and 70 days after the first drug administration, and subjected to re-exposure to observe the tumor growth. At 4 and 7 days after the second re-exposure, the number of memory T cells from the mouse spleen was analyzed using a FACS Canto II (Becton Dickinson) device.

Figure 5A:
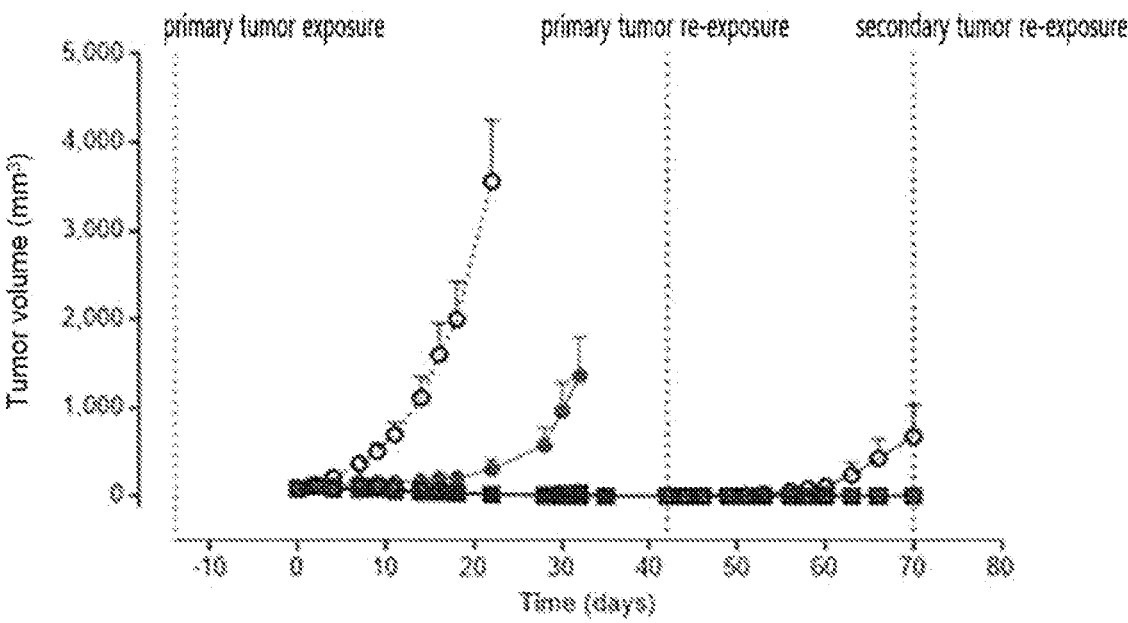
FIGS. 5A and 5B are the result confirming the memory T cell change in an animal model of the long-acting conjugate of interleukin-2 analogs. A shows the tumor growth inhibitory effect of an interleukin-2 analog conjugate 21, interleukin-2 analog conjugate 41, and interleukin-2 analog conjugate 52, and B is the result of analyzing the number of memory T cells of an interleukin-2 analog conjugate 21, interleukin-2 analog conjugate 41, and interleukin-2 analog conjugate 52.
Figure 5B:
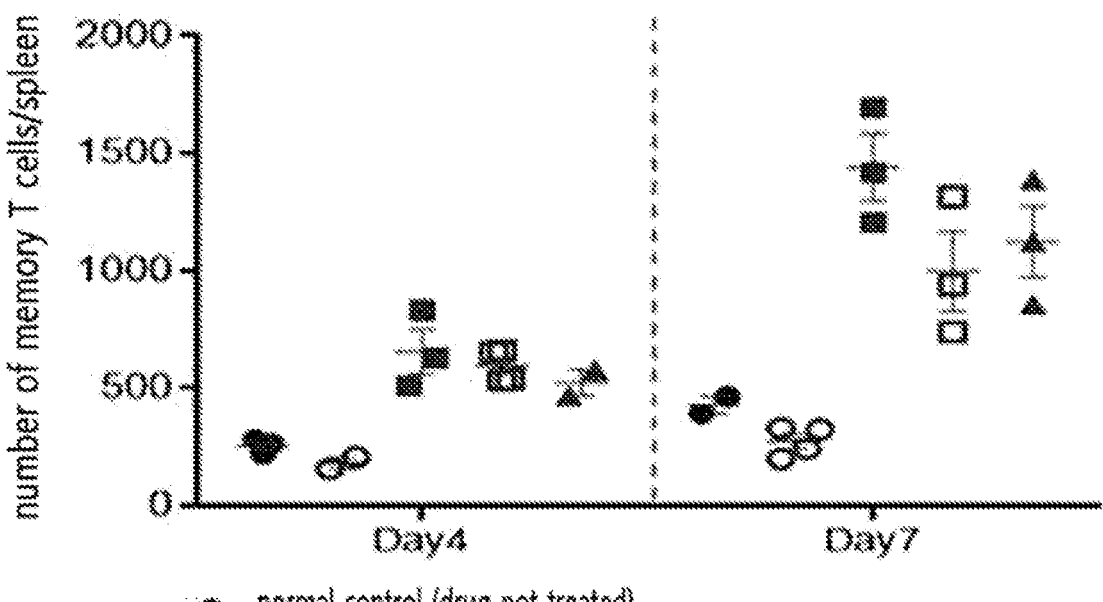

As a result, in all drug administration groups except for the negative control group, tumor growth was suppressed according to re-exposure, and a significant increase in memory T cells was observed in the spleen (FIGS. 5A and 5B). In conclusion, the interleukin-2 analog conjugates according to the present invention induced a memory immune response in the CT26 colon tumor syngeneic mouse model with only a single agent, and thus strong anticancer efficacy was maintained not only in the first tumor exposure but also in the re-exposure of the tumor.

Example 12: Evaluation of Anticancer Efficacy of Interleukin-2 Analog Long-Acting Conjugate in Malignant Melanoma In order to evaluate the anticancer efficacy of the inter-leukin-2 analog conjugate according to the present inven-tion, interleukin-2 analog conjugate 86 and aldesleukin as a control material were each administered to B16F10 mela-noma tumor syngeneic mouse model to evaluate the tumor size and individual survival rate.

Specifically, B16F10 cells (ATCC) cultured in a cell culture flask were subcutaneously injected into the thigh of C57BL/6 mice, and when tumors were observed with the naked eye a few days later, 9 mice were assigned to each group so that the tumors were similar in size. Among the long-acting conjugates, based on the weight of the inter-leukin-2 analog region, 0.08 mg/kg to 10 mg/kg of inter-leukin-2 analog conjugate 86 was each administered subcu-taneously, once a week, for a total of 4 repeated times. In addition, in the aldesleukin administration group as a control group, 3.0 mg/kg of proleukin (Novartis) was administered once a day by intraperitoneal route for 5 consecutive days, followed by a 2-day rest period, and the administration was repeatedly performed for a total of 4 times.

On day 15 from the first dosing day, the tumor size of each group (FIG. 6A) and the survival rate of each individual for 60 days (FIG. 6B) were observed. As a result, it was confirmed that the group administered with interleukin-2 analog conjugate 86 of the present invention had a smaller tumor size and improved individual survival rate compared to the group administered with aldesleukin, and the dose-dependent anticancer efficacy of the long-acting conjugate of the present invention was confirmed. In particular, in the group administered with interleukin-2 analog conjugate 86 at 4.0 mg/kg or more per week, complete remission with complete tumor removal was observed in some individuals. In contrast, in the group in which aldesleukin was admin-istered at 3.0 mg/kg consecutively for 5 days, no complete remission was found in any individual.

This means that the interleukin-2 analog conjugates of the present invention were designed to have a characteristic of binding to the beta subunit of the human interleukin-2 receptor, which is relatively strong compared to aldesleukin, and thus can exhibit excellent anticancer effect. In addition, it effectively controls excessive immune response through binding to the alpha subunit of the human interleukin-2 receptor, which does not cause undesired side effects, so that no side effects were observed to the extent that the drug administration was discontinued even in the high-dosing group of 10 mg/kg or more based on the weight of the interleukin-2 analog region in the long-acting conjugates.

The experimental results described above show that the long-acting conjugate including the interleukin-2 analog in which an amino acid mutation was introduced into native interleukin-2 according to the present invention has altered binding affinity for the interleukin-2 alpha receptors and binding affinity for the interleukin-2 beta receptors, thereby suggesting that it can be used for the development of various drugs using the conjugate, particularly the development of anticancer drugs.

Based on the above description, it will be understood by those skilled in the art that the present disclosure may be implemented in a different specific form without changing the technical spirit or essential characteristics thereof. In this regard, it should be understood that the above embodiment is not limitative, but illustrative in all aspects. The scope of the disclosure is defined by the appended claims rather than by the description preceding them, and therefore all changes and modifications that fall within metes and bounds of the claims, or equivalents of such metes and bounds, are therefore intended to be embraced by the claims.

The invention claimed is:

1. A method for treating cancer, comprising administering to a human cancer patient in need thereof a pharmaceutical composition comprising a pharmaceutically effective amount of a long-acting conjugate and a pharmaceutically acceptable excipient, wherein the long-acting conjugate comprises an interleukin-2 analog, and is represented by Chemical Formula 1 below:

X—La—F            [Chemical Formula 1]

wherein, X is an interleukin-2 analog having an increased binding affinity for interleukin-2 beta receptors compared to aldesleukin under a same condition;

L is a polyethylene glycol linker;

a is 0 or a natural number, with the proviso that when a is 2 or more, each L is independent of each other;

F is an immunoglobulin Fc region in the form of a dimer; and

— indicates a covalent linkage between X and L and between L and F;

wherein the interleukin-2 analog comprises the amino acid sequence of SEQ ID NO: 87, wherein the cancer is selected from the group consisting of metastatic renal cell cancer, metastatic melanoma, colorectal cancer, pancreatic cancer, kidney cancer, lung cancer, melanoma, and breast cancer.

2. The method of claim 1, wherein the pharmaceutical composition exhibits one or more of the following properties:

(i) high blood exposure relative to aldesleukin;

(ii) high tumor growth inhibitory activity compared to aldesleukin, (iii) high memory T cell-generating response compared to aldesleukin; wherein the pharmaceutical composition is administered via an intraperitoneal, intravenous, intramuscular, subcutaneous, intradermal, oral, topical, intranasal, intrapulmonary, or intrarectal route; or wherein the pharmaceutical composition is administered at a time interval ranging from 1 week to 1 month.

3. The method of claim 1, wherein the polyethylene glycol linker has a molecular weight of 2 kDa to 30 kDa.

4. The method of claim 1, wherein the immunoglobulin Fc region is those derived from IgG, IgA, IgD, IgE, IgM, or a combination thereof, or a hybrid thereof;

wherein the immunoglobulin Fc region is an IgG4 Fc region;

wherein the immunoglobulin Fc region is non-glycosylated;

wherein the L contains ethylene glycol repeating units, and the formula weight of the ethylene glycol repeating unit moiety is in the range of 1 kDa to 100 kDa; or wherein the long-acting conjugate is a long-acting conjugate in which one molecule of X is covalently linked to one of the Fc regions of the dimeric immunoglobulin Fc region via the polyethylene glycol linker.

5. The method of claim 3, wherein the immunoglobulin Fc region is an immunoglobulin Fc region of IgG, IgA, IgD, IgE, IgM, or a combination thereof, or a hybrid thereof; or wherein the immunoglobulin Fc region is non-glycosylated.

6. The method of claim 5, wherein the immunoglobulin Fc region is an IgG4 Fc region.

7. A method for treating cancer, comprising administering to a human cancer patient in need thereof a pharmaceutical composition comprising a pharmaceutically effective amount of a long-acting conjugate and a pharmaceutically acceptable excipient, wherein the long-acting conjugate comprises an interleukin-2 analog, and is represented by Chemical Formula 1 below:

X—La—F          [Chemical Formula 1]

wherein, X is an interleukin-2 analog having an increased binding affinity for interleukin-2 beta receptors compared to aldesleukin under a same condition;

L is a polyethylene glycol linker;

a is 0 or a natural number, with the proviso that when a is 2 or more, each L is independent of each other;

F is an immunoglobulin Fc region in the form of a dimer; and

— indicates a covalent linkage between X and L and between L and F;

wherein the interleukin-2 analog comprises the amino acid sequence selected from the group consisting of SEQ ID NO: 22, 42, and 53, wherein the cancer is selected from the group consisting of metastatic renal cell cancer, metastatic melanoma, and colorectal cancer.

8. The method of claim 7, wherein the pharmaceutical composition exhibits one or more of the following properties:

(i) high blood exposure relative to aldesleukin;

(ii) high tumor growth inhibitory activity compared to aldesleukin, (iii) high memory T cell-generating response compared to aldesleukin; wherein the pharmaceutical composition is administered via an intraperitoneal, intravenous, intramuscular, subcutaneous, intradermal, oral, topical, intranasal, intrapulmonary, or intrarectal route; or wherein the pharmaceutical composition is administered at a time interval ranging from 1 week to 1 month.

9. The method of claim 7, wherein the polyethylene glycol linker has a molecular weight of 2 kDa to 30 kDa.

10. The method of claim 7, wherein the immunoglobulin Fc region is those derived from IgG, IgA, IgD, IgE, IgM, or a combination thereof, or a hybrid thereof;

wherein the immunoglobulin Fc region is an IgG4 Fc region;

wherein the immunoglobulin Fc region is non-glycosylated;

wherein the L contains ethylene glycol repeating units, and the formula weight of the ethylene glycol repeating unit moiety is in the range of 1 kDa to 100 kDa; or wherein the long-acting conjugate is a long-acting conjugate in which one molecule of X is covalently linked to one of the Fc regions of the dimeric immunoglobulin Fc region via the polyethylene glycol linker.

11. The method of claim 10, wherein the immunoglobulin Fc region is an immunoglobulin Fc region of IgG, IgA, IgD, IgE, IgM, or a combination thereof, or a hybrid thereof; or wherein the immunoglobulin Fc region is non-glycosylated.

12. The method of claim 11, wherein the immunoglobulin Fc region is an IgG4 Fc region.

\* \* \* \* \*

SEQUENCE LISTING

```
<160> NUMBER OF SEQ ID NOS: 439

<210> SEQ ID NO 1
<211> LENGTH: 133
<212> TYPE: PRT
<213> ORGANISM: homo sapiens

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 2
<211> LENGTH: 132
<212> TYPE: PRT
<213> ORGANISM: Artificial Sequence
<220> FEATURE:
<223> OTHER INFORMATION: IL-2 analog 1

<400> SEQUENCE: 2

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
            85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 3
```

```
<211> LENGTH: 132
<212> TYPE: PRT
<213> ORGANISM: Artificial Sequence
<220> FEATURE:
<223> OTHER INFORMATION: IL-2 analog 2

<400> SEQUENCE: 3

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Cys Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 4
<211> LENGTH: 132
<212> TYPE: PRT
<213> ORGANISM: Artificial Sequence
<220> FEATURE:
<223> OTHER INFORMATION: IL-2 analog 3

<400> SEQUENCE: 4

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Cys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 5
<211> LENGTH: 132
<212> TYPE: PRT
<213> ORGANISM: Artificial Sequence
<220> FEATURE:
<223> OTHER INFORMATION: IL-2 analog 4
```

<400> SEQUENCE: 5

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Cys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 6
<211> LENGTH: 132
<212> TYPE: PRT
<213> ORGANISM: Artificial Sequence
<220> FEATURE:
<223> OTHER INFORMATION: IL-2 analog 5

<400> SEQUENCE: 6

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Cys Phe Tyr Met Pro Lys Lys
        35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 7
<211> LENGTH: 132
<212> TYPE: PRT
<213> ORGANISM: Artificial Sequence
<220> FEATURE:
<223> OTHER INFORMATION: IL-2 analog 6

<400> SEQUENCE: 7

Pro Thr Ser Ser Ser Thr Lys Lys Thr Gln Leu Gln Leu Glu His Leu
1               5                   10                  15

```
Leu Leu Asp Leu Gln Met Ile Leu Asn Gly Ile Asn Asn Tyr Lys Asn
        20              25              30

Pro Lys Leu Thr Arg Met Leu Thr Phe Lys Phe Tyr Met Pro Cys Lys
        35              40              45

Ala Thr Glu Leu Lys His Leu Gln Cys Leu Glu Glu Glu Leu Lys Pro
    50              55              60

Leu Glu Glu Val Leu Asn Leu Ala Gln Ser Lys Asn Phe His Leu Arg
65              70              75              80

Pro Arg Asp Leu Ile Ser Asn Ile Asn Val Ile Val Leu Glu Leu Lys
                85              90              95

Gly Ser Glu Thr Thr Phe Met Cys Glu Tyr Ala Asp Glu Thr Ala Thr
            100             105             110

Ile Val Glu Phe Leu Asn Arg Trp Ile Thr Phe Ser Gln Ser Ile Ile
        115             120             125

Ser Thr Leu Thr
    130

<210> SEQ ID NO 8
<211> LENGTH: 132
<212> TYPE: PRT
<213> ORGANISM: Artificial Sequence
<220> FEATURE:
<223> OTHER INFORMATION: IL-2 analog 7

<400> SEQUENCE: 8

Pro Thr Ser Ser Ser Thr Lys Lys Thr Gln Leu Gln Leu Glu His Leu
1               5               10              15

Leu Leu Asp Leu Gln Met Ile Leu Asn Gly Ile Asn Asn Tyr Lys Asn
        20              25              30

Pro Lys Leu Thr Arg Met Leu Thr Phe Lys Phe Tyr Met Pro Lys Cys
        35              40              45

Ala Thr Glu Leu Lys His Leu Gln Cys Leu Glu Glu Glu Leu Lys Pro
    50              55              60

Leu Glu Glu Val Leu Asn Leu Ala Gln Ser Lys Asn Phe His Leu Arg
65              70              75              80

Pro Arg Asp Leu Ile Ser Asn Ile Asn Val Ile Val Leu Glu Leu Lys
                85              90              95

Gly Ser Glu Thr Thr Phe Met Cys Glu Tyr Ala Asp Glu Thr Ala Thr
            100             105             110

Ile Val Glu Phe Leu Asn Arg Trp Ile Thr Phe Ser Gln Ser Ile Ile
        115             120             125

Ser Thr Leu Thr
    130

<210> SEQ ID NO 9
<211> LENGTH: 132
<212> TYPE: PRT
<213> ORGANISM: Artificial Sequence
<220> FEATURE:
<223> OTHER INFORMATION: IL-2 analog 9

<400> SEQUENCE: 9

Pro Thr Ser Ser Ser Thr Lys Lys Thr Gln Leu Gln Leu Glu His Leu
1               5               10              15

Leu Leu Asp Leu Gln Met Ile Leu Asn Gly Ile Asn Asn Tyr Lys Asn
        20              25              30

Pro Lys Leu Thr Arg Met Leu Thr Phe Lys Phe Tyr Met Pro Lys Lys
```

```
            35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Cys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 10
<211> LENGTH: 132
<212> TYPE: PRT
<213> ORGANISM: Artificial Sequence
<220> FEATURE:
<223> OTHER INFORMATION: IL-2 analog 10

<400> SEQUENCE: 10

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Ala Met Leu Thr Phe Lys Phe Tyr Met Pro Lys Lys
            35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 11
<211> LENGTH: 132
<212> TYPE: PRT
<213> ORGANISM: Artificial Sequence
<220> FEATURE:
<223> OTHER INFORMATION: IL-2 analog 10

<400> SEQUENCE: 11

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Arg Met Leu Thr Lys Lys Phe Tyr Met Pro Lys Lys
            35                  40                  45

Ala Thr Glu Leu Lys His Leu Gln Cys Leu Glu Glu Glu Leu Lys Pro
    50                  55                  60
```

```
Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 12
<211> LENGTH: 132
<212> TYPE: PRT
<213> ORGANISM: Artificial Sequence
<220> FEATURE:
<223> OTHER INFORMATION: IL-2 analog 11

<400> SEQUENCE: 12

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Arg Met Leu Thr Ala Lys Phe Tyr Met Pro Lys Lys
            35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 13
<211> LENGTH: 132
<212> TYPE: PRT
<213> ORGANISM: Artificial Sequence
<220> FEATURE:
<223> OTHER INFORMATION: IL-2 analog 12

<400> SEQUENCE: 13

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Ala Met Leu Thr Lys Lys Phe Tyr Met Pro Lys Lys
            35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95
```

```
Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
        130

<210> SEQ ID NO 14
<211> LENGTH: 132
<212> TYPE: PRT
<213> ORGANISM: Artificial Sequence
<220> FEATURE:
<223> OTHER INFORMATION: IL-2 analog 13

<400> SEQUENCE: 14

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Ala Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
        130

<210> SEQ ID NO 15
<211> LENGTH: 132
<212> TYPE: PRT
<213> ORGANISM: Artificial Sequence
<220> FEATURE:
<223> OTHER INFORMATION: IL-2 analog 14

<400> SEQUENCE: 15

Pro Thr Ser Ser Ser Thr Lys Lys Thr Gln Leu Gln Leu Glu His Leu
1               5                   10                  15

Leu Tyr Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
```

-continued

```
               115                 120                 125

Ser Thr Leu Thr
    130

<210> SEQ ID NO 16
<211> LENGTH: 132
<212> TYPE: PRT
<213> ORGANISM: Artificial Sequence
<220> FEATURE:
<223> OTHER INFORMATION: IL-2 analog 15

<400> SEQUENCE: 16

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Glu Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 17
<211> LENGTH: 132
<212> TYPE: PRT
<213> ORGANISM: Artificial Sequence
<220> FEATURE:
<223> OTHER INFORMATION: IL-2 analog 16

<400> SEQUENCE: 17

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Gln Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

-continued

<210> SEQ ID NO 18
<211> LENGTH: 132
<212> TYPE: PRT
<213> ORGANISM: Artificial Sequence
<220> FEATURE:
<223> OTHER INFORMATION: IL-2 analog 17

<400> SEQUENCE: 18

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Thr Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 19
<211> LENGTH: 132
<212> TYPE: PRT
<213> ORGANISM: Artificial Sequence
<220> FEATURE:
<223> OTHER INFORMATION: IL-2 analog 18

<400> SEQUENCE: 19

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Gln Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 20
<211> LENGTH: 132
<212> TYPE: PRT
<213> ORGANISM: Artificial Sequence

```
<220> FEATURE:
<223> OTHER INFORMATION: IL-2 analog 19

<400> SEQUENCE: 20

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Asp
65                  70                  75                  80

Pro Arg Asp Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 21
<211> LENGTH: 132
<212> TYPE: PRT
<213> ORGANISM: Artificial Sequence
<220> FEATURE:
<223> OTHER INFORMATION: IL-2 analog 20

<400> SEQUENCE: 21

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 22
<211> LENGTH: 132
<212> TYPE: PRT
<213> ORGANISM: Artificial Sequence
<220> FEATURE:
<223> OTHER INFORMATION: IL-2 analog 21

<400> SEQUENCE: 22
```

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Asp
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130
```

<210> SEQ ID NO 23
<211> LENGTH: 132
<212> TYPE: PRT
<213> ORGANISM: Artificial Sequence
<220> FEATURE:
<223> OTHER INFORMATION: IL-2 analog 22

<400> SEQUENCE: 23

```
Pro Thr Ser Ser Ser Thr Lys Lys Thr Gln Val Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130
```

<210> SEQ ID NO 24
<211> LENGTH: 132
<212> TYPE: PRT
<213> ORGANISM: Artificial Sequence
<220> FEATURE:
<223> OTHER INFORMATION: IL-2 analog 23

<400> SEQUENCE: 24

```
Pro Thr Ser Ser Ser Thr Lys Lys Thr Gln Phe Gln Leu Glu His Leu
1               5                   10                  15

Leu Leu Asp Leu Gln Met Ile Leu Asn Gly Ile Asn Asn Tyr Lys Asn
            20                  25                  30
```

-continued

```
Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 25
<211> LENGTH: 132
<212> TYPE: PRT
<213> ORGANISM: Artificial Sequence
<220> FEATURE:
<223> OTHER INFORMATION: IL-2 analog 24

<400> SEQUENCE: 25

Pro Thr Ser Ser Ser Thr Lys Lys Thr Gln Leu Gln Leu Glu His Leu
1               5                   10                  15

Leu Val Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 26
<211> LENGTH: 132
<212> TYPE: PRT
<213> ORGANISM: Artificial Sequence
<220> FEATURE:
<223> OTHER INFORMATION: IL-2 analog 25

<400> SEQUENCE: 26

Pro Thr Ser Ser Ser Thr Lys Lys Thr Gln Leu Gln Leu Glu His Leu
1               5                   10                  15

Leu Phe Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
```

```
        50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 27
<211> LENGTH: 132
<212> TYPE: PRT
<213> ORGANISM: Artificial Sequence
<220> FEATURE:
<223> OTHER INFORMATION: IL-2 analog 26

<400> SEQUENCE: 27

Pro Thr Ser Ser Ser Thr Lys Lys Thr Gln Leu Gln Leu Glu His Leu
1                   5                   10                  15

Leu Leu Asp Leu Gln Met Ile Leu Asn Gly Ile Asn Asn Tyr Lys Asn
                20                  25                  30

Pro Lys Leu Thr Ala Met Leu Thr Lys Lys Phe Tyr Met Pro Lys Lys
            35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Leu Arg
65                  70                  75                  80

Pro Arg Asp Leu Ile Ser Asn Phe Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 28
<211> LENGTH: 132
<212> TYPE: PRT
<213> ORGANISM: Artificial Sequence
<220> FEATURE:
<223> OTHER INFORMATION: IL-2 analog 27

<400> SEQUENCE: 28

Pro Thr Ser Ser Ser Thr Lys Lys Thr Gln Leu Gln Leu Glu His Leu
1                   5                   10                  15

Leu Leu Asp Leu Gln Met Ile Leu Asn Gly Ile Asn Asn Tyr Lys Asn
                20                  25                  30

Pro Lys Leu Thr Ala Met Leu Thr Lys Lys Phe Tyr Met Pro Lys Lys
            35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Leu Arg
65                  70                  75                  80
```

```
Pro Arg Asp Leu Ile Ser Asn Ile Asn Phe Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 29
<211> LENGTH: 132
<212> TYPE: PRT
<213> ORGANISM: Artificial Sequence
<220> FEATURE:
<223> OTHER INFORMATION: IL-2 analog 28

<400> SEQUENCE: 29

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Val Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 30
<211> LENGTH: 132
<212> TYPE: PRT
<213> ORGANISM: Artificial Sequence
<220> FEATURE:
<223> OTHER INFORMATION: IL-2 analog 29

<400> SEQUENCE: 30

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110
```

Ile Val Glu Phe Leu Asn Arg Trp Ile Thr Phe Ser Thr Ser Ile Ile
        115                 120                 125

Ser Thr Leu Thr
    130

<210> SEQ ID NO 31
<211> LENGTH: 132
<212> TYPE: PRT
<213> ORGANISM: Artificial Sequence
<220> FEATURE:
<223> OTHER INFORMATION: IL-2 analog 30

<400> SEQUENCE: 31

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Asp
65                  70                  75                  80

Pro Arg Asp Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 32
<211> LENGTH: 132
<212> TYPE: PRT
<213> ORGANISM: Artificial Sequence
<220> FEATURE:
<223> OTHER INFORMATION: IL-2 analog 31

<400> SEQUENCE: 32

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Glu Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr

130

<210> SEQ ID NO 33
<211> LENGTH: 132
<212> TYPE: PRT
<213> ORGANISM: Artificial Sequence
<220> FEATURE:
<223> OTHER INFORMATION: IL-2 analog 32

<400> SEQUENCE: 33

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Asp
65                  70                  75                  80

Pro Arg Glu Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130
```

<210> SEQ ID NO 34
<211> LENGTH: 132
<212> TYPE: PRT
<213> ORGANISM: Artificial Sequence
<220> FEATURE:
<223> OTHER INFORMATION: IL-2 analog 33

<400> SEQUENCE: 34

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130
```

<210> SEQ ID NO 35
<211> LENGTH: 132

-continued

```
<212> TYPE: PRT
<213> ORGANISM: Artificial Sequence
<220> FEATURE:
<223> OTHER INFORMATION: IL-2 analog 34

<400> SEQUENCE: 35

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Arg
65                  70                  75                  80

Pro Arg Glu Leu Ile Ser Asn Ile Asn Val Ile Val Leu Glu Leu Lys
            85                  90                  95

Gly Ser Glu Thr Thr Phe Met Cys Glu Tyr Ala Asp Glu Thr Ala Thr
        100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 36
<211> LENGTH: 132
<212> TYPE: PRT
<213> ORGANISM: Artificial Sequence
<220> FEATURE:
<223> OTHER INFORMATION: IL-2 analog 35

<400> SEQUENCE: 36

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Phe Glu Phe Lys
            85                  90                  95

Gly Ser Glu Thr Thr Phe Met Cys Glu Tyr Ala Asp Glu Thr Ala Thr
        100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 37
<211> LENGTH: 132
<212> TYPE: PRT
<213> ORGANISM: Artificial Sequence
<220> FEATURE:
<223> OTHER INFORMATION: IL-2 analog 36
```

-continued

<400> SEQUENCE: 37

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Phe Glu Val Lys
            85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 38
<211> LENGTH: 132
<212> TYPE: PRT
<213> ORGANISM: Artificial Sequence
<220> FEATURE:
<223> OTHER INFORMATION: IL-2 analog 37

<400> SEQUENCE: 38

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Phe Glu Ile Lys
            85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 39
<211> LENGTH: 132
<212> TYPE: PRT
<213> ORGANISM: Artificial Sequence
<220> FEATURE:
<223> OTHER INFORMATION: IL-2 analog 38

<400> SEQUENCE: 39

Pro Thr Ser Ser Ser Thr Lys Lys Thr Gln Leu Gln Leu Glu His Leu
1               5                   10                  15

```
Leu Leu Asp Leu Gln Met Ile Leu Asn Gly Ile Asn Asn Tyr Lys Asn
        20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Leu Asp
65                  70                  75                  80

Pro Arg Asp Leu Ile Ser Asn Ile Asn Val Phe Val Phe Glu Phe Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

```
<210> SEQ ID NO 40
<211> LENGTH: 132
<212> TYPE: PRT
<213> ORGANISM: Artificial Sequence
<220> FEATURE:
<223> OTHER INFORMATION: IL-2 analog 39

<400> SEQUENCE: 40
```

```
Pro Thr Ser Ser Ser Thr Lys Lys Thr Gln Leu Gln Leu Glu His Leu
1                   5                   10                  15

Leu Leu Asp Leu Gln Met Ile Leu Asn Gly Ile Asn Asn Tyr Lys Asn
        20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Leu Asp
65                  70                  75                  80

Pro Arg Asp Leu Ile Ser Asn Ile Asn Val Phe Val Phe Glu Val Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

```
<210> SEQ ID NO 41
<211> LENGTH: 132
<212> TYPE: PRT
<213> ORGANISM: Artificial Sequence
<220> FEATURE:
<223> OTHER INFORMATION: IL-2 analog 40

<400> SEQUENCE: 41
```

```
Pro Thr Ser Ser Ser Thr Lys Lys Thr Gln Leu Gln Leu Glu His Leu
1                   5                   10                  15

Leu Leu Asp Leu Gln Met Ile Leu Asn Gly Ile Asn Asn Tyr Lys Asn
        20                  25                  30

Pro Lys Leu Thr Ala Met Leu Thr Lys Lys Phe Tyr Met Pro Lys Lys
        35                  40                  45
```

```
Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Asp
65                  70                  75                  80

Pro Arg Asp Leu Ile Ser Asn Ile Asn Val Phe Val Phe Glu Ile Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 42
<211> LENGTH: 132
<212> TYPE: PRT
<213> ORGANISM: Artificial Sequence
<220> FEATURE:
<223> OTHER INFORMATION: IL-2 analog 41

<400> SEQUENCE: 42

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Asp
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 43
<211> LENGTH: 132
<212> TYPE: PRT
<213> ORGANISM: Artificial Sequence
<220> FEATURE:
<223> OTHER INFORMATION: IL-2 analog 42

<400> SEQUENCE: 43

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Ala Met Leu Thr Lys Lys Phe Tyr Met Pro Lys Lys
            35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Glu
```

```
65                  70                  75                  80

Pro Arg Asp Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 44
<211> LENGTH: 132
<212> TYPE: PRT
<213> ORGANISM: Artificial Sequence
<220> FEATURE:
<223> OTHER INFORMATION: IL-2 analog 43

<400> SEQUENCE: 44

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Ala Met Leu Thr Lys Lys Phe Tyr Met Pro Lys Lys
            35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Asp
65                  70                  75                  80

Pro Arg Asp Leu Ile Ser Asn Ile Asn Val Leu Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 45
<211> LENGTH: 132
<212> TYPE: PRT
<213> ORGANISM: Artificial Sequence
<220> FEATURE:
<223> OTHER INFORMATION: IL-2 analog 44

<400> SEQUENCE: 45

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Ala Met Leu Thr Lys Lys Phe Tyr Met Pro Lys Lys
            35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Asp
65                  70                  75                  80

Pro Arg Val Leu Ile Ser Asn Ile Asn Val Phe Val Leu Glu Leu Lys
                85                  90                  95
```

-continued

```
Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

<210> SEQ ID NO 46
<211> LENGTH: 132
<212> TYPE: PRT
<213> ORGANISM: Artificial Sequence
<220> FEATURE:
<223> OTHER INFORMATION: IL-2 analog 45

<400> SEQUENCE: 46

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Asp
65                  70                  75                  80

Pro Arg Phe Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

<210> SEQ ID NO 47
<211> LENGTH: 132
<212> TYPE: PRT
<213> ORGANISM: Artificial Sequence
<220> FEATURE:
<223> OTHER INFORMATION: IL-2 analog 46

<400> SEQUENCE: 47

```
Pro Thr Ser Ser Ser Thr Lys Lys Thr Gln Leu Gln Leu Glu His Leu
1               5                   10                  15

Leu Leu Val Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Asp
65                  70                  75                  80

Pro Arg Asp Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125
```

-continued

```
Ser Thr Leu Thr
    130

<210> SEQ ID NO 48
<211> LENGTH: 132
<212> TYPE: PRT
<213> ORGANISM: Artificial Sequence
<220> FEATURE:
<223> OTHER INFORMATION: IL-2 analog 47

<400> SEQUENCE: 48

Pro Thr Ser Ser Ser Thr Lys Lys Thr Gln Leu Gln Leu Glu His Leu
1               5                   10                  15

Leu Leu Phe Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Asp
65                  70                  75                  80

Pro Arg Asp Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 49
<211> LENGTH: 132
<212> TYPE: PRT
<213> ORGANISM: Artificial Sequence
<220> FEATURE:
<223> OTHER INFORMATION: IL-2 analog 48

<400> SEQUENCE: 49

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Asp
65                  70                  75                  80

Pro Arg Asp Leu Ile Ser Val Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

<210> SEQ ID NO 50
<211> LENGTH: 132
<212> TYPE: PRT
<213> ORGANISM: Artificial Sequence
<220> FEATURE:
<223> OTHER INFORMATION: IL-2 analog 49

<400> SEQUENCE: 50

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Asp
65                  70                  75                  80

Pro Arg Asp Leu Ile Ser Phe Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 51
<211> LENGTH: 132
<212> TYPE: PRT
<213> ORGANISM: Artificial Sequence
<220> FEATURE:
<223> OTHER INFORMATION: IL-2 analog 50

<400> SEQUENCE: 51

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Asp
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 52
<211> LENGTH: 132
<212> TYPE: PRT
<213> ORGANISM: Artificial Sequence
<220> FEATURE:

-continued

```
<223> OTHER INFORMATION: IL-2 analog 51

<400> SEQUENCE: 52

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Gln Glu Leu Lys Pro
    50                  55                  60

Leu Glu Glu Val Leu Asn Leu Ala Gln Ser Lys Asn Phe His Leu Asp
65                  70                  75                  80

Pro Arg Asp Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 53
<211> LENGTH: 132
<212> TYPE: PRT
<213> ORGANISM: Artificial Sequence
<220> FEATURE:
<223> OTHER INFORMATION: IL-2 analog 52

<400> SEQUENCE: 53

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Asp
65                  70                  75                  80

Pro Arg Asp Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 54
<211> LENGTH: 132
<212> TYPE: PRT
<213> ORGANISM: Artificial Sequence
<220> FEATURE:
<223> OTHER INFORMATION: IL-2 analog 53

<400> SEQUENCE: 54

Pro Thr Ser Ser Ser Thr Lys Lys Thr Gln Leu Gln Leu Glu His Leu
```

```
1                5               10              15

Leu Leu Asp Leu Gln Met Ile Leu Asn Gly Ile Asn Asn Tyr Lys Asn
        20              25              30

Pro Lys Leu Thr Ala Met Leu Thr Lys Lys Phe Tyr Met Pro Lys Lys
        35              40              45

Ala Thr Glu Leu Lys His Leu Gln Cys Leu Glu Glu Glu Leu Lys Pro
    50              55              60

Leu Glu Glu Val Leu Asn Leu Ala Gln Ser Lys Asn Phe His Phe Asp
65              70              75              80

Pro Arg Glu Leu Ile Ser Asn Ile Asn Val Phe Val Leu Glu Leu Lys
                85              90              95

Gly Ser Glu Thr Thr Phe Met Cys Glu Tyr Ala Asp Glu Thr Ala Thr
            100             105             110

Ile Val Glu Phe Leu Asn Arg Trp Ile Thr Phe Ser Gln Ser Ile Ile
            115             120             125

Ser Thr Leu Thr
    130
```

```
<210> SEQ ID NO 55
<211> LENGTH: 132
<212> TYPE: PRT
<213> ORGANISM: Artificial Sequence
<220> FEATURE:
<223> OTHER INFORMATION: IL-2 analog 54

<400> SEQUENCE: 55
```

```
Pro Thr Ser Ser Ser Thr Lys Lys Thr Gln Leu Gln Leu Glu His Leu
1                5               10              15

Leu Leu Asp Leu Gln Met Ile Leu Asn Gly Ile Asn Asn Tyr Lys Asn
        20              25              30

Pro Lys Leu Thr Ala Met Leu Thr Lys Lys Phe Tyr Met Pro Lys Lys
        35              40              45

Ala Thr Glu Leu Lys His Leu Gln Cys Leu Glu Glu Glu Leu Lys Pro
    50              55              60

Leu Glu Glu Val Leu Asn Leu Ala His Ser Lys Asn Phe His Leu Asp
65              70              75              80

Pro Arg Asp Leu Ile Ser Asn Ile Asn Val Phe Val Leu Glu Leu Lys
                85              90              95

Gly Ser Glu Thr Thr Phe Met Cys Glu Tyr Ala Asp Glu Thr Ala Thr
            100             105             110

Ile Val Glu Phe Leu Asn Arg Trp Ile Thr Phe Ser Gln Ser Ile Ile
            115             120             125

Ser Thr Leu Thr
    130
```

```
<210> SEQ ID NO 56
<211> LENGTH: 132
<212> TYPE: PRT
<213> ORGANISM: Artificial Sequence
<220> FEATURE:
<223> OTHER INFORMATION: IL-2 analog 55

<400> SEQUENCE: 56
```

```
Pro Thr Ser Ser Ser Thr Lys Lys Thr Gln Leu Gln Leu Glu His Leu
1                5               10              15

Leu Leu Asp Leu Gln Met Ile Leu Asn Gly Ile Asn Asn Tyr Lys Asn
        20              25              30
```

```
Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala His Ser Lys Asn Phe His Phe Asp
65                  70                  75                  80

Pro Arg Asp Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

<210> SEQ ID NO 57
<211> LENGTH: 132
<212> TYPE: PRT
<213> ORGANISM: Artificial Sequence
<220> FEATURE:
<223> OTHER INFORMATION: IL-2 analog 56

<400> SEQUENCE: 57

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Ala Met Leu Thr Lys Lys Phe Ala Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala His Ser Lys Asn Phe His Leu Asp
65                  70                  75                  80

Pro Arg Asp Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

<210> SEQ ID NO 58
<211> LENGTH: 132
<212> TYPE: PRT
<213> ORGANISM: Artificial Sequence
<220> FEATURE:
<223> OTHER INFORMATION: IL-2 analog 57

<400> SEQUENCE: 58

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Ala Met Leu Thr Lys Lys Phe Ala Met Pro Lys Lys
        35                  40                  45

Ala Thr Glu Leu Lys His Leu Gln Cys Leu Glu Glu Glu Leu Lys Pro
    50                  55                  60
```

```
Leu Glu Glu Val Leu Asn Leu Ala His Ser Lys Asn Phe His Phe Asp
65              70                  75                  80

Pro Arg Asp Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 59
<211> LENGTH: 132
<212> TYPE: PRT
<213> ORGANISM: Artificial Sequence
<220> FEATURE:
<223> OTHER INFORMATION: IL-2 analog 61

<400> SEQUENCE: 59

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Asp
65              70                  75                  80

Pro Arg Asp Ala Ala Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 60
<211> LENGTH: 132
<212> TYPE: PRT
<213> ORGANISM: Artificial Sequence
<220> FEATURE:
<223> OTHER INFORMATION: IL-2 analog 59

<400> SEQUENCE: 60

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Asp
65              70                  75                  80

Pro Arg Asp Ala Ala Ser Asn Ile Asn Val Tyr Val Leu Glu Leu Lys
```

```
                85              90              95

Gly Ser Glu Thr Thr Phe Met Cys Glu Tyr Ala Asp Glu Thr Ala Thr
            100             105             110

Ile Val Glu Phe Leu Asn Arg Trp Ile Thr Phe Ser Gln Ser Ile Ile
        115             120             125

Ser Thr Leu Thr
    130

<210> SEQ ID NO 61
<211> LENGTH: 132
<212> TYPE: PRT
<213> ORGANISM: Artificial Sequence
<220> FEATURE:
<223> OTHER INFORMATION: IL-2 analog 60

<400> SEQUENCE: 61

Pro Thr Ser Ser Ser Thr Lys Lys Thr Gln Leu Gln Leu Glu His Leu
1               5               10              15

Leu Leu Asp Leu Gln Met Ile Leu Asn Gly Ile Asn Asn Tyr Lys Asn
            20              25              30

Pro Lys Leu Thr Ala Met Leu Thr Lys Lys Phe Ala Met Pro Lys Lys
        35              40              45

Ala Thr Glu Leu Lys His Leu Gln Cys Leu Glu Glu Glu Leu Lys Pro
    50              55              60

Leu Glu Glu Val Leu Asn Leu Ala Gln Ser Lys Asn Phe His Tyr Arg
65              70              75              80

Pro Arg Asp Ala Ala Ser Asn Ile Asn Val Tyr Val Leu Glu Leu Lys
            85              90              95

Gly Ser Glu Thr Thr Phe Met Cys Glu Tyr Ala Asp Glu Thr Ala Thr
            100             105             110

Ile Val Glu Phe Leu Asn Arg Trp Ile Thr Phe Ser Gln Ser Ile Ile
        115             120             125

Ser Thr Leu Thr
    130

<210> SEQ ID NO 62
<211> LENGTH: 132
<212> TYPE: PRT
<213> ORGANISM: Artificial Sequence
<220> FEATURE:
<223> OTHER INFORMATION: IL-2 analog 61

<400> SEQUENCE: 62

Pro Thr Ser Ser Ser Thr Lys Lys Thr Gln Leu Gln Leu Glu His Leu
1               5               10              15

Leu Leu Asp Leu Gln Met Ile Leu Asn Gly Ile Asn Asn Tyr Lys Asn
            20              25              30

Pro Lys Leu Thr Ala Met Leu Thr Lys Lys Phe Tyr Met Pro Lys Lys
        35              40              45

Ala Thr Glu Leu Lys His Leu Gln Cys Leu Glu Glu Glu Leu Lys Pro
    50              55              60

Leu Glu Glu Val Leu Asn Leu Ala Gln Ser Lys Asn Phe His Tyr Asp
65              70              75              80

Pro Arg Asp Gly Val Ser Asn Ile Asn Val Tyr Val Leu Glu Leu Lys
            85              90              95

Gly Ser Glu Thr Thr Phe Met Cys Glu Tyr Ala Asp Glu Thr Ala Thr
            100             105             110
```

```
Ile Val Glu Phe Leu Asn Arg Trp Ile Thr Phe Ser Gln Ser Ile Ile
    115                 120                 125

Ser Thr Leu Thr
    130

<210> SEQ ID NO 63
<211> LENGTH: 132
<212> TYPE: PRT
<213> ORGANISM: Artificial Sequence
<220> FEATURE:
<223> OTHER INFORMATION: IL-2 analog 62

<400> SEQUENCE: 63

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Trp Glu
65                  70                  75                  80

Pro Arg Asp Gly Ala Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
    115                 120                 125

Ser Thr Leu Thr
    130

<210> SEQ ID NO 64
<211> LENGTH: 132
<212> TYPE: PRT
<213> ORGANISM: Artificial Sequence
<220> FEATURE:
<223> OTHER INFORMATION: IL-2 analog 63

<400> SEQUENCE: 64

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Asp Glu
65                  70                  75                  80

Pro Arg Asp Thr Gly Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
    115                 120                 125

Ser Thr Leu Thr
    130
```

-continued

```
<210> SEQ ID NO 65
<211> LENGTH: 132
<212> TYPE: PRT
<213> ORGANISM: Artificial Sequence
<220> FEATURE:
<223> OTHER INFORMATION: IL-2 analog 64

<400> SEQUENCE: 65

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Tyr Asn
65                  70                  75                  80

Pro Arg Asp Val Val Ser Asn Ile Asn Val Tyr Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 66
<211> LENGTH: 132
<212> TYPE: PRT
<213> ORGANISM: Artificial Sequence
<220> FEATURE:
<223> OTHER INFORMATION: IL-2 analog 65

<400> SEQUENCE: 66

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Tyr Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 67
<211> LENGTH: 132
<212> TYPE: PRT
```

-continued

<213> ORGANISM: Artificial Sequence
<220> FEATURE:
<223> OTHER INFORMATION: IL-2 analog 66

<400> SEQUENCE: 67

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Glu
65                  70                  75                  80

Pro Arg Asp Phe Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130
```

<210> SEQ ID NO 68
<211> LENGTH: 132
<212> TYPE: PRT
<213> ORGANISM: Artificial Sequence
<220> FEATURE:
<223> OTHER INFORMATION: IL-2 analog 67

<400> SEQUENCE: 68

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Tyr Asp
65                  70                  75                  80

Pro Arg Asp Phe Val Ser Asn Ile Asn Val Trp Val Leu Asp Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130
```

<210> SEQ ID NO 69
<211> LENGTH: 132
<212> TYPE: PRT
<213> ORGANISM: Artificial Sequence
<220> FEATURE:
<223> OTHER INFORMATION: IL-2 analog 68

<400> SEQUENCE: 69

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Glu
65                  70                  75                  80

Pro Arg Asp Ile Val Ser Asn Ile Asn Glu Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

```
<210> SEQ ID NO 70
<211> LENGTH: 132
<212> TYPE: PRT
<213> ORGANISM: Artificial Sequence
<220> FEATURE:
<223> OTHER INFORMATION: IL-2 analog 69

<400> SEQUENCE: 70
```

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Tyr Glu
65                  70                  75                  80

Pro Arg Asp Phe Leu Ser Asn Ile Asn Glu Trp Val Leu Asp Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

```
<210> SEQ ID NO 71
<211> LENGTH: 132
<212> TYPE: PRT
<213> ORGANISM: Artificial Sequence
<220> FEATURE:
<223> OTHER INFORMATION: IL-2 analog 70

<400> SEQUENCE: 71
```

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
```

```
            20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Tyr Asp
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 72
<211> LENGTH: 132
<212> TYPE: PRT
<213> ORGANISM: Artificial Sequence
<220> FEATURE:
<223> OTHER INFORMATION: IL-2 analog 71

<400> SEQUENCE: 72

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 73
<211> LENGTH: 132
<212> TYPE: PRT
<213> ORGANISM: Artificial Sequence
<220> FEATURE:
<223> OTHER INFORMATION: IL-2 analog 72

<400> SEQUENCE: 73

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Ala Met Leu Thr Lys Lys Phe Tyr Met Pro Lys Lys
        35                  40                  45
```

-continued

```
Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Asp
65                  70                  75                  80

Pro Arg Asp Val Gly Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 74
<211> LENGTH: 132
<212> TYPE: PRT
<213> ORGANISM: Artificial Sequence
<220> FEATURE:
<223> OTHER INFORMATION: IL-2 analog 73

<400> SEQUENCE: 74

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Ala Met Leu Thr Lys Lys Phe Tyr Met Pro Lys Lys
            35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Asp
65                  70                  75                  80

Pro Arg Asp Trp Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 75
<211> LENGTH: 132
<212> TYPE: PRT
<213> ORGANISM: Artificial Sequence
<220> FEATURE:
<223> OTHER INFORMATION: IL-2 analog 74

<400> SEQUENCE: 75

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Asp Met Leu Thr Lys Lys Phe Tyr Met Pro Lys Lys
            35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Tyr Asp
65                  70                  75                  80
```

```
Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 76
<211> LENGTH: 132
<212> TYPE: PRT
<213> ORGANISM: Artificial Sequence
<220> FEATURE:
<223> OTHER INFORMATION: IL-2 analog 75

<400> SEQUENCE: 76

Pro Thr Ser Ser Ser Thr Lys Lys Thr Gln Leu Gln Leu Glu His Leu
1               5                  10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Lys Phe Ala Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 77
<211> LENGTH: 132
<212> TYPE: PRT
<213> ORGANISM: Artificial Sequence
<220> FEATURE:
<223> OTHER INFORMATION: IL-2 analog 76

<400> SEQUENCE: 77

Pro Thr Ser Ser Ser Thr Lys Lys Thr Gln Leu Gln Leu Glu His Leu
1               5                  10                  15

Leu Leu Asp Leu Gln Met Ile Leu Asn Gly Ile Asn Asn Tyr Lys Asn
            20                  25                  30

Pro Lys Leu Thr Ala Met Leu Thr Lys Gln Phe Tyr Met Pro Lys Lys
        35                  40                  45

Ala Thr Glu Leu Lys His Leu Gln Cys Leu Glu Arg Glu Leu Lys Pro
    50                  55                  60

Leu Glu Glu Val Leu Asn Leu Ala Gln Ser Lys Asn Phe His Phe Asp
65                  70                  75                  80

Pro Arg Asp Val Gly Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
```

```
              100             105             110

Ile Val Glu Phe Leu Asn Arg Trp Ile Thr Phe Ser Gln Ser Ile Ile
        115             120             125

Ser Thr Leu Thr
    130

<210> SEQ ID NO 78
<211> LENGTH: 132
<212> TYPE: PRT
<213> ORGANISM: Artificial Sequence
<220> FEATURE:
<223> OTHER INFORMATION: IL-2 analog 77

<400> SEQUENCE: 78

Pro Thr Ser Ser Ser Thr Lys Lys Thr Gln Leu Gln Leu Glu His Leu
1               5               10              15

Leu Leu Asp Leu Gln Met Ile Leu Asn Gly Ile Asn Asn Tyr Lys Asn
            20              25              30

Pro Lys Leu Thr Ala Met Leu Thr Lys Glu Phe Tyr Met Pro Lys Lys
        35              40              45

Ala Thr Glu Leu Lys His Leu Gln Cys Leu Glu Arg Glu Leu Lys Pro
    50              55              60

Leu Glu Glu Val Leu Asn Leu Ala Gln Ser Lys Asn Phe His Phe Asp
65              70              75              80

Pro Arg Asp Trp Val Ser Asn Ile Asn Val Phe Val Leu Glu Leu Lys
            85              90              95

Gly Ser Glu Thr Thr Phe Met Cys Glu Tyr Ala Asp Glu Thr Ala Thr
            100             105             110

Ile Val Glu Phe Leu Asn Arg Trp Ile Thr Phe Ser Gln Ser Ile Ile
        115             120             125

Ser Thr Leu Thr
    130

<210> SEQ ID NO 79
<211> LENGTH: 132
<212> TYPE: PRT
<213> ORGANISM: Artificial Sequence
<220> FEATURE:
<223> OTHER INFORMATION: IL-2 analog 78

<400> SEQUENCE: 79

Pro Thr Ser Ser Ser Thr Lys Lys Thr Gln Leu Gln Leu Glu His Leu
1               5               10              15

Leu Leu Asp Leu Gln Met Ile Leu Asn Gly Ile Asn Asn Tyr Lys Asn
            20              25              30

Pro Glu Leu Thr Ala Met Leu Thr Lys Lys Phe Tyr Met Pro Lys Lys
        35              40              45

Ala Thr Glu Leu Lys His Leu Gln Cys Leu Glu Glu Glu Leu Lys Pro
    50              55              60

Leu Glu Glu Val Leu Asn Leu Ala Gln Ser Lys Asn Phe His Phe Glu
65              70              75              80

Pro Arg Asp Val Val Ser Asn Ile Asn Val Phe Val Leu Glu Leu Lys
            85              90              95

Gly Ser Glu Thr Thr Phe Met Cys Glu Tyr Ala Asp Glu Thr Ala Thr
            100             105             110

Ile Val Glu Phe Leu Asn Arg Trp Ile Thr Phe Ser Gln Ser Ile Ile
        115             120             125
```

```
Ser Thr Leu Thr
    130

<210> SEQ ID NO 80
<211> LENGTH: 132
<212> TYPE: PRT
<213> ORGANISM: Artificial Sequence
<220> FEATURE:
<223> OTHER INFORMATION: IL-2 analog 79

<400> SEQUENCE: 80

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Glu Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala His Ser Lys Asn Phe His Phe Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 81
<211> LENGTH: 132
<212> TYPE: PRT
<213> ORGANISM: Artificial Sequence
<220> FEATURE:
<223> OTHER INFORMATION: IL-2 analog 80

<400> SEQUENCE: 81

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Glu Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala His Ser Lys Asn Phe His Phe Glu
65                  70                  75                  80

Gly Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 82
```

```
<211> LENGTH: 132
<212> TYPE: PRT
<213> ORGANISM: Artificial Sequence
<220> FEATURE:
<223> OTHER INFORMATION: IL-2 analog 81

<400> SEQUENCE: 82

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Glu Leu Thr Ala Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala His Ser Lys Asn Phe His Phe Glu
65                  70                  75                  80

Val Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 83
<211> LENGTH: 132
<212> TYPE: PRT
<213> ORGANISM: Artificial Sequence
<220> FEATURE:
<223> OTHER INFORMATION: IL-2 analog 82

<400> SEQUENCE: 83

Pro Thr Ser Ser Ser Thr Lys Lys Thr Gln Leu Gln Leu Glu His Leu
1               5                   10                  15

Arg Leu Asp Leu Glu Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Asp
65                  70                  75                  80

Pro Arg Asp Glu Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 84
<211> LENGTH: 132
<212> TYPE: PRT
<213> ORGANISM: Artificial Sequence
<220> FEATURE:
<223> OTHER INFORMATION: IL-2 analog 83
```

-continued

<400> SEQUENCE: 84

```
Pro Thr Ser Ser Ser Thr Lys Lys Thr Gln Leu Gln Leu Glu His Leu
1               5                   10                  15

Arg Arg Asp Leu Glu Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Asp
65                  70                  75                  80

Pro Arg Asp Glu Val Ser Asn Ile Asn Val Phe Val Leu Glu Leu Lys
            85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

<210> SEQ ID NO 85
<211> LENGTH: 132
<212> TYPE: PRT
<213> ORGANISM: Artificial Sequence
<220> FEATURE:
<223> OTHER INFORMATION: IL-2 analog 84

<400> SEQUENCE: 85

```
Pro Thr Ser Ser Ser Thr Lys Lys Thr Gln Leu Gln Leu Glu His Leu
1               5                   10                  15

Arg Leu Asp Leu Glu Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Val Asp
65                  70                  75                  80

Pro Arg Asp Glu Val Ser Asn Ile Asn Val Phe Val Leu Glu Leu Lys
            85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

<210> SEQ ID NO 86
<211> LENGTH: 132
<212> TYPE: PRT
<213> ORGANISM: Artificial Sequence
<220> FEATURE:
<223> OTHER INFORMATION: IL-2 analog 85

<400> SEQUENCE: 86

```
Pro Thr Ser Ser Ser Thr Lys Lys Thr Gln Leu Gln Leu Glu His Leu
1               5                   10                  15
```

-continued

```
Leu Leu Asp Leu Gln Met Ile Leu Asn Gly Ile Asn Asn Tyr Lys Asn
        20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 87
<211> LENGTH: 132
<212> TYPE: PRT
<213> ORGANISM: Artificial Sequence
<220> FEATURE:
<223> OTHER INFORMATION: IL-2 analog 86

<400> SEQUENCE: 87

Pro Thr Ser Ser Ser Thr Lys Lys Thr Gln Leu Gln Leu Glu His Leu
1               5                   10                  15

Arg Leu Asp Leu Glu Met Ile Leu Asn Gly Ile Asn Asn Tyr Lys Asn
        20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 88
<211> LENGTH: 132
<212> TYPE: PRT
<213> ORGANISM: Artificial Sequence
<220> FEATURE:
<223> OTHER INFORMATION: IL-2 analog 87

<400> SEQUENCE: 88

Pro Thr Ser Ser Ser Thr Lys Lys Thr Gln Leu Gln Leu Glu His Leu
1               5                   10                  15

Arg Arg Asp Leu Glu Met Ile Leu Asn Gly Ile Asn Asn Tyr Lys Asn
        20                  25                  30

Pro Lys Leu Thr Arg Met Leu Thr Phe Lys Phe Tyr Met Pro Lys Lys
```

-continued

```
              35                    40                    45

Ala Thr Glu Leu Lys His Leu Gln Cys Leu Glu Glu Glu Leu Lys Pro
    50                    55                    60

Leu Glu Glu Val Leu Asn Leu Ala Gln Ser Lys Asn Phe His Phe Glu
65                    70                    75                    80

Pro Arg Asp Val Val Ser Asn Ile Asn Val Phe Val Leu Glu Leu Lys
                      85                    90                    95

Gly Ser Glu Thr Thr Phe Met Cys Glu Tyr Ala Asp Glu Thr Ala Thr
                  100                   105                   110

Ile Val Glu Phe Leu Asn Arg Trp Ile Thr Phe Ser Gln Ser Ile Ile
              115                   120                   125

Ser Thr Leu Thr
    130

<210> SEQ ID NO 89
<211> LENGTH: 132
<212> TYPE: PRT
<213> ORGANISM: Artificial Sequence
<220> FEATURE:
<223> OTHER INFORMATION: IL-2 analog 88

<400> SEQUENCE: 89

Pro Thr Ser Ser Ser Thr Lys Lys Thr Gln Leu Gln Leu Glu His Leu
1                 5                    10                    15

Leu Leu Asp Leu Gln Met Ile Leu Asn Gly Ile Asn Asn Tyr Lys Asn
                  20                    25                    30

Pro Lys Leu Thr Arg Met Leu Thr Phe Lys Phe Tyr Met Pro Lys Lys
              35                    40                    45

Ala Thr Glu Leu Lys His Leu Gln Cys Leu Glu Asp Glu Leu Lys Pro
    50                    55                    60

Leu Glu Glu Val Leu Asn Leu Ala Gln Ser Lys Asn Phe His Phe Glu
65                    70                    75                    80

Pro Arg Asp Val Val Ser Asn Ile Asn Val Phe Val Leu Glu Leu Lys
                      85                    90                    95

Gly Ser Glu Thr Thr Phe Met Cys Glu Tyr Ala Asp Glu Thr Ala Thr
                  100                   105                   110

Ile Val Glu Phe Leu Asn Arg Trp Ile Thr Phe Ser Gln Ser Ile Ile
              115                   120                   125

Ser Thr Leu Thr
    130

<210> SEQ ID NO 90
<211> LENGTH: 132
<212> TYPE: PRT
<213> ORGANISM: Artificial Sequence
<220> FEATURE:
<223> OTHER INFORMATION: IL-2 analog 89

<400> SEQUENCE: 90

Pro Thr Ser Ser Ser Thr Lys Lys Thr Gln Leu Gln Leu Glu His Leu
1                 5                    10                    15

Leu Leu Asp Leu Gln Met Ile Leu Asn Gly Ile Asn Asn Tyr Lys Asn
                  20                    25                    30

Pro Lys Leu Thr Ala Met Leu Thr Phe Lys Phe Tyr Met Pro Lys Lys
              35                    40                    45

Ala Thr Glu Leu Lys His Leu Gln Cys Leu Glu Glu Glu Leu Lys Pro
    50                    55                    60
```

```
Leu Glu Gln Val Leu Asn Leu Ala Gln Ser Lys Asn Phe His Phe Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 91
<211> LENGTH: 132
<212> TYPE: PRT
<213> ORGANISM: Artificial Sequence
<220> FEATURE:
<223> OTHER INFORMATION: IL-2 analog 90

<400> SEQUENCE: 91

Pro Thr Ser Ser Ser Thr Lys Lys Thr Gln Leu Gln Leu Glu His Leu
1                   5                   10                  15

Leu Leu Asp Leu Gln Met Ile Leu Asn Gly Ile Asn Asn Tyr Lys Asn
                20                  25                  30

Pro Lys Leu Thr Arg Met Leu Thr Trp Lys Phe Tyr Met Pro Lys Lys
            35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 92
<211> LENGTH: 132
<212> TYPE: PRT
<213> ORGANISM: Artificial Sequence
<220> FEATURE:
<223> OTHER INFORMATION: IL-2 analog 91

<400> SEQUENCE: 92

Pro Thr Ser Ser Ser Thr Lys Lys Thr Gln Leu Gln Leu Glu His Leu
1                   5                   10                  15

Leu Leu Asp Leu Gln Met Ile Leu Asn Gly Ile Asn Asn Tyr Lys Asn
                20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Gln Glu Leu Lys Pro
    50                  55                  60

Leu Glu Glu Val Leu Asn Leu Ala Gln Ser Lys Asn Phe His Phe Glu
65                  70                  75                  80

Pro Arg Asp Val Val Ser Asn Ile Asn Val Phe Val Leu Glu Leu Lys
                85                  90                  95
```

-continued

```
Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 93
<211> LENGTH: 132
<212> TYPE: PRT
<213> ORGANISM: Artificial Sequence
<220> FEATURE:
<223> OTHER INFORMATION: IL-2 analog 92

<400> SEQUENCE: 93

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Glu
65                  70                  75                  80

Pro Arg Asp Val Val Ser Asn Ile Asn Thr Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 94
<211> LENGTH: 132
<212> TYPE: PRT
<213> ORGANISM: Artificial Sequence
<220> FEATURE:
<223> OTHER INFORMATION: IL-2 analog 93

<400> SEQUENCE: 94

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Glu
65                  70                  75                  80

Pro Arg Glu Val Val Ser Asn Ile Asn Thr Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
```

-continued

```
          115               120               125

Ser Thr Leu Thr
    130

<210> SEQ ID NO 95
<211> LENGTH: 132
<212> TYPE: PRT
<213> ORGANISM: Artificial Sequence
<220> FEATURE:
<223> OTHER INFORMATION: IL-2 analog 94

<400> SEQUENCE: 95

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Glu
65                  70                  75                  80

Pro Arg Asp Val Val Ser Asn Ile Asn Val Phe Val Phe Glu Phe Lys
            85                  90                  95

Gly Ser Glu Thr Thr Phe Met Cys Glu Tyr Ala Asp Glu Thr Ala Thr
        100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 96
<211> LENGTH: 132
<212> TYPE: PRT
<213> ORGANISM: Artificial Sequence
<220> FEATURE:
<223> OTHER INFORMATION: IL-2 analog 95

<400> SEQUENCE: 96

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Gly Leu Asn Leu Ala Gln Ser Lys Asn Phe His Phe Glu
65                  70                  75                  80

Pro Arg Asp Val Val Ser Asn Ile Asn Val Phe Val Leu Glu Leu Lys
            85                  90                  95

Gly Ser Glu Thr Thr Phe Met Cys Glu Tyr Ala Asp Glu Thr Ala Thr
        100                 105                 110

Ile Val Glu Phe Leu Asn Arg Trp Ile Thr Phe Ser Gln Ser Ile Ile
        115                 120                 125

Ser Thr Leu Thr
    130
```

-continued

<210> SEQ ID NO 97
<211> LENGTH: 132
<212> TYPE: PRT
<213> ORGANISM: Artificial Sequence
<220> FEATURE:
<223> OTHER INFORMATION: IL-2 analog 96

<400> SEQUENCE: 97

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Gly Leu Asn Leu Ala Ala Ser Lys Asn Phe His Phe Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 98
<211> LENGTH: 132
<212> TYPE: PRT
<213> ORGANISM: Artificial Sequence
<220> FEATURE:
<223> OTHER INFORMATION: IL-2 analog 97

<400> SEQUENCE: 98

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Asp
65                  70                  75                  80

Pro Arg Asp Leu Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 99
<211> LENGTH: 132
<212> TYPE: PRT
<213> ORGANISM: Artificial Sequence

```
<220> FEATURE:
<223> OTHER INFORMATION: IL-2 analog 98

<400> SEQUENCE: 99

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Glu
65                  70                  75                  80

Pro Arg Asp Val Ile Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 100
<211> LENGTH: 132
<212> TYPE: PRT
<213> ORGANISM: Artificial Sequence
<220> FEATURE:
<223> OTHER INFORMATION: IL-2 analog 99

<400> SEQUENCE: 100

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Glu
65                  70                  75                  80

Pro Arg Asp Leu Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 101
<211> LENGTH: 132
<212> TYPE: PRT
<213> ORGANISM: Artificial Sequence
<220> FEATURE:
<223> OTHER INFORMATION: IL-2 analog 100

<400> SEQUENCE: 101
```

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Glu
65                  70                  75                  80

Pro Arg Asp Tyr Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

<210> SEQ ID NO 102
<211> LENGTH: 132
<212> TYPE: PRT
<213> ORGANISM: Artificial Sequence
<220> FEATURE:
<223> OTHER INFORMATION: IL-2 analog 101

<400> SEQUENCE: 102

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Glu
65                  70                  75                  80

Pro Arg Asp Leu Ala Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

<210> SEQ ID NO 103
<211> LENGTH: 132
<212> TYPE: PRT
<213> ORGANISM: Artificial Sequence
<220> FEATURE:
<223> OTHER INFORMATION: IL-2 analog 102

<400> SEQUENCE: 103

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30
```

-continued

```
Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Glu
65                  70                  75                  80

Pro Arg Asp Val Val Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

```
<210> SEQ ID NO 104
<211> LENGTH: 132
<212> TYPE: PRT
<213> ORGANISM: Artificial Sequence
<220> FEATURE:
<223> OTHER INFORMATION: IL-2 analog 103

<400> SEQUENCE: 104
```

```
Pro Thr Ser Ser Ser Thr Lys Lys Thr Gln Leu Gln Leu Glu His Leu
1               5                   10                  15

Arg Leu Asp Leu Glu Met Ile Leu Asn Gly Ile Asn Asn Tyr Lys Asn
            20                  25                  30

Pro Lys Leu Thr Ala Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Phe Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

```
<210> SEQ ID NO 105
<211> LENGTH: 132
<212> TYPE: PRT
<213> ORGANISM: Artificial Sequence
<220> FEATURE:
<223> OTHER INFORMATION: IL-2 analog 104

<400> SEQUENCE: 105
```

```
Pro Thr Ser Ser Ser Thr Lys Lys Thr Gln Leu Gln Leu Glu His Leu
1               5                   10                  15

Arg Leu Asp Leu Glu Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Asp Glu Leu Lys Pro
```

```
                50                  55                  60

Leu Glu Glu Val Leu Asn Leu Ala Gln Ser Lys Asn Phe His Phe Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
        115                 120                 125

Ser Thr Leu Thr
    130
```

```
<210> SEQ ID NO 106
<211> LENGTH: 132
<212> TYPE: PRT
<213> ORGANISM: Artificial Sequence
<220> FEATURE:
<223> OTHER INFORMATION: IL-2 analog 105

<400> SEQUENCE: 106

Pro Thr Ser Ser Ser Thr Lys Lys Thr Gln Leu Gln Leu Glu His Leu
1               5                   10                  15

Arg Leu Asp Leu Glu Met Ile Leu Asn Gly Ile Asn Asn Tyr Lys Asn
                20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
        50                  55                  60

Leu Glu Asp Val Leu Asn Leu Ala Gln Ser Lys Asn Phe His Phe Glu
65                  70                  75                  80

Pro Arg Asp Val Val Ser Asn Ile Asn Val Phe Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
        115                 120                 125

Ser Thr Leu Thr
    130
```

```
<210> SEQ ID NO 107
<211> LENGTH: 399
<212> TYPE: DNA
<213> ORGANISM: Artificial Sequence
<220> FEATURE:
<223> OTHER INFORMATION: IL-2 analog 1

<400> SEQUENCE: 107
cctacttcaa gttctacaaa gaaaacacag ctacaactgg agcatttact gctggattta    60
cagatgattt tgaatggaat taataattac aagaatccca aactcaccag gatgctcaca   120
tttaagtttt acatgcccaa gaaggccaca gaactgaaac atcttcagtg tctagaagaa   180
gaactcaaac tctggagga agtgctaaat ttagctcaaa gcaaaaactt tcacttaaga    240
cccagggact taatcagcaa tatcaacgta atagttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                         399
```

-continued

```
<210> SEQ ID NO 108
<211> LENGTH: 399
<212> TYPE: DNA
<213> ORGANISM: Artificial Sequence
<220> FEATURE:
<223> OTHER INFORMATION: IL-2 analog 2

<400> SEQUENCE: 108
cctacttcaa gttctacaaa gaaaacacag ctacaactgg agcatttact gctggattta      60
cagatgattt tgaatggaat taataattac aagaatccca aactcaccag gatgctcaca     120
tttaagtttt acatgcccaa gaaggccaca gaactgaaac atcttcagtg tctagaagaa     180
gaactcaaac ctctggagga agtgctaaat ttagctcaaa gcaaaaactt tcacttaaga     240
cccagggact taatctgcaa tatcaacgta atagttctgg aactaaaggg atctgaaaca     300
acattcatgt gtgaatatgc tgatgagaca gcaaccattg tagaatttct gaacagatgg     360 attacctttta gtcaaagcat catctcaaca ctgacttga                          399

<210> SEQ ID NO 109
<211> LENGTH: 399
<212> TYPE: DNA
<213> ORGANISM: Artificial Sequence
<220> FEATURE:
<223> OTHER INFORMATION: IL-2 analog 3

<400> SEQUENCE: 109
cctacttcaa gttctacaaa gaaaacacag ctacaactgg agcatttact gctggattta      60
cagatgattt tgaatggaat taataattac tgtaatccca aactcaccag gatgctcaca     120
tttaagtttt acatgcccaa gaaggccaca gaactgaaac atcttcagtg tctagaagaa     180
gaactcaaac ctctggagga agtgctaaat ttagctcaaa gcaaaaactt tcacttaaga     240
cccagggact taatcagcaa tatcaacgta atagttctgg aactaaaggg atctgaaaca     300
acattcatgt gtgaatatgc tgatgagaca gcaaccattg tagaatttct gaacagatgg     360 attacctttta gtcaaagcat catctcaaca ctgacttga                          399

<210> SEQ ID NO 110
<211> LENGTH: 399
<212> TYPE: DNA
<213> ORGANISM: Artificial Sequence
<220> FEATURE:
<223> OTHER INFORMATION: IL-2 analog 4

<400> SEQUENCE: 110
cctacttcaa gttctacaaa gaaaacacag ctacaactgg agcatttact gctggattta      60
cagatgattt tgaatggaat taataattac aagaatccct gtctcaccag gatgctcaca     120
tttaagtttt acatgcccaa gaaggccaca gaactgaaac atcttcagtg tctagaagaa     180
gaactcaaac ctctggagga agtgctaaat ttagctcaaa gcaaaaactt tcacttaaga     240
cccagggact taatcagcaa tatcaacgta atagttctgg aactaaaggg atctgaaaca     300
acattcatgt gtgaatatgc tgatgagaca gcaaccattg tagaatttct gaacagatgg     360 attacctttta gtcaaagcat catctcaaca ctgacttga                          399

<210> SEQ ID NO 111
<211> LENGTH: 399
<212> TYPE: DNA
<213> ORGANISM: Artificial Sequence
<220> FEATURE:
<223> OTHER INFORMATION: IL-2 analog 5
```

-continued

```
<400> SEQUENCE: 111
cctacttcaa gttctacaaa gaaaacacag ctacaactgg agcatttact gctggattta      60
cagatgattt tgaatggaat taataattac aagaatccca aactcaccag gatgctcaca     120
ttttgttttt acatgcccaa gaaggccaca gaactgaaac atcttcagtg tctagaagaa     180
gaactcaaac ctctggagga agtgctaaat ttagctcaaa gcaaaaactt tcacttaaga     240
cccagggact taatcagcaa tatcaacgta atagttctgg aactaaaggg atctgaaaca     300
acattcatgt gtgaatatgc tgatgagaca gcaaccattg tagaatttct gaacagatgg     360 attacccttta gtcaaagcat catctcaaca ctgacttga                           399

<210> SEQ ID NO 112
<211> LENGTH: 399
<212> TYPE: DNA
<213> ORGANISM: Artificial Sequence
<220> FEATURE:
<223> OTHER INFORMATION: IL-2 analog 6

<400> SEQUENCE: 112
cctacttcaa gttctacaaa gaaaacacag ctacaactgg agcatttact gctggattta      60
cagatgattt tgaatggaat taataattac aagaatccca aactcaccag gatgctcaca     120
tttaagtttt acatgccctg taaggccaca gaactgaaac atcttcagtg tctagaagaa     180
gaactcaaac ctctggagga agtgctaaat ttagctcaaa gcaaaaactt tcacttaaga     240
cccagggact taatcagcaa tatcaacgta atagttctgg aactaaaggg atctgaaaca     300
acattcatgt gtgaatatgc tgatgagaca gcaaccattg tagaatttct gaacagatgg     360 attacccttta gtcaaagcat catctcaaca ctgacttga                           399

<210> SEQ ID NO 113
<211> LENGTH: 399
<212> TYPE: DNA
<213> ORGANISM: Artificial Sequence
<220> FEATURE:
<223> OTHER INFORMATION: IL-2 analog 7

<400> SEQUENCE: 113
cctacttcaa gttctacaaa gaaaacacag ctacaactgg agcatttact gctggattta      60
cagatgattt tgaatggaat taataattac aagaatccca aactcaccag gatgctcaca     120
tttaagtttt acatgcccaa gtgtgccaca gaactgaaac atcttcagtg tctagaagaa     180
gaactcaaac ctctggagga agtgctaaat ttagctcaaa gcaaaaactt tcacttaaga     240
cccagggact taatcagcaa tatcaacgta atagttctgg aactaaaggg atctgaaaca     300
acattcatgt gtgaatatgc tgatgagaca gcaaccattg tagaatttct gaacagatgg     360 attacccttta gtcaaagcat catctcaaca ctgacttga                           399

<210> SEQ ID NO 114
<211> LENGTH: 399
<212> TYPE: DNA
<213> ORGANISM: Artificial Sequence
<220> FEATURE:
<223> OTHER INFORMATION: IL-2 analog 8

<400> SEQUENCE: 114
cctacttcaa gttctacaaa gaaaacacag ctacaactgg agcatttact gctggattta      60
cagatgattt tgaatggaat taataattac aagaatccca aactcaccag gatgctcaca     120
tttaagtttt acatgcccaa gaaggccaca gaactgaaac atcttcagtg tctagaagaa     180
```

```
gaactcaaac ctctggagga agtgctaaat ttagctcaaa gctgtaactt tcacttaaga      240
cccagggact taatcagcaa tatcaacgta atagttctgg aactaaaggg atctgaaaca      300
acattcatgt gtgaatatgc tgatgagaca gcaaccattg tagaatttct gaacagatgg      360 attacctta gtcaaagcat catctcaaca ctgacttga                            399
```

```
<210> SEQ ID NO 115
<211> LENGTH: 399
<212> TYPE: DNA
<213> ORGANISM: Artificial Sequence
<220> FEATURE:
<223> OTHER INFORMATION: IL-2 analog 9

<400> SEQUENCE: 115
cctacttcaa gttctacaaa gaaaacacag ctacaactgg agcatttact gctggattta      60
cagatgattt tgaatggaat taataattac aagaatccca aactcaccgc gatgctcaca      120
tttaagtttt acatgcccaa gaaggccaca gaactgaaac atcttcagtg tctagaagaa      180
gaactcaaac ctctggagga agtgctaaat ttagctcaaa gcaaaaactt tcacttaaga      240
cccagggact taatcagcaa tatcaacgta atagttctgg aactaaaggg atctgaaaca      300
acattcatgt gtgaatatgc tgatgagaca gcaaccattg tagaatttct gaacagatgg      360 attacctta gtcaaagcat catctcaaca ctgacttga                            399
```

```
<210> SEQ ID NO 116
<211> LENGTH: 399
<212> TYPE: DNA
<213> ORGANISM: Artificial Sequence
<220> FEATURE:
<223> OTHER INFORMATION: IL-2 analog 10

<400> SEQUENCE: 116
cctacttcaa gttctacaaa gaaaacacag ctacaactgg agcatttact gctggattta      60
cagatgattt tgaatggaat taataattac aagaatccca aactcaccag gatgctcaca      120
aagaagtttt acatgcccaa gaaggccaca gaactgaaac atcttcagtg tctagaagaa      180
gaactcaaac ctctggagga agtgctaaat ttagctcaaa gcaaaaactt tcacttaaga      240
cccagggact taatcagcaa tatcaacgta atagttctgg aactaaaggg atctgaaaca      300
acattcatgt gtgaatatgc tgatgagaca gcaaccattg tagaatttct gaacagatgg      360 attacctta gtcaaagcat catctcaaca ctgacttga                            399
```

```
<210> SEQ ID NO 117
<211> LENGTH: 399
<212> TYPE: DNA
<213> ORGANISM: Artificial Sequence
<220> FEATURE:
<223> OTHER INFORMATION: IL-2 analog 11

<400> SEQUENCE: 117
cctacttcaa gttctacaaa gaaaacacag ctacaactgg agcatttact gctggattta      60
cagatgattt tgaatggaat taataattac aagaatccca aactcaccag gatgctcaca      120
gctaagtttt acatgcccaa gaaggccaca gaactgaaac atcttcagtg tctagaagaa      180
gaactcaaac ctctggagga agtgctaaat ttagctcaaa gcaaaaactt tcacttaaga      240
cccagggact taatcagcaa tatcaacgta atagttctgg aactaaaggg atctgaaaca      300
acattcatgt gtgaatatgc tgatgagaca gcaaccattg tagaatttct gaacagatgg      360
```
attaccttta gtcaaagcat catctcaaca ctgacttga                              399

<210> SEQ ID NO 118
<211> LENGTH: 399
<212> TYPE: DNA
<213> ORGANISM: Artificial Sequence
<220> FEATURE:
<223> OTHER INFORMATION: IL-2 analog 12

<400> SEQUENCE: 118
cctacttcaa gttctacaaa gaaaacacag ctacaactgg agcatttact gctggattta       60
cagatgattt tgaatggaat taataattac aagaatccca aactcaccgc gatgctcaca      120
aagaagtttt acatgcccaa gaaggccaca gaactgaaac atcttcagtg tctagaagaa      180
gaactcaaac ctctggagga agtgctaaat ttagctcaaa gcaaaaactt tcacttaaga      240
cccagggact taatcagcaa tatcaacgta atagttctgg aactaaaggg atctgaaaca      300
acattcatgt gtgaatatgc tgatgagaca gcaaccattg tagaatttct gaacagatgg      360
attaccttta gtcaaagcat catctcaaca ctgacttga                              399

<210> SEQ ID NO 119
<211> LENGTH: 399
<212> TYPE: DNA
<213> ORGANISM: Artificial Sequence
<220> FEATURE:
<223> OTHER INFORMATION: IL-2 analog 13

<400> SEQUENCE: 119
cctacttcaa gttctacaaa gaaaacacag ctacaactgg agcatttact gctggattta       60
cagatgattt tgaatggaat taataattac aagaatccca aactcaccgc gatgctcaca      120
gctaagtttt acatgcccaa gaaggccaca gaactgaaac atcttcagtg tctagaagaa      180
gaactcaaac ctctggagga agtgctaaat ttagctcaaa gcaaaaactt tcacttaaga      240
cccagggact taatcagcaa tatcaacgta atagttctgg aactaaaggg atctgaaaca      300
acattcatgt gtgaatatgc tgatgagaca gcaaccattg tagaatttct gaacagatgg      360
attaccttta gtcaaagcat catctcaaca ctgacttga                              399

<210> SEQ ID NO 120
<211> LENGTH: 399
<212> TYPE: DNA
<213> ORGANISM: Artificial Sequence
<220> FEATURE:
<223> OTHER INFORMATION: IL-2 analog 14

<400> SEQUENCE: 120
cctacttcaa gttctacaaa gaaaacacag ctacaactgg agcatttact gtacgattta       60
cagatgattt tgaatggaat taataattac aagaatccca aactcaccgc gatgctcaca      120
aagaagtttt acatgcccaa gaaggccaca gaactgaaac atcttcagtg tctagaagaa      180
gaactcaaac ctctggagga agtgctaaat ttagctcaaa gcaaaaactt tcacttaaga      240
cccagggact taatcagcaa tatcaacgta atagttctgg aactaaaggg atctgaaaca      300
acattcatgt gtgaatatgc tgatgagaca gcaaccattg tagaatttct gaacagatgg      360
attaccttta gtcaaagcat catctcaaca ctgacttga                              399

<210> SEQ ID NO 121
<211> LENGTH: 399
<212> TYPE: DNA
<213> ORGANISM: Artificial Sequence -continued

```
<220> FEATURE:
<223> OTHER INFORMATION: IL-2 analog 15

<400> SEQUENCE: 121
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttaaga   240
cccagggagt taatcagcaa tatcaacgta atagttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                          399

<210> SEQ ID NO 122
<211> LENGTH: 399
<212> TYPE: DNA
<213> ORGANISM: Artificial Sequence
<220> FEATURE:
<223> OTHER INFORMATION: IL-2 analog 16

<400> SEQUENCE: 122
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttaaga   240
cccagggact taatcagcca aatcaacgta atagttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                          399

<210> SEQ ID NO 123
<211> LENGTH: 399
<212> TYPE: DNA
<213> ORGANISM: Artificial Sequence
<220> FEATURE:
<223> OTHER INFORMATION: IL-2 analog 17

<400> SEQUENCE: 123
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacttaaga   240
cccagggact taatcagcaa tatcaacaca atagttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                          399

<210> SEQ ID NO 124
<211> LENGTH: 399
<212> TYPE: DNA
<213> ORGANISM: Artificial Sequence
<220> FEATURE:
<223> OTHER INFORMATION: IL-2 analog 18

<400> SEQUENCE: 124
cctacttcaa gttctacaaa gaaaacacag ctacaactgg agcatttact gctggattta    60
```

-continued

```
cagatgattt tgaatggaat taataattac aagaatccca aactcaccgc gatgctcaca    120
aagaagtttt acatgcccaa gaaggccaca gaactgaaac atcttcagtg tctagaacag    180
gaactcaaac ctctggagga agtgctaaat ttagctcaaa gcaaaaactt tcacttaaga    240
cccagggact taatcagcaa tatcaacgta atagttctgg aactaaaggg atctgaaaca    300
acattcatgt gtgaatatgc tgatgagaca gcaaccattg tagaatttct gaacagatgg    360 attacctttta gtcaaagcat catctcaaca ctgacttga                          399
```

<210> SEQ ID NO 125
<211> LENGTH: 399
<212> TYPE: DNA
<213> ORGANISM: Artificial Sequence
<220> FEATURE:
<223> OTHER INFORMATION: IL-2 analog 19

<400> SEQUENCE: 125

```
cctacttcaa gttctacaaa gaaaacacag ctacaactgg agcatttact gctggattta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcacttagac    240
cccagggact taatcagcaa tatcaacgta tttgttctgg aactaaaggg atctgaaaca    300
acattcatgt gtgaatatgc tgatgagaca gcaaccattg tagaatttct gaacagatgg    360 attacctttta gtcaaagcat catctcaaca ctgacttga                          399
```

<210> SEQ ID NO 126
<211> LENGTH: 399
<212> TYPE: DNA
<213> ORGANISM: Artificial Sequence
<220> FEATURE:
<223> OTHER INFORMATION: IL-2 analog 20

<400> SEQUENCE: 126

```
cctacttcaa gttctacaaa gaaaacacag ctacaactgg agcatttact gctggattta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcacttaaga    240
cccagggacg tagtcagcaa tatcaacgta tttgttctgg aactaaaggg atctgaaaca    300
acattcatgt gtgaatatgc tgatgagaca gcaaccattg tagaatttct gaacagatgg    360 attacctttta gtcaaagcat catctcaaca ctgacttga                          399
```

<210> SEQ ID NO 127
<211> LENGTH: 399
<212> TYPE: DNA
<213> ORGANISM: Artificial Sequence
<220> FEATURE:
<223> OTHER INFORMATION: IL-2 analog 21

<400> SEQUENCE: 127

```
cctacttcaa gttctacaaa gaaaacacag ctacaactgg agcatttact gctggattta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcactttgac    240
cccagggacg tagtcagcaa tatcaacgta tttgttctgg aactaaaggg atctgaaaca    300
```

-continued

```
acattcatgt gtgaatatgc tgatgagaca gcaaccattg tagaatttct gaacagatgg      360
attaccttta gtcaaagcat catctcaaca ctgacttga                              399

<210> SEQ ID NO 128
<211> LENGTH: 399
<212> TYPE: DNA
<213> ORGANISM: Artificial Sequence
<220> FEATURE:
<223> OTHER INFORMATION: IL-2 analog 22

<400> SEQUENCE: 128
cctacttcaa gttctacaaa gaaaacacag gtacaactgg agcatttact gctggattta       60
cagatgattt tgaatggaat taataattac aagaatccca aactcaccgc gatgctcaca      120
aagaagtttt acatgcccaa gaaggccaca gaactgaaac atcttcagtg tctagaagaa      180
gaactcaaac ctctggagga agtgctaaat ttagctcaaa gcaaaaactt tcacttaaga      240
cccagggact taatcagcaa tatcaacgta atagttctgg aactaaaggg atctgaaaca      300
acattcatgt gtgaatatgc tgatgagaca gcaaccattg tagaatttct gaacagatgg      360
attaccttta gtcaaagcat catctcaaca ctgacttga                              399

<210> SEQ ID NO 129
<211> LENGTH: 399
<212> TYPE: DNA
<213> ORGANISM: Artificial Sequence
<220> FEATURE:
<223> OTHER INFORMATION: IL-2 analog 23

<400> SEQUENCE: 129
cctacttcaa gttctacaaa gaaaacacag tttcaactgg agcatttact gctggattta       60
cagatgattt tgaatggaat taataattac aagaatccca aactcaccgc gatgctcaca      120
aagaagtttt acatgcccaa gaaggccaca gaactgaaac atcttcagtg tctagaagaa      180
gaactcaaac ctctggagga agtgctaaat ttagctcaaa gcaaaaactt tcacttaaga      240
cccagggact taatcagcaa tatcaacgta atagttctgg aactaaaggg atctgaaaca      300
acattcatgt gtgaatatgc tgatgagaca gcaaccattg tagaatttct gaacagatgg      360
attaccttta gtcaaagcat catctcaaca ctgacttga                              399

<210> SEQ ID NO 130
<211> LENGTH: 399
<212> TYPE: DNA
<213> ORGANISM: Artificial Sequence
<220> FEATURE:
<223> OTHER INFORMATION: IL-2 analog 24

<400> SEQUENCE: 130
cctacttcaa gttctacaaa gaaaacacag ctacaactgg agcatttact ggtggattta       60
cagatgattt tgaatggaat taataattac aagaatccca aactcaccgc gatgctcaca      120
aagaagtttt acatgcccaa gaaggccaca gaactgaaac atcttcagtg tctagaagaa      180
gaactcaaac ctctggagga agtgctaaat ttagctcaaa gcaaaaactt tcacttaaga      240
cccagggact taatcagcaa tatcaacgta atagttctgg aactaaaggg atctgaaaca      300
acattcatgt gtgaatatgc tgatgagaca gcaaccattg tagaatttct gaacagatgg      360
attaccttta gtcaaagcat catctcaaca ctgacttga                              399

<210> SEQ ID NO 131
```

-continued

```
<211> LENGTH: 399
<212> TYPE: DNA
<213> ORGANISM: Artificial Sequence
<220> FEATURE:
<223> OTHER INFORMATION: IL-2 analog 25

<400> SEQUENCE: 131
cctacttcaa gttctacaaa gaaaacacag ctacaactgg agcatttact gttcgattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcacttaaga     240
cccagggact taatcagcaa tatcaacgta atagttctgg aactaaaggg atctgaaaca     300
acattcatgt gtgaatatgc tgatgagaca gcaaccattg tagaatttct gaacagatgg     360 attacctttta gtcaaagcat catctcaaca ctgacttga                          399

<210> SEQ ID NO 132
<211> LENGTH: 399
<212> TYPE: DNA
<213> ORGANISM: Artificial Sequence
<220> FEATURE:
<223> OTHER INFORMATION: IL-2 analog 26

<400> SEQUENCE: 132
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcacttaaga     240
cccagggact taatcagcaa tttcaacgta atagttctgg aactaaaggg atctgaaaca     300
acattcatgt gtgaatatgc tgatgagaca gcaaccattg tagaatttct gaacagatgg     360 attacctttta gtcaaagcat catctcaaca ctgacttga                          399

<210> SEQ ID NO 133
<211> LENGTH: 399
<212> TYPE: DNA
<213> ORGANISM: Artificial Sequence
<220> FEATURE:
<223> OTHER INFORMATION: IL-2 analog 27

<400> SEQUENCE: 133
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcacttaaga     240
cccagggact taatcagcaa tatcaacttt atagttctgg aactaaaggg atctgaaaca     300
acattcatgt gtgaatatgc tgatgagaca gcaaccattg tagaatttct gaacagatgg     360 attacctttta gtcaaagcat catctcaaca ctgacttga                          399

<210> SEQ ID NO 134
<211> LENGTH: 399
<212> TYPE: DNA
<213> ORGANISM: Artificial Sequence
<220> FEATURE:
<223> OTHER INFORMATION: IL-2 analog 28

<400> SEQUENCE: 134
```

-continued

```
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcacttaaga     240
cccagggact aatcagcaa tatcaacgta atagttgtgg aactaaaggg atctgaaaca      300
acattcatgt gtgaatatgc tgatgagaca gcaaccattg tagaatttct gaacagatgg     360 attacctta gtcaaagcat catctcaaca ctgacttga                             399
```

<210> SEQ ID NO 135
<211> LENGTH: 399
<212> TYPE: DNA
<213> ORGANISM: Artificial Sequence
<220> FEATURE:
<223> OTHER INFORMATION: IL-2 analog 29

<400> SEQUENCE: 135

```
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcacttaaga     240
cccagggact aatcagcaa tatcaacgta atagttctgg aactaaaggg atctgaaaca      300
acattcatgt gtgaatatgc tgatgagaca gcaaccattg tagaatttct gaacagatgg     360 attacctta gtacaagcat catctcaaca ctgacttga                             399
```

<210> SEQ ID NO 136
<211> LENGTH: 399
<212> TYPE: DNA
<213> ORGANISM: Artificial Sequence
<220> FEATURE:
<223> OTHER INFORMATION: IL-2 analog 30

<400> SEQUENCE: 136

```
cctacttcaa gttctacaaa gaaaacacag ctacaactgg agcatttact gctggattta      60
cagatgattt tgaatggaat taataattac aagaatccca aactcaccgc gatgctcaca     120
tttaagtttt acatgcccaa gaaggccaca gaactgaaac atcttcagtg tctagaagaa     180
gaactcaaac ctctggagga agtgctaaat ttagctcaaa gcaaaaactt tcacttagac     240
cccagggact aatcagcaa tatcaacgta tttgttctgg aactaaaggg atctgaaaca      300
acattcatgt gtgaatatgc tgatgagaca gcaaccattg tagaatttct gaacagatgg     360 attacctta gtcaaagcat catctcaaca ctgacttga                             399
```

<210> SEQ ID NO 137
<211> LENGTH: 399
<212> TYPE: DNA
<213> ORGANISM: Artificial Sequence
<220> FEATURE:
<223> OTHER INFORMATION: IL-2 analog 31

<400> SEQUENCE: 137

```
cctacttcaa gttctacaaa gaaaacacag ctacaactgg agcatttact gctggattta      60
cagatgattt tgaatggaat taataattac aagaatccca aactcaccgc gatgctcaca     120
tttaagtttt acatgcccaa gaaggccaca gaactgaaac atcttcagtg tctagaagaa     180
```

-continued

```
gaactcaaac ctctggagga agtgctaaat ttagctcaaa gcaaaaactt tcacttaaga      240
cccagggagt taatcagcaa tatcaacgta atagttctgg aactaaaggg atctgaaaca      300
acattcatgt gtgaatatgc tgatgagaca gcaaccattg tagaatttct gaacagatgg      360 attacctttta gtcaaagcat catctcaaca ctgacttga                           399

<210> SEQ ID NO 138
<211> LENGTH: 399
<212> TYPE: DNA
<213> ORGANISM: Artificial Sequence
<220> FEATURE:
<223> OTHER INFORMATION: IL-2 analog 32

<400> SEQUENCE: 138
cctacttcaa gttctacaaa gaaaacacag ctacaactgg agcatttact gctggattta       60
cagatgattt tgaatggaat taataattac aagaatccca aactcaccgc gatgctcaca      120
tttaagtttt acatgcccaa gaaggccaca gaactgaaac atcttcagtg tctagaagaa      180
gaactcaaac ctctggagga agtgctaaat ttagctcaaa gcaaaaactt tcacttagac      240
cccagggagt taatcagcaa tatcaacgta tttgttctgg aactaaaggg atctgaaaca      300
acattcatgt gtgaatatgc tgatgagaca gcaaccattg tagaatttct gaacagatgg      360 attacctttta gtcaaagcat catctcaaca ctgacttga                           399

<210> SEQ ID NO 139
<211> LENGTH: 399
<212> TYPE: DNA
<213> ORGANISM: Artificial Sequence
<220> FEATURE:
<223> OTHER INFORMATION: IL-2 analog 33

<400> SEQUENCE: 139
cctacttcaa gttctacaaa gaaaacacag ctacaactgg agcatttact gctggattta       60
cagatgattt tgaatggaat taataattac aagaatccca aactcaccgc gatgctcaca      120
tttaagtttt acatgcccaa gaaggccaca gaactgaaac atcttcagtg tctagaagaa      180
gaactcaaac ctctggagga agtgctaaat ttagctcaaa gcaaaaactt tcactttaga      240
cccagggact taatcagcaa tatcaacgta atagttctgg aactaaaggg atctgaaaca      300
acattcatgt gtgaatatgc tgatgagaca gcaaccattg tagaatttct gaacagatgg      360 attacctttta gtcaaagcat catctcaaca ctgacttga                           399

<210> SEQ ID NO 140
<211> LENGTH: 399
<212> TYPE: DNA
<213> ORGANISM: Artificial Sequence
<220> FEATURE:
<223> OTHER INFORMATION: IL-2 analog 34

<400> SEQUENCE: 140
cctacttcaa gttctacaaa gaaaacacag ctacaactgg agcatttact gctggattta       60
cagatgattt tgaatggaat taataattac aagaatccca aactcaccgc gatgctcaca      120
tttaagtttt acatgcccaa gaaggccaca gaactgaaac atcttcagtg tctagaagaa      180
gaactcaaac ctctggagga agtgctaaat ttagctcaaa gcaaaaactt tcactttaga      240
cccagggagt taatcagcaa tatcaacgta atagttctgg aactaaaggg atctgaaaca      300
acattcatgt gtgaatatgc tgatgagaca gcaaccattg tagaatttct gaacagatgg      360 attacctttta gtcaaagcat catctcaaca ctgacttga                           399
```

```
<210> SEQ ID NO 141
<211> LENGTH: 399
<212> TYPE: DNA
<213> ORGANISM: Artificial Sequence
<220> FEATURE:
<223> OTHER INFORMATION: IL-2 analog 35

<400> SEQUENCE: 141
cctacttcaa gttctacaaa gaaaacacag ctacaactgg agcatttact gctggattta        60
cagatgattt tgaatggaat taataattac aagaatccca aactcaccgc gatgctcaca       120
tttaagtttt acatgcccaa gaaggccaca gaactgaaac atcttcagtg tctagaagaa       180
gaactcaaac ctctggagga agtgctaaat ttagctcaaa gcaaaaactt tcacttaaga       240
cccagggact taatcagcaa tatcaacgta atagttttcg aatttaaggg atctgaaaca       300
acattcatgt gtgaatatgc tgatgagaca gcaaccattg tagaatttct gaacagatgg       360 attacccttta gtcaaagcat catctcaaca ctgacttga                            399

<210> SEQ ID NO 142
<211> LENGTH: 399
<212> TYPE: DNA
<213> ORGANISM: Artificial Sequence
<220> FEATURE:
<223> OTHER INFORMATION: IL-2 analog 36

<400> SEQUENCE: 142
cctacttcaa gttctacaaa gaaaacacag ctacaactgg agcatttact gctggattta        60
cagatgattt tgaatggaat taataattac aagaatccca aactcaccgc gatgctcaca       120
tttaagtttt acatgcccaa gaaggccaca gaactgaaac atcttcagtg tctagaagaa       180
gaactcaaac ctctggagga agtgctaaat ttagctcaaa gcaaaaactt tcacttaaga       240
cccagggact taatcagcaa tatcaacgta atagttttcg aagtaaaggg atctgaaaca       300
acattcatgt gtgaatatgc tgatgagaca gcaaccattg tagaatttct gaacagatgg       360 attacccttta gtcaaagcat catctcaaca ctgacttga                            399

<210> SEQ ID NO 143
<211> LENGTH: 399
<212> TYPE: DNA
<213> ORGANISM: Artificial Sequence
<220> FEATURE:
<223> OTHER INFORMATION: IL-2 analog 37

<400> SEQUENCE: 143
cctacttcaa gttctacaaa gaaaacacag ctacaactgg agcatttact gctggattta        60
cagatgattt tgaatggaat taataattac aagaatccca aactcaccgc gatgctcaca       120
aagaagtttt acatgcccaa gaaggccaca gaactgaaac atcttcagtg tctagaagaa       180
gaactcaaac ctctggagga agtgctaaat ttagctcaaa gcaaaaactt tcacttagac       240
cccagggact taatcagcaa tatcaacgta ttagttctgg aactaaaggg atctgaaaca       300
acattcatgt gtgaatatgc tgatgagaca gcaaccattg tagaatttct gaacagatgg       360 attacccttta gtcaaagcat catctcaaca ctgacttga                            399

<210> SEQ ID NO 144
<211> LENGTH: 399
<212> TYPE: DNA
<213> ORGANISM: Artificial Sequence
<220> FEATURE:
```

<223> OTHER INFORMATION: IL-2 analog 38

<400> SEQUENCE: 144
cctacttcaa gttctacaaa gaaaacacag ctacaactgg agcatttact gctggattta          60
cagatgattt tgaatggaat taataattac aagaatccca aactcaccgc gatgctcaca         120
aagaagtttt acatgcccaa gaaggccaca gaactgaaac atcttcagtg tctagaagaa         180
gaactcaaac ctctggagga agtgctaaat ttagctcaaa gcaaaaactt tcacttagac         240
cccagggact taatcagcaa tatcaacgta tttgtttttcg aatttaaggg atctgaaaca        300
acattcatgt gtgaatatgc tgatgagaca gcaaccattg tagaatttct gaacagatgg         360 attacctttta gtcaaagcat catctcaaca ctgacttga                               399

<210> SEQ ID NO 145
<211> LENGTH: 399
<212> TYPE: DNA
<213> ORGANISM: Artificial Sequence
<220> FEATURE:
<223> OTHER INFORMATION: IL-2 analog 39

<400> SEQUENCE: 145
cctacttcaa gttctacaaa gaaaacacag ctacaactgg agcatttact gctggattta          60
cagatgattt tgaatggaat taataattac aagaatccca aactcaccgc gatgctcaca         120
aagaagtttt acatgcccaa gaaggccaca gaactgaaac atcttcagtg tctagaagaa         180
gaactcaaac ctctggagga agtgctaaat ttagctcaaa gcaaaaactt tcacttagac         240
cccagggact taatcagcaa tatcaacgta tttgtttttcg aagtaaaggg atctgaaaca        300
acattcatgt gtgaatatgc tgatgagaca gcaaccattg tagaatttct gaacagatgg         360 attacctttta gtcaaagcat catctcaaca ctgacttga                               399

<210> SEQ ID NO 146
<211> LENGTH: 399
<212> TYPE: DNA
<213> ORGANISM: Artificial Sequence
<220> FEATURE:
<223> OTHER INFORMATION: IL-2 analog 40

<400> SEQUENCE: 146
cctacttcaa gttctacaaa gaaaacacag ctacaactgg agcatttact gctggattta          60
cagatgattt tgaatggaat taataattac aagaatccca aactcaccgc gatgctcaca         120
aagaagtttt acatgcccaa gaaggccaca gaactgaaac atcttcagtg tctagaagaa         180
gaactcaaac ctctggagga agtgctaaat ttagctcaaa gcaaaaactt tcacttagac         240
cccagggact taatcagcaa tatcaacgta tttgtttttcg aaattaaggg atctgaaaca        300
acattcatgt gtgaatatgc tgatgagaca gcaaccattg tagaatttct gaacagatgg         360 attacctttta gtcaaagcat catctcaaca ctgacttga                               399

<210> SEQ ID NO 147
<211> LENGTH: 399
<212> TYPE: DNA
<213> ORGANISM: Artificial Sequence
<220> FEATURE:
<223> OTHER INFORMATION: IL-2 analog 41

<400> SEQUENCE: 147
cctacttcaa gttctacaaa gaaaacacag ctacaactgg agcatttact gctggattta          60
cagatgattt tgaatggaat taataattac aagaatccca aactcaccag gatgctcaca         120

-continued

```
tttaagtttt acatgcccaa gaaggccaca gaactgaaac atcttcagtg tctagaagaa    180
gaactcaaac ctctggagga agtgctaaat ttagctcaaa gcaaaaactt tcactttgac    240
cccagggacg tagtcagcaa tatcaacgta tttgttctgg aactaaaggg atctgaaaca    300
acattcatgt gtgaatatgc tgatgagaca gcaaccattg tagaatttct gaacagatgg    360 attacctttta gtcaaagcat catctcaaca ctgacttga                          399

<210> SEQ ID NO 148
<211> LENGTH: 399
<212> TYPE: DNA
<213> ORGANISM: Artificial Sequence
<220> FEATURE:
<223> OTHER INFORMATION: IL-2 analog 42

<400> SEQUENCE: 148
cctacttcaa gttctacaaa gaaaacacag ctacaactgg agcatttact gctggattta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcacttagaa    240
cccagggact taatcagcaa tatcaacgta tttgttctgg aactaaaggg atctgaaaca    300
acattcatgt gtgaatatgc tgatgagaca gcaaccattg tagaatttct gaacagatgg    360 attacctttta gtcaaagcat catctcaaca ctgacttga                          399

<210> SEQ ID NO 149
<211> LENGTH: 399
<212> TYPE: DNA
<213> ORGANISM: Artificial Sequence
<220> FEATURE:
<223> OTHER INFORMATION: IL-2 analog 43

<400> SEQUENCE: 149
cctacttcaa gttctacaaa gaaaacacag ctacaactgg agcatttact gctggattta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcacttagac    240
cccagggact taatcagcaa tatcaacgta ttagttctgg aactaaaggg atctgaaaca    300
acattcatgt gtgaatatgc tgatgagaca gcaaccattg tagaatttct gaacagatgg    360 attacctttta gtcaaagcat catctcaaca ctgacttga                          399

<210> SEQ ID NO 150
<211> LENGTH: 399
<212> TYPE: DNA
<213> ORGANISM: Artificial Sequence
<220> FEATURE:
<223> OTHER INFORMATION: IL-2 analog 44

<400> SEQUENCE: 150
cctacttcaa gttctacaaa gaaaacacag ctacaactgg agcatttact gctggattta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcacttagac    240
cccagggtct taatcagcaa tatcaacgta tttgttctgg aactaaaggg atctgaaaca    300
```

-continued

```
acattcatgt gtgaatatgc tgatgagaca gcaaccattg tagaatttct gaacagatgg    360
attaccttta gtcaaagcat catctcaaca ctgacttga                           399

<210> SEQ ID NO 151
<211> LENGTH: 399
<212> TYPE: DNA
<213> ORGANISM: Artificial Sequence
<220> FEATURE:
<223> OTHER INFORMATION: IL-2 analog 45

<400> SEQUENCE: 151
cctacttcaa gttctacaaa gaaaacacag ctacaactgg agcatttact gctggattta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcacttagac    240
cccaggttct taatcagcaa tatcaacgta tttgttctgg aactaaaggg atctgaaaca    300
acattcatgt gtgaatatgc tgatgagaca gcaaccattg tagaatttct gaacagatgg    360
attacctttg gtcaaagcat catctcaaca ctgacttga                           399

<210> SEQ ID NO 152
<211> LENGTH: 399
<212> TYPE: DNA
<213> ORGANISM: Artificial Sequence
<220> FEATURE:
<223> OTHER INFORMATION: IL-2 analog 46

<400> SEQUENCE: 152
cctacttcaa gttctacaaa gaaaacacag ctacaactgg agcatttact gctggtttta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcacttagac    240
cccagggact taatcagcaa tatcaacgta tttgttctgg aactaaaggg atctgaaaca    300
acattcatgt gtgaatatgc tgatgagaca gcaaccattg tagaatttct gaacagatgg    360
attacctttg gtcaaagcat catctcaaca ctgacttga                           399

<210> SEQ ID NO 153
<211> LENGTH: 399
<212> TYPE: DNA
<213> ORGANISM: Artificial Sequence
<220> FEATURE:
<223> OTHER INFORMATION: IL-2 analog 47

<400> SEQUENCE: 153
cctacttcaa gttctacaaa gaaaacacag ctacaactgg agcatttact gctgttttta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcacttagac    240
cccagggact taatcagcaa tatcaacgta tttgttctgg aactaaaggg atctgaaaca    300
acattcatgt gtgaatatgc tgatgagaca gcaaccattg tagaatttct gaacagatgg    360
attacctttg gtcaaagcat catctcaaca ctgacttga                           399

<210> SEQ ID NO 154
<211> LENGTH: 399
```

<212> TYPE: DNA
<213> ORGANISM: Artificial Sequence
<220> FEATURE:
<223> OTHER INFORMATION: IL-2 analog 48

<400> SEQUENCE: 154
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcacttagac     240
cccagggact taatcagcgt tatcaacgta tttgttctgg aactaaaggg atctgaaaca     300
acattcatgt gtgaatatgc tgatgagaca gcaaccattg tagaatttct gaacagatgg     360 attacctttta gtcaaagcat catctcaaca ctgacttga                          399

<210> SEQ ID NO 155
<211> LENGTH: 399
<212> TYPE: DNA
<213> ORGANISM: Artificial Sequence
<220> FEATURE:
<223> OTHER INFORMATION: IL-2 analog 49

<400> SEQUENCE: 155
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcacttagac     240
cccagggact taatcagctt tatcaacgta tttgttctgg aactaaaggg atctgaaaca     300
acattcatgt gtgaatatgc tgatgagaca gcaaccattg tagaatttct gaacagatgg     360 attacctttta gtcaaagcat catctcaaca ctgacttga                          399

<210> SEQ ID NO 156
<211> LENGTH: 399
<212> TYPE: DNA
<213> ORGANISM: Artificial Sequence
<220> FEATURE:
<223> OTHER INFORMATION: IL-2 analog 50

<400> SEQUENCE: 156
cctacttcaa gttctacaaa gaaaacacag ctacaactgg agcatttact gctggattta      60
cagatgattt tgaatggaat taataattac aagaatccca aactcaccag gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcactttgac     240
cccagggacg tagtcagcaa tatcaacgta tttgttctgg aactaaaggg atctgaaaca     300
acattcatgt gtgaatatgc tgatgagaca gcaaccattg tagaatttct gaacagatgg     360 attacctttta gtcaaagcat catctcaaca ctgacttga                          399

<210> SEQ ID NO 157
<211> LENGTH: 399
<212> TYPE: DNA
<213> ORGANISM: Artificial Sequence
<220> FEATURE:
<223> OTHER INFORMATION: IL-2 analog 51

<400> SEQUENCE: 157

-continued

```
cctacttcaa gttctacaaa gaaaacacag ctacaactgg agcatttact gctggattta      60
cagatgattt tgaatggaat taataattac aagaatccca aactcaccag gatgctcaca     120
tttaagtttt acatgcccaa gaaggccaca gaactgaaac atcttcagtg tctagaacag     180
gaactcaaac ctctggagga agtgctaaat ttagctcaaa gcaaaaactt tcacttagac     240
cccagggact taatcagcaa tatcaacgta tttgttctgg aactaaaggg atctgaaaca     300
acattcatgt gtgaatatgc tgatgagaca gcaaccattg tagaatttct gaacagatgg     360
attaccttta gtcaaagcat catctcaaca ctgacttga                            399
```

```
<210> SEQ ID NO 158
<211> LENGTH: 399
<212> TYPE: DNA
<213> ORGANISM: Artificial Sequence
<220> FEATURE:
<223> OTHER INFORMATION: IL-2 analog 52

<400> SEQUENCE: 158
```

```
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcactttgac     240
cccagggact taatcagcaa tatcaacgta tttgttctgg aactaaaggg atctgaaaca     300
acattcatgt gtgaatatgc tgatgagaca gcaaccattg tagaatttct gaacagatgg     360
attaccttta gtcaaagcat catctcaaca ctgacttga                            399
```

```
<210> SEQ ID NO 159
<211> LENGTH: 399
<212> TYPE: DNA
<213> ORGANISM: Artificial Sequence
<220> FEATURE:
<223> OTHER INFORMATION: IL-2 analog 53

<400> SEQUENCE: 159
```

```
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcactttgac     240
cccagggagt taatcagcaa tatcaacgta tttgttctgg aactaaaggg atctgaaaca     300
acattcatgt gtgaatatgc tgatgagaca gcaaccattg tagaatttct gaacagatgg     360
attaccttta gtcaaagcat catctcaaca ctgacttga                            399
```

```
<210> SEQ ID NO 160
<211> LENGTH: 399
<212> TYPE: DNA
<213> ORGANISM: Artificial Sequence
<220> FEATURE:
<223> OTHER INFORMATION: IL-2 analog 54

<400> SEQUENCE: 160
```

```
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaca gcaaaaactt tcacttagac     240
```

-continued

```
cccagggact taatcagcaa tatcaacgta tttgttctgg aactaaaggg atctgaaaca    300
acattcatgt gtgaatatgc tgatgagaca gcaaccattg tagaatttct gaacagatgg    360 attacctttta gtcaaagcat catctcaaca ctgacttga                          399
```

```
<210> SEQ ID NO 161
<211> LENGTH: 399
<212> TYPE: DNA
<213> ORGANISM: Artificial Sequence
<220> FEATURE:
<223> OTHER INFORMATION: IL-2 analog 55

<400> SEQUENCE: 161
cctacttcaa gttctacaaa gaaaacacag ctacaactgg agcatttact gctggattta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaca gcaaaaactt tcactttgac    240
cccagggact taatcagcaa tatcaacgta tttgttctgg aactaaaggg atctgaaaca    300
acattcatgt gtgaatatgc tgatgagaca gcaaccattg tagaatttct gaacagatgg    360 attacctttta gtcaaagcat catctcaaca ctgacttga                          399
```

```
<210> SEQ ID NO 162
<211> LENGTH: 399
<212> TYPE: DNA
<213> ORGANISM: Artificial Sequence
<220> FEATURE:
<223> OTHER INFORMATION: IL-2 analog 56

<400> SEQUENCE: 162
cctacttcaa gttctacaaa gaaaacacag ctacaactgg agcatttact gctggattta     60
cagatgattt tgaatggaat taataattac aagaatccca aactcaccgc gatgctcaca    120
aagaagtttg ccatgcccaa gaaggccaca gaactgaaac atcttcagtg tctagaagaa    180
gaactcaaac ctctggagga agtgctaaat ttagctcaca gcaaaaactt tcacttagac    240
cccagggact taatcagcaa tatcaacgta tttgttctgg aactaaaggg atctgaaaca    300
acattcatgt gtgaatatgc tgatgagaca gcaaccattg tagaatttct gaacagatgg    360 attacctttta gtcaaagcat catctcaaca ctgacttga                          399
```

```
<210> SEQ ID NO 163
<211> LENGTH: 399
<212> TYPE: DNA
<213> ORGANISM: Artificial Sequence
<220> FEATURE:
<223> OTHER INFORMATION: IL-2 analog 57

<400> SEQUENCE: 163
cctacttcaa gttctacaaa gaaaacacag ctacaactgg agcatttact gctggattta     60
cagatgattt tgaatggaat taataattac aagaatccca aactcaccgc gatgctcaca    120
aagaagtttg ccatgcccaa gaaggccaca gaactgaaac atcttcagtg tctagaagaa    180
gaactcaaac ctctggagga agtgctaaat ttagctcaca gcaaaaactt tcactttgac    240
cccagggact taatcagcaa tatcaacgta tttgttctgg aactaaaggg atctgaaaca    300
acattcatgt gtgaatatgc tgatgagaca gcaaccattg tagaatttct gaacagatgg    360 attacctttta gtcaaagcat catctcaaca ctgacttga                          399
```

<210> SEQ ID NO 164
<211> LENGTH: 399
<212> TYPE: DNA
<213> ORGANISM: Artificial Sequence
<220> FEATURE:
<223> OTHER INFORMATION: IL-2 analog 58

<400> SEQUENCE: 164
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcactttgac     240
cccagggacg ctgccagcaa tatcaacgta tttgttctgg aactaaaggg atctgaaaca     300
acattcatgt gtgaatatgc tgatgagaca gcaaccattg tagaatttct gaacagatgg     360 attacctttta gtcaaagcat catctcaaca ctgacttga                          399

<210> SEQ ID NO 165
<211> LENGTH: 399
<212> TYPE: DNA
<213> ORGANISM: Artificial Sequence
<220> FEATURE:
<223> OTHER INFORMATION: IL-2 analog 59

<400> SEQUENCE: 165
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcactttgac     240
cccagggacg ctgccagcaa tatcaacgta tatgttctgg aactaaaggg atctgaaaca     300
acattcatgt gtgaatatgc tgatgagaca gcaaccattg tagaatttct gaacagatgg     360 attacctttta gtcaaagcat catctcaaca ctgacttga                          399

<210> SEQ ID NO 166
<211> LENGTH: 399
<212> TYPE: DNA
<213> ORGANISM: Artificial Sequence
<220> FEATURE:
<223> OTHER INFORMATION: IL-2 analog 60

<400> SEQUENCE: 166
cctacttcaa gttctacaaa gaaaacacag ctacaactgg agcatttact gctggattta      60
cagatgattt tgaatggaat taataattac aagaatccca aactcaccgc gatgctcaca     120
aagaagtttg ccatgcccaa gaaggccaca gaactgaaac atcttcagtg tctagaagaa     180
gaactcaaac ctctggagga agtgctaaat ttagctcaaa gcaaaaactt tcactataga     240
cccagggacg ctgccagcaa tatcaacgta tatgttctgg aactaaaggg atctgaaaca     300
acattcatgt gtgaatatgc tgatgagaca gcaaccattg tagaatttct gaacagatgg     360 attacctttta gtcaaagcat catctcaaca ctgacttga                          399

<210> SEQ ID NO 167
<211> LENGTH: 399
<212> TYPE: DNA
<213> ORGANISM: Artificial Sequence
<220> FEATURE:
<223> OTHER INFORMATION: IL-2 analog 61

-continued

<400> SEQUENCE: 167
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcactatgac   240
cccagggacg tgttagcaa tatcaacgta tatgttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                         399

<210> SEQ ID NO 168
<211> LENGTH: 399
<212> TYPE: DNA
<213> ORGANISM: Artificial Sequence
<220> FEATURE:
<223> OTHER INFORMATION: IL-2 analog 62

<400> SEQUENCE: 168
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcactgggaa   240
cccagggacg gagccagcaa tatcaacgta tttgttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                         399

<210> SEQ ID NO 169
<211> LENGTH: 399
<212> TYPE: DNA
<213> ORGANISM: Artificial Sequence
<220> FEATURE:
<223> OTHER INFORMATION: IL-2 analog 63

<400> SEQUENCE: 169
cctacttcaa gttctacaaa gaaaacacag ctacaactgg agcatttact gctggattta    60
cagatgattt tgaatggaat taataattac aagaatccca aactcaccgc gatgctcaca   120
aagaagtttt acatgcccaa gaaggccaca gaactgaaac atcttcagtg tctagaagaa   180
gaactcaaac ctctggagga agtgctaaat ttagctcaaa gcaaaaactt tcacgacgaa   240
cccagggaca caggcagcaa tatcaacgta tttgttctgg aactaaaggg atctgaaaca   300
acattcatgt gtgaatatgc tgatgagaca gcaaccattg tagaatttct gaacagatgg   360
attaccttta gtcaaagcat catctcaaca ctgacttga                         399

<210> SEQ ID NO 170
<211> LENGTH: 399
<212> TYPE: DNA
<213> ORGANISM: Artificial Sequence
<220> FEATURE:
<223> OTHER INFORMATION: IL-2 analog 64

<400> SEQUENCE: 170
cctacttcaa gttctacaaa gaaaacacag ctacaactgg agcatttact gctggattta    60
cagatgattt tgaatggaat taataattac aagaatccca aactcaccgc gatgctcaca   120

-continued

```
aagaagtttt acatgcccaa gaaggccaca gaactgaaac atcttcagtg tctagaagaa      180
gaactcaaac ctctggagga agtgctaaat ttagctcaaa gcaaaaactt tcactacaac      240
cccagggacg tagtcagcaa tatcaacgta tttgttctgg aactaaaggg atctgaaaca      300
acattcatgt gtgaatatgc tgatgagaca gcaaccattg tagaatttct gaacagatgg      360 attacctttta gtcaaagcat catctcaaca ctgacttga                           399
```

<210> SEQ ID NO 171
<211> LENGTH: 399
<212> TYPE: DNA
<213> ORGANISM: Artificial Sequence
<220> FEATURE:
<223> OTHER INFORMATION: IL-2 analog 65

<400> SEQUENCE: 171

```
cctacttcaa gttctacaaa gaaaacacag ctacaactgg agcatttact gctggattta       60
cagatgattt tgaatggaat taataattac aagaatccca aactcaccgc gatgctcaca      120
aagaagtttt acatgcccaa gaaggccaca gaactgaaac atcttcagtg tctagaagaa      180
gaactcaaac ctctggagga agtgctaaat ttagctcaaa gcaaaaactt tcactacgaa      240
cccagggacg tagtcagcaa tatcaacgta tttgttctgg aactaaaggg atctgaaaca      300
acattcatgt gtgaatatgc tgatgagaca gcaaccattg tagaatttct gaacagatgg      360 attacctttta gtcaaagcat catctcaaca ctgacttga                           399
```

<210> SEQ ID NO 172
<211> LENGTH: 399
<212> TYPE: DNA
<213> ORGANISM: Artificial Sequence
<220> FEATURE:
<223> OTHER INFORMATION: IL-2 analog 66

<400> SEQUENCE: 172

```
cctacttcaa gttctacaaa gaaaacacag ctacaactgg agcatttact gctggattta       60
cagatgattt tgaatggaat taataattac aagaatccca aactcaccgc gatgctcaca      120
aagaagtttt acatgcccaa gaaggccaca gaactgaaac atcttcagtg tctagaagaa      180
gaactcaaac ctctggagga agtgctaaat ttagctcaaa gcaaaaactt tcacttcgaa      240
cccagggact tcgtcagcaa tatcaacgta tttgttctgg aactaaaggg atctgaaaca      300
acattcatgt gtgaatatgc tgatgagaca gcaaccattg tagaatttct gaacagatgg      360 attacctttta gtcaaagcat catctcaaca ctgacttga                           399
```

<210> SEQ ID NO 173
<211> LENGTH: 399
<212> TYPE: DNA
<213> ORGANISM: Artificial Sequence
<220> FEATURE:
<223> OTHER INFORMATION: IL-2 analog 67

<400> SEQUENCE: 173

```
cctacttcaa gttctacaaa gaaaacacag ctacaactgg agcatttact gctggattta       60
cagatgattt tgaatggaat taataattac aagaatccca aactcaccgc gatgctcaca      120
aagaagtttt acatgcccaa gaaggccaca gaactgaaac atcttcagtg tctagaagaa      180
gaactcaaac ctctggagga agtgctaaat ttagctcaaa gcaaaaactt tcactatgac      240
cccagggact tcgtcagcaa tatcaacgta tgggttctgg acctaaaggg atctgaaaca      300
acattcatgt gtgaatatgc tgatgagaca gcaaccattg tagaatttct gaacagatgg      360
```

-continued

```
attacctttta gtcaaagcat catctcaaca ctgacttga                       399

<210> SEQ ID NO 174
<211> LENGTH: 399
<212> TYPE: DNA
<213> ORGANISM: Artificial Sequence
<220> FEATURE:
<223> OTHER INFORMATION: IL-2 analog 68

<400> SEQUENCE: 174
cctacttcaa gttctacaaa gaaaacacag ctacaactgg agcatttact gctggattta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcacttcgaa    240
cccagggaca tagtcagcaa tatcaacgaa ttcgttctgg aactaaaggg atctgaaaca    300
acattcatgt gtgaatatgc tgatgagaca gcaaccattg tagaatttct gaacagatgg    360 attacctttta gtcaaagcat catctcaaca ctgacttga                       399

<210> SEQ ID NO 175
<211> LENGTH: 399
<212> TYPE: DNA
<213> ORGANISM: Artificial Sequence
<220> FEATURE:
<223> OTHER INFORMATION: IL-2 analog 69

<400> SEQUENCE: 175
cctacttcaa gttctacaaa gaaaacacag ctacaactgg agcatttact gctggattta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcactacgaa    240
cccagggact tcctcagcaa tatcaacgaa tgggttctgg acctaaaggg atctgaaaca    300
acattcatgt gtgaatatgc tgatgagaca gcaaccattg tagaatttct gaacagatgg    360 attacctttta gtcaaagcat catctcaaca ctgacttga                       399

<210> SEQ ID NO 176
<211> LENGTH: 399
<212> TYPE: DNA
<213> ORGANISM: Artificial Sequence
<220> FEATURE:
<223> OTHER INFORMATION: IL-2 analog 70

<400> SEQUENCE: 176
cctacttcaa gttctacaaa gaaaacacag ctacaactgg agcatttact gctggattta     60
cagatgattt tgaatggaat taataattac aagaatccca aactcaccgc gatgctcaca    120
aagaagtttt acatgcccaa gaaggccaca gaactgaaac atcttcagtg tctagaagaa    180
gaactcaaac ctctggagga agtgctaaat ttagctcaaa gcaaaaactt tcactatgac    240
cccagggacg tagtcagcaa tatcaacgta tttgttctgg aactaaaggg atctgaaaca    300
acattcatgt gtgaatatgc tgatgagaca gcaaccattg tagaatttct gaacagatgg    360 attacctttta gtcaaagcat catctcaaca ctgacttga                       399

<210> SEQ ID NO 177
<211> LENGTH: 399
<212> TYPE: DNA
```

-continued

<213> ORGANISM: Artificial Sequence
<220> FEATURE:
<223> OTHER INFORMATION: IL-2 analog 71

<400> SEQUENCE: 177

```
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcacttcgaa     240
cccagggacg tagtcagcaa tatcaacgta tttgttctgg aactaaaggg atctgaaaca     300
acattcatgt gtgaatatgc tgatgagaca gcaaccattg tagaatttct gaacagatgg     360 attacctttta gtcaaagcat catctcaaca ctgacttga                          399
```

<210> SEQ ID NO 178
<211> LENGTH: 399
<212> TYPE: DNA
<213> ORGANISM: Artificial Sequence
<220> FEATURE:
<223> OTHER INFORMATION: IL-2 analog 72

<400> SEQUENCE: 178

```
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcactttgac     240
cccagggacg taggcagcaa tatcaacgta tttgttctgg aactaaaggg atctgaaaca     300
acattcatgt gtgaatatgc tgatgagaca gcaaccattg tagaatttct gaacagatgg     360 attacctttta gtcaaagcat catctcaaca ctgacttga                          399
```

<210> SEQ ID NO 179
<211> LENGTH: 399
<212> TYPE: DNA
<213> ORGANISM: Artificial Sequence
<220> FEATURE:
<223> OTHER INFORMATION: IL-2 analog 73

<400> SEQUENCE: 179

```
cctacttcaa gttctacaaa gaaaacacag ctacaactgg agcatttact gctggattta      60
cagatgattt tgaatggaat taataattac aagaatccca aactcaccgc gatgctcaca     120
aagaagtttt acatgcccaa gaaggccaca gaactgaaac atcttcagtg tctagaagaa     180
gaactcaaac ctctggagga agtgctaaat ttagctcaaa gcaaaaactt tcactttgac     240
cccagggact gggtcagcaa tatcaacgta tttgttctgg aactaaaggg atctgaaaca     300
acattcatgt gtgaatatgc tgatgagaca gcaaccattg tagaatttct gaacagatgg     360 attacctttta gtcaaagcat catctcaaca ctgacttga                          399
```

<210> SEQ ID NO 180
<211> LENGTH: 399
<212> TYPE: DNA
<213> ORGANISM: Artificial Sequence
<220> FEATURE:
<223> OTHER INFORMATION: IL-2 analog 74

<400> SEQUENCE: 180

```
cctacttcaa gttctacaaa gaaaacacag ctacaactgg agcatttact gctggattta      60
```

```
cagatgattt tgaatggaat taataattac aagaatccca aactcaccga tatgctcaca      120
aagaagtttt acatgcccaa gaaggccaca gaactgaaac atcttcagtg tctagaagaa      180
gaactcaaac ctctggagga agtgctaaat ttagctcaaa gcaaaaactt tcactatgac      240
cccagggacg tagtcagcaa tatcaacgta tttgttctgg aactaaaggg atctgaaaca      300
acattcatgt gtgaatatgc tgatgagaca gcaaccattg tagaatttct gaacagatgg      360
attaccttta gtcaaagcat catctcaaca ctgacttga                             399

<210> SEQ ID NO 181
<211> LENGTH: 399
<212> TYPE: DNA
<213> ORGANISM: Artificial Sequence
<220> FEATURE:
<223> OTHER INFORMATION: IL-2 analog 75

<400> SEQUENCE: 181
cctacttcaa gttctacaaa gaaaacacag ctacaactgg agcatttact gctggattta       60
cagatgattt tgaatggaat taataattac aagaatccca aactcaccgc gatgctcaca      120
aagaagtttg ccatgcccaa gaaggccaca gaactgaaac atcttcagtg tctagaagaa      180
gaactcaaac ctctggagga agtgctaaat ttagctcaaa gcaaaaactt tcacttcgaa      240
cccagggacg tagtcagcaa tatcaacgta tttgttctgg aactaaaggg atctgaaaca      300
acattcatgt gtgaatatgc tgatgagaca gcaaccattg tagaatttct gaacagatgg      360
attaccttta gtcaaagcat catctcaaca ctgacttga                             399

<210> SEQ ID NO 182
<211> LENGTH: 399
<212> TYPE: DNA
<213> ORGANISM: Artificial Sequence
<220> FEATURE:
<223> OTHER INFORMATION: IL-2 analog 76

<400> SEQUENCE: 182
cctacttcaa gttctacaaa gaaaacacag ctacaactgg agcatttact gctggattta       60
cagatgattt tgaatggaat taataattac aagaatccca aactcaccgc gatgctcaca      120
aagcagtttt acatgcccaa gaaggccaca gaactgaaac atcttcagtg tctagaacgg      180
gaactcaaac ctctggagga agtgctaaat ttagctcaaa gcaaaaactt tcactttgac      240
cccagggacg taggcagcaa tatcaacgta tttgttctgg aactaaaggg atctgaaaca      300
acattcatgt gtgaatatgc tgatgagaca gcaaccattg tagaatttct gaacagatgg      360
attaccttta gtcaaagcat catctcaaca ctgacttga                             399

<210> SEQ ID NO 183
<211> LENGTH: 399
<212> TYPE: DNA
<213> ORGANISM: Artificial Sequence
<220> FEATURE:
<223> OTHER INFORMATION: IL-2 analog 77

<400> SEQUENCE: 183
cctacttcaa gttctacaaa gaaaacacag ctacaactgg agcatttact gctggattta       60
cagatgattt tgaatggaat taataattac aagaatccca aactcaccgc gatgctcaca      120
aaggagtttt acatgcccaa gaaggccaca gaactgaaac atcttcagtg tctagaacgg      180
gaactcaaac ctctggagga agtgctaaat ttagctcaaa gcaaaaactt tcactttgac      240
```

-continued

```
cccagggact gggtcagcaa tatcaacgta tttgttctgg aactaaaggg atctgaaaca      300
acattcatgt gtgaatatgc tgatgagaca gcaaccattg tagaatttct gaacagatgg      360 attacctta gtcaaagcat catctcaaca ctgacttga                               399

<210> SEQ ID NO 184
<211> LENGTH: 399
<212> TYPE: DNA
<213> ORGANISM: Artificial Sequence
<220> FEATURE:
<223> OTHER INFORMATION: IL-2 analog 78

<400> SEQUENCE: 184
cctacttcaa gttctacaaa gaaaacacag ctacaactgg agcatttact gctggattta       60
cagatgattt tgaatggaat taataattac aagaatcccg aactcaccgc gatgctcaca      120
aagaagtttt acatgcccaa gaaggccaca gaactgaaac atcttcagtg tctagaagaa      180
gaactcaaac ctctggagga agtgctaaat ttagctcaaa gcaaaaactt tcacttcgaa      240
cccagggacg tagtcagcaa tatcaacgta tttgttctgg aactaaaggg atctgaaaca      300
acattcatgt gtgaatatgc tgatgagaca gcaaccattg tagaatttct gaacagatgg      360 attacctta gtcaaagcat catctcaaca ctgacttga                               399

<210> SEQ ID NO 185
<211> LENGTH: 399
<212> TYPE: DNA
<213> ORGANISM: Artificial Sequence
<220> FEATURE:
<223> OTHER INFORMATION: IL-2 analog 79

<400> SEQUENCE: 185
cctacttcaa gttctacaaa gaaaacacag ctacaactgg agcatttact gctggattta       60
cagatgattt tgaatggaat taataattac aagaatcccg aactcaccgc gatgctcaca      120
aagaagtttt acatgcccaa gaaggccaca gaactgaaac atcttcagtg tctagaagaa      180
gaactcaaac ctctggagga agtgctaaat ttagctcaca gcaaaaactt tcacttcgaa      240
cccagggacg tagtcagcaa tatcaacgta tttgttctgg aactaaaggg atctgaaaca      300
acattcatgt gtgaatatgc tgatgagaca gcaaccattg tagaatttct gaacagatgg      360 attacctta gtcaaagcat catctcaaca ctgacttga                               399

<210> SEQ ID NO 186
<211> LENGTH: 399
<212> TYPE: DNA
<213> ORGANISM: Artificial Sequence
<220> FEATURE:
<223> OTHER INFORMATION: IL-2 analog 80

<400> SEQUENCE: 186
cctacttcaa gttctacaaa gaaaacacag ctacaactgg agcatttact gctggattta       60
cagatgattt tgaatggaat taataattac aagaatcccg aactcaccgc gatgctcaca      120
aagaagtttt acatgcccaa gaaggccaca gaactgaaac atcttcagtg tctagaagaa      180
gaactcaaac ctctggagga agtgctaaat ttagctcaca gcaaaaactt tcacttcgaa      240
ggcagggacg tagtcagcaa tatcaacgta tttgttctgg aactaaaggg atctgaaaca      300
acattcatgt gtgaatatgc tgatgagaca gcaaccattg tagaatttct gaacagatgg      360 attacctta gtcaaagcat catctcaaca ctgacttga                               399
```

-continued

```
<210> SEQ ID NO 187
<211> LENGTH: 399
<212> TYPE: DNA
<213> ORGANISM: Artificial Sequence
<220> FEATURE:
<223> OTHER INFORMATION: IL-2 analog 81

<400> SEQUENCE: 187
cctacttcaa gttctacaaa gaaaacacag ctacaactgg agcatttact gctggattta       60
cagatgattt tgaatggaat taataattac aagaatcccg aactcaccgc gatgctcaca      120
aagaagtttt acatgcccaa gaaggccaca gaactgaaac atcttcagtg tctagaagaa      180
gaactcaaac ctctggagga agtgctaaat ttagctcaca gcaaaaactt tcacttcgaa      240
gtcagggacg tagtcagcaa tatcaacgta tttgttctgg aactaaaggg atctgaaaca      300
acattcatgt gtgaatatgc tgatgagaca gcaaccattg tagaatttct gaacagatgg      360 attacctttta gtcaaagcat catctcaaca ctgacttga                            399

<210> SEQ ID NO 188
<211> LENGTH: 399
<212> TYPE: DNA
<213> ORGANISM: Artificial Sequence
<220> FEATURE:
<223> OTHER INFORMATION: IL-2 analog 82

<400> SEQUENCE: 188
cctacttcaa gttctacaaa gaaaacacag ctacaactgg agcatttacg tctggattta       60
gaaatgattt tgaatggaat taataattac aagaatccca aactcaccag gatgctcaca      120
tttaagtttt acatgcccaa gaaggccaca gaactgaaac atcttcagtg tctagaagaa      180
gaactcaaac ctctggagga agtgctaaat ttagctcaaa gcaaaaactt tcactttgac      240
cccagggacg aagtgagcaa tatcaacgta tttgttctgg aactaaaggg atctgaaaca      300
acattcatgt gtgaatatgc tgatgagaca gcaaccattg tagaatttct gaacagatgg      360 attacctttta gtcaaagcat catctcaaca ctgacttga                            399

<210> SEQ ID NO 189
<211> LENGTH: 399
<212> TYPE: DNA
<213> ORGANISM: Artificial Sequence
<220> FEATURE:
<223> OTHER INFORMATION: IL-2 analog 83

<400> SEQUENCE: 189
cctacttcaa gttctacaaa gaaaacacag ctacaactgg agcatttacg tcgtgattta       60
gaaatgattt tgaatggaat taataattac aagaatccca aactcaccag gatgctcaca      120
tttaagtttt acatgcccaa gaaggccaca gaactgaaac atcttcagtg tctagaagaa      180
gaactcaaac ctctggagga agtgctaaat ttagctcaaa gcaaaaactt tcactttgac      240
cccagggacg aagtgagcaa tatcaacgta tttgttctgg aactaaaggg atctgaaaca      300
acattcatgt gtgaatatgc tgatgagaca gcaaccattg tagaatttct gaacagatgg      360 attacctttta gtcaaagcat catctcaaca ctgacttga                            399

<210> SEQ ID NO 190
<211> LENGTH: 399
<212> TYPE: DNA
<213> ORGANISM: Artificial Sequence
<220> FEATURE:
<223> OTHER INFORMATION: IL-2 analog 84
```

-continued

```
<400> SEQUENCE: 190
cctacttcaa gttctacaaa gaaaacacag ctacaactgg agcatttacg tctggattta     60
gaaatgattt tgaatggaat taataattac aagaatccca aactcaccag gatgctcaca    120
tttaagtttt acatgcccaa gaaggccaca gaactgaaac atcttcagtg tctagaagaa    180
gaactcaaac ctctggagga agtgctaaat ttagctcaaa gcaaaaactt tcacgtggat    240
cccagggacg aagtgagcaa tatcaacgta tttgttctgg aactaaaggg atctgaaaca    300
acattcatgt gtgaatatgc tgatgagaca gcaaccattg tagaatttct gaacagatgg    360 attacccttta gtcaaagcat catctcaaca ctgacttga                         399

<210> SEQ ID NO 191
<211> LENGTH: 399
<212> TYPE: DNA
<213> ORGANISM: Artificial Sequence
<220> FEATURE:
<223> OTHER INFORMATION: IL-2 analog 85

<400> SEQUENCE: 191
cctacttcaa gttctacaaa gaaaacacag ctacaactgg agcatttact gctggattta     60
cagatgattt tgaatggaat taataattac aagaatccca aactcaccag gatgctcaca    120
tttaagtttt acatgcccaa gaaggccaca gaactgaaac atcttcagtg tctagaagaa    180
gaactcaaac ctctggagga agtgctaaat ttagctcaaa gcaaaaactt tcacttcgaa    240
cccagggacg tagtcagcaa tatcaacgta tttgttctgg aactaaaggg atctgaaaca    300
acattcatgt gtgaatatgc tgatgagaca gcaaccattg tagaatttct gaacagatgg    360 attacccttta gtcaaagcat catctcaaca ctgacttga                         399

<210> SEQ ID NO 192
<211> LENGTH: 399
<212> TYPE: DNA
<213> ORGANISM: Artificial Sequence
<220> FEATURE:
<223> OTHER INFORMATION: IL-2 analog 86

<400> SEQUENCE: 192
cctacttcaa gttctacaaa gaaaacacag ctacaactgg agcatttacg tctggattta     60
gaaatgattt tgaatggaat taataattac aagaatccca aactcaccag gatgctcaca    120
tttaagtttt acatgcccaa gaaggccaca gaactgaaac atcttcagtg tctagaagaa    180
gaactcaaac ctctggagga agtgctaaat ttagctcaaa gcaaaaactt tcacttcgaa    240
cccagggacg tagtcagcaa tatcaacgta tttgttctgg aactaaaggg atctgaaaca    300
acattcatgt gtgaatatgc tgatgagaca gcaaccattg tagaatttct gaacagatgg    360 attacccttta gtcaaagcat catctcaaca ctgacttga                         399

<210> SEQ ID NO 193
<211> LENGTH: 399
<212> TYPE: DNA
<213> ORGANISM: Artificial Sequence
<220> FEATURE:
<223> OTHER INFORMATION: IL-2 analog 87

<400> SEQUENCE: 193
cctacttcaa gttctacaaa gaaaacacag ctacaactgg agcatttacg tcgtgattta     60
gaaatgattt tgaatggaat taataattac aagaatccca aactcaccag gatgctcaca    120
tttaagtttt acatgcccaa gaaggccaca gaactgaaac atcttcagtg tctagaagaa    180
```

-continued

```
gaactcaaac ctctggagga agtgctaaat ttagctcaaa gcaaaaactt tcacttcgaa        240
cccagggacg tagtcagcaa tatcaacgta tttgttctgg aactaaaggg atctgaaaca        300
acattcatgt gtgaatatgc tgatgagaca gcaaccattg tagaatttct gaacagatgg        360 attacctttta gtcaaagcat catctcaaca ctgacttga                             399
```

```
<210> SEQ ID NO 194
<211> LENGTH: 399
<212> TYPE: DNA
<213> ORGANISM: Artificial Sequence
<220> FEATURE:
<223> OTHER INFORMATION: IL-2 analog 88

<400> SEQUENCE: 194
cctacttcaa gttctacaaa gaaaacacag ctacaactgg agcatttact gctggattta         60
cagatgattt tgaatggaat taataattac aagaatccca aactcaccag gatgctcaca        120
tttaagtttt acatgcccaa gaaggccaca gaactgaaac atcttcagtg tctagaagac        180
gaactcaaac ctctggagga agtgctaaat ttagctcaaa gcaaaaactt tcacttcgaa        240
cccagggacg tagtcagcaa tatcaacgta tttgttctgg aactaaaggg atctgaaaca        300
acattcatgt gtgaatatgc tgatgagaca gcaaccattg tagaatttct gaacagatgg        360 attacctttta gtcaaagcat catctcaaca ctgacttga                             399
```

```
<210> SEQ ID NO 195
<211> LENGTH: 399
<212> TYPE: DNA
<213> ORGANISM: Artificial Sequence
<220> FEATURE:
<223> OTHER INFORMATION: IL-2 analog 89

<400> SEQUENCE: 195
cctacttcaa gttctacaaa gaaaacacag ctacaactgg agcatttact gctggattta         60
cagatgattt tgaatggaat taataattac aagaatccca aactcaccgc gatgctcaca        120
tttaagtttt acatgcccaa gaaggccaca gaactgaaac atcttcagtg tctagaagaa        180
gaactcaaac ctctggagca ggtgctaaat ttagctcaaa gcaaaaactt tcacttcgaa        240
cccagggacg tagtcagcaa tatcaacgta tttgttctgg aactaaaggg atctgaaaca        300
acattcatgt gtgaatatgc tgatgagaca gcaaccattg tagaatttct gaacagatgg        360 attacctttta gtcaaagcat catctcaaca ctgacttga                             399
```

```
<210> SEQ ID NO 196
<211> LENGTH: 399
<212> TYPE: DNA
<213> ORGANISM: Artificial Sequence
<220> FEATURE:
<223> OTHER INFORMATION: IL-2 analog 90

<400> SEQUENCE: 196
cctacttcaa gttctacaaa gaaaacacag ctacaactgg agcatttact gctggattta         60
cagatgattt tgaatggaat taataattac aagaatccca aactcaccag gatgctcaca        120
tggaagtttt acatgcccaa gaaggccaca gaactgaaac atcttcagtg tctagaagaa        180
gaactcaaac ctctggagga agtgctaaat ttagctcaaa gcaaaaactt tcacttcgaa        240
cccagggacg tagtcagcaa tatcaacgta tttgttctgg aactaaaggg atctgaaaca        300
acattcatgt gtgaatatgc tgatgagaca gcaaccattg tagaatttct gaacagatgg        360
```

-continued attaccttta gtcaaagcat catctcaaca ctgacttga                              399

<210> SEQ ID NO 197
<211> LENGTH: 399
<212> TYPE: DNA
<213> ORGANISM: Artificial Sequence
<220> FEATURE:
<223> OTHER INFORMATION: IL-2 analog 91

<400> SEQUENCE: 197
cctacttcaa gttctacaaa gaaaacacag ctacaactgg agcatttact gctggattta       60
cagatgattt tgaatggaat taataattac aagaatccca aactcaccag gatgctcaca      120
tttaagtttt acatgcccaa gaaggccaca gaactgaaac atcttcagtg tctagaacaa      180
gaactcaaac ctctggagga agtgctaaat ttagctcaaa gcaaaaactt tcacttcgaa      240 cccaggggacg tagtcagcaa tatcaacgta tttgttctgg aactaaaggg atctgaaaca      300
acattcatgt gtgaatatgc tgatgagaca gcaaccattg tagaatttct gaacagatgg      360 attacctttta gtcaaagcat catctcaaca ctgacttga                            399

<210> SEQ ID NO 198
<211> LENGTH: 399
<212> TYPE: DNA
<213> ORGANISM: Artificial Sequence
<220> FEATURE:
<223> OTHER INFORMATION: IL-2 analog 92

<400> SEQUENCE: 198
cctacttcaa gttctacaaa gaaaacacag ctacaactgg agcatttact gctggattta       60
cagatgattt tgaatggaat taataattac aagaatccca aactcaccag gatgctcaca      120
tttaagtttt acatgcccaa gaaggccaca gaactgaaac atcttcagtg tctagaagaa      180
gaactcaaac ctctggagga agtgctaaat ttagctcaaa gcaaaaactt tcacttcgaa      240
cccagggacg tagtcagcaa tatcaacaca tttgttctgg aactaaaggg atctgaaaca      300
acattcatgt gtgaatatgc tgatgagaca gcaaccattg tagaatttct gaacagatgg      360 attacctttta gtcaaagcat catctcaaca ctgacttga                            399

<210> SEQ ID NO 199
<211> LENGTH: 399
<212> TYPE: DNA
<213> ORGANISM: Artificial Sequence
<220> FEATURE:
<223> OTHER INFORMATION: IL-2 analog 93

<400> SEQUENCE: 199
cctacttcaa gttctacaaa gaaaacacag ctacaactgg agcatttact gctggattta       60
cagatgattt tgaatggaat taataattac aagaatccca aactcaccag gatgctcaca      120
tttaagtttt acatgcccaa gaaggccaca gaactgaaac atcttcagtg tctagaagaa      180
gaactcaaac ctctggagga agtgctaaat ttagctcaaa gcaaaaactt tcacttcgaa      240
cccagggagg tagtcagcaa tatcaacaca tttgttctgg aactaaaggg atctgaaaca      300
acattcatgt gtgaatatgc tgatgagaca gcaaccattg tagaatttct gaacagatgg      360 attacctttta gtcaaagcat catctcaaca ctgacttga                            399

<210> SEQ ID NO 200
<211> LENGTH: 399
<212> TYPE: DNA
<213> ORGANISM: Artificial Sequence -continued

```
<220> FEATURE:
<223> OTHER INFORMATION: IL-2 analog 94

<400> SEQUENCE: 200
cctacttcaa gttctacaaa gaaaacacag ctacaactgg agcatttact gctggattta      60
cagatgattt tgaatggaat taataattac aagaatccca aactcaccag gatgctcaca     120
tttaagtttt acatgcccaa gaaggccaca gaactgaaac atcttcagtg tctagaagaa     180
gaactcaaac ctctggagga agtgctaaat ttagctcaaa gcaaaaactt tcacttcgaa     240
cccagggacg tagtcagcaa tatcaacgta tttgttttcg aattcaaggg atctgaaaca     300
acattcatgt gtgaatatgc tgatgagaca gcaaccattg tagaatttct gaacagatgg     360
attaccttta gtcaaagcat catctcaaca ctgacttga                            399

<210> SEQ ID NO 201
<211> LENGTH: 399
<212> TYPE: DNA
<213> ORGANISM: Artificial Sequence
<220> FEATURE:
<223> OTHER INFORMATION: IL-2 analog 95

<400> SEQUENCE: 201
cctacttcaa gttctacaaa gaaaacacag ctacaactgg agcatttact gctggattta      60
cagatgattt tgaatggaat taataattac aagaatccca aactcaccag gatgctcaca     120
tttaagtttt acatgcccaa gaaggccaca gaactgaaac atcttcagtg tctagaagaa     180
gaactcaaac ctctggagga agggctaaat ttagctcaaa gcaaaaactt tcacttcgaa     240
cccagggacg tagtcagcaa tatcaacgta tttgttctgg aactaaaggg atctgaaaca     300
acattcatgt gtgaatatgc tgatgagaca gcaaccattg tagaatttct gaacagatgg     360
attaccttta gtcaaagcat catctcaaca ctgacttga                            399

<210> SEQ ID NO 202
<211> LENGTH: 399
<212> TYPE: DNA
<213> ORGANISM: Artificial Sequence
<220> FEATURE:
<223> OTHER INFORMATION: IL-2 analog 96

<400> SEQUENCE: 202
cctacttcaa gttctacaaa gaaaacacag ctacaactgg agcatttact gctggattta      60
cagatgattt tgaatggaat taataattac aagaatccca aactcaccag gatgctcaca     120
tttaagtttt acatgcccaa gaaggccaca gaactgaaac atcttcagtg tctagaagaa     180
gaactcaaac ctctggagga agggctaaat ttagctgcaa gcaaaaactt tcacttcgaa     240
cccagggacg tagtcagcaa tatcaacgta tttgttctgg aactaaaggg atctgaaaca     300
acattcatgt gtgaatatgc tgatgagaca gcaaccattg tagaatttct gaacagatgg     360
attaccttta gtcaaagcat catctcaaca ctgacttga                            399

<210> SEQ ID NO 203
<211> LENGTH: 399
<212> TYPE: DNA
<213> ORGANISM: Artificial Sequence
<220> FEATURE:
<223> OTHER INFORMATION: IL-2 analog 97

<400> SEQUENCE: 203
cctacttcaa gttctacaaa gaaaacacag ctacaactgg agcatttact gctggattta      60
```

-continued

```
cagatgattt tgaatggaat taataattac aagaatccca aactcaccgc gatgctcaca        120
tttaagtttt acatgcccaa gaaggccaca gaactgaaac atcttcagtg tctagaagaa        180
gaactcaaac ctctggagga agtgctaaat ttagctcaaa gcaaaaactt tcactttgac        240
cccagggact taatcagcaa tatcaacgta tttgttctgg aactaaaggg atctgaaaca        300
acattcatgt gtgaatatgc tgatgagaca gcaaccattg tagaatttct gaacagatgg        360
attaccttta gtcaaagcat catctcaaca ctgacttga        399

<210> SEQ ID NO 204
<211> LENGTH: 399
<212> TYPE: DNA
<213> ORGANISM: Artificial Sequence
<220> FEATURE:
<223> OTHER INFORMATION: IL-2 analog 98

<400> SEQUENCE: 204
cctacttcaa gttctacaaa gaaaacacag ctacaactgg agcatttact gctggattta         60
cagatgattt tgaatggaat taataattac aagaatccca aactcaccgc gatgctcaca        120
tttaagtttt acatgcccaa gaaggccaca gaactgaaac atcttcagtg tctagaagaa        180
gaactcaaac ctctggagga agtgctaaat ttagctcaaa gcaaaaactt tcactttgag        240
cccagggacg taatcagcaa tatcaacgta tttgttctgg aactaaaggg atctgaaaca        300
acattcatgt gtgaatatgc tgatgagaca gcaaccattg tagaatttct gaacagatgg        360
attaccttta gtcaaagcat catctcaaca ctgacttga        399

<210> SEQ ID NO 205
<211> LENGTH: 399
<212> TYPE: DNA
<213> ORGANISM: Artificial Sequence
<220> FEATURE:
<223> OTHER INFORMATION: IL-2 analog 99

<400> SEQUENCE: 205
cctacttcaa gttctacaaa gaaaacacag ctacaactgg agcatttact gctggattta         60
cagatgattt tgaatggaat taataattac aagaatccca aactcaccgc gatgctcaca        120
tttaagtttt acatgcccaa gaaggccaca gaactgaaac atcttcagtg tctagaagaa        180
gaactcaaac ctctggagga agtgctaaat ttagctcaaa gcaaaaactt tcactttgag        240
cccagggact tagtcagcaa tatcaacgta tttgttctgg aactaaaggg atctgaaaca        300
acattcatgt gtgaatatgc tgatgagaca gcaaccattg tagaatttct gaacagatgg        360
attaccttta gtcaaagcat catctcaaca ctgacttga        399

<210> SEQ ID NO 206
<211> LENGTH: 399
<212> TYPE: DNA
<213> ORGANISM: Artificial Sequence
<220> FEATURE:
<223> OTHER INFORMATION: IL-2 analog 100

<400> SEQUENCE: 206
cctacttcaa gttctacaaa gaaaacacag ctacaactgg agcatttact gctggattta         60
cagatgattt tgaatggaat taataattac aagaatccca aactcaccag gatgctcaca        120
tttaagtttt acatgcccaa gaaggccaca gaactgaaac atcttcagtg tctagaagaa        180
gaactcaaac ctctggagga agtgctaaat ttagctcaaa gcaaaaactt tcacttcgaa        240
cccagggact acgtcagcaa tatcaacgta tttgttctgg aactaaaggg atctgaaaca        300
```

```
acattcatgt gtgaatatgc tgatgagaca gcaaccattg tagaatttct gaacagatgg     360 attacctta gtcaaagcat catctcaaca ctgacttga                             399

<210> SEQ ID NO 207
<211> LENGTH: 399
<212> TYPE: DNA
<213> ORGANISM: Artificial Sequence
<220> FEATURE:
<223> OTHER INFORMATION: IL-2 analog 101

<400> SEQUENCE: 207
cctacttcaa gttctacaaa gaaaacacag ctacaactgg agcatttact gctggattta      60
cagatgattt tgaatggaat taataattac aagaatccca aactcaccag gatgctcaca     120
tttaagtttt acatgcccaa gaaggccaca gaactgaaac atcttcagtg tctagaagaa     180
gaactcaaac ctctggagga agtgctaaat ttagctcaaa gcaaaaactt tcacttcgaa     240
cccagggacc tggccagcaa tatcaacgta tttgttctgg aactaaaggg atctgaaaca     300
acattcatgt gtgaatatgc tgatgagaca gcaaccattg tagaatttct gaacagatgg     360 attacctta gtcaaagcat catctcaaca ctgacttga                             399

<210> SEQ ID NO 208
<211> LENGTH: 399
<212> TYPE: DNA
<213> ORGANISM: Artificial Sequence
<220> FEATURE:
<223> OTHER INFORMATION: IL-2 analog 102

<400> SEQUENCE: 208
cctacttcaa gttctacaaa gaaaacacag ctacaactgg agcatttact gctggattta      60
cagatgattt tgaatggaat taataattac aagaatccca aactcaccag gatgctcaca     120
tttaagtttt acatgcccaa gaaggccaca gaactgaaac atcttcagtg tctagaagaa     180
gaactcaaac ctctggagga agtgctaaat ttagctcaaa gcaaaaactt tcacttcgaa     240
cccagggacg tagtcagcaa tatcaacgta attgttctgg aactaaaggg atctgaaaca     300
acattcatgt gtgaatatgc tgatgagaca gcaaccattg tagaatttct gaacagatgg     360 attacctta gtcaaagcat catctcaaca ctgacttga                             399

<210> SEQ ID NO 209
<211> LENGTH: 399
<212> TYPE: DNA
<213> ORGANISM: Artificial Sequence
<220> FEATURE:
<223> OTHER INFORMATION: IL-2 analog 103

<400> SEQUENCE: 209
cctacttcaa gttctacaaa gaaaacacag ctacaactgg agcatttacg tctggattta      60
gaaatgattt tgaatggaat taataattac aagaatccca aactcaccgc gatgctcaca     120
tttaagtttt acatgcccaa gaaggccaca gaactgaaac atcttcagtg tctagaagaa     180
gaactcaaac ctctggagga agtgctaaat ttagctcaaa gcaaaaactt tcacttcgaa     240
cccagggacg tagtcagcaa tatcaacgta tttgttctgg aactaaaggg atctgaaaca     300
acattcatgt gtgaatatgc tgatgagaca gcaaccattg tagaatttct gaacagatgg     360 attacctta gtcaaagcat catctcaaca ctgacttga                             399

<210> SEQ ID NO 210
```

-continued

```
<211> LENGTH: 399
<212> TYPE: DNA
<213> ORGANISM: Artificial Sequence
<220> FEATURE:
<223> OTHER INFORMATION: IL-2 analog 104

<400> SEQUENCE: 210
cctacttcaa gttctacaaa gaaaacacag ctacaactgg agcatttacg tctggattta        60
gaaatgattt tgaatggaat taataattac aagaatccca aactcaccag gatgctcaca       120
tttaagtttt acatgcccaa gaaggccaca gaactgaaac atcttcagtg tctagaagac       180
gaactcaaac ctctggagga agtgctaaat ttagctcaaa gcaaaaactt tcacttcgaa       240
cccagggacg tagtcagcaa tatcaacgta tttgttctgg aactaaaggg atctgaaaca       300
acattcatgt gtgaatatgc tgatgagaca gcaaccattg tagaatttct gaacagatgg       360
attaccttta gtcaaagcat catctcaaca ctgacttga                             399

<210> SEQ ID NO 211
<211> LENGTH: 399
<212> TYPE: DNA
<213> ORGANISM: Artificial Sequence
<220> FEATURE:
<223> OTHER INFORMATION: IL-2 analog 105

<400> SEQUENCE: 211
cctacttcaa gttctacaaa gaaaacacag ctacaactgg agcatttacg tctggattta        60
gaaatgattt tgaatggaat taataattac aagaatccca aactcaccag gatgctcaca       120
tttaagtttt acatgcccaa gaaggccaca gaactgaaac atcttcagtg tctagaagaa       180
gaactcaaac ctctggagga cgtgctaaat ttagctcaaa gcaaaaactt tcacttcgaa       240
cccagggacg tagtcagcaa tatcaacgta tttgttctgg aactaaaggg atctgaaaca       300
acattcatgt gtgaatatgc tgatgagaca gcaaccattg tagaatttct gaacagatgg       360
attaccttta gtcaaagcat catctcaaca ctgacttga                             399

<210> SEQ ID NO 212
<211> LENGTH: 133
<212> TYPE: PRT
<213> ORGANISM: Artificial Sequence
<220> FEATURE:
<223> OTHER INFORMATION: General Formula 1
<220> FEATURE:
<221> NAME/KEY: MISC_FEATURE
<222> LOCATION: (1)
<223> OTHER INFORMATION: Xaa is a deletion
<220> FEATURE:
<221> NAME/KEY: MISC_FEATURE
<222> LOCATION: (18)
<223> OTHER INFORMATION: Xaa is leucine (L) or arginine (R)
<220> FEATURE:
<221> NAME/KEY: MISC_FEATURE
<222> LOCATION: (19)
<223> OTHER INFORMATION: Xaa is leucine (L) or tyrosine (Y)
<220> FEATURE:
<221> NAME/KEY: MISC_FEATURE
<222> LOCATION: (22)
<223> OTHER INFORMATION: Xaa is glutamic acid (E) or glutamine (Q)
<220> FEATURE:
<221> NAME/KEY: MISC_FEATURE
<222> LOCATION: (38)
<223> OTHER INFORMATION: Xaa is alanine (A), aspartic acid (D), or
      arginine (R)
<220> FEATURE:
<221> NAME/KEY: MISC_FEATURE
<222> LOCATION: (42)
<223> OTHER INFORMATION: Xaa is alanine (A), phenylalanine (F), lysine
      (K), or tryptophan (W)
```

-continued

```
<220> FEATURE:
<221> NAME/KEY: MISC_FEATURE
<222> LOCATION: (43)
<223> OTHER INFORMATION: Xaa is glutamic acid (E), lysine (K), or
      glutamine (Q)
<220> FEATURE:
<221> NAME/KEY: MISC_FEATURE
<222> LOCATION: (45)
<223> OTHER INFORMATION: Xaa is alanine (A) or tyrosine (Y)
<220> FEATURE:
<221> NAME/KEY: MISC_FEATURE
<222> LOCATION: (61)
<223> OTHER INFORMATION: Xaa is aspartic acid (D), glutamic acid (E),
      glutamine (Q), or arginine (R)
<220> FEATURE:
<221> NAME/KEY: MISC_FEATURE
<222> LOCATION: (68)
<223> OTHER INFORMATION: Xaa is aspartic acid (D) or glutamic acid (E)
<220> FEATURE:
<221> NAME/KEY: MISC_FEATURE
<222> LOCATION: (74)
<223> OTHER INFORMATION: Xaa is histidine (H) or glutamine (Q)
<220> FEATURE:
<221> NAME/KEY: MISC_FEATURE
<222> LOCATION: (80)
<223> OTHER INFORMATION: Xaa is phenylalanine (F), leucine (L), valine
      (V), or tyrosine (Y)
<220> FEATURE:
<221> NAME/KEY: MISC_FEATURE
<222> LOCATION: (81)
<223> OTHER INFORMATION: Xaa is aspartic acid (D), glutamic acid (E), or
      arginine (R)
<220> FEATURE:
<221> NAME/KEY: MISC_FEATURE
<222> LOCATION: (84)
<223> OTHER INFORMATION: Xaa is aspartic acid (D) or glutamic acid (E)
<220> FEATURE:
<221> NAME/KEY: MISC_FEATURE
<222> LOCATION: (85)
<223> OTHER INFORMATION: Xaa is alanine (A), glutamic acid (E), glycine
      (G), leucine (L), valine (V), tryptophan (W), or tyrosine (Y)
<220> FEATURE:
<221> NAME/KEY: MISC_FEATURE
<222> LOCATION: (86)
<223> OTHER INFORMATION: Xaa is alanine (A), glycine (G), isoleucine
      (I), or valine (V)
<220> FEATURE:
<221> NAME/KEY: MISC_FEATURE
<222> LOCATION: (91)
<223> OTHER INFORMATION: Xaa is threonine (T) or valine (V)
<220> FEATURE:
<221> NAME/KEY: MISC_FEATURE
<222> LOCATION: (92)
<223> OTHER INFORMATION: Xaa is phenylalanine (F), isoleucine (I), or
      tyrosine (Y)
<220> FEATURE:
<221> NAME/KEY: MISC_FEATURE
<222> LOCATION: (94)
<223> OTHER INFORMATION: Xaa is phenylalanine (F) or leucine (L)
<220> FEATURE:
<221> NAME/KEY: MISC_FEATURE
<222> LOCATION: (96)
<223> OTHER INFORMATION: Xaa is phenylalanine (F) or leucine (L)

<400> SEQUENCE: 212

Xaa Pro Thr Ser Ser Ser Thr Lys Lys Thr Gln Leu Gln Leu Glu His
1               5                   10                  15

Leu Xaa Xaa Asp Leu Xaa Met Ile Leu Asn Gly Ile Asn Asn Tyr Lys
            20                  25                  30

Asn Pro Lys Leu Thr Xaa Met Leu Thr Xaa Xaa Phe Xaa Met Pro Lys
        35                  40                  45

Lys Ala Thr Glu Leu Lys His Leu Gln Cys Leu Glu Xaa Glu Leu Lys
    50                  55                  60

Pro Leu Glu Xaa Val Leu Asn Leu Ala Xaa Ser Lys Asn Phe His Xaa
```

```
65              70              75              80

Xaa Pro Arg Xaa Xaa Xaa Ser Asn Ile Asn Xaa Xaa Val Xaa Glu Xaa
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130
```

```
<210> SEQ ID NO 213
<211> LENGTH: 133
<212> TYPE: PRT
<213> ORGANISM: Artificial Sequence
<220> FEATURE:
<223> OTHER INFORMATION: General Formula 2
<220> FEATURE:
<221> NAME/KEY: MISC_FEATURE
<222> LOCATION: (1)
<223> OTHER INFORMATION: Xaa is a deletion
<220> FEATURE:
<221> NAME/KEY: MISC_FEATURE
<222> LOCATION: (18)
<223> OTHER INFORMATION: Xaa is leucine (L) or arginine (R)
<220> FEATURE:
<221> NAME/KEY: MISC_FEATURE
<222> LOCATION: (22)
<223> OTHER INFORMATION: Xaa is glutamic acid (E) or glutamine (Q)
<220> FEATURE:
<221> NAME/KEY: MISC_FEATURE
<222> LOCATION: (38)
<223> OTHER INFORMATION: Xaa is alanine (A) or arginine (R)
<220> FEATURE:
<221> NAME/KEY: MISC_FEATURE
<222> LOCATION: (42)
<223> OTHER INFORMATION: Xaa is phenylalanine (F) or lysine (K)
<220> FEATURE:
<221> NAME/KEY: MISC_FEATURE
<222> LOCATION: (61)
<223> OTHER INFORMATION: Xaa is aspartic acid (D) or glutamic acid (E)
<220> FEATURE:
<221> NAME/KEY: MISC_FEATURE
<222> LOCATION: (68)
<223> OTHER INFORMATION: Xaa is aspartic acid (D) or glutamic acid (E)
<220> FEATURE:
<221> NAME/KEY: MISC_FEATURE
<222> LOCATION: (81)
<223> OTHER INFORMATION: Xaais aspartic acid (D) or glutamic acid (E)
<220> FEATURE:
<221> NAME/KEY: MISC_FEATURE
<222> LOCATION: (85)
<223> OTHER INFORMATION: Xaa is leucine (L) or valine (V)
<220> FEATURE:
<221> NAME/KEY: MISC_FEATURE
<222> LOCATION: (86)
<223> OTHER INFORMATION: Xaa is isoleucine (I) or valine (V)

<400> SEQUENCE: 213

Xaa Pro Thr Ser Ser Ser Thr Lys Lys Thr Gln Leu Gln Leu Glu His
1               5                   10                  15

Leu Xaa Leu Asp Leu Xaa Met Ile Leu Asn Gly Ile Asn Asn Tyr Lys
            20                  25                  30

Asn Pro Lys Leu Thr Xaa Met Leu Thr Xaa Lys Phe Tyr Met Pro Lys
        35                  40                  45

Lys Ala Thr Glu Leu Lys His Leu Gln Cys Leu Glu Xaa Glu Leu Lys
    50                  55                  60

Pro Leu Glu Xaa Val Leu Asn Leu Ala Gln Ser Lys Asn Phe His Phe
65                  70                  75                  80
```

-continued

```
Xaa Pro Arg Asp Xaa Xaa Ser Asn Ile Asn Val Phe Val Leu Glu Leu
             85              90              95

Lys Gly Ser Glu Thr Thr Phe Met Cys Glu Tyr Ala Asp Glu Thr Ala
         100             105             110

Thr Ile Val Glu Phe Leu Asn Arg Trp Ile Thr Phe Ser Gln Ser Ile
     115             120             125

Ile Ser Thr Leu Thr
     130

<210> SEQ ID NO 214
<211> LENGTH: 33
<212> TYPE: DNA
<213> ORGANISM: Artificial Sequence
<220> FEATURE:
<223> OTHER INFORMATION: primer #1 (IL2_L12F_F)

<400> SEQUENCE: 214
caaagaaaac acagtttcaa ctggagcatt tac                              33

<210> SEQ ID NO 215
<211> LENGTH: 33
<212> TYPE: DNA
<213> ORGANISM: Artificial Sequence
<220> FEATURE:
<223> OTHER INFORMATION: primer #2 (IL2_L12F_R)

<400> SEQUENCE: 215
gtaaatgctc cagttgaaac tgtgtttct ttg                              33

<210> SEQ ID NO 216
<211> LENGTH: 33
<212> TYPE: DNA
<213> ORGANISM: Artificial Sequence
<220> FEATURE:
<223> OTHER INFORMATION: primer #3 (IL2_L12V_F)

<400> SEQUENCE: 216
caaagaaaac acaggtacaa ctggagcatt tac                              33

<210> SEQ ID NO 217
<211> LENGTH: 33
<212> TYPE: DNA
<213> ORGANISM: Artificial Sequence
<220> FEATURE:
<223> OTHER INFORMATION: primer #4 (IL2_L12V_R)

<400> SEQUENCE: 217
gtaaatgctc cagttgtacc tgtgtttct ttg                              33

<210> SEQ ID NO 218
<211> LENGTH: 39
<212> TYPE: DNA
<213> ORGANISM: Artificial Sequence
<220> FEATURE:
<223> OTHER INFORMATION: primer #5 (IL2_L18R_L19R_Q22E_F)

<400> SEQUENCE: 218
ctggagcatt tacgtcgtga tttagaaatg attttgaat                        39

<210> SEQ ID NO 219
<211> LENGTH: 39
<212> TYPE: DNA
<213> ORGANISM: Artificial Sequence
<220> FEATURE:
<223> OTHER INFORMATION: primer #6 (IL2_L18R_L19R_Q22E_R)
```

-continued

```
<400> SEQUENCE: 219
attcaaaatc atttctaaat cacgacgtaa atgctccag                               39

<210> SEQ ID NO 220
<211> LENGTH: 39
<212> TYPE: DNA
<213> ORGANISM: Artificial Sequence
<220> FEATURE:
<223> OTHER INFORMATION: primer #7 (IL2_L18R_Q22E_F)

<400> SEQUENCE: 220
ctggagcatt tacgtctgga tttagaaatg attttgaat                               39

<210> SEQ ID NO 221
<211> LENGTH: 39
<212> TYPE: DNA
<213> ORGANISM: Artificial Sequence
<220> FEATURE:
<223> OTHER INFORMATION: primer #8 (IL2_L18R_Q22E_R)

<400> SEQUENCE: 221
attcaaaatc atttctaaat ccagacgtaa atgctccag                               39

<210> SEQ ID NO 222
<211> LENGTH: 33
<212> TYPE: DNA
<213> ORGANISM: Artificial Sequence
<220> FEATURE:
<223> OTHER INFORMATION: primer #9 (IL2_L19F_F)

<400> SEQUENCE: 222
gagcatttac tgttcgattt acagatgatt ttg                                     33

<210> SEQ ID NO 223
<211> LENGTH: 33
<212> TYPE: DNA
<213> ORGANISM: Artificial Sequence
<220> FEATURE:
<223> OTHER INFORMATION: primer #10 (IL2_L19F_R)

<400> SEQUENCE: 223
caaaatcatc tgtaaatcga acagtaaatg ctc                                     33

<210> SEQ ID NO 224
<211> LENGTH: 33
<212> TYPE: DNA
<213> ORGANISM: Artificial Sequence
<220> FEATURE:
<223> OTHER INFORMATION: primer #11 (IL2_L19V_F)

<400> SEQUENCE: 224
gagcatttac tggtggattt acagatgatt ttg                                     33

<210> SEQ ID NO 225
<211> LENGTH: 33
<212> TYPE: DNA
<213> ORGANISM: Artificial Sequence
<220> FEATURE:
<223> OTHER INFORMATION: primer #12 (IL2_L19V_R)

<400> SEQUENCE: 225
caaaatcatc tgtaaatcca ccagtaaatg ctc                                     33

<210> SEQ ID NO 226
```

-continued

```
<211> LENGTH: 33
<212> TYPE: DNA
<213> ORGANISM: Artificial Sequence
<220> FEATURE:
<223> OTHER INFORMATION: primer #13 (IL2_L19Y_F)

<400> SEQUENCE: 226
caactggagc atttactgta cgatttacag atg                                 33

<210> SEQ ID NO 227
<211> LENGTH: 33
<212> TYPE: DNA
<213> ORGANISM: Artificial Sequence
<220> FEATURE:
<223> OTHER INFORMATION: primer #14 (IL2_L19Y_R)

<400> SEQUENCE: 227
catctgtaaa tcgtacagta aatgctccag ttg                                 33

<210> SEQ ID NO 228
<211> LENGTH: 34
<212> TYPE: DNA
<213> ORGANISM: Artificial Sequence
<220> FEATURE:
<223> OTHER INFORMATION: primer #15 (IL2_D20F_F)

<400> SEQUENCE: 228
ggagcattta ctgctgtttt tacagatgat tttg                                34

<210> SEQ ID NO 229
<211> LENGTH: 34
<212> TYPE: DNA
<213> ORGANISM: Artificial Sequence
<220> FEATURE:
<223> OTHER INFORMATION: primer #16 (IL2_D20F_R)

<400> SEQUENCE: 229
caaaatcatc tgtaaaaaca gcagtaaatg ctcc                                34

<210> SEQ ID NO 230
<211> LENGTH: 33
<212> TYPE: DNA
<213> ORGANISM: Artificial Sequence
<220> FEATURE:
<223> OTHER INFORMATION: primer #17 (IL2_D20V_F)

<400> SEQUENCE: 230
gagcatttac tgctggtttt acagatgatt ttg                                 33

<210> SEQ ID NO 231
<211> LENGTH: 33
<212> TYPE: DNA
<213> ORGANISM: Artificial Sequence
<220> FEATURE:
<223> OTHER INFORMATION: primer #18 (IL2_D20V_R)

<400> SEQUENCE: 231
caaaatcatc tgtaaaacca gcagtaaatg ctc                                 33

<210> SEQ ID NO 232
<211> LENGTH: 33
<212> TYPE: DNA
<213> ORGANISM: Artificial Sequence
<220> FEATURE:
<223> OTHER INFORMATION: primer #19 (IL2_K32C_F)

<400> SEQUENCE: 232
```

-continued ggaattaata attactgtaa tcccaaactc acc                                      33

<210> SEQ ID NO 233
<211> LENGTH: 33
<212> TYPE: DNA
<213> ORGANISM: Artificial Sequence
<220> FEATURE:
<223> OTHER INFORMATION: primer #20 (IL2_K32C_R)

<400> SEQUENCE: 233
ggtgagtttg ggattacagt aattattaat tcc                                      33

<210> SEQ ID NO 234
<211> LENGTH: 33
<212> TYPE: DNA
<213> ORGANISM: Artificial Sequence
<220> FEATURE:
<223> OTHER INFORMATION: primer #21 (IL2_K35C_F)

<400> SEQUENCE: 234
aattacaaga atccctgtct caccaggatg ctc                                      33

<210> SEQ ID NO 235
<211> LENGTH: 33
<212> TYPE: DNA
<213> ORGANISM: Artificial Sequence
<220> FEATURE:
<223> OTHER INFORMATION: primer #22 (IL2_K35C_R)

<400> SEQUENCE: 235
gagcatcctg gtgagacagg gattcttgta att                                      33

<210> SEQ ID NO 236
<211> LENGTH: 33
<212> TYPE: DNA
<213> ORGANISM: Artificial Sequence
<220> FEATURE:
<223> OTHER INFORMATION: primer #23 (IL2_K35E_F)

<400> SEQUENCE: 236
taattacaag aatcccgaac tcaccgcgat gct                                      33

<210> SEQ ID NO 237
<211> LENGTH: 33
<212> TYPE: DNA
<213> ORGANISM: Artificial Sequence
<220> FEATURE:
<223> OTHER INFORMATION: primer #24 (IL2_K35E_R)

<400> SEQUENCE: 237
agcatcgcgg tgagttcggg attcttgtaa tta                                      33

<210> SEQ ID NO 238
<211> LENGTH: 25
<212> TYPE: DNA
<213> ORGANISM: Artificial Sequence
<220> FEATURE:
<223> OTHER INFORMATION: primer #25 (IL2_R38A_F)

<400> SEQUENCE: 238
ccaaactcac cgcgatgctc acatt                                               25

<210> SEQ ID NO 239
<211> LENGTH: 25
<212> TYPE: DNA

-continued

<213> ORGANISM: Artificial Sequence
<220> FEATURE:
<223> OTHER INFORMATION: primer #26 (IL2_R38A_R)

<400> SEQUENCE: 239
aatgtgagca tcgcggtgag tttgg                                          25

<210> SEQ ID NO 240
<211> LENGTH: 33
<212> TYPE: DNA
<213> ORGANISM: Artificial Sequence
<220> FEATURE:
<223> OTHER INFORMATION: primer #27 (IL2_R38A_F42F_F)

<400> SEQUENCE: 240
caccgcgatg ctcacattta agttttacat gcc                                33

<210> SEQ ID NO 241
<211> LENGTH: 33
<212> TYPE: DNA
<213> ORGANISM: Artificial Sequence
<220> FEATURE:
<223> OTHER INFORMATION: primer #28 (IL2_R38A_F42F_R)

<400> SEQUENCE: 241
ggcatgtaaa acttaaatgt gagcatcgcg gtg                                33

<210> SEQ ID NO 242
<211> LENGTH: 25
<212> TYPE: DNA
<213> ORGANISM: Artificial Sequence
<220> FEATURE:
<223> OTHER INFORMATION: primer #29 (IL2_A38R_F)

<400> SEQUENCE: 242
ccaaactcac caggatgctc acatt                                          25

<210> SEQ ID NO 243
<211> LENGTH: 25
<212> TYPE: DNA
<213> ORGANISM: Artificial Sequence
<220> FEATURE:
<223> OTHER INFORMATION: primer #30 (IL2_A38R_R)

<400> SEQUENCE: 243
aatgtgagca tcctggtgag tttgg                                          25

<210> SEQ ID NO 244
<211> LENGTH: 30
<212> TYPE: DNA
<213> ORGANISM: Artificial Sequence
<220> FEATURE:
<223> OTHER INFORMATION: primer #31 (IL2_R38D_F)

<400> SEQUENCE: 244
aagaatccca aactcaccga tatgctcaca                                     30

<210> SEQ ID NO 245
<211> LENGTH: 30
<212> TYPE: DNA
<213> ORGANISM: Artificial Sequence
<220> FEATURE:
<223> OTHER INFORMATION: primer #32 (IL2_R38D_R)

<400> SEQUENCE: 245
tgtgagcata tcggtgagtt tgggattctt                                     30

```
<210> SEQ ID NO 246
<211> LENGTH: 30
<212> TYPE: DNA
<213> ORGANISM: Artificial Sequence
<220> FEATURE:
<223> OTHER INFORMATION: primer #33 (IL2_F42A_F)

<400> SEQUENCE: 246
ccaggatgct cacagctaag ttttacatgc                                     30

<210> SEQ ID NO 247
<211> LENGTH: 30
<212> TYPE: DNA
<213> ORGANISM: Artificial Sequence
<220> FEATURE:
<223> OTHER INFORMATION: primer #34 (IL2_F42A_R)

<400> SEQUENCE: 247
gcatgtaaaa cttagctgtg agcatcctgg                                     30

<210> SEQ ID NO 248
<211> LENGTH: 30
<212> TYPE: DNA
<213> ORGANISM: Artificial Sequence
<220> FEATURE:
<223> OTHER INFORMATION: primer #35 (IL2_F42K_F)

<400> SEQUENCE: 248
ccaggatgct cacaaagaag ttttacatgc                                     30

<210> SEQ ID NO 249
<211> LENGTH: 30
<212> TYPE: DNA
<213> ORGANISM: Artificial Sequence
<220> FEATURE:
<223> OTHER INFORMATION: primer #36 (IL2_F42K_R)

<400> SEQUENCE: 249
gcatgtaaaa cttctttgtg agcatcctgg                                     30

<210> SEQ ID NO 250
<211> LENGTH: 30
<212> TYPE: DNA
<213> ORGANISM: Artificial Sequence
<220> FEATURE:
<223> OTHER INFORMATION: primer #37 (IL2_F42K_K43E_F)

<400> SEQUENCE: 250
atgctcacaa aggagtttta catgcccaag                                     30

<210> SEQ ID NO 251
<211> LENGTH: 30
<212> TYPE: DNA
<213> ORGANISM: Artificial Sequence
<220> FEATURE:
<223> OTHER INFORMATION: primer #38 (IL2_F42K_K43E_R)

<400> SEQUENCE: 251
cttgggcatg taaaactcct ttgtgagcat                                     30

<210> SEQ ID NO 252
<211> LENGTH: 30
<212> TYPE: DNA
<213> ORGANISM: Artificial Sequence
<220> FEATURE:
```

-continued

<223> OTHER INFORMATION: primer #39 (IL2_F42K_K43Q_F)

<400> SEQUENCE: 252
atgctcacaa agcagtttta catgcccaag                                         30

<210> SEQ ID NO 253
<211> LENGTH: 30
<212> TYPE: DNA
<213> ORGANISM: Artificial Sequence
<220> FEATURE:
<223> OTHER INFORMATION: primer #40 (IL2_F42K_K43Q_R)

<400> SEQUENCE: 253
cttgggcatg taaaactgct ttgtgagcat                                         30

<210> SEQ ID NO 254
<211> LENGTH: 30
<212> TYPE: DNA
<213> ORGANISM: Artificial Sequence
<220> FEATURE:
<223> OTHER INFORMATION: primer #41 (IL2_K42F_F)

<400> SEQUENCE: 254
ccaggatgct cacatttaag ttttacatgc                                         30

<210> SEQ ID NO 255
<211> LENGTH: 30
<212> TYPE: DNA
<213> ORGANISM: Artificial Sequence
<220> FEATURE:
<223> OTHER INFORMATION: primer #42 (IL2_K42F_R)

<400> SEQUENCE: 255
gcatgtaaaa cttaaatgtg agcatcctgg                                         30

<210> SEQ ID NO 256
<211> LENGTH: 39
<212> TYPE: DNA
<213> ORGANISM: Artificial Sequence
<220> FEATURE:
<223> OTHER INFORMATION: primer #43 (IL2_K42F_F_long)

<400> SEQUENCE: 256
ctcaccagga tgctcacatt taagttttac atgcccaag                               39

<210> SEQ ID NO 257
<211> LENGTH: 39
<212> TYPE: DNA
<213> ORGANISM: Artificial Sequence
<220> FEATURE:
<223> OTHER INFORMATION: primer #44 (IL2_K42F_R_long)

<400> SEQUENCE: 257
cttgggcatg taaaacttaa atgtgagcat cctggtgag                               39

<210> SEQ ID NO 258
<211> LENGTH: 33
<212> TYPE: DNA
<213> ORGANISM: Artificial Sequence
<220> FEATURE:
<223> OTHER INFORMATION: primer #45 (IL2_F42W_F)

<400> SEQUENCE: 258
accaggatgc tcacatggaa gttttacatg ccc                                     33

-continued

```
<210> SEQ ID NO 259
<211> LENGTH: 33
<212> TYPE: DNA
<213> ORGANISM: Artificial Sequence
<220> FEATURE:
<223> OTHER INFORMATION: primer #46 (IL2_F42W_R)

<400> SEQUENCE: 259
gggcatgtaa aacttccatg tgagcatcct ggt                                33

<210> SEQ ID NO 260
<211> LENGTH: 33
<212> TYPE: DNA
<213> ORGANISM: Artificial Sequence
<220> FEATURE:
<223> OTHER INFORMATION: primer #47 (IL2_K43C_F)

<400> SEQUENCE: 260
aggatgctca cattttgttt ttacatgccc aag                                33

<210> SEQ ID NO 261
<211> LENGTH: 33
<212> TYPE: DNA
<213> ORGANISM: Artificial Sequence
<220> FEATURE:
<223> OTHER INFORMATION: primer #48 (IL2_K43C_R)

<400> SEQUENCE: 261
cttgggcatg taaaaacaaa atgtgagcat cct                                33

<210> SEQ ID NO 262
<211> LENGTH: 19
<212> TYPE: DNA
<213> ORGANISM: Artificial Sequence
<220> FEATURE:
<223> OTHER INFORMATION: primer #49 (IL2_Y45A_F)

<400> SEQUENCE: 262
gaagtttgcc atgcccaag                                                19

<210> SEQ ID NO 263
<211> LENGTH: 19
<212> TYPE: DNA
<213> ORGANISM: Artificial Sequence
<220> FEATURE:
<223> OTHER INFORMATION: primer #50 (IL2_Y45A_R)

<400> SEQUENCE: 263
cttgggcatg gcaaacttc                                                19

<210> SEQ ID NO 264
<211> LENGTH: 34
<212> TYPE: DNA
<213> ORGANISM: Artificial Sequence
<220> FEATURE:
<223> OTHER INFORMATION: primer #51 (IL2_Y45A_F_long)

<400> SEQUENCE: 264
gctcacaaag aagtttgcca tgcccaagaa ggcc                               34

<210> SEQ ID NO 265
<211> LENGTH: 34
<212> TYPE: DNA
<213> ORGANISM: Artificial Sequence
<220> FEATURE:
<223> OTHER INFORMATION: primer #52 (IL2_Y45A_R_long)
```

-continued 263 264

<400> SEQUENCE: 265
ggccttcttg ggcatggcaa acttctttgt gagc                                    34

<210> SEQ ID NO 266
<211> LENGTH: 33
<212> TYPE: DNA
<213> ORGANISM: Artificial Sequence
<220> FEATURE:
<223> OTHER INFORMATION: primer #53 (IL2_K48C_F)

<400> SEQUENCE: 266 aagtttaca tgccctgtaa ggccacagaa ctg                                      33

<210> SEQ ID NO 267
<211> LENGTH: 33
<212> TYPE: DNA
<213> ORGANISM: Artificial Sequence
<220> FEATURE:
<223> OTHER INFORMATION: primer #54 (IL2_K48C_R)

<400> SEQUENCE: 267
cagttctgtg gccttacagg gcatgtaaaa ctt                                     33

<210> SEQ ID NO 268
<211> LENGTH: 33
<212> TYPE: DNA
<213> ORGANISM: Artificial Sequence
<220> FEATURE:
<223> OTHER INFORMATION: primer #55 (IL2_K49C_F)

<400> SEQUENCE: 268
ttttacatgc ccaagtgtgc cacagaactg aaa                                     33

<210> SEQ ID NO 269
<211> LENGTH: 33
<212> TYPE: DNA
<213> ORGANISM: Artificial Sequence
<220> FEATURE:
<223> OTHER INFORMATION: primer #56 (IL2_K49C_R)

<400> SEQUENCE: 269
tttcagttct gtggcacact gggcatgta aaa                                      33

<210> SEQ ID NO 270
<211> LENGTH: 33
<212> TYPE: DNA
<213> ORGANISM: Artificial Sequence
<220> FEATURE:
<223> OTHER INFORMATION: primer #57 (IL2_E61D_F)

<400> SEQUENCE: 270
cttcagtgtc tagaagacga actcaaacct ctg                                     33

<210> SEQ ID NO 271
<211> LENGTH: 33
<212> TYPE: DNA
<213> ORGANISM: Artificial Sequence
<220> FEATURE:
<223> OTHER INFORMATION: primer #58 (IL2_E61D_R)

<400> SEQUENCE: 271
cagaggtttg agttcgtctt ctagacactg aag                                     33

<210> SEQ ID NO 272
<211> LENGTH: 33

<212> TYPE: DNA
<213> ORGANISM: Artificial Sequence
<220> FEATURE:
<223> OTHER INFORMATION: primer #59 (IL2_E61Q_F)

<400> SEQUENCE: 272
cttcagtgtc tagaacaaga actcaaacct ctg                                      33

<210> SEQ ID NO 273
<211> LENGTH: 33
<212> TYPE: DNA
<213> ORGANISM: Artificial Sequence
<220> FEATURE:
<223> OTHER INFORMATION: primer #60 (IL2_E61Q_R)

<400> SEQUENCE: 273
cagaggtttg agttcttgtt ctagacactg aag                                      33

<210> SEQ ID NO 274
<211> LENGTH: 30
<212> TYPE: DNA
<213> ORGANISM: Artificial Sequence
<220> FEATURE:
<223> OTHER INFORMATION: primer #61 (IL2_E61R_F)

<400> SEQUENCE: 274
cttcagtgtc tagaacggga actcaaacct                                          30

<210> SEQ ID NO 275
<211> LENGTH: 30
<212> TYPE: DNA
<213> ORGANISM: Artificial Sequence
<220> FEATURE:
<223> OTHER INFORMATION: primer #62 (IL2_E61R_R)

<400> SEQUENCE: 275
aggtttgagt tcccgttcta gacactgaag                                          30

<210> SEQ ID NO 276
<211> LENGTH: 33
<212> TYPE: DNA
<213> ORGANISM: Artificial Sequence
<220> FEATURE:
<223> OTHER INFORMATION: primer #63 (IL2_E68D_F)

<400> SEQUENCE: 276
ctcaaacctc tggaggacgt gctaaattta gct                                      33

<210> SEQ ID NO 277
<211> LENGTH: 33
<212> TYPE: DNA
<213> ORGANISM: Artificial Sequence
<220> FEATURE:
<223> OTHER INFORMATION: primer #64 (IL2_E68D_R)

<400> SEQUENCE: 277
agctaaattt agcacgtcct ccagaggttt gag                                      33

<210> SEQ ID NO 278
<211> LENGTH: 33
<212> TYPE: DNA
<213> ORGANISM: Artificial Sequence
<220> FEATURE:
<223> OTHER INFORMATION: primer #65 (IL2_E68Q_F)

<400> SEQUENCE: 278

-continued ctcaaacctc tggagcaggt gctaaattta gct                                      33

<210> SEQ ID NO 279
<211> LENGTH: 33
<212> TYPE: DNA
<213> ORGANISM: Artificial Sequence
<220> FEATURE:
<223> OTHER INFORMATION: primer #66 (IL2_E68Q_R)

<400> SEQUENCE: 279
agctaaattt agcacctgct ccagaggttt gag                                      33

<210> SEQ ID NO 280
<211> LENGTH: 32
<212> TYPE: DNA
<213> ORGANISM: Artificial Sequence
<220> FEATURE:
<223> OTHER INFORMATION: primer #67 (IL2_V69G_F)

<400> SEQUENCE: 280
caaacctctg gaggaagggc taaatttagc tc                                       32

<210> SEQ ID NO 281
<211> LENGTH: 32
<212> TYPE: DNA
<213> ORGANISM: Artificial Sequence
<220> FEATURE:
<223> OTHER INFORMATION: primer #68 (IL2_V69G_R)

<400> SEQUENCE: 281
gagctaaatt tagcccttcc tccagaggtt tg                                       32

<210> SEQ ID NO 282
<211> LENGTH: 40
<212> TYPE: DNA
<213> ORGANISM: Artificial Sequence
<220> FEATURE:
<223> OTHER INFORMATION: primer #69 (IL2_V69G_Q74A_F)

<400> SEQUENCE: 282
ctggaggaag ggctaaattt agctgcaagc aaaaactttc                                40

<210> SEQ ID NO 283
<211> LENGTH: 40
<212> TYPE: DNA
<213> ORGANISM: Artificial Sequence
<220> FEATURE:
<223> OTHER INFORMATION: primer #70 (IL2_V69G_Q74A_R)

<400> SEQUENCE: 283
gaaagttttt gcttgcagct aaatttagcc cttcctccag                                40

<210> SEQ ID NO 284
<211> LENGTH: 24
<212> TYPE: DNA
<213> ORGANISM: Artificial Sequence
<220> FEATURE:
<223> OTHER INFORMATION: primer #71 (IL2_Q74H_F)

<400> SEQUENCE: 284
ctaaatttag ctcacagcaa aaac                                                24

<210> SEQ ID NO 285
<211> LENGTH: 24
<212> TYPE: DNA
<213> ORGANISM: Artificial Sequence
<220> FEATURE:
<223> OTHER INFORMATION: primer #72 (IL2_Q74H_R)

<400> SEQUENCE: 285
gtttttgctg tgagctaaat ttag                                          24

<210> SEQ ID NO 286
<211> LENGTH: 33
<212> TYPE: DNA
<213> ORGANISM: Artificial Sequence
<220> FEATURE:
<223> OTHER INFORMATION: primer #73 (IL2_K76C_F)

<400> SEQUENCE: 286
aatttagctc aaagctgtaa ctttcactta aga                                33

<210> SEQ ID NO 287
<211> LENGTH: 33
<212> TYPE: DNA
<213> ORGANISM: Artificial Sequence
<220> FEATURE:
<223> OTHER INFORMATION: primer #74 (IL2_K76C_R)

<400> SEQUENCE: 287
tcttaagtga aagttacagc tttgagctaa att                                33

<210> SEQ ID NO 288
<211> LENGTH: 32
<212> TYPE: DNA
<213> ORGANISM: Artificial Sequence
<220> FEATURE:
<223> OTHER INFORMATION: primer #75 (IL2_L80D_R81E_F)

<400> SEQUENCE: 288
aaagcaaaaa ctttcacgac gaacccaggg ac                                 32

<210> SEQ ID NO 289
<211> LENGTH: 32
<212> TYPE: DNA
<213> ORGANISM: Artificial Sequence
<220> FEATURE:
<223> OTHER INFORMATION: primer #76 (IL2_L80D_R81E_R)

<400> SEQUENCE: 289
gtccctgggt tcgtcgtgaa agttttttgct tt                                32

<210> SEQ ID NO 290
<211> LENGTH: 29
<212> TYPE: DNA
<213> ORGANISM: Artificial Sequence
<220> FEATURE:
<223> OTHER INFORMATION: primer #77 (IL2_L80F_F)

<400> SEQUENCE: 290
gcaaaaactt tcactttaga cccagggac                                     29

<210> SEQ ID NO 291
<211> LENGTH: 29
<212> TYPE: DNA
<213> ORGANISM: Artificial Sequence
<220> FEATURE:
<223> OTHER INFORMATION: primer #78 (IL2_L80F_R)

<400> SEQUENCE: 291
gtccctgggt ctaaagtgaa agttttttgc                                    29

<210> SEQ ID NO 292
<211> LENGTH: 29
<212> TYPE: DNA
<213> ORGANISM: Artificial Sequence
<220> FEATURE:
<223> OTHER INFORMATION: primer #79 (IL2_L80F_R81D_F)

<400> SEQUENCE: 292
gcaaaaactt tcactttgac cccagggac                                                   29

<210> SEQ ID NO 293
<211> LENGTH: 29
<212> TYPE: DNA
<213> ORGANISM: Artificial Sequence
<220> FEATURE:
<223> OTHER INFORMATION: primer #80 (IL2_L80F_R81D_R)

<400> SEQUENCE: 293
gtccctgggg tcaaagtgaa agtttttgc                                                   29

<210> SEQ ID NO 294
<211> LENGTH: 32
<212> TYPE: DNA
<213> ORGANISM: Artificial Sequence
<220> FEATURE:
<223> OTHER INFORMATION: primer #81 (IL2_L80F_R81E_F)

<400> SEQUENCE: 294
aaagcaaaaa ctttcacttc gaacccaggg ac                                              32

<210> SEQ ID NO 295
<211> LENGTH: 32
<212> TYPE: DNA
<213> ORGANISM: Artificial Sequence
<220> FEATURE:
<223> OTHER INFORMATION: primer #82 (IL2_L80F_R81E_R)

<400> SEQUENCE: 295
gtccctgggt tcgaagtgaa agtttttgct tt                                              32

<210> SEQ ID NO 296
<211> LENGTH: 32
<212> TYPE: DNA
<213> ORGANISM: Artificial Sequence
<220> FEATURE:
<223> OTHER INFORMATION: primer #83 (IL2_L80V_R81D_F)

<400> SEQUENCE: 296
aaagcaaaaa ctttcacgtg gatcccaggg ac                                              32

<210> SEQ ID NO 297
<211> LENGTH: 32
<212> TYPE: DNA
<213> ORGANISM: Artificial Sequence
<220> FEATURE:
<223> OTHER INFORMATION: primer #84 (IL2_L80V_R81D_R)

<400> SEQUENCE: 297
gtccctggga tccacgtgaa agtttttgct tt                                              32

<210> SEQ ID NO 298
<211> LENGTH: 32
<212> TYPE: DNA
<213> ORGANISM: Artificial Sequence
<220> FEATURE:
<223> OTHER INFORMATION: primer #85 (IL2_L80W_R81E_F)

-continued

```
<400> SEQUENCE: 298
aaagcaaaaa ctttcactgg gaacccaggg ac                                    32

<210> SEQ ID NO 299
<211> LENGTH: 32
<212> TYPE: DNA
<213> ORGANISM: Artificial Sequence
<220> FEATURE:
<223> OTHER INFORMATION: primer #86 (IL2_L80W_R81E_R)

<400> SEQUENCE: 299
gtccctgggt tcccagtgaa agtttttgct tt                                    32

<210> SEQ ID NO 300
<211> LENGTH: 29
<212> TYPE: DNA
<213> ORGANISM: Artificial Sequence
<220> FEATURE:
<223> OTHER INFORMATION: primer #87 (IL2_L80Y_R81D_F)

<400> SEQUENCE: 300
gcaaaaactt tcactatgac cccagggac                                        29

<210> SEQ ID NO 301
<211> LENGTH: 29
<212> TYPE: DNA
<213> ORGANISM: Artificial Sequence
<220> FEATURE:
<223> OTHER INFORMATION: primer #88 (IL2_L80Y_R81D_R)

<400> SEQUENCE: 301
gtccctgggg tcatagtgaa agtttttgc                                        29

<210> SEQ ID NO 302
<211> LENGTH: 32
<212> TYPE: DNA
<213> ORGANISM: Artificial Sequence
<220> FEATURE:
<223> OTHER INFORMATION: primer #89 (IL2_L80Y_R81E_F)

<400> SEQUENCE: 302
aaagcaaaaa ctttcactac gaacccaggg ac                                    32

<210> SEQ ID NO 303
<211> LENGTH: 32
<212> TYPE: DNA
<213> ORGANISM: Artificial Sequence
<220> FEATURE:
<223> OTHER INFORMATION: primer #90 (IL2_L80Y_R81E_R)

<400> SEQUENCE: 303
gtccctgggt tcgtagtgaa agtttttgct tt                                    32

<210> SEQ ID NO 304
<211> LENGTH: 32
<212> TYPE: DNA
<213> ORGANISM: Artificial Sequence
<220> FEATURE:
<223> OTHER INFORMATION: primer #91 (IL2_L80Y_R81N_F)

<400> SEQUENCE: 304
aaagcaaaaa ctttcactac aaccccaggg ac                                    32

<210> SEQ ID NO 305
```

-continued

```
<211> LENGTH: 32
<212> TYPE: DNA
<213> ORGANISM: Artificial Sequence
<220> FEATURE:
<223> OTHER INFORMATION: primer #92 (IL2_L80Y_R81N_R)

<400> SEQUENCE: 305
gtccctgggg ttgtagtgaa agtttttgct tt                                          32

<210> SEQ ID NO 306
<211> LENGTH: 29
<212> TYPE: DNA
<213> ORGANISM: Artificial Sequence
<220> FEATURE:
<223> OTHER INFORMATION: primer #93 (IL2_L80Y_R81R_F)

<400> SEQUENCE: 306
gcaaaaactt tcactataga cccagggac                                             29

<210> SEQ ID NO 307
<211> LENGTH: 29
<212> TYPE: DNA
<213> ORGANISM: Artificial Sequence
<220> FEATURE:
<223> OTHER INFORMATION: primer #94 (IL2_L80Y_R81R_R)

<400> SEQUENCE: 307
gtccctgggt ctatagtgaa agtttttgc                                             29

<210> SEQ ID NO 308
<211> LENGTH: 31
<212> TYPE: DNA
<213> ORGANISM: Artificial Sequence
<220> FEATURE:
<223> OTHER INFORMATION: primer #95 (IL2_R81D_D84E_F)

<400> SEQUENCE: 308
ctttcactta gaccccaggg agttaatcag c                                          31

<210> SEQ ID NO 309
<211> LENGTH: 31
<212> TYPE: DNA
<213> ORGANISM: Artificial Sequence
<220> FEATURE:
<223> OTHER INFORMATION: primer #96 (IL2_R81D_D84E_R)

<400> SEQUENCE: 309
gctgattaac tccctggggt ctaagtgaaa g                                          31

<210> SEQ ID NO 310
<211> LENGTH: 34
<212> TYPE: DNA
<213> ORGANISM: Artificial Sequence
<220> FEATURE:
<223> OTHER INFORMATION: primer #97 (IL2_R81D_F)

<400> SEQUENCE: 310
caaaaacttt cacttagacc ccagggactt aatc                                       34

<210> SEQ ID NO 311
<211> LENGTH: 34
<212> TYPE: DNA
<213> ORGANISM: Artificial Sequence
<220> FEATURE:
<223> OTHER INFORMATION: primer #98 (IL2_R81D_R)

<400> SEQUENCE: 311
```

-continued gattaagtcc ctggggtcta agtgaaagtt tttg                        34

<210> SEQ ID NO 312
<211> LENGTH: 51
<212> TYPE: DNA
<213> ORGANISM: Artificial Sequence
<220> FEATURE:
<223> OTHER INFORMATION: primer #99 (IL2_R81D_F_long)

<400> SEQUENCE: 312
ctcaaagcaa aaactttcac ttagacccca gggacttaat cagcaaatat c     51

<210> SEQ ID NO 313
<211> LENGTH: 51
<212> TYPE: DNA
<213> ORGANISM: Artificial Sequence
<220> FEATURE:
<223> OTHER INFORMATION: primer #100 (IL2_R81D_R_long)

<400> SEQUENCE: 313
gatatttgct gattaagtcc ctggggtcta agtgaaagtt tttgctttga g     51

<210> SEQ ID NO 314
<211> LENGTH: 43
<212> TYPE: DNA
<213> ORGANISM: Artificial Sequence
<220> FEATURE:
<223> OTHER INFORMATION: primer #101
      (IL2_R81E_D84E_L85V_I86V_V91T_I92F_F)

<400> SEQUENCE: 314
gaacccaggg aggtagtcag caatatcaac acatttgttc tgg              43

<210> SEQ ID NO 315
<211> LENGTH: 43
<212> TYPE: DNA
<213> ORGANISM: Artificial Sequence
<220> FEATURE:
<223> OTHER INFORMATION: primer #102
      (IL2_R81E_D84E_L85V_I86V_V91T_I92F_R)

<400> SEQUENCE: 315
ccagaacaaa tgtgttgata ttgctgacta cctccctggg ttc              43

<210> SEQ ID NO 316
<211> LENGTH: 31
<212> TYPE: DNA
<213> ORGANISM: Artificial Sequence
<220> FEATURE:
<223> OTHER INFORMATION: primer #103 (IL2_R81E_F)

<400> SEQUENCE: 316
aaactttcac ttagaaccca gggacttaat c                           31

<210> SEQ ID NO 317
<211> LENGTH: 31
<212> TYPE: DNA
<213> ORGANISM: Artificial Sequence
<220> FEATURE:
<223> OTHER INFORMATION: primer #104 (IL2_R81E_R)

<400> SEQUENCE: 317
gattaagtcc ctgggttcta agtgaaagtt t                           31

<210> SEQ ID NO 318

-continued

```
<211> LENGTH: 33
<212> TYPE: DNA
<213> ORGANISM: Artificial Sequence
<220> FEATURE:
<223> OTHER INFORMATION: primer #105 (IL2_P82G_F)

<400> SEQUENCE: 318
aactttcact tcgaaggcag ggacgtagtc agc                                  33

<210> SEQ ID NO 319
<211> LENGTH: 33
<212> TYPE: DNA
<213> ORGANISM: Artificial Sequence
<220> FEATURE:
<223> OTHER INFORMATION: primer #106 (IL2_P82G_R)

<400> SEQUENCE: 319
gctgactacg tccctgcctt cgaagtgaaa gtt                                  33

<210> SEQ ID NO 320
<211> LENGTH: 33
<212> TYPE: DNA
<213> ORGANISM: Artificial Sequence
<220> FEATURE:
<223> OTHER INFORMATION: primer #107 (IL2_P82V_F)

<400> SEQUENCE: 320
aactttcact tcgaagtcag ggacgtagtc agc                                  33

<210> SEQ ID NO 321
<211> LENGTH: 33
<212> TYPE: DNA
<213> ORGANISM: Artificial Sequence
<220> FEATURE:
<223> OTHER INFORMATION: primer #108 (IL2_P82V_R)

<400> SEQUENCE: 321
gctgactacg tccctgactt cgaagtgaaa gtt                                  33

<210> SEQ ID NO 322
<211> LENGTH: 34
<212> TYPE: DNA
<213> ORGANISM: Artificial Sequence
<220> FEATURE:
<223> OTHER INFORMATION: primer #109 (IL2_D84E_F)

<400> SEQUENCE: 322
cttaagaccc agggagttaa tcagcaatat caac                                 34

<210> SEQ ID NO 323
<211> LENGTH: 34
<212> TYPE: DNA
<213> ORGANISM: Artificial Sequence
<220> FEATURE:
<223> OTHER INFORMATION: primer #110 (IL2_D84E_R)

<400> SEQUENCE: 323
gttgatattg ctgattaact ccctgggtct taag                                 34

<210> SEQ ID NO 324
<211> LENGTH: 32
<212> TYPE: DNA
<213> ORGANISM: Artificial Sequence
<220> FEATURE:
<223> OTHER INFORMATION: primer #111 (IL2_D84F_F)

<400> SEQUENCE: 324
```

-continued

```
cacttagacc ccaggttctt aatcagcaat at                                32

<210> SEQ ID NO 325
<211> LENGTH: 32
<212> TYPE: DNA
<213> ORGANISM: Artificial Sequence
<220> FEATURE:
<223> OTHER INFORMATION: primer #112 (IL2_D84F_R)

<400> SEQUENCE: 325
atattgctga ttaagaacct ggggtctaag tg                                32

<210> SEQ ID NO 326
<211> LENGTH: 31
<212> TYPE: DNA
<213> ORGANISM: Artificial Sequence
<220> FEATURE:
<223> OTHER INFORMATION: primer #113 (IL2_D84V_F)

<400> SEQUENCE: 326
acttagaccc cagggtctta atcagcaata t                                 31

<210> SEQ ID NO 327
<211> LENGTH: 31
<212> TYPE: DNA
<213> ORGANISM: Artificial Sequence
<220> FEATURE:
<223> OTHER INFORMATION: primer #114 (IL2_D84V_R)

<400> SEQUENCE: 327
atattgctga ttaagaccct ggggtctaag t                                 31

<210> SEQ ID NO 328
<211> LENGTH: 35
<212> TYPE: DNA
<213> ORGANISM: Artificial Sequence
<220> FEATURE:
<223> OTHER INFORMATION: primer #115 (IL2_L85A_I86A_F)

<400> SEQUENCE: 328
ctttgacccc agggacgctg ccagcaatat caacg                             35

<210> SEQ ID NO 329
<211> LENGTH: 35
<212> TYPE: DNA
<213> ORGANISM: Artificial Sequence
<220> FEATURE:
<223> OTHER INFORMATION: primer #116 (IL2_L85A_I86A_R)

<400> SEQUENCE: 329
cgttgatatt gctggcagcg tccctggggt caaag                             35

<210> SEQ ID NO 330
<211> LENGTH: 30
<212> TYPE: DNA
<213> ORGANISM: Artificial Sequence
<220> FEATURE:
<223> OTHER INFORMATION: primer #117 (IL2_L85E_I86V_F)

<400> SEQUENCE: 330
cccagggacg aagtgagcaa tatcaacgta                                   30

<210> SEQ ID NO 331
<211> LENGTH: 30
<212> TYPE: DNA
```

-continued

```
<213> ORGANISM: Artificial Sequence
<220> FEATURE:
<223> OTHER INFORMATION: primer #118 (IL2_L85E_I86V_R)

<400> SEQUENCE: 331
tacgttgata ttgctcactt cgtccctggg                                      30

<210> SEQ ID NO 332
<211> LENGTH: 27
<212> TYPE: DNA
<213> ORGANISM: Artificial Sequence
<220> FEATURE:
<223> OTHER INFORMATION: primer #119 (IL2_L85F_I86L_F)

<400> SEQUENCE: 332
cccagggact tcctcagcaa tatcaac                                         27

<210> SEQ ID NO 333
<211> LENGTH: 27
<212> TYPE: DNA
<213> ORGANISM: Artificial Sequence
<220> FEATURE:
<223> OTHER INFORMATION: primer #120 (IL2_L85F_I86L_R)

<400> SEQUENCE: 333
gttgatattg ctgaggaagt ccctggg                                         27

<210> SEQ ID NO 334
<211> LENGTH: 27
<212> TYPE: DNA
<213> ORGANISM: Artificial Sequence
<220> FEATURE:
<223> OTHER INFORMATION: primer #121 (IL2_L85F_I86V_F)

<400> SEQUENCE: 334
cccagggact tcgtcagcaa tatcaac                                         27

<210> SEQ ID NO 335
<211> LENGTH: 27
<212> TYPE: DNA
<213> ORGANISM: Artificial Sequence
<220> FEATURE:
<223> OTHER INFORMATION: primer #122 (IL2_L85F_I86V_R)

<400> SEQUENCE: 335
gttgatattg ctgacgaagt ccctggg                                         27

<210> SEQ ID NO 336
<211> LENGTH: 27
<212> TYPE: DNA
<213> ORGANISM: Artificial Sequence
<220> FEATURE:
<223> OTHER INFORMATION: primer #123 (IL2_L85G_I86A_F)

<400> SEQUENCE: 336
cccagggacg gagccagcaa tatcaac                                         27

<210> SEQ ID NO 337
<211> LENGTH: 27
<212> TYPE: DNA
<213> ORGANISM: Artificial Sequence
<220> FEATURE:
<223> OTHER INFORMATION: primer #124 (IL2_L85G_I86A_R)

<400> SEQUENCE: 337
gttgatattg ctggctccgt ccctggg                                         27
```

-continued

```
<210> SEQ ID NO 338
<211> LENGTH: 35
<212> TYPE: DNA
<213> ORGANISM: Artificial Sequence
<220> FEATURE:
<223> OTHER INFORMATION: primer #125 (IL2_L85G_I86V_F)

<400> SEQUENCE: 338
ctttgacccc agggacggtg ttagcaatat caacg                              35

<210> SEQ ID NO 339
<211> LENGTH: 35
<212> TYPE: DNA
<213> ORGANISM: Artificial Sequence
<220> FEATURE:
<223> OTHER INFORMATION: primer #126 (IL2_L85G_I86V_R)

<400> SEQUENCE: 339
cgttgatatt gctaacccag tccctggggt caaag                              35

<210> SEQ ID NO 340
<211> LENGTH: 27
<212> TYPE: DNA
<213> ORGANISM: Artificial Sequence
<220> FEATURE:
<223> OTHER INFORMATION: primer #127 (IL2_L85I_I86V_F)

<400> SEQUENCE: 340
cccagggaca tagtcagcaa tatcaac                                       27

<210> SEQ ID NO 341
<211> LENGTH: 27
<212> TYPE: DNA
<213> ORGANISM: Artificial Sequence
<220> FEATURE:
<223> OTHER INFORMATION: primer #128 (IL2_L85I_I86V_R)

<400> SEQUENCE: 341
gttgatattg ctgactatgt ccctggg                                      27

<210> SEQ ID NO 342
<211> LENGTH: 34
<212> TYPE: DNA
<213> ORGANISM: Artificial Sequence
<220> FEATURE:
<223> OTHER INFORMATION: primer #129 (IL2_L85L_I86A_F)

<400> SEQUENCE: 342
cttcgaaccc agggacctgg ccagcaatat caac                              34

<210> SEQ ID NO 343
<211> LENGTH: 34
<212> TYPE: DNA
<213> ORGANISM: Artificial Sequence
<220> FEATURE:
<223> OTHER INFORMATION: primer #130 (IL2_L85L_I86A_R)

<400> SEQUENCE: 343
gttgatattg ctggccaggt ccctgggttc gaag                              34

<210> SEQ ID NO 344
<211> LENGTH: 34
<212> TYPE: DNA
<213> ORGANISM: Artificial Sequence
<220> FEATURE:
```

-continued

<223> OTHER INFORMATION: primer #131 (IL2_L85L_I86V_F)

<400> SEQUENCE: 344
ctttgagccc agggacttag tcagcaatat caac                                34

<210> SEQ ID NO 345
<211> LENGTH: 34
<212> TYPE: DNA
<213> ORGANISM: Artificial Sequence
<220> FEATURE:
<223> OTHER INFORMATION: primer #132 (IL2_L85L_I86V_R)

<400> SEQUENCE: 345
gttgatattg ctgactaagt ccctgggctc aaag                                34

<210> SEQ ID NO 346
<211> LENGTH: 27
<212> TYPE: DNA
<213> ORGANISM: Artificial Sequence
<220> FEATURE:
<223> OTHER INFORMATION: primer #133 (IL2_L85T_I86G_F)

<400> SEQUENCE: 346
cccagggaca caggcagcaa tatcaac                                        27

<210> SEQ ID NO 347
<211> LENGTH: 27
<212> TYPE: DNA
<213> ORGANISM: Artificial Sequence
<220> FEATURE:
<223> OTHER INFORMATION: primer #134 (IL2_L85T_I86G_R)

<400> SEQUENCE: 347
gttgatattg ctgcctgtgt ccctggg                                        27

<210> SEQ ID NO 348
<211> LENGTH: 29
<212> TYPE: DNA
<213> ORGANISM: Artificial Sequence
<220> FEATURE:
<223> OTHER INFORMATION: primer #135 (IL2_L85V_I86G_F)

<400> SEQUENCE: 348
cccagggacg taggcagcaa tatcaacgt                                      29

<210> SEQ ID NO 349
<211> LENGTH: 29
<212> TYPE: DNA
<213> ORGANISM: Artificial Sequence
<220> FEATURE:
<223> OTHER INFORMATION: primer #136 (IL2_L85V_I86G_R)

<400> SEQUENCE: 349
acgttgatat tgctgcctac gtccctggg                                      29

<210> SEQ ID NO 350
<211> LENGTH: 31
<212> TYPE: DNA
<213> ORGANISM: Artificial Sequence
<220> FEATURE:
<223> OTHER INFORMATION: primer #137 (IL2_L85V_I86I_codon_F)

<400> SEQUENCE: 350
gaacccaggg acgtaatcag caatatcaac g                                   31

-continued

```
<210> SEQ ID NO 351
<211> LENGTH: 31
<212> TYPE: DNA
<213> ORGANISM: Artificial Sequence
<220> FEATURE:
<223> OTHER INFORMATION: primer #138 (IL2_L85V_I86I_codon_R)

<400> SEQUENCE: 351
cgttgatatt gctgattacg tccctgggtt c                                        31

<210> SEQ ID NO 352
<211> LENGTH: 30
<212> TYPE: DNA
<213> ORGANISM: Artificial Sequence
<220> FEATURE:
<223> OTHER INFORMATION: primer #139 (IL2_L85V_I86V_F)

<400> SEQUENCE: 352
gacccaggga cgtagtcagc aatatcaacg                                          30

<210> SEQ ID NO 353
<211> LENGTH: 30
<212> TYPE: DNA
<213> ORGANISM: Artificial Sequence
<220> FEATURE:
<223> OTHER INFORMATION: primer #140 (IL2_L85V_I86V_R)

<400> SEQUENCE: 353
cgttgatatt gctgactacg tccctgggtc                                          30

<210> SEQ ID NO 354
<211> LENGTH: 29
<212> TYPE: DNA
<213> ORGANISM: Artificial Sequence
<220> FEATURE:
<223> OTHER INFORMATION: primer #141 (IL2_L85W_I86V_F)

<400> SEQUENCE: 354
cccagggact gggtcagcaa tatcaacgt                                           29

<210> SEQ ID NO 355
<211> LENGTH: 29
<212> TYPE: DNA
<213> ORGANISM: Artificial Sequence
<220> FEATURE:
<223> OTHER INFORMATION: primer #142 (IL2_L85W_I86V_R)

<400> SEQUENCE: 355
acgttgatat tgctgaccca gtccctggg                                           29

<210> SEQ ID NO 356
<211> LENGTH: 30
<212> TYPE: DNA
<213> ORGANISM: Artificial Sequence
<220> FEATURE:
<223> OTHER INFORMATION: primer #143 (IL2_L85W_I86V_Long_F)

<400> SEQUENCE: 356
tttgacccca gggactgggt cagcaatatc                                          30

<210> SEQ ID NO 357
<211> LENGTH: 30
<212> TYPE: DNA
<213> ORGANISM: Artificial Sequence
<220> FEATURE:
<223> OTHER INFORMATION: primer #144 (IL2_L85W_I86V_Long_R)
```

-continued

<400> SEQUENCE: 357
gatattgctg acccagtccc tggggtcaaa                                    30

<210> SEQ ID NO 358
<211> LENGTH: 34
<212> TYPE: DNA
<213> ORGANISM: Artificial Sequence
<220> FEATURE:
<223> OTHER INFORMATION: primer #145 (IL2_L85Y_I86V_F)

<400> SEQUENCE: 358
cttcgaaccc agggactacg tcagcaatat caac                               34

<210> SEQ ID NO 359
<211> LENGTH: 34
<212> TYPE: DNA
<213> ORGANISM: Artificial Sequence
<220> FEATURE:
<223> OTHER INFORMATION: primer #146 (IL2_L85Y_I86V_R)

<400> SEQUENCE: 359
gttgatattg ctgacgtagt ccctgggttc gaag                               34

<210> SEQ ID NO 360
<211> LENGTH: 31
<212> TYPE: DNA
<213> ORGANISM: Artificial Sequence
<220> FEATURE:
<223> OTHER INFORMATION: primer #147 (IL2_I86V_V91T_I92F_F)

<400> SEQUENCE: 360
gtcagcaata tcaacacatt tgttctggaa c                                  31

<210> SEQ ID NO 361
<211> LENGTH: 31
<212> TYPE: DNA
<213> ORGANISM: Artificial Sequence
<220> FEATURE:
<223> OTHER INFORMATION: primer #148 (IL2_I86V_V91T_I92F_R)

<400> SEQUENCE: 361
gttccagaac aaatgtgttg atattgctga c                                  31

<210> SEQ ID NO 362
<211> LENGTH: 33
<212> TYPE: DNA
<213> ORGANISM: Artificial Sequence
<220> FEATURE:
<223> OTHER INFORMATION: primer #149 (IL2_S87C_F)

<400> SEQUENCE: 362
cccagggact taatctgcaa tatcaacgta ata                                33

<210> SEQ ID NO 363
<211> LENGTH: 33
<212> TYPE: DNA
<213> ORGANISM: Artificial Sequence
<220> FEATURE:
<223> OTHER INFORMATION: primer #150 (IL2_S87C_R)

<400> SEQUENCE: 363
tattacgttg atattgcaga ttaagtccct ggg                                33

<210> SEQ ID NO 364
<211> LENGTH: 34

```
<212> TYPE: DNA
<213> ORGANISM: Artificial Sequence
<220> FEATURE:
<223> OTHER INFORMATION: primer #151 (IL2_N88F_F)

<400> SEQUENCE: 364
cagggactta atcagcttta tcaacgtatt tgtt                              34

<210> SEQ ID NO 365
<211> LENGTH: 34
<212> TYPE: DNA
<213> ORGANISM: Artificial Sequence
<220> FEATURE:
<223> OTHER INFORMATION: primer #152 (IL2_N88F_R)

<400> SEQUENCE: 365
aacaaatacg ttgataaagc tgattaagtc cctg                             34

<210> SEQ ID NO 366
<211> LENGTH: 33
<212> TYPE: DNA
<213> ORGANISM: Artificial Sequence
<220> FEATURE:
<223> OTHER INFORMATION: primer #153 (IL2_N88Q_F)

<400> SEQUENCE: 366
gggacttaat cagccaaatc aacgtaatag ttc                              33

<210> SEQ ID NO 367
<211> LENGTH: 33
<212> TYPE: DNA
<213> ORGANISM: Artificial Sequence
<220> FEATURE:
<223> OTHER INFORMATION: primer #154 (IL2_N88Q_R)

<400> SEQUENCE: 367
gaactattac gttgatttgg ctgattaagt ccc                              33

<210> SEQ ID NO 368
<211> LENGTH: 34
<212> TYPE: DNA
<213> ORGANISM: Artificial Sequence
<220> FEATURE:
<223> OTHER INFORMATION: primer #155 (IL2_N88V_F)

<400> SEQUENCE: 368
cagggactta atcagcgtta tcaacgtatt tgtt                             34

<210> SEQ ID NO 369
<211> LENGTH: 34
<212> TYPE: DNA
<213> ORGANISM: Artificial Sequence
<220> FEATURE:
<223> OTHER INFORMATION: primer #156 (IL2_N88V_R)

<400> SEQUENCE: 369
aacaaatacg ttgataacgc tgattaagtc cctg                             34

<210> SEQ ID NO 370
<211> LENGTH: 33
<212> TYPE: DNA
<213> ORGANISM: Artificial Sequence
<220> FEATURE:
<223> OTHER INFORMATION: primer #157 (IL2_I89F_F)

<400> SEQUENCE: 370
```

```
gacttaatca gcaatttcaa cgtaatagtt ctg                                    33

<210> SEQ ID NO 371
<211> LENGTH: 33
<212> TYPE: DNA
<213> ORGANISM: Artificial Sequence
<220> FEATURE:
<223> OTHER INFORMATION: primer #158 (IL2_I89F_R)

<400> SEQUENCE: 371
cagaactatt acgttgaaat tgctgattaa gtc                                    33

<210> SEQ ID NO 372
<211> LENGTH: 33
<212> TYPE: DNA
<213> ORGANISM: Artificial Sequence
<220> FEATURE:
<223> OTHER INFORMATION: primer #159 (IL2_V91E_I92F_F)

<400> SEQUENCE: 372
agcaatatca acgaattcgt tctggaacta aag                                    33

<210> SEQ ID NO 373
<211> LENGTH: 33
<212> TYPE: DNA
<213> ORGANISM: Artificial Sequence
<220> FEATURE:
<223> OTHER INFORMATION: primer #160 (IL2_V91E_I92F_R)

<400> SEQUENCE: 373
ctttagttcc agaacgaatt cgttgatatt gct                                    33

<210> SEQ ID NO 374
<211> LENGTH: 33
<212> TYPE: DNA
<213> ORGANISM: Artificial Sequence
<220> FEATURE:
<223> OTHER INFORMATION: primer #161 (IL2_V91E_I92W_F)

<400> SEQUENCE: 374
agcaatatca acgaatgggt tctggaacta aag                                    33

<210> SEQ ID NO 375
<211> LENGTH: 33
<212> TYPE: DNA
<213> ORGANISM: Artificial Sequence
<220> FEATURE:
<223> OTHER INFORMATION: primer #162 (IL2_V91E_I92W_R)

<400> SEQUENCE: 375
ctttagttcc agaacccatt cgttgatatt gct                                    33

<210> SEQ ID NO 376
<211> LENGTH: 34
<212> TYPE: DNA
<213> ORGANISM: Artificial Sequence
<220> FEATURE:
<223> OTHER INFORMATION: primer #163 (IL2_V91F_F)

<400> SEQUENCE: 376
cagcaatatc aactttatag ttctggaact aaag                                   34

<210> SEQ ID NO 377
<211> LENGTH: 34
<212> TYPE: DNA
<213> ORGANISM: Artificial Sequence
```

<220> FEATURE:
<223> OTHER INFORMATION: primer #164 (IL2_V91F_R)

<400> SEQUENCE: 377
ctttagttcc agaactataa agttgatatt gctg                                     34

<210> SEQ ID NO 378
<211> LENGTH: 34
<212> TYPE: DNA
<213> ORGANISM: Artificial Sequence
<220> FEATURE:
<223> OTHER INFORMATION: primer #165 (IL2_V91T_F)

<400> SEQUENCE: 378
cagcaatatc aacacaatag ttctggaact aaag                                     34

<210> SEQ ID NO 379
<211> LENGTH: 34
<212> TYPE: DNA
<213> ORGANISM: Artificial Sequence
<220> FEATURE:
<223> OTHER INFORMATION: primer #166 (IL2_V91T_R)

<400> SEQUENCE: 379
ctttagttcc agaactattg tgttgatatt gctg                                     34

<210> SEQ ID NO 380
<211> LENGTH: 32
<212> TYPE: DNA
<213> ORGANISM: Artificial Sequence
<220> FEATURE:
<223> OTHER INFORMATION: primer #167 (IL2_I92F_F)

<400> SEQUENCE: 380
gcaatatcaa cgtatttgtt ctggaactaa ag                                       32

<210> SEQ ID NO 381
<211> LENGTH: 32
<212> TYPE: DNA
<213> ORGANISM: Artificial Sequence
<220> FEATURE:
<223> OTHER INFORMATION: primer #168 (IL2_I92F_R)

<400> SEQUENCE: 381
ctttagttcc agaacaaata cgttgatatt gc                                       32

<210> SEQ ID NO 382
<211> LENGTH: 49
<212> TYPE: DNA
<213> ORGANISM: Artificial Sequence
<220> FEATURE:
<223> OTHER INFORMATION: primer #169 (IL2_I92F_F_long)

<400> SEQUENCE: 382
gacttaatca gcaatatcaa cgtatttgtt ctggaactaa agggatctg                     49

<210> SEQ ID NO 383
<211> LENGTH: 49
<212> TYPE: DNA
<213> ORGANISM: Artificial Sequence
<220> FEATURE:
<223> OTHER INFORMATION: primer #170 (IL2_I92F_R_long)

<400> SEQUENCE: 383
cagatccctt tagttccaga acaaatacgt tgatattgct gattaagtc                     49

-continued

```
<210> SEQ ID NO 384
<211> LENGTH: 45
<212> TYPE: DNA
<213> ORGANISM: Artificial Sequence
<220> FEATURE:
<223> OTHER INFORMATION: primer #171 (IL2_I92F_F_long2)

<400> SEQUENCE: 384
cttaatcagc aatatcaacg tatttgttct ggaactaaag ggatc                    45

<210> SEQ ID NO 385
<211> LENGTH: 45
<212> TYPE: DNA
<213> ORGANISM: Artificial Sequence
<220> FEATURE:
<223> OTHER INFORMATION: primer #172 (IL2_I92F_R_long2)

<400> SEQUENCE: 385
gatcccttta gttccagaac aaatacgttg atattgctga ttaag                    45

<210> SEQ ID NO 386
<211> LENGTH: 32
<212> TYPE: DNA
<213> ORGANISM: Artificial Sequence
<220> FEATURE:
<223> OTHER INFORMATION: primer #173 (IL2_I92F_L94F_L96F_F)

<400> SEQUENCE: 386
caacgtattt gttttcgaat tcaagggatc tg                                  32

<210> SEQ ID NO 387
<211> LENGTH: 32
<212> TYPE: DNA
<213> ORGANISM: Artificial Sequence
<220> FEATURE:
<223> OTHER INFORMATION: primer #174 (IL2_I92F_L94F_L96F_R)

<400> SEQUENCE: 387
cagatccctt gaattcgaaa acaaatacgt tg                                  32

<210> SEQ ID NO 388
<211> LENGTH: 39
<212> TYPE: DNA
<213> ORGANISM: Artificial Sequence
<220> FEATURE:
<223> OTHER INFORMATION: primer #175 (IL2_I92F_L94F_L96F_F)

<400> SEQUENCE: 388
gcaatatcaa cgtatttgtt ttcgaattta agggatctg                           39

<210> SEQ ID NO 389
<211> LENGTH: 39
<212> TYPE: DNA
<213> ORGANISM: Artificial Sequence
<220> FEATURE:
<223> OTHER INFORMATION: primer #176 (IL2_I92F_L94F_L96F_R)

<400> SEQUENCE: 389
cagatccctt aaattcgaaa acaaatacgt tgatattgc                           39

<210> SEQ ID NO 390
<211> LENGTH: 39
<212> TYPE: DNA
<213> ORGANISM: Artificial Sequence
<220> FEATURE:
<223> OTHER INFORMATION: primer #177 (IL2_I92F_L94F_L96I_F)
```

<400> SEQUENCE: 390
gcaatatcaa cgtatttgtt ttcgaaatta agggatctg                          39

<210> SEQ ID NO 391
<211> LENGTH: 39
<212> TYPE: DNA
<213> ORGANISM: Artificial Sequence
<220> FEATURE:
<223> OTHER INFORMATION: primer #178 (IL2_I92F_L94F_L96I_R)

<400> SEQUENCE: 391
cagatcccTT aatttcgaaa acaaatacgt tgatattgc                          39

<210> SEQ ID NO 392
<211> LENGTH: 39
<212> TYPE: DNA
<213> ORGANISM: Artificial Sequence
<220> FEATURE:
<223> OTHER INFORMATION: primer #179 (IL2_I92F_L94F_L96V_F)

<400> SEQUENCE: 392
gcaatatcaa cgtatttgtt ttcgaagtaa agggatctg                          39

<210> SEQ ID NO 393
<211> LENGTH: 39
<212> TYPE: DNA
<213> ORGANISM: Artificial Sequence
<220> FEATURE:
<223> OTHER INFORMATION: primer #180 (IL2_I92F_L94F_L96V_R)

<400> SEQUENCE: 393
cagatcccTT tacttcgaaa acaaatacgt tgatattgc                          39

<210> SEQ ID NO 394
<211> LENGTH: 33
<212> TYPE: DNA
<213> ORGANISM: Artificial Sequence
<220> FEATURE:
<223> OTHER INFORMATION: primer #181 (IL2_I92I_F)

<400> SEQUENCE: 394
gcaatatcaa cgtaattgtt ctggaactaa agg                                33

<210> SEQ ID NO 395
<211> LENGTH: 33
<212> TYPE: DNA
<213> ORGANISM: Artificial Sequence
<220> FEATURE:
<223> OTHER INFORMATION: primer #182 (IL2_I92I_R)

<400> SEQUENCE: 395
cctttagttc cagaacaatt acgttgatat tgc                                33

<210> SEQ ID NO 396
<211> LENGTH: 33
<212> TYPE: DNA
<213> ORGANISM: Artificial Sequence
<220> FEATURE:
<223> OTHER INFORMATION: primer #183 (IL2_I92L_F)

<400> SEQUENCE: 396
gcaatatcaa cgtattagtt ctggaactaa agg                                33

<210> SEQ ID NO 397

<211> LENGTH: 33
<212> TYPE: DNA
<213> ORGANISM: Artificial Sequence
<220> FEATURE:
<223> OTHER INFORMATION: primer #184 (IL2_I92L_R)

<400> SEQUENCE: 397
cctttagttc cagaactaat acgttgatat tgc                                33

<210> SEQ ID NO 398
<211> LENGTH: 33
<212> TYPE: DNA
<213> ORGANISM: Artificial Sequence
<220> FEATURE:
<223> OTHER INFORMATION: primer #185 (IL2_I92W_F)

<400> SEQUENCE: 398
agcaatatca acgtatgggt tctggaacta aag                                33

<210> SEQ ID NO 399
<211> LENGTH: 33
<212> TYPE: DNA
<213> ORGANISM: Artificial Sequence
<220> FEATURE:
<223> OTHER INFORMATION: primer #186 (IL2_I92W_R)

<400> SEQUENCE: 399
ctttagttcc agaacccata cgttgatatt gct                                33

<210> SEQ ID NO 400
<211> LENGTH: 32
<212> TYPE: DNA
<213> ORGANISM: Artificial Sequence
<220> FEATURE:
<223> OTHER INFORMATION: primer #187 (IL2_I92Y_F)

<400> SEQUENCE: 400
gcaatatcaa cgtatatgtt ctggaactaa ag                                 32

<210> SEQ ID NO 401
<211> LENGTH: 32
<212> TYPE: DNA
<213> ORGANISM: Artificial Sequence
<220> FEATURE:
<223> OTHER INFORMATION: primer #188 (IL2_I92Y_R)

<400> SEQUENCE: 401
ctttagttcc agaacatata cgttgatatt gc                                 32

<210> SEQ ID NO 402
<211> LENGTH: 33
<212> TYPE: DNA
<213> ORGANISM: Artificial Sequence
<220> FEATURE:
<223> OTHER INFORMATION: primer #189 (IL2_L94F_L96F_F)

<400> SEQUENCE: 402
cgtaatagtt ttcgaattta agggatctga aac                                33

<210> SEQ ID NO 403
<211> LENGTH: 33
<212> TYPE: DNA
<213> ORGANISM: Artificial Sequence
<220> FEATURE:
<223> OTHER INFORMATION: primer #190 (IL2_L94F_L96F_R)

<400> SEQUENCE: 403
gtttcagatc ccttaaattc gaaaactatt acg                                    33

<210> SEQ ID NO 404
<211> LENGTH: 33
<212> TYPE: DNA
<213> ORGANISM: Artificial Sequence
<220> FEATURE:
<223> OTHER INFORMATION: primer #191 (IL2_L94F_L96I_F)

<400> SEQUENCE: 404
cgtaatagtt ttcgaaatta agggatctga aac                                    33

<210> SEQ ID NO 405
<211> LENGTH: 33
<212> TYPE: DNA
<213> ORGANISM: Artificial Sequence
<220> FEATURE:
<223> OTHER INFORMATION: primer #192 (IL2_L94F_L96I_R)

<400> SEQUENCE: 405
gtttcagatc ccttaatttc gaaaactatt acg                                    33

<210> SEQ ID NO 406
<211> LENGTH: 33
<212> TYPE: DNA
<213> ORGANISM: Artificial Sequence
<220> FEATURE:
<223> OTHER INFORMATION: primer #193 (IL2_L94F_L96V_F)

<400> SEQUENCE: 406
cgtaatagtt ttcgaagtaa agggatctga aac                                    33

<210> SEQ ID NO 407
<211> LENGTH: 33
<212> TYPE: DNA
<213> ORGANISM: Artificial Sequence
<220> FEATURE:
<223> OTHER INFORMATION: primer #194 (IL2_L94F_L96V_R)

<400> SEQUENCE: 407
gtttcagatc cctttacttc gaaaactatt acg                                    33

<210> SEQ ID NO 408
<211> LENGTH: 30
<212> TYPE: DNA
<213> ORGANISM: Artificial Sequence
<220> FEATURE:
<223> OTHER INFORMATION: primer #195 (IL2_E95D_F)

<400> SEQUENCE: 408
gttctggacc taaagggatc tgaaacaaca                                        30

<210> SEQ ID NO 409
<211> LENGTH: 30
<212> TYPE: DNA
<213> ORGANISM: Artificial Sequence
<220> FEATURE:
<223> OTHER INFORMATION: primer #196 (IL2_E95D_R)

<400> SEQUENCE: 409
tgttgtttca gatcccttta ggtccagaac                                        30

<210> SEQ ID NO 410
<211> LENGTH: 33
<212> TYPE: DNA

<213> ORGANISM: Artificial Sequence
<220> FEATURE:
<223> OTHER INFORMATION: primer #197 (IL2_C125S_F)

<400> SEQUENCE: 410
agatggatta cctttagtca aagcatcatc tca                                    33

<210> SEQ ID NO 411
<211> LENGTH: 33
<212> TYPE: DNA
<213> ORGANISM: Artificial Sequence
<220> FEATURE:
<223> OTHER INFORMATION: primer #198 (IL2_C125S_R)

<400> SEQUENCE: 411
tgagatgatg ctttgactaa aggtaatcca tct                                    33

<210> SEQ ID NO 412
<211> LENGTH: 34
<212> TYPE: DNA
<213> ORGANISM: Artificial Sequence
<220> FEATURE:
<223> OTHER INFORMATION: primer #199 (IL2_Q126T_F)

<400> SEQUENCE: 412
gatggattac ctttagtaca agcatcatct caac                                   34

<210> SEQ ID NO 413
<211> LENGTH: 34
<212> TYPE: DNA
<213> ORGANISM: Artificial Sequence
<220> FEATURE:
<223> OTHER INFORMATION: primer #200 (IL2_Q126T_R)

<400> SEQUENCE: 413
gttgagatga tgcttgtact aaaggtaatc catc                                   34

<210> SEQ ID NO 414
<211> LENGTH: 33
<212> TYPE: DNA
<213> ORGANISM: Artificial Sequence
<220> FEATURE:
<223> OTHER INFORMATION: primer #201 (IL2_desA1_F)

<400> SEQUENCE: 414
taagaatata catatgccta cttcaagttc tac                                    33

<210> SEQ ID NO 415
<211> LENGTH: 33
<212> TYPE: DNA
<213> ORGANISM: Artificial Sequence
<220> FEATURE:
<223> OTHER INFORMATION: primer #202 (IL2_desA1_R)

<400> SEQUENCE: 415
gtagaacttg aagtaggcat atgtatattc tta                                    33

<210> SEQ ID NO 416
<211> LENGTH: 34
<212> TYPE: DNA
<213> ORGANISM: Artificial Sequence
<220> FEATURE:
<223> OTHER INFORMATION: primer #203 (IL2_NdeI_desA1_N-term)

<400> SEQUENCE: 416
cgccatatgc ctacttcaag ttctacaaag aaaa                                   34

```
<210> SEQ ID NO 417
<211> LENGTH: 34
<212> TYPE: DNA
<213> ORGANISM: Artificial Sequence
<220> FEATURE:
<223> OTHER INFORMATION: primer #204 (IL2_BHI_C-term)

<400> SEQUENCE: 417
cgggatcctc aagtcagtgt tgagatgatg cttt                                 34

<210> SEQ ID NO 418
<211> LENGTH: 12
<212> TYPE: PRT
<213> ORGANISM: HOMO SAPIENS

<400> SEQUENCE: 418

Glu Ser Lys Tyr Gly Pro Pro Cys Pro Ser Cys Pro
1               5                   10

<210> SEQ ID NO 419
<211> LENGTH: 11
<212> TYPE: PRT
<213> ORGANISM: Artificial Sequence
<220> FEATURE:
<223> OTHER INFORMATION: Variant of hinge region

<400> SEQUENCE: 419

Glu Ser Lys Tyr Gly Pro Pro Pro Ser Cys Pro
1               5                   10

<210> SEQ ID NO 420
<211> LENGTH: 11
<212> TYPE: PRT
<213> ORGANISM: Artificial Sequence
<220> FEATURE:
<223> OTHER INFORMATION: Variant of hinge region

<400> SEQUENCE: 420

Glu Ser Lys Tyr Gly Pro Pro Cys Pro Ser Pro
1               5                   10

<210> SEQ ID NO 421
<211> LENGTH: 10
<212> TYPE: PRT
<213> ORGANISM: Artificial Sequence
<220> FEATURE:
<223> OTHER INFORMATION: Variant of hinge region

<400> SEQUENCE: 421

Glu Ser Lys Tyr Gly Pro Pro Cys Pro Ser
1               5                   10

<210> SEQ ID NO 422
<211> LENGTH: 10
<212> TYPE: PRT
<213> ORGANISM: Artificial Sequence
<220> FEATURE:
<223> OTHER INFORMATION: Variant of hinge region

<400> SEQUENCE: 422

Glu Ser Lys Tyr Gly Pro Pro Cys Pro Pro
1               5                   10

<210> SEQ ID NO 423
<211> LENGTH: 8
```

-continued

```
<212> TYPE: PRT
<213> ORGANISM: Artificial Sequence
<220> FEATURE:
<223> OTHER INFORMATION: Variant of hinge region

<400> SEQUENCE: 423

Lys Tyr Gly Pro Pro Cys Pro Ser
1               5

<210> SEQ ID NO 424
<211> LENGTH: 8
<212> TYPE: PRT
<213> ORGANISM: Artificial Sequence
<220> FEATURE:
<223> OTHER INFORMATION: Variant of hinge region

<400> SEQUENCE: 424

Glu Ser Lys Tyr Gly Pro Pro Cys
1               5

<210> SEQ ID NO 425
<211> LENGTH: 7
<212> TYPE: PRT
<213> ORGANISM: Artificial Sequence
<220> FEATURE:
<223> OTHER INFORMATION: Variant of hinge region

<400> SEQUENCE: 425

Glu Lys Tyr Gly Pro Pro Cys
1               5

<210> SEQ ID NO 426
<211> LENGTH: 6
<212> TYPE: PRT
<213> ORGANISM: Artificial Sequence
<220> FEATURE:
<223> OTHER INFORMATION: Variant of hinge region

<400> SEQUENCE: 426

Glu Ser Pro Ser Cys Pro
1               5

<210> SEQ ID NO 427
<211> LENGTH: 5
<212> TYPE: PRT
<213> ORGANISM: Artificial Sequence
<220> FEATURE:
<223> OTHER INFORMATION: Variant of hinge region

<400> SEQUENCE: 427

Glu Pro Ser Cys Pro
1               5

<210> SEQ ID NO 428
<211> LENGTH: 4
<212> TYPE: PRT
<213> ORGANISM: Artificial Sequence
<220> FEATURE:
<223> OTHER INFORMATION: Variant of hinge region

<400> SEQUENCE: 428

Pro Ser Cys Pro
1

<210> SEQ ID NO 429
<211> LENGTH: 10
<212> TYPE: PRT
```

-continued

```
<213> ORGANISM: Artificial Sequence
<220> FEATURE:
<223> OTHER INFORMATION: Variant of hinge region

<400> SEQUENCE: 429

Glu Ser Lys Tyr Gly Pro Pro Ser Cys Pro
1               5                   10

<210> SEQ ID NO 430
<211> LENGTH: 9
<212> TYPE: PRT
<213> ORGANISM: Artificial Sequence
<220> FEATURE:
<223> OTHER INFORMATION: Variant of hinge region

<400> SEQUENCE: 430

Lys Tyr Gly Pro Pro Pro Ser Cys Pro
1               5

<210> SEQ ID NO 431
<211> LENGTH: 9
<212> TYPE: PRT
<213> ORGANISM: Artificial Sequence
<220> FEATURE:
<223> OTHER INFORMATION: Variant of hinge region

<400> SEQUENCE: 431

Glu Ser Lys Tyr Gly Pro Ser Cys Pro
1               5

<210> SEQ ID NO 432
<211> LENGTH: 8
<212> TYPE: PRT
<213> ORGANISM: Artificial Sequence
<220> FEATURE:
<223> OTHER INFORMATION: Variant of hinge region

<400> SEQUENCE: 432

Glu Ser Lys Tyr Gly Pro Pro Cys
1               5

<210> SEQ ID NO 433
<211> LENGTH: 7
<212> TYPE: PRT
<213> ORGANISM: Artificial Sequence
<220> FEATURE:
<223> OTHER INFORMATION: Variant of hinge region

<400> SEQUENCE: 433

Lys Tyr Gly Pro Pro Cys Pro
1               5

<210> SEQ ID NO 434
<211> LENGTH: 7
<212> TYPE: PRT
<213> ORGANISM: Artificial Sequence
<220> FEATURE:
<223> OTHER INFORMATION: Variant of hinge region

<400> SEQUENCE: 434

Glu Ser Lys Pro Ser Cys Pro
1               5

<210> SEQ ID NO 435
<211> LENGTH: 6
<212> TYPE: PRT
<213> ORGANISM: Artificial Sequence
```

```
<220> FEATURE:
<223> OTHER INFORMATION: Variant of hinge region

<400> SEQUENCE: 435

Glu Ser Pro Ser Cys Pro
1               5

<210> SEQ ID NO 436
<211> LENGTH: 4
<212> TYPE: PRT
<213> ORGANISM: Artificial Sequence
<220> FEATURE:
<223> OTHER INFORMATION: Variant of hinge region

<400> SEQUENCE: 436

Glu Pro Ser Cys
1

<210> SEQ ID NO 437
<211> LENGTH: 3
<212> TYPE: PRT
<213> ORGANISM: Artificial Sequence
<220> FEATURE:
<223> OTHER INFORMATION: Variant of hinge region

<400> SEQUENCE: 437

Ser Cys Pro
1

<210> SEQ ID NO 438
<211> LENGTH: 221
<212> TYPE: PRT
<213> ORGANISM: homo sapiens

<400> SEQUENCE: 438

Pro Ser Cys Pro Ala Pro Glu Phe Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser Gln Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Phe Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
```

-continued

```
         195             200             205
His Tyr Thr Gln Lys Ser Leu Ser Leu Ser Leu Gly Lys
    210             215             220
```

```
<210> SEQ ID NO 439
<211> LENGTH: 442
<212> TYPE: PRT
<213> ORGANISM: Homo sapiens
<220> FEATURE:
<221> NAME/KEY: MISC_FEATURE
<222> LOCATION: (1)..(442)
<223> OTHER INFORMATION: Amino acids at position 1 to 442 form Human
      Immunoglobulin G4 Fc Fragment (homodimer)
<220> FEATURE:
<221> NAME/KEY: MISC_FEATURE
<222> LOCATION: (1)..(221)
<223> OTHER INFORMATION: Amino acids at position 1 to 221 form one
      monomer
<220> FEATURE:
<221> NAME/KEY: MISC_FEATURE
<222> LOCATION: (222)..(442)
<223> OTHER INFORMATION: Amino acids at position 222 to 442 form one
      monomer
<220> FEATURE:
<221> NAME/KEY: DISULFID
<222> LOCATION: (3)..(224)
<223> OTHER INFORMATION: Amino acids at position 3 and position 224 form
      an inter-disulfide bond
<220> FEATURE:
<221> NAME/KEY: DISULFID
<222> LOCATION: (35)..(95)
<223> OTHER INFORMATION: Amino acids at position 35 and position 95 form
      an intra-chain disulfide bond
<220> FEATURE:
<221> NAME/KEY: DISULFID
<222> LOCATION: (141)..(199)
<223> OTHER INFORMATION: Amino acids at position 141 and position 199
      form an intra-chain disulfide bond
<220> FEATURE:
<221> NAME/KEY: DISULFID
<222> LOCATION: (256)..(316)
<223> OTHER INFORMATION: Amino acids at position 256 and position 316
      form an intra-chain disulfide bond
<220> FEATURE:
<221> NAME/KEY: DISULFID
<222> LOCATION: (362)..(420)
<223> OTHER INFORMATION: Amino acids at position 362 and position 420
      form an intra-chain disulfide bond

<400> SEQUENCE: 439

Pro Ser Cys Pro Ala Pro Glu Phe Leu Gly Gly Pro Ser Val Phe Leu
1               5               10              15

Phe Pro Pro Lys Pro Lys Asp Thr Leu Met Ile Ser Arg Thr Pro Glu
        20              25              30

Val Thr Cys Val Val Val Asp Val Ser Gln Glu Asp Pro Glu Val Gln
        35              40              45

Phe Asn Trp Tyr Val Asp Gly Val Glu Val His Asn Ala Lys Thr Lys
    50              55              60

Pro Arg Glu Glu Gln Phe Asn Ser Thr Tyr Arg Val Val Ser Val Leu
65              70              75              80

Thr Val Leu His Gln Asp Trp Leu Asn Gly Lys Glu Tyr Lys Cys Lys
            85              90              95

Val Ser Asn Lys Gly Leu Pro Ser Ser Ile Glu Lys Thr Ile Ser Lys
            100             105             110

Ala Lys Gly Gln Pro Arg Glu Pro Gln Val Tyr Thr Leu Pro Pro Ser
        115             120             125

Gln Glu Glu Met Thr Lys Asn Gln Val Ser Leu Thr Cys Leu Val Lys
        130             135             140
```

-continued

```
Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
            195                 200                 205

His Tyr Thr Gln Lys Ser Leu Ser Leu Ser Leu Gly Lys Pro Ser Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
    275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
            405                 410                 415

Val Phe Ser Cys Ser Val Met His Glu Ala Leu His Asn His Tyr Thr
            420                 425                 430

Gln Lys Ser Leu Ser Leu Ser Leu Gly Lys
            435                 440
```